United States Patent
Pulici et al.

(10) Patent No.: US 8,541,575 B2
(45) Date of Patent: Sep. 24, 2013

(54) 3,4-DIARYLPYRAZOLES AS PROTEIN KINASE INHIBITORS

(75) Inventors: Maurizio Pulici, Caponago (IT); Fabio Zuccotto, Milan (IT); Alessandra Badari, Vedano al Lambro (IT); Stefano Nuvoloni, Genoa (IT); Giovanni Cervi, Como (IT); Gabriella Traquandi, Milan (IT); Sonia Biondaro, Roncà (IT); Paolo Trifiro', Genoa (IT); Chiara Marchionni, Milan (IT); Michele Modugno, Cernusco sul Naviglio (IT)

(73) Assignee: Nerviano Medical Sciences S.R.L., Nerviano (IT)

( * ) Notice: Subject to any disclaimer, the term of this patent is extended or adjusted under 35 U.S.C. 154(b) by 207 days.

(21) Appl. No.: 13/054,853

(22) PCT Filed: Jul. 23, 2009

(86) PCT No.: PCT/EP2009/059506
§ 371 (c)(1),
(2), (4) Date: Feb. 4, 2011

(87) PCT Pub. No.: WO2010/010154
PCT Pub. Date: Jan. 28, 2010

(65) Prior Publication Data
US 2011/0144068 A1 Jun. 16, 2011

(30) Foreign Application Priority Data
Jul. 24, 2008 (EP) .................. 08161076

(51) Int. Cl.
*C07D 239/02* (2006.01)
*C07D 213/04* (2006.01)
*A01N 43/54* (2006.01)

(52) U.S. Cl.
USPC ........... 544/242; 546/255; 514/256; 514/269; 514/275

(58) Field of Classification Search
None
See application file for complete search history.

(56) References Cited

U.S. PATENT DOCUMENTS
2013/0053419 A1* 2/2013 Pulici et al. .................. 514/341

FOREIGN PATENT DOCUMENTS
WO  WO 2005/068452 A1  7/2005
WO  WO 2007/105058 A2  9/2007
WO  WO 2008/042639 A1  4/2008

OTHER PUBLICATIONS
International Search Report dated Sep. 23, 2009 received from the European Patent Office.

* cited by examiner

*Primary Examiner* — James O Wilson
*Assistant Examiner* — Oluwafemi Masha
(74) *Attorney, Agent, or Firm* — Brinks Hofer Gilson & Lione; William R. Boudreaux

(57) ABSTRACT

3,4-diarylpyrazole derivatives of formula (I) as defined in the specification, and pharmaceutically acceptable salts thereof, process for their preparation and pharmaceutical compositions comprising them are disclosed; the compounds of the invention may be useful, in therapy, in the treatment of diseases associated with a disregulated protein kinase activity, like cancer.

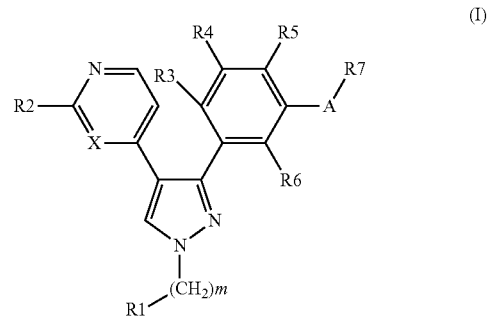

21 Claims, No Drawings

3,4-DIARYLPYRAZOLES AS PROTEIN KINASE INHIBITORS

The present invention relates to certain substituted 3,4-diarylpyrazole compounds, which modulate the activity of protein kinases. The compounds of this invention are therefore useful in treating diseases caused by deregulated protein kinase activity. The present invention also provides methods for preparing these compounds, pharmaceutical compositions comprising these compounds, and methods of treating diseases utilizing pharmaceutical compositions comprising these compounds.

The classical Ras, Raf, MEK (mitogen activated protein kinase/extracellular signal-regulated kinase kinase), ERK (extracellular signal-regulated kinase) pathway plays a central role in the regulation of a variety of cellular functions dependent upon cellular context, including cellular proliferation, differentiation, survival, immortalization and angiogenesis (reviewed in Peyssonnaux and Eychene, Biology of the Cell, 2001, 93, 3-62). In this pathway, Raf family members are recruited to the plasma membrane upon binding to guanosine triphosphate (GTP) loaded Ras resulting in the phosphorylation and activation of Raf proteins. Activated Rafs then phosphorylate and activate MEKs, which in turn phosphorylate and activate ERKs. Upon activation, ERKs translocate from the cytoplasm to the nucleus resulting in the phosphorylation and regulation of activity of transcription factors such as Elk-I and Myc. The Ras/Raf/MEK/ERK pathway has been reported to contribute to the tumorigenic phenotype by inducing immortalisation, growth factor-independent growth, insensitivity to growth-inhibitory signals, ability to invade and metastasize, by stimulating angiogenesis and by inhibiting apoptosis (reviewed in Kolch et al., Exp. Rev. Mol. Med., 2002, 25 April, http://www.expertreviews.org/02004386h.htm). In fact, ERK phosphorylation is enhanced in approximately 30% of all human tumours (Hoshino et al., Oncogene, 1999, 18, 813-822). This may be a result of overexpression and/or mutation of key members of the pathway.

Three Raf serine/threonine protein kinase isoforms have been reported Raf-1/c-Raf, B-Raf and A-Raf (reviewed in Mercer and Pritchard, Biochim. Biophys. Acta, 2003, 1653, 25-40), the genes for which are thought to have arisen from gene duplication. All three Raf genes are expressed in most tissues but with differences: c-Raf is expressed ubiquitously at high levels, whereas B-Raf high-level expression is found in neuronal tissue and A-Raf in urogenital tissue. The highly homologous Raf family members have overlapping but distinct biochemical activities and biological functions (Hagemann and Rapp, Expt. Cell Res. 1999, 253, 34-46). Expression of all three Raf genes is required for normal murine development however both c-Raf and B-Raf are required to complete gestation. B-Raf –/– mice die at E12.5 due to vascular haemorrhaging caused by increased apoptosis of endothelial cells (Wojnowski et al, Nature Genet., 1997, 16, 293-297). B-Raf is reportedly the major isoform involved in cell proliferation and the primary target of oncogenic Ras. Activating 5 somatic missense mutations have been identified exclusively for B-Raf, occurring with a frequency of 66% in malignant cutaneous melanomas (Davies et al., Nature, 2002, 417, 949-954) and also present in a wide range of human cancers, including but not limited to papillary thyroid tumours (Cohen et al., J. Natl. Cancer Inst., 2003, 95, 625-627), cholangiocarcinomas (Tannapfel et al., Gut, 2003, 52, 706-712), colon and ovarian cancers (Davies et al., Nature, 10 2002, 417, 949-954). The most frequent mutation in B-Raf (80%) is a glutamic acid for valine substitution at position 600. These mutations increase the basal kinase activity of B-Raf and are thought to uncouple Raf/MEK/ERK signalling from upstream proliferation drives including Ras and growth factor receptor activation resulting in constitutive activation of ERK. Mutated B-Raf proteins are transforming in NIH3T3 cells (Davies et al., Nature, 2002, 15 417, 949-954) and melanocytes (Wellbrock et al., Cancer Res., 2004, 64, 2338-2342) and have also been shown to be essential for melanoma cell viability and transformation (Hingorani et al., Cancer Res., 2003, 63, 5198-5202). As a key driver of the Raf/MEK/ERK signalling cascade, B-Raf represents a likely point of intervention in tumours dependent on this pathway Substituted pyrazole derivatives for the treatment of cytokine-mediated diseases such as inflammation and arthritis are disclosed in WO98/52940 and WO00/31063 in the name of G.D. Searle & Co.

Hydroxyaryl-pyrazole derivatives for the treatment of cancer are disclosed in WO03/055860 in the name of Cancer Research Institute and in WO07/105,058 in the name of Pfizer Inc.

Pyrimidinyl-pyrazole derivatives for the treatment of hyperproliferative disorders such as cancer are disclosed in WO07/24843 in the name of SmithKline Beecham Corporation. Despite these developments, there is still need for effective agents for said diseases.

The present inventors have now discovered that compounds of formula (I), described below, are kinase inhibitors and are thus useful in therapy as antitumor agents.

Accordingly, a first object of the present invention is to provide a substituted 3,4-diarylpyrazole compound represented by formula (I),

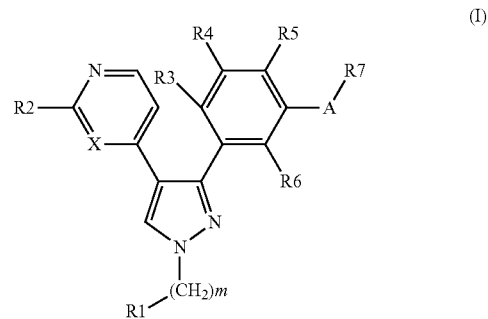

wherein:

m is an integer from 0 to 6;

R1 is hydrogen, trichloromethyl, trifluoromethyl, halogen, cyano, OH, OR8, NR9R10, NR21COR22, COOH, COOR11, CONR12R13, or a group optionally substituted selected from straight or branched $(C_1-C_8)$ alkyl, $(C_2-C_8)$ alkenyl or $(C_2-C_8)$ alkynyl, $(C_3-C_8)$ cycloalkyl, $(C_3-C_8)$ cycloalkenyl, heterocyclyl, aryl and heteroaryl, wherein:

R8 and R11 are each independently a group optionally substituted selected from straight or branched $(C_1-C_8)$ alkyl, $(C_3-C_8)$ cycloalkyl, heterocyclyl, aryl and heteroaryl;

R9, R10, R12 and R13 the same or different, are each independently hydrogen or a group optionally substituted selected from straight or branched $(C_1-C_8)$ alkyl, $(C_3-C_8)$ cycloalkyl, heterocyclyl, aryl and heteroaryl, or taken together with the nitrogen atom to which they are bonded either R9 and R10 as well as R12 and R13 may form an optionally substituted heterocyclyl or heteroaryl, optionally containing one additional heteroatom or heteroatomic group selected from S, O, N or NH;

R21 and R22 the same or different, are each independently hydrogen or a group optionally substituted selected from straight or branched $(C_1-C_8)$ alkyl, $(C_3-C_8)$ cycloalkyl, heterocyclyl, aryl and heteroaryl, or taken together with the atoms to which they are bonded R21 and R22 may form an optionally substituted heterocyclyl, optionally containing one additional heteroatom or heteroatomic group selected from S, O, N or NH;

X is —CH or N;

R2 is hydrogen, halogen, NR14R15, SR23 or $SO_2R23$, wherein:

R14 and R15 are independently hydrogen or a group optionally substituted selected from straight or branched $(C_1-C_8)$ alkyl, $(C_3-C_8)$ cycloalkyl, heterocyclyl, aryl and heteroaryl; or taken together with the nitrogen atom to which they are bonded R14 and R15 may form an optionally substituted 3 to 8 membered heterocyclyl or heteroaryl, optionally containing one additional heteroatom or heteroatomic group selected from S, O, N or NH; or R14 is hydrogen and R15 is COR16, wherein:

R16 is OR17, NR18R19 or a group optionally substituted selected from straight or branched $(C_1-C_8)$ alkyl, $(C_2-C_8)$ alkenyl or $(C_2-C_8)$ alkynyl, $(C_3-C_8)$ cycloalkyl, $(C_3-C_8)$ cylcoalkenyl, heterocyclyl, aryl and heteroaryl, wherein:

R17 is a group optionally substituted selected from straight or branched $(C_1-C_8)$ alkyl, $(C_3-C_8)$ cycloalkyl, heterocyclyl, aryl and heteroaryl;

R18 and R19 are each independently a group optionally substituted selected from straight or branched $(C_1-C_8)$ alkyl, $(C_3-C_8)$ cycloalkyl, heterocyclyl, aryl and heteroaryl, or taken together with the nitrogen atom to which they are bonded R18 and R19 may form an optionally substituted 3 to 8 membered heterocyclyl or heteroaryl, optionally containing one additional heteroatom or heteroatomic group selected from S, O, N or NH;

R23 is a group optionally substituted selected from straight or branched $(C_1-C_8)$ alkyl, $(C_3-C_8)$ cycloalkyl, heterocyclyl, aryl and heteroaryl, R3, R4, R5 and R6 are each independently hydrogen, halogen, trifluoromethyl, trichloromethyl, cyano, OR20 or a group optionally substituted selected from straight or branched $(C_1-C_8)$ alkyl, and $(C_3-C_8)$ cycloalkyl, wherein: R20 is a group optionally substituted selected from straight or branched $(C_1-C_8)$ alkyl and $(C_3-C_8)$ cycloalkyl;

A is —CON(Y), —CON(Y)O—, —CON(Y)N(Y)—, —CON(Y)SO$_2$—, —SO$_2$N(Y)—, —SO$_2$N(Y)O—, —SO$_2$N(Y)N(Y)—, —SO$_2$N(Y)CO—, —SO$_2$N(Y)CON(Y)—, —SO$_2$N(Y)SO$_2$—, —N(Y)CO—, —N(Y)SO$_2$—, —N(Y)CON(Y)—, —N(Y)CSN(Y)—, —N(Y)CON(Y)N(Y)—, —N(Y)COO—, —N(Y)CON(Y)SO$_2$—, —N(Y)SO$_2$N(Y)—, —C(R'R")CON(Y)—, —C(R'R")CSN(Y)—, —C(R'R")CON(Y)O—, —C(R'R")CON(Y)N(Y)—, —C(R'R")CON(Y)SO$_2$—, —C(R'R")SO$_2$N(Y)—, —C(R'R")SO$_2$N(Y)O—, —C(R'R")SO$_2$N(Y)N(Y)—, —C(R'R")SO$_2$N(Y)CO—, —C(R'R")SO$_2$N(Y)SO$_2$—, —C(R'R")N(Y)CO, —C(R'R")N(Y)SO$_2$—, —C(R'R")N(Y)CON(Y)—, —C(R'R")N(Y)CSN(Y)—, —C(R'R")N(Y)COO—, —C(R'R")N(Y)SO$_2$N(Y)— or —N(Y)C(R'R")—, wherein:

Y is hydrogen or an optionally substituted straight or branched $(C_1-C_3)$ alkyl;

and R' and R" are independently hydrogen or an optionally further substituted straight or branched $(C_1-C_6)$ alkyl, or taken together with the carbon atom to which they are bonded R' and R" may form an optionally substituted $(C_3-C_8)$ cycloalkyl;

R7 is hydrogen or an optionally substituted group selected from straight or branched $(C_1-C_8)$ alkyl, $(C_2-C_8)$ alkenyl, or $(C_3-C_8)$ cycloalkyl, $(C_2-C_8)$ alkynyl, $(C_3-C_8)$ cylcoalkenyl, heterocyclyl, aryl and heteroaryl;

and pharmaceutically acceptable salts thereof.

The present invention also provides methods of preparing the substituted 3,4-diarylpyrazole compounds, represented by formula (I), prepared through a process consisting of standard synthetic transformations.

The present invention also provides a method for treating diseases caused by and/or associated with deregulated protein kinase activity, particularly the RAF family, PLK family, protein kinase C in different isoforms, Met, PAK-4, PAK-5, ZC-1, STLK-2, DDR-2, Aurora A, Aurora B, Aurora C, Bub-1, Chk1, Chk2, HER2, MEK1, MAPK, EGF-R, PDGF-R, FGF-R, IGF-R, PI3K, weel kinase, Src, Abl, Akt, MAPK, ILK, MK-2, IKK-2, Cdc7, Nek, Cdk/cyclin kinase family, more particularly the RAF family, which comprises administering to a mammal, in need thereof, an effective amount of a substituted 3,4-diarylpyrazole compound represented by formula (I) as defined above.

A preferred method of the present invention is to treat a disease caused by and/or associated with deregulated protein kinase activity selected from the group consisting of cancer, cell proliferative disorders, viral infections, autoimmune and neurodegenerative disorders.

Another preferred method of the present invention is to treat specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Another preferred method of the present invention is to treat specific cellular proliferation disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

Another preferred method of the present invention is to treat viral infections, in particular the prevention of AIDS development in HIV-infected individuals.

In addition, the method of the present invention also provides tumor angiogenesis and metastasis inhibition as well as the treatment of organ transplant rejection and host versus graft disease.

In a further preferred embodiment, the method of the present invention further comprises subjecting the mammal in need thereof to a radiation therapy or chemotherapy regimen in combination with at least one cytostatic or cytotoxic agent.

Moreover the invention provides an in vitro method for inhibiting the RAF family protein activity which comprises contacting the said protein with an effective amount of a compound of formula (I).

The present invention also provides a pharmaceutical composition comprising one or more compounds of formula (I) or a pharmaceutically acceptable salt thereof and a pharmaceutically acceptable excipient, carrier or diluent.

The present invention further provides a pharmaceutical composition comprising a compound of formula (I) in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like. Additionally, the invention provides a product or kit comprising a compound of formula (I) or a pharmaceutically acceptable salt thereof, as defined above, or pharmaceutical compositions thereof and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament.

Moreover the invention provides the use of a compound of formula (I) or a pharmaceutically acceptable salt thereof, as defined above, in the manufacture of a medicament with antitumor activity.

Finally, the invention provides a compound of formula (I) or a pharmaceutically acceptable salt thereof, as defined above, for use in a method of treating cancer.

Unless otherwise specified, when referring to the compounds of formula (I) per se as well as to any pharmaceutical composition thereof or to any therapeutic treatment comprising them, the present invention includes all of the isomers, tautomers, hydrates, solvates, complexes, metabolites, prodrugs, carriers, N-oxides and pharmaceutically acceptable salts of the compounds of this invention.

A metabolite of a compound of formula (I) is any compound into which this same compound of formula (I) is converted in vivo, for instance upon administration to a mammal in need thereof. Typically, without however representing a limiting example, upon administration of a compound of formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of formula (I). Prodrugs are any covalently bonded compounds, which release in vivo the active parent drug according to formula (I).

N-oxides are compounds of formula (I) wherein nitrogen and oxygen are tethered through a dative bond.

If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases when compounds can exist in tautomeric forms, each form is contemplated as being included within this invention whether existing in equilibrium or predominantly in one form.

As such, unless otherwise provided, when in compounds of formula (I) m is 0 and R1 is hydrogen, only one of the following tautomeric forms of formula (Ia) or (Ib) is indicated, the remaining one has still to be intended as comprised within the scope of the invention:

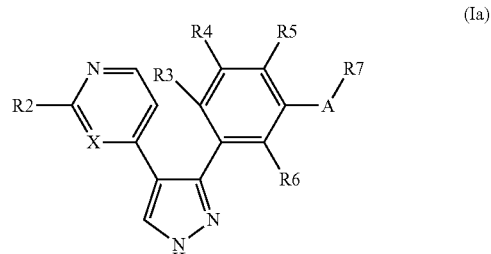

(Ia)

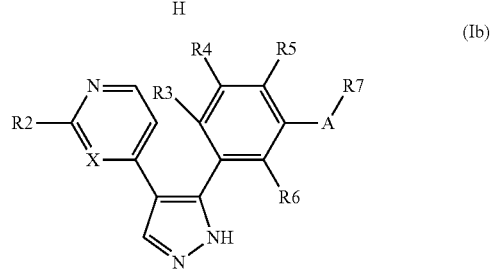

(Ib)

In cases wherein compounds may exist in other tautomeric forms, such as keto-enol tautomers, each tautomeric form is contemplated as being included within this invention whether existing in equilibrium or predominantly in one form.

With the term "straight or branched $C_1$-$C_8$ alkyl", we intend any of the groups such as, for instance, methyl, ethyl, n-propyl, isopropyl, n-butyl, isobutyl, tert-butyl, sec-butyl, n-pentyl, n-hexyl, n-heptyl, n-octyl and the like.

With the term "straight or branched $C_1$-$C_6$ alkyl", we intend any of the groups such as, for instance, methyl, ethyl, n-propyl, isopropyl, n-butyl, isobutyl, tert-butyl, sec-butyl, n-pentyl, n-hexyl, and the like.

With the term "straight or branched $C_1$-$C_3$ alkyl", we intend any of the groups such as, for instance, methyl, ethyl, n-propyl, isopropyl.

With the term "$C_3$-$C_8$ cycloalkyl" we intend, unless otherwise provided, 3- to 8-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene and cyclohexadiene.

With the term "heterocyclyl" we intend a 3- to 8-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

With the term "$C_2$-$C_8$ alkenyl" we intend an aliphatic $C_2$-$C_8$ hydrocarbon chain containing at least one carbon-carbon double bond and which can be straight or branched. Representative examples include, but are not limited to, ethenyl, 1-propenyl, 2-propenyl, 1- or 2-butenyl, and the like.

With the term "$C_2$-$C_8$ alkynyl" we intend an aliphatic $C_2$-$C_8$ hydrocarbon chain containing at least one carbon-carbon triple bond and which can be straight or branched. Representative examples include, but are not limited to, ethynyl, 1-propynyl, 2-propynyl, 1- or 2-butynyl, and the like.

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated π-electron bond system. Non-limiting examples of such aryl groups are phenyl, α- or β-naphthyl or biphenyl groups.

The term "heteroaryl" refers to aromatic heterocyclic rings, typically 5- to 8-membered heterocycles with from 1 to 3 heteroatoms selected among N, O or S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl; benzopyranyl, 2,3-dihydrobenzoxazinyl, 2,3-dihydroquinoxalinyl and the like.

According to the present invention and unless otherwise provided, any of the above R1, R2, R3, R4, R5, R6 and R7 group may be optionally substituted, in any of their free positions, by one or more groups, for instance 1 to 6 groups, independently selected from: halogen, nitro, oxo groups (=O), cyano, $C_1$-$C_8$ alkyl, polyfluorinated alkyl, polyfluorinated alkoxy, $C_2$-$C_8$ alkenyl, $C_2$-$C_8$ alkynyl, hydroxyalkyl, aryl, arylalkyl, heteroaryl, heteroarylalkyl, heterocyclyl, heterocyclylalkyl, $C_3$-$C_8$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclylalkyloxycarbonylamino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate. In their turn, whenever appropriate, each of the above substituent may be further substituted by one or more of the aforementioned groups.

With the term halogen atom we intend a fluorine, chlorine, bromine or iodine atom.

With the term cyano we intend a —CN residue.

With the term nitro we intend a —$NO_2$ group.

With the term polyfluorinated alkyl or polyfluorinated alkoxy we intend any of the above straight or branched $C_1$-$C_8$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term hydroxyalkyl we intend any of the above $C_1$-$C_8$ alkyl, bearing an hydroxyl group such as, for instance, hydroxymethyl, 2-hydroxyethyl, 3-hydroxypropyl and the like.

From all of the above, it is clear to the skilled person that any group which name is a composite name such as, for instance, arylamino has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, $C_3$-$C_8$ cycloalkyl and heterocyclyl moieties are as above defined.

Pharmaceutically acceptable salts of the compounds of formula (I) include the acid addition salts with inorganic or organic acids, e.g., nitric, hydrochloric, hydrobromic, sulfuric, perchloric, phosphoric, acetic, trifluoroacetic, propionic, glycolic, lactic, oxalic, fumaric, malonic, malic, maleic, tartaric, citric, benzoic, cinnamic, mandelic, methanesulphonic, isethionic and salicylic acid.

Pharmaceutically acceptable salts of the compounds of formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines, preferably methylamine, ethylamine, diethylamine, triethylamine, piperidine and the like.

A preferred class of compounds of formula (I) are the compounds wherein:

m is an integer from 0 to 2.

Another preferred class of compounds of formula (I) are the compounds wherein:

A is —CON(Y), —CON(Y)O—, —CON(Y)N(Y)—, —CON(Y)$SO_2$—, —$SO_2$N(Y)—, —N(Y)CO—, —N(Y)$SO_2$—, —N(Y)CON(Y)—, —N(Y)CSN(Y)—, —N(Y)COO—, —C(R'R")CON(Y)—, —C(R'R")N(Y)CO, —C(R'R")N(Y)CON(Y)—, wherein:

Y and R' and R" are as defined above.

A further preferred class of compounds of formula (I) are the compounds wherein:

R1 is hydrogen, trichloromethyl, trifluoromethyl, halogen, cyano, OH, OR8, NR9R10, CONR12R13, or a group optionally substituted selected from straight or branched ($C_1$-$C_8$) alkyl, ($C_2$-$C_8$) alkenyl or ($C_2$-$C_8$) alkynyl, ($C_3$-$C_8$) cycloalkyl, ($C_3$-$C_8$) cycloalkenyl, heterocyclyl, aryl and heteroaryl, wherein:

R8, R9, R10, R12 and R13 are as defined above.

A particularly preferred class of compounds of formula (I) are the compounds wherein:

R1 is hydrogen, trichloromethyl, trifluoromethyl, halogen and cyano.

Another further preferred class of compounds of formula (I) are the compounds wherein:

R2 is hydrogen or NR14R15, wherein:

R14 and R15 are independently hydrogen or a group optionally substituted selected from straight or branched ($C_1$-$C_8$) alkyl, ($C_3$-$C_8$) cycloalkyl, heterocyclyl, aryl and heteroaryl.

Another further preferred class of compounds of formula (I) are the compounds wherein:

R3, R4, R5 and R6 are each independently hydrogen, halogen, trifluoromethyl, trichloromethyl or cyano.

Another further preferred class of compounds of formula (I) are the compounds wherein:

R7 is an optionally substituted group selected from straight or branched ($C_1$-$C_8$) alkyl, ($C_3$-$C_8$) cylcoalkyl, ($C_3$-$C_8$) cycloalkenyl, heterocyclyl, aryl and heteroaryl.

Preferred specific compounds of formula (I) are the compounds listed below:

1) 1-[3-(4-pyridin-4-yl-1H-pyrazol-3-yl)-phenyl]-3-(4-trifluoromethyl-phenyl)-urea,
2) 2,5-difluoro-N-[3-(4-pyridin-4-yl-1H-pyrazol-3-yl)-phenyl]-benzenesulfonamide,
3) N-(4-chloro-phenyl)-3-(4-pyridin-4-yl-1H-pyrazol-3-yl)-benzamide,
4) N-(4-tert-Butyl-phenyl)-3-(4-pyridin-4-yl-1H-pyrazol-3-yl)-benzamide,
5) 1-(4-chloro-3-trifluoromethyl-phenyl)-3-{3-[1-(2-fluoro-ethyl)-4-pyridin-4-yl-1H-pyrazol-3-yl]-phenyl}-urea,
6) furan-2-sulfonic acid [3-(4-pyridin-4-yl-1H-pyrazol-3-yl)-phenyl]-amide,
7) thiophene-3-sulfonic acid [3-(4-pyridin-4-yl-1H-pyrazol-3-yl)-phenyl]-amide,
8) 1-[3-(4-pyridin-4-yl-1H-pyrazol-3-yl)-phenyl]-3-p-tolyl-urea,
9) 1-(4-chloro-phenyl)-3-[3-(4-pyridin-4-yl-1H-pyrazol-3-yl)-phenyl]-urea,
10) 1-[3-(1-ethyl-4-pyridin-4-yl-1H-pyrazol-3-yl)-phenyl]-3-(4-trifluoromethyl-phenyl)-urea,
11) 1-[3-(1-cyanomethyl-4-pyridin-4-yl-1H-pyrazol-3-yl)-phenyl]-3-(4-trifluoromethyl-phenyl)-urea,
12) 1-{3-[4-(2-amino-pyridin-4-yl)-1H-pyrazol-3-yl]-phenyl}-3-(4-trifluoromethyl-phenyl)-urea,
13) 1-{3-[1-(2-fluoro-ethyl)-4-pyridin-4-yl-1H-pyrazol-3-yl]-phenyl}-3-(4-trifluoromethyl-phenyl)-urea,
14) 1-{3-[1-(2-hydroxy-ethyl)-4-pyridin-4-yl-1H-pyrazol-3-yl]-phenyl}-3-(4-trifluoromethyl-phenyl)-urea,
15) 1-[3-(1-piperidin-4-yl-4-pyridin-4-yl-1H-pyrazol-3-yl)-phenyl]-3-(4-trifluoromethyl-phenyl)-urea,
16) N-[3-(4-pyridin-4-yl-1H-pyrazol-3-yl)-phenyl]-2-(4-trifluoromethyl-phenyl)-acetamide,
17) N-[4-(3-{3-[3-(4-trifluoromethyl-phenyl)-ureido]-phenyl}-1H-pyrazol-4-yl)-pyridin-2-yl]-acetamide,
18) N-[2,4-difluoro-3-(4-pyridin-4-yl-1H-pyrazol-3-yl)-phenyl]-2,5-difluoro-benzenesulfonamide,
19) thiophene-3-sulfonic acid [2,4-difluoro-3-(4-pyridin-4-yl-1H-pyrazol-3-yl)-phenyl]-amide,
20) furan-2-sulfonic acid [2,4-difluoro-3-(4-pyridin-4-yl-1H-pyrazol-3-yl)-phenyl]-amide,
21) propane-1-sulfonic acid [2,4-difluoro-3-(4-pyridin-4-yl-1H-pyrazol-3-yl)-phenyl]-amide,
22) 1-(4-tert-butyl-phenyl)-3-[3-(4-pyridin-4-yl-1H-pyrazol-3-yl)-phenyl]-urea,
23) 1-[4-(cyano-dimethyl-methyl)-phenyl]-3-[3-(4-pyridin-4-yl-1H-pyrazol-3-yl)-phenyl]-urea,
24) 1-[2-ffluoro-5-(4-pyridin-4-yl-1H-pyrazol-3-yl)-phenyl]-3-(4-trifluoromethyl-phenyl)-urea,
25) 1-(2-fluoro-4-trifluoromethyl-phenyl)-3-[3-(4-pyridin-4-yl-1H-pyrazol-3-yl)-phenyl]-urea,
26) cyclopropanesulfonic acid [2,4-difluoro-3-(4-pyridin-4-yl-1H-pyrazol-3-yl)-phenyl]-amide,
27) 2,2,2-trifluoro-ethanesulfonic acid [2,4-difluoro-3-(4-pyridin-4-yl-1H-pyrazol-3-yl)-phenyl]-amide,
28) N-[2,4-difluoro-3-(4-pyridin-4-yl-1H-pyrazol-3-yl)-phenyl]-C,C,C-trifluoro-methanesulfonamide,
29) cyclohexanesulfonic acid [2,4-difluoro-3-(4-pyridin-4-yl-1H-pyrazol-3-yl)-phenyl]-amide,
30) 1-[3-(4-pyrimidin-4-yl-1H-pyrazol-3-yl)-phenyl]-3-(4-trifluoromethyl-phenyl)-urea,
31) 1-{3-[4-(2-amino-pyrimidin-4-yl)-1H-pyrazol-3-yl]-phenyl}-3-(4-trifluoromethyl-phenyl)-urea,
32) N-[4-(3-{3-[3-(4-trifluoromethyl-phenyl)-ureido]-phenyl}-1H-pyrazol-4-yl)-pyrimidin-2-yl]-acetamide,
33) 2,5-difluoro-N-[3-(4-pyrimidin-4-yl-1H-pyrazol-3-yl)-phenyl]-benzenesulfonamide,
34) N-{3-[4-(2-amino-pyrimidin-4-yl)-1H-pyrazol-3-yl]-phenyl}-2,5-difluoro-benzenesulfonamide, to 35) N-(4-{3-[3-(2,5-difluoro-benzenesulfonylamino)-phenyl]-1H-pyrazol-4-yl}-pyrimidin-2-yl)-acetamide,
36) N-[2,4-difluoro-3-(4-pyrimidin-4-yl-1H-pyrazol-3-yl)-phenyl]-2,5-difluoro-benzenesulfonamide,
37) N-{3-[4-(2-amino-pyrimidin-4-yl)-1H-pyrazol-3-yl]-2,4-difluoro-phenyl}-2,5-difluoro-benzenesulfonamide,
38) N-(4-{3-[3-(2,5-difluoro-benzenesulfonylamino)-2,6-difluoro-phenyl]-1H-pyrazol-4-yl}-pyrimidin-2-yl)-acetamide,
39) N-[4-(3-{3-[3-(4-trifluoromethyl-phenyl)-ureido]-phenyl}-1H-pyrazol-4-yl)-pyridin-2-yl]-propionamide,
40) N-[4-(3-{3-[3-(4-trifluoromethyl-phenyl)-ureido]-phenyl}-1H-pyrazol-4-yl)-pyridin-2-yl]-isobutyramide,
41) cyclopentanecarboxylic acid [4-(3-{3-[3-(4-trifluoromethyl-phenyl)-ureido]-phenyl}-1H-pyrazol-4-yl)-pyridin-2-yl]-amide,
42) 2-[3-(4-pyridin-4-yl-1H-pyrazol-3-yl)-phenyl]-N-(4-trifluoromethyl-phenyl)-acetamide,
43) 4-hydroxy-N-[4-(3-{3-[3-(4-trifluoromethyl-phenyl)-ureido]-phenyl}-1H-pyrazol-4-yl)-pyridin-2-yl]-butyramide,
44) N-(4-{3-[3-(2,5-difluoro-benzenesulfonylamino)-phenyl]-1H-pyrazol-4-yl}-pyridin-2-yl)-acetamide,
45) N-(4-{3-[3-(2,5-difluoro-benzenesulfonylamino)-2,6-difluoro-phenyl]-1H-pyrazol-4-yl}-pyridin-2-yl)-acetamide,
46) 3-(4-pyridin-4-yl-1H-pyrazol-3-yl)-N-(4-trifluoromethyl-phenyl)-benzamide,
47) 4-pyridin-4-yl-3-{3-[3-(4-trifluoromethyl-phenyl)-ureido]-phenyl}-pyrazole-1-carboxylic acid ethyl ester
48) 1-[3-(1-methyl-4-pyridin-4-yl-1H-pyrazol-3-yl)-phenyl]-3-(4-trifluoromethyl-phenyl)-urea,
49) 1-[3-(1-butyl-4-pyridin-4-yl-1H-pyrazol-3-yl)-phenyl]-3-(4-trifluoromethyl-phenyl)-urea,
50) 1-[3-(1-Isobutyl-4-pyridin-4-yl-1H-pyrazol-3-yl)-phenyl]-3-(4-trifluoromethyl-phenyl)-urea,
51) N-[3-(1-ethyl-4-pyridin-4-yl-1H-pyrazol-3-yl)-2,4-difluoro-phenyl]-2,5-difluoro-benzenesulfonamide, 52) N-[2,4-difluoro-3-(1-methyl-4-pyridin-4-yl-1H-pyrazol-3-yl)-phenyl]-2,5-difluoro-benzenesulfonamide,
53) N-{2,4-difluoro-3-[4-(2-methylamino-pyridin-4-yl)-1H-pyrazol-3-yl]-phenyl}-2,5-difluoro-benzenesulfonamide,
54) N-{3-[4-(2-ethylamino-pyridin-4-yl)-1H-pyrazol-3-yl]-2,4-difluoro-phenyl}-2,5-difluoro-benzenesulfonamide,
55) N-{3-[4-(2-ethylamino-pyrimidin-4-yl)-1H-pyrazol-3-yl]-phenyl}-2,5-difluoro-benzenesulfonamide,
56) N-[2,4-difluoro-3-(1-isobutyl-4-pyridin-4-yl-1H-pyrazol-3-yl)-phenyl]-2,5-difluoro-benzenesulfonamide,
57) N-[3-(1-ethyl-4-pyridin-4-yl-1H-pyrazol-3-yl)-2,4-difluoro-phenyl]-2-fluoro-benzenesulfonamide,
58) N-[3-(1-ethyl-4-pyridin-4-yl-1H-pyrazol-3-yl)-2,4-difluoro-phenyl]-3-fluoro-benzenesulfonamide,
59) N-[3-(1-ethyl-4-pyridin-4-yl-1H-pyrazol-3-yl)-4-fluoro-phenyl]-2,5-difluoro-benzenesulfonamide,
60) N-[3-(1-ethyl-4-pyridin-4-yl-1H-pyrazol-3-yl)-2-fluoro-phenyl]-2,5-difluoro-benzenesulfonamide,
61) N-{3-[4-(2-amino-pyrimidin-4-yl)-1-ethyl-1H-pyrazol-3-yl]-2,4-difluoro-phenyl}-2,5-difluoro-benzenesulfonamide,
62) N-{2,4-difluoro-3-[1-(2-piperidin-1-yl-ethyl)-4-pyridin-4-yl-1H-pyrazol-3-yl]-phenyl}-2,5-difluoro-benzenesulfonamide,
63) N-{2,4-difluoro-3-[1-(2-morpholin-4-yl-ethyl)-4-pyridin-4-yl-1H-pyrazol-3-yl]-phenyl}-2,5-difluoro-benzenesulfonamide,
64) N-(2,4-difluoro-3-{1-[2-(4-methyl-piperazin-1-yl)-ethyl]-4-pyridin-4-yl-1H-pyrazol-3-yl}-phenyl)-2,5-difluoro-benzenesulfonamide,
65) N-{3-[1-(2-dimethylamino-ethyl)-4-pyridin-4-yl-1H-pyrazol-3-yl]-2,4-difluoro-phenyl}-2,5-difluoro-benzenesulfonamide,
66) (2,5-difluoro-benzyl)-[3-(1-ethyl-4-pyridin-4-yl-1H-pyrazol-3-yl)-2,4-difluoro-phenyl]-amine,
67) 4-{3-[3-(2,5-difluoro-benzyloxy)-2,6-difluoro-phenyl]-1-ethyl-1H-pyrazol-4-yl}-pyridine and
68) N-{3-[4-(2-Amino-pyridin-4-yl)-1-ethyl-1H-pyrazol-3-yl]-2,4-difluoro-phenyl}-2,5-difluoro-benzenesulfonamide.

The present invention also provides a process for the preparation of a compound of formula (I) as defined above, by using the reaction routes and synthertic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis on non-exemplified compounds according to the invention may be performed by modifications apparent to those skilled in the art, for instance by appropriately protecting interfering groups, by changing to other suitable reagents known in the art, or by making routine modifications of reaction conditions. Alternatively other reactions referred to herein or known in the art will be recognized as having adaptability for preparing other compounds of the invention. The reported Scheme 1 shows the preparation of a compound of formula (I).

Scheme 1

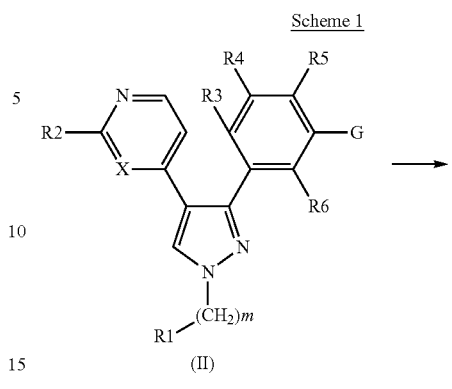

(II)

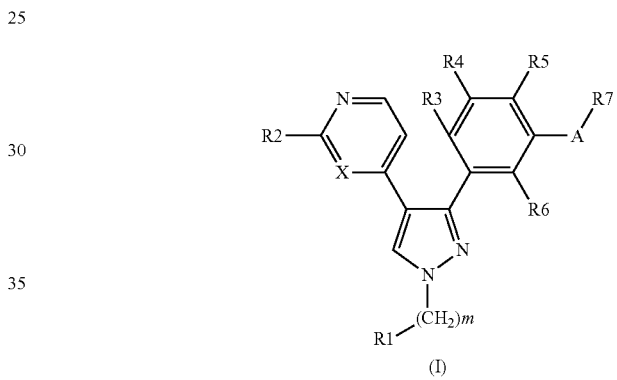

(I)

wherein
G is a suitable precursor of the A-R7 groups defined above, such as an optionally protected amino group, a nitro group, a halogen, a cyano group or a suitable carboxylic ester; and
X, m, R1, R2, R3, R4, R5, R6 and R7 are as defined above.
The intermediate compound of formula (II) is prepared according to method A, B, C and D described below.
A compound of formula (II) can be optionally converted into another compound of formula (II) according to any of the methods E and F described below.
A compound of formula (I) is prepared following one of the synthetic methods described hereafter in method G, H, I, J, and M.
A compound of formula (I) can be optionally converted into another compound of formula (I) according to any of the methods K and L described below.
All those with ordinary skills in the art will appreciate that any transformation performed according to said methods may require standard modifications such as, for instance, protection of interfering groups, change to other suitable reagents known in the art, or make routine modifications of reaction conditions.

Method A

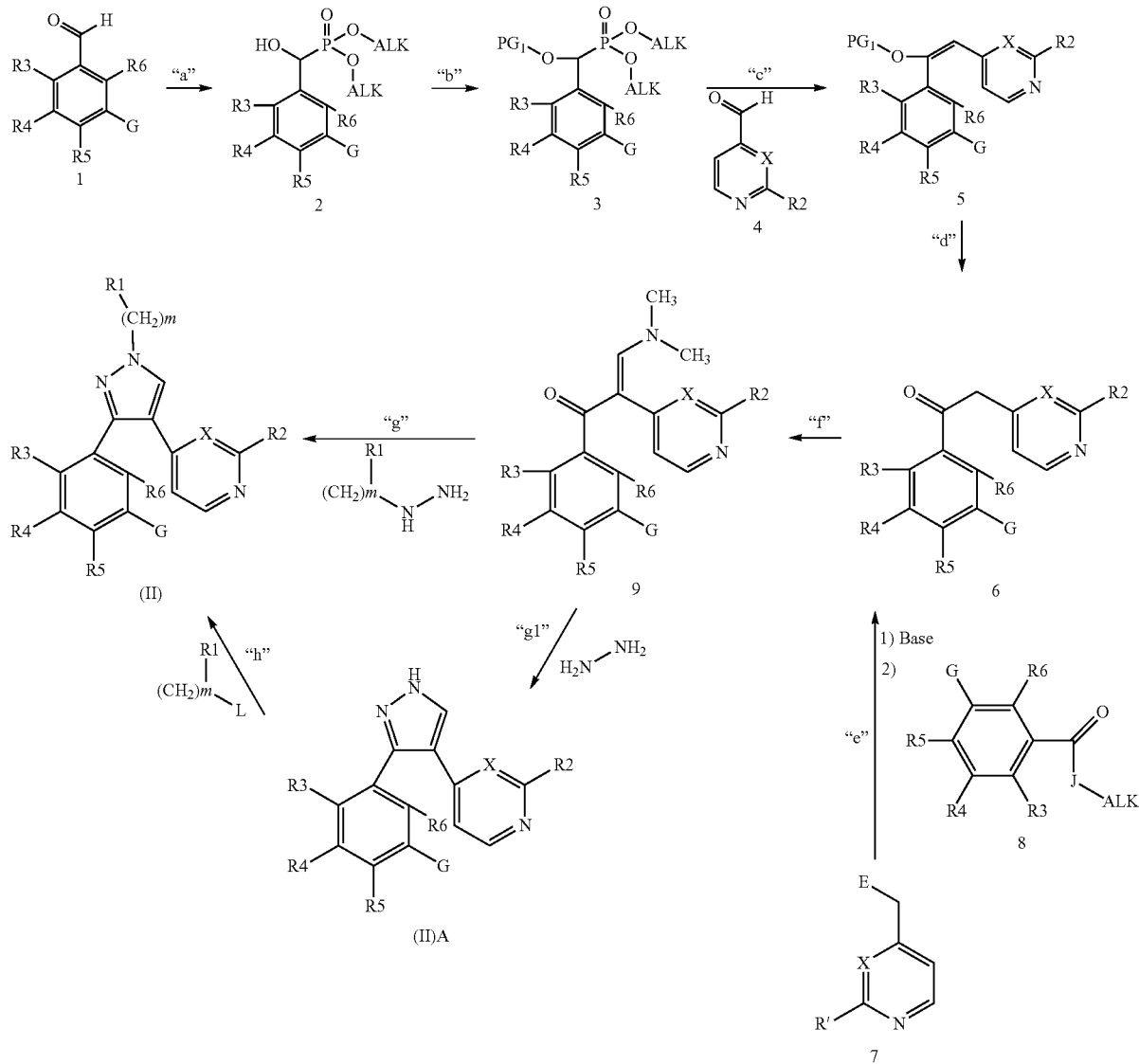

In the above scheme, X, m, R1, R2, R3, R4, R5, R6 and G are as defined above, J is oxygen or a group —N(CH₃)O—, PG₁ is a protecting group such as silyl or acyl derivatives or tetrahydropyranyl, Alk is $C_1$-$C_6$ alkyl, E is hydrogen or alkoxycarbonyl, L is OH or a group that may work as a leaving group, such as a halogen atom, a tosylate, mesylate or triflate.

In a synthetic process for the preparation of a compound of formula (II), which is described in method A, in step "a" a compound of formula 1 is reacted with a dialkylphosphite to yield a hydroxyalkyl phosphonate of formula 2. In steps "b" and "c" protection of the alcoholic function followed by Wittig-type reaction with a suitable 4-pyridyl or 4-pyrimidinyl carboxaldehyde of formula 4 yields a compound of formula 5 that in step "d" is conveniently hydrolyzed to yield a ketone represented by formula 6. In step "e" the latter may be obtained alternatively starting from a compound of formula 7 which is transformed in the corresponding metal anion and reacted with an aromatic alkyl carboxylate or Weinreb amide of formula 8. In step "f" transformation of a compound of formula 6 to pyrazoles is accomplished by forming an enaminone derivative of formula 9, followed in step "g" and "g1" by condensation with an appropriate hydrazine to give a compound of formula (II). With a substituted hydrazine the latter reaction yields a mixture of regioisomers from which the desired isomer is purified by known methods such as silica gel chromatography or preparative HPLC. When hydrazine is used, a N-unsubstituted pyrazole of formula (II)A is obtained (m is 0 and R1 is hydrogen).

In the latter case in step "h" introduction of the —(CH₂)mR1 group to form a compound of formula (II) is accomplished through N-alkylation of a suitable alkylating agent L-(CH₂)mR1, where L is a group that, optionally upon activation, may work as a leaving group. The latter reaction could yield a mixture of regioisomers from which the desired isomer is purified by known methods such as silica gel chromatography or preparative HPLC.

According to step "a" of method A, the condensation between an aromatic aldehyde of formula 1 with a dialkyl phosphite can be accomplished in a variety of ways according to conventional methods. Preferably it is carried out in presence of a base, such as triethylamine (TEA) 1,8-diazabicyclo[5.4.0]undec-7ene (DBU), lithium diisopropylamide (LDA), sodium methoxide or the like, preferably in a solvent such as, for instance, ethylacetate, dichloromethane, toluene, tetrahydrofuran, 1,4-dioxane, 1,2-dimethoxyethane, acetonitrile at a temperature ranging from 0° C. to reflux and for a time ranging from 30 minutes to about 24 hours.

According to step "b" of method A, the protection of the alcoholic function can be accomplished in a variety of ways according to conventional methods that can be readily appreciated by all those skilled in the art. For instance, such alcoholic group can be protected as silyl derivatives by treatment with a suitable silylating agent, such as any alkylsilyl halide or azide in the presence of a base, such as, for instance, 1,8-diazabicyclo[5.4.0]undec-7ene (DBU), or by treatment with 1,1,1,3,3,3-hexamethyldisilazane in the presence of submolar amounts of Iodine or of a suitable acid, such as, for instance, sulphuric acid. Such reactions can be performed using a variety of solvents such as dichloromethane, toluene, tetrahydrofuran, 1,4-dioxane, 1,2-dimethoxyethane, acetonitrile at a temperature ranging from 0° C. to reflux and for a time ranging from 30 minutes to about 24 hours. Again, said protection can be accomplished by acylation following treatment with a suitable acylating agent such as an acid chloride or anhydride in the presence of a base using a variety of solvents such as dichloromethane, toluene, tetrahydrofuran, 1,4-dioxane, 1,2-dimethoxyethane, N,N-dimethylformamide, N,N-dimethylacetamide, acetonitrile or the like at a temperature ranging from 0° C. to reflux and for a time ranging from 30 minutes to about 24 hours. More preferably such a protection can be accomplished using 3,4-dihydro-2H-pyran in the presence of a suitable acidic catalyst, such as, for instance, p-Toluensulfonic acid (PTSA) using solvents such as toluene, tetrahydrofuran, 1,4-dioxane, 1,2-dimethoxyethane at a temperature ranging from 0° C. to reflux and for a time ranging from 30 minutes to about 24 hours.

According to step "c" of method A, the reaction of a compound of formula 3 with a compound of formula 4 can be accomplished in the presence of a suitable base such as, for instance sodium methoxide, sodium ethoxide, sodium hydride, lithium diisopropylamide or triethylamine in a variety of solvents such as tetrahydrofuran, 1,4-dioxane, 1,2-dimethoxyethane, toluene, dichloromethane, or the like at a temperature ranging from 0° C. to reflux and for a time ranging from 30 minutes to about 24 hours.

According to step "d" of method A, the conversion of a compound of formula 5 to a compound of formula 6 can be accomplished in a variety of ways known in the art depending on the nature of the protecting group itself. For example, when the protective group introduced in step "b" of method A is tetrahydropyranyl, the conversion is made using any of the hydrolytic method known in the literature, for instance using an aqueous solution of hydrochloric acid in a suitable cosolvent, for instance methanol, ethanol, tetrahydrofuran, acetonitrile or the like at a temperature ranging from 0° C. to reflux and for a time ranging from 30 minutes to about 24 hours. When, for example, such a protecting group is a silyl group, deprotection can be accomplished using strong acids like trifluoroacetic acid, perchloric acid, hydrochloric acid, hydrofluoric acid, as well as tetrabutyl ammonium fluoride and derivatives thereof, in a suitable solvent such as tetrahydrofuran, 1,4-dioxane, 1,2-dimethoxyethane, methanol, ethanol, acetonitrile, dichloromethane, or the like at a temperature ranging from 0° C. to reflux and for a time ranging from 30 minutes to about 24 hours. When, for example, such a protecting group is an acyl group, deprotection can be accomplished using aqueous alkali, such as NaOH, KOH, LiOH or the like, optionally in the presence of a suitable solvent such as ethanol, methanol, tetrahydrofuran or the like.

According to step "e" of method A, a compound of formula 7 is converted to a compound of formula 6 by reaction with a strong base such as sodium hexamethyldisilazane (NaHMDS), lithium hexamethyldisilazane (LiHMDS), lithium diisopropylamide (LDA), a Grignard reagent and the like, following condensation with an aromatic alkyl carboxylate or Weinreb amide of formula 8. Said reaction is typically performed using a variety of solvents such as toluene, N,N-dimethylformamide, tetrahydrofuran, 1,4-dioxane, 1,2-dimethoxyethane, or the like at a temperature ranging from 0° C. to reflux and for a time ranging from 30 minutes to about 24 hours.

According to step "f" of method A, the synthesis of the enaminone derivative of formula 9 is accomplished using a N,N-dimethylformamide dialkyl acetal, such as, for instance N,N-dimethylformamide dimethyl acetal, N,N-dimethylformamide ditertbutyl acetal and the like in a suitable solvent such as tetrahydrofuran, 1,4-dioxane, 1,2-dimethoxyethane, acetonitrile, N,N-dimethylformamide, N,N-dimethylacetamide, or the like at a temperature ranging from 0° C. to reflux and for a time ranging from 30 minutes to about 24 hours.

According to step "g" of method A, the conversion of a compound of formula 9 into a compound of formula (II) is accomplished by using a hydrazine derivative of formula $NH_2NH-(CH_2)mR1$ in a suitable solvent such as tetrahydrofuran, 1,4-dioxane, 1,2-dimethoxyethane, methanol, ethanol, acetonitrile, acetic acid, N,N-dimethylformamide or mixtures thereof at a temperature ranging from 0° C. to reflux and for a time ranging from 30 minutes to about 24 hours. When hydrazine is used (m is O and R1 is hydrogen), the reaction proceeds according to step "g1" of method A yielding a N-unsubstituted pyrazole of formula (II)A.

According to step "h" of method A, the conversion of said N-unsubstituted pyrazole of formula (II)A in another compound of formula (II) can be accomplished using a compound of formula $L-(CH_2)mR1$ wherein L is OH, in which case the Mitsunobu conditions can be employed, or L is a group that optionally upon activation, may work as a leaving group, such as a halogen atom, a tosylate, mesylate or triflate.

In the former instance, that is, when a Mitsunobu protocol is employed, the reaction can be accomplished using a dialkyl azodicarboxylate, such as diethyl azodicarboxylate (DEAD), diisopropyl azodicarboxylate (DIAD) or the like, in the presence of a trialkyl or triaryl phosphine, preferably triphenyl phosphine in a suitable solvent such as tetrahydrofuran, 1,4-dioxane, 1,2-dimethoxyethane, acetonitrile. When L is a halogen atom or a group such as tosylate, mesylate or triflate or the like the conversion can be accomplished using a suitable base such as, for instance, NaH, $K_2CO_3$, $Cs_2CO_3$, NaOH, DBU, LiHMDS and the like, in a suitable solvent such as dichloromethane, tetrahydrofuran, 1,4-dioxane, 1,2-dimethoxyethane, methanol, ethanol, isopropanol, acetonitrile, acetic acid, N,N-dimethylformamide, N,N-dimethylacetamide, dimethylsulfoxide and the like. Said reactions can be carried out at temperatures ranging from 0° C. to reflux and for a time ranging from 30 minutes to about 48 hours. If required compounds of formula (II) can be separated and purified by silica gel chromatography or preparative HPLC.

Method B

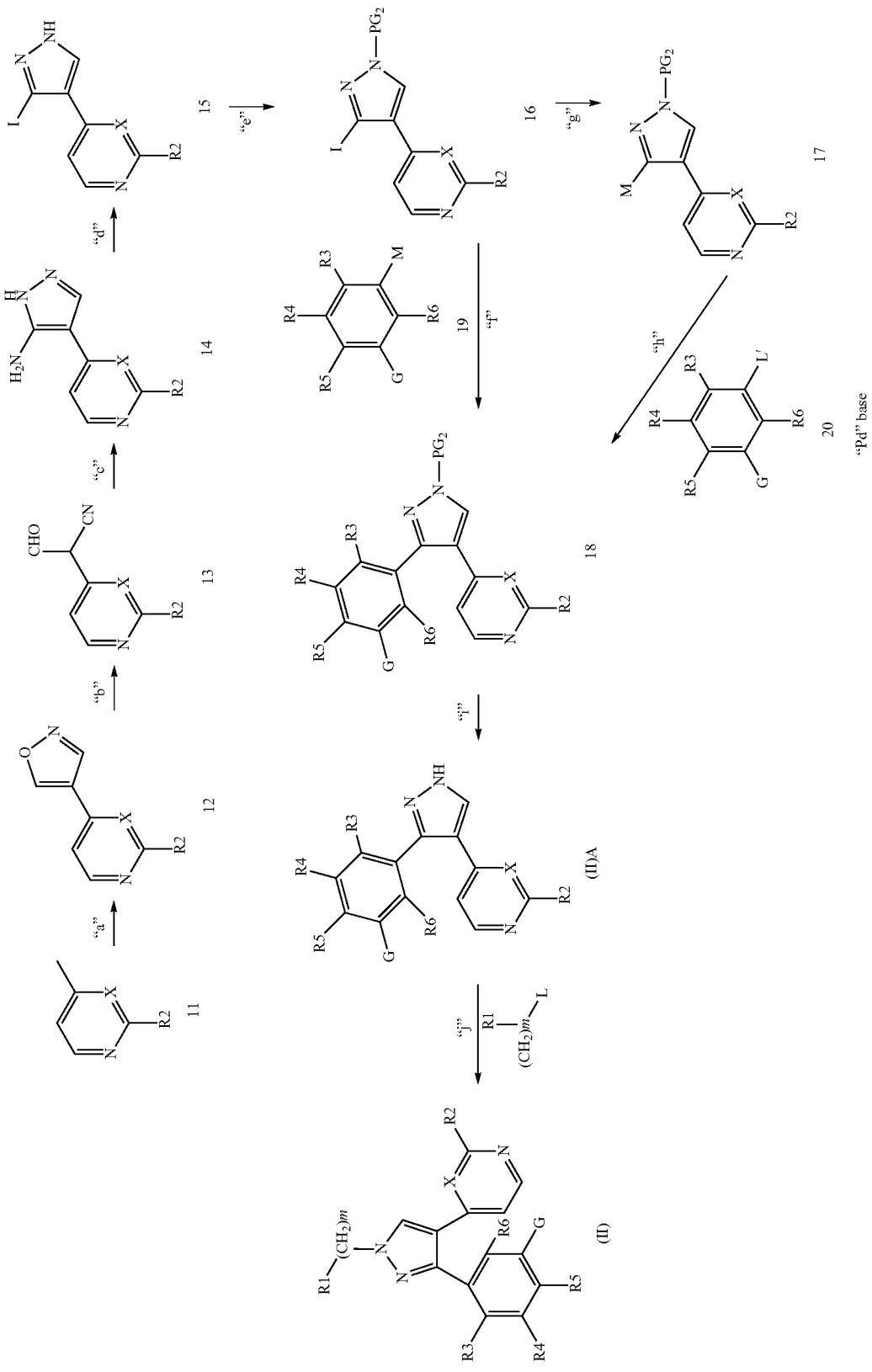

In the above scheme, X, m, R1, R2, R3, R4, R5, R6, G and L are as defined above, L' is a group that may work as a leaving group, such as a halogen atom, a tosylate, mesylate or triflate, and $PG_2$ is a protecting group such as p-methoxybenzyl, tetrahydropyranyl, trityl or a silyl derivative such as trimethylsilylethoxymethyl (SEM) and 2-trimethylsilylethanesulfonyl (SES), and M is $B(OH)_2$, $B(Oalk)_2$, $Sn(Alk)_3$, $Al(Alk)_2$, ZnHal, MgHal or $ZrCp_2Hal$.

In another synthetic process for the preparation of a compound of formula (II), which is described in method B, in step "a" 4-picoline or 4-methylpyrimidine derivative of formula 11 is reacted with phosphoryl trichloride under the Vilsmeier condition to form a malonaldehyde derivative, which is condensed with hydroxylamine to form the isoxazole compound of formula 12. In step "b" ring-opening of the isoxazole derivative yields a compound of formula 13, then in step "c" the condensation with hydrazine yields the pyrazole derivative of formula 14. In step "d" a Sandmeier reaction is used to convert a compound of formula 14 into a iodopyrazole derivative of formula 15. In step "e" the pyrazole nitrogen protection of a compound of formula 15 with a suitable protecting group such as, for instance, p-methoxybenzyl, tetrahydropyranyl or trytyl yields an intermediate of formula 16. In step "f" the latter can be transformed into a compound of formula 18 by exploiting any of the cross-coupling reactions suitable for the formation of carbon-carbon bonds. Said reactions, which are well known in the art, imply coupling with a suitable organometal reagent, such as, for instance, an organoboron, organotin, organozinc, organoaluminum or organozirconium compound and the like. Alternatively, in step "g" a compound of formula 16 is transformed in an organometal derivative, such as a boron-pyrazolo derivative, which in turn in step"h" is cross-coupled to a suitable electrophile, such as an aryl halide compound of formula 20, to form a compound of formula 18. In step "i" a compound of formula 18 is then deprotected to give a compound of formula (II)A. Finally, in step "j" the introduction of the —$(CH_2)mR1$ group to form a compound of formula (II) is accomplished through N-alkylation of a suitable alkylating agent L-$(CH_2)mR1$. The latter reaction could yield a mixture of regioisomers from which the desired isomer is purified by known methods such as silica gel chromatography or preparative HPLC.

According to step "a" of method B, a compound of formula 11 is reacted with the Vilsmeier reagent, which can be prepared according to methods well known by those skilled in the art, following conditions such as those reported by Arnold (Arnold, Z. Coll. Czech. *Chem. Commun.*, 1963, 28, 863). Condensation of the malonaldehyde derivative with hydroxylamine is accomplished using solvent such as ethanol, tetrahydrofuran or the like at a temperature ranging from 0° C. to reflux and for a time ranging from 30 minutes to about 24 hours.

According to step "b" of method B, ring-opening of the isoxazole of formula 12 is accomplished using aqueous alkali, such as NaOH, KOH, LiOH or the like, optionally in the presence of a suitable solvent such as ethanol, methanol, tetrahydrofuran or the like.

According to step "c" of method B, the conversion of a compound of formula 13 into a compound of formula 14 is accomplished by using hydrazine in a suitable solvent such as tetrahydrofuran, 1,4-dioxane, 1,2-dimethoxyethane, methanol, ethanol, acetonitrile, acetic acid, N,N-dimethylformamide or mixtures thereof at a temperature ranging from 0° C. to reflux and for a time ranging from 30 minutes to about 24 hours.

According to step "d" of method B, the conversion of a compound of formula 14 into a compound of formula 15 is accomplished preparing a diazonium salt, which can be done using sodium nitrite in water or aqueous solvents, in the presence of a mineral acid, such as hydrochloric acid, sulphuric acid and the like, following treatment with a iodide salt such as KI, NaI, CsI, CuI optionally in the presence of iodine. Alternatively the diazonium salt can be obtained using isoamyl nitrite in a suitable solvent such as dichloromethane dimethoxyethane, tetrahydrofuran and the like at a temperature ranging from 0° C. to reflux and for a time ranging from 30 minutes to about 24 hours.

According to step "e" of method B, protection of a iodopyrazole derivative of formula 15 can be accomplished in a number of ways which are well-known to those skilled in the art, depending on the nature of such a protecting groups. For instance protection can be carried out using p-methoxybenzyl bromide in solvents such as N,N-dimethylformamide in the presence of a suitable base such as $Cs_2CO_3$, $K_2CO_3$ or the like at temperature ranging from 20° C. to reflux and for a time ranging from 30 minutes to about 24 hours. As an alternative the protection may be accomplished using dihydropyrane in solvents such as dichloromethane, tetrahydrofuran or the like, in the presence of a suitable catalyst such as, for instance, p-toluenesulfonic acid (PTSA) at temperature ranging from 20° C. to reflux and for a time ranging from 30 minutes to about 24 hours. Yet, in a further context, said protection may be accomplished using trityl chloride in solvents such as toluene dichloromethane, tetrahydrofuran or the like in the presence of a base such as triethyl amine, DBU, or the like. Again, when such a protective group is represented by a SEM or SES group, protection can be accomplished using a suitable silylating agent, such as SEM halide or SES halide in the presence of a base, such as, for instance, 1,8-diazabicyclo[5.4.0]undec-7ene (DBU). Such reactions can be performed using a variety of solvents such as dichloromethane, toluene, tetrahydrofuran, 1,4-dioxane, 1,2-dimethoxyethane, acetonitrile at a temperature ranging from 0° C. to reflux and for a time ranging from 30 minutes to about 24 hours.

According to step "f" of method B, an intermediate of formula 16 is cross-coupled with a suitable organometal, such as, for instance, an organoboron compound (Suzuki reaction), an organotin compound (Stille reaction), an organozinc, organoalluminium or organozirconium compound (Negishi reaction), and the like. Said reactions are well known among those with ordinary skills in the art. Preferred reaction is the Suzuki reaction where an appropriate aryl or heteroaryl boronate is used in the presence of a palladium-based catalyst, such as, for instance, palladium tetrakis triphenyl phosphine, and a suitable base, such as $Cs_2CO_3$, $K_2CO_3$, $Rb_2CO_3$, NaOH, CsF, and the like.

According to step "g" of method B, a compound of formula 18 can be obtained also by transforming a compound of formula 16 into a suitable organometal derivative, such as an organoboron, an organotin or the like. Preferred organometal are organoboron compounds that can be obtained for instance reacting a compound of formula 16 with a suitable boron compound, such as bis(pinacolato)diboron, pinacolborane, or the like in the presence of a suitable palladium catalyst such as palladium acetate, PdCl2(dppf) and of a suitable base, such as KOAc, triethylamine and the like, in solvents such as N,N-dimethylformamide, dimethylsulfoxide, dimethoxyethane, dioxane, tetrahydrofuran or the like, at temperature ranging from 20° C. to reflux and for a time ranging from 30 minutes to about 24 hours.

According to step "h" of method B, the organometal derivative is reacted with an appropriate electrophile of formula 20, such as an aryl halide or a trifluoromethanesulfonate (triflate), a methanesulfonate (mesylate) or a p-toluenesulfonate (tosylate) in the presence of a palladium or nickel-based catalyst, such as, for instance, palladium tetrakis triphenyl phosphine, and a suitable base, such as $Cs_2CO_3$, $K_2CO_3$, $Rb_2CO_3$, NaOH, CsF, and the like to give a compound of formula 18.

According to step "i" of methods B, the removal of the protecting group $PG_2$ can be accomplished in a number of ways depending on the nature of said protecting group. For instance, when $PG_2$ is a tetrahydropyranyl group, transformation of a compound of formula 18 to a compound of formula (II)A can be accomplished using hydrochloric acid in methanol or ethanol. When said protecting group is, for instance, p-methoxybenzyl or trityl, transformation of a compound of formula 18 into a compound of formula (II)A can be accomplished using strong acids such as for instance trifluoroacetic acid in a suitable cosolvent such as dichloromethane at temperature ranging from 20° C. to reflux or above, provided that the reaction is carried out in a sealed vial heating for instance with a microwave oven, for a time ranging from 30 minutes to about 24 hours.

According to step "j" of method B, the conversion of a compounds of formula (II)A into another compound of formula (II) is accomplished as described under step "h" of method A.

Method C

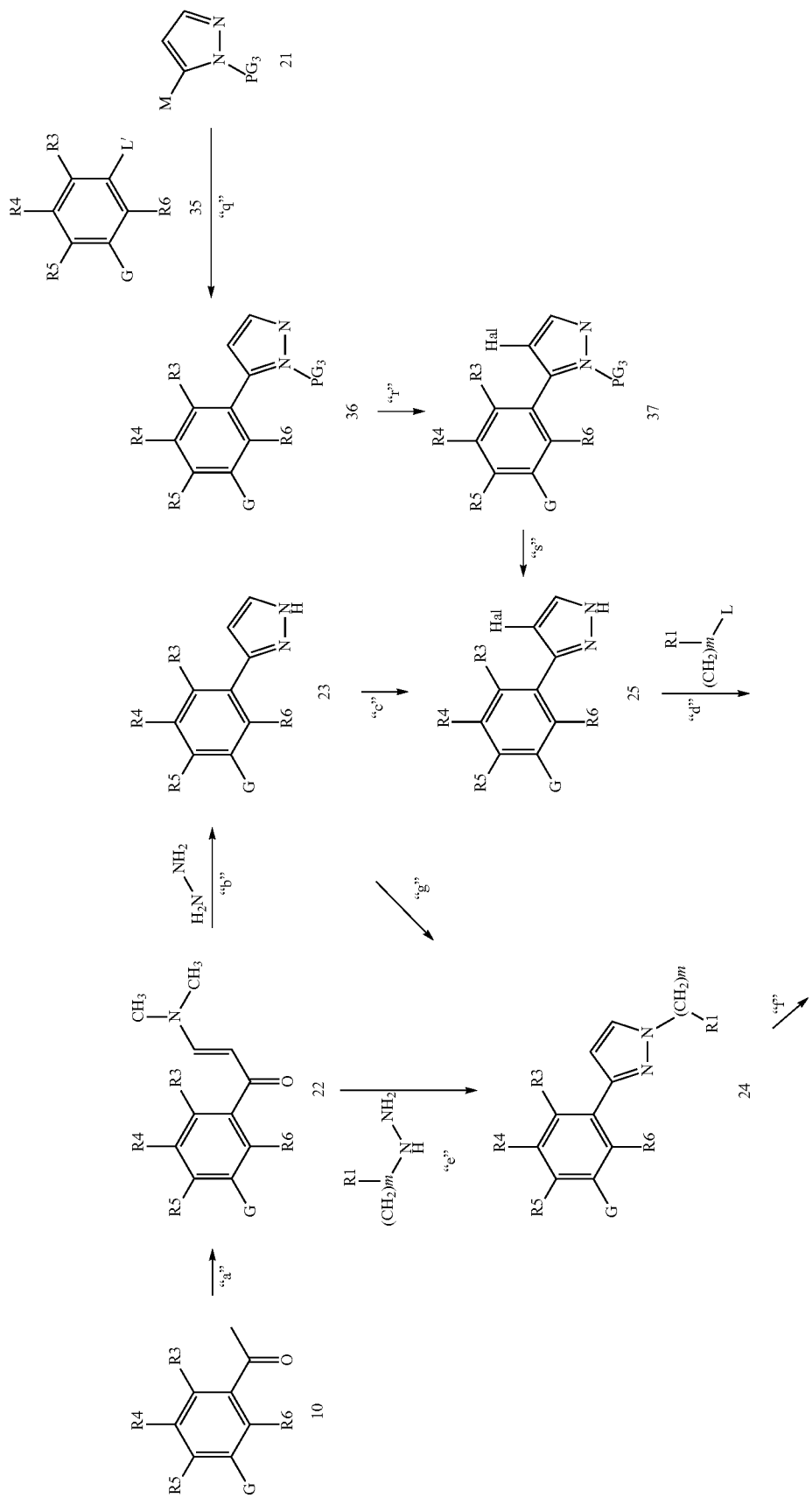

-continued
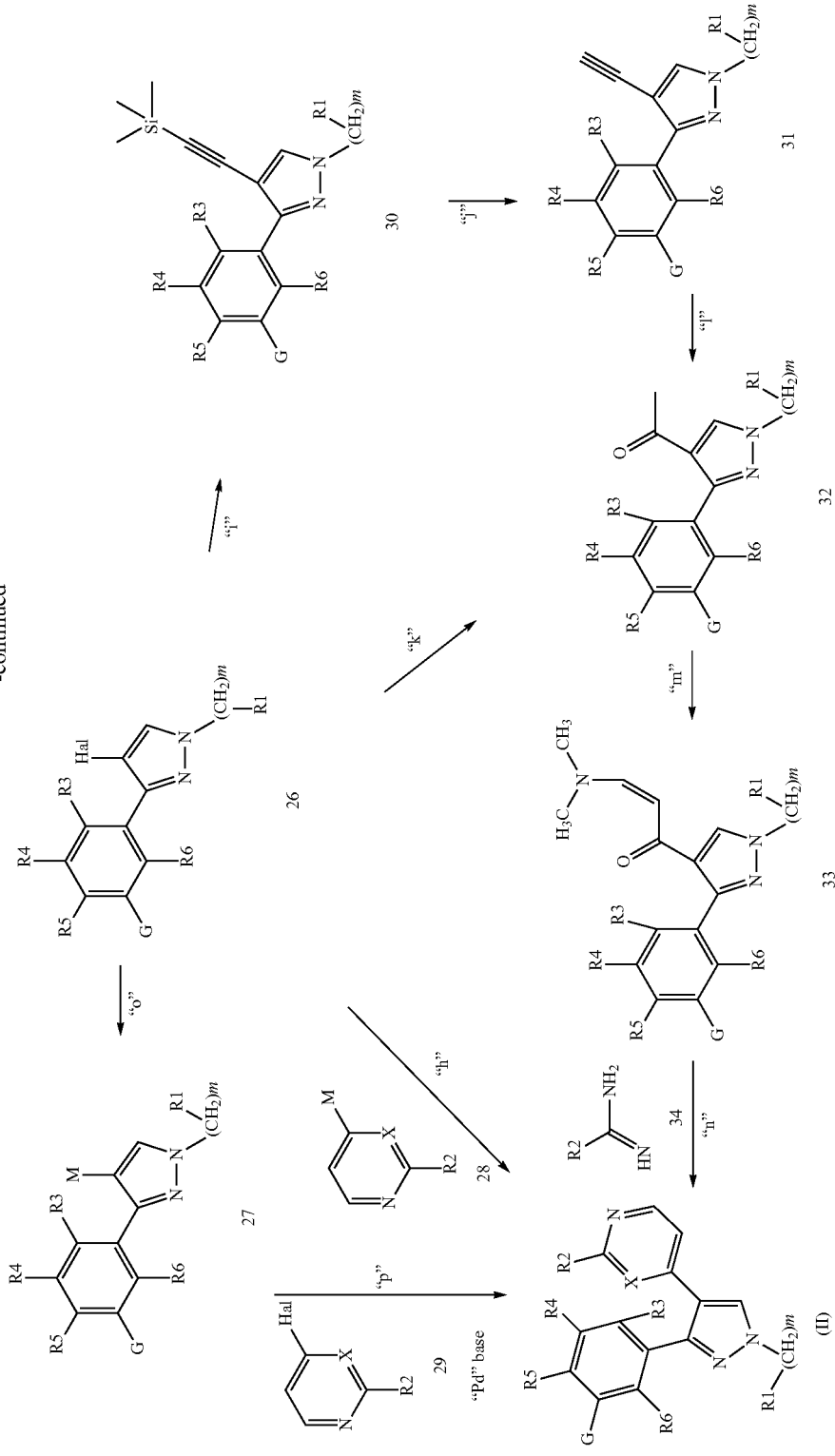

In the above scheme, X, m, R1, R2, R3, R4, R5, R6, G, L and M are as defined above, Hal is halogen and $PG_3$ is an ortho-directing protecting group such as tetrahydropyranyl, trimethylsilylethoxymethyl (SEM), methoxyethoxymethyl (MEM) or benzyloxymethyl (BOM).

In a further synthetic process for the preparation of a compound of formula (II), which is described in method C, in step "a" an aromatic ketone of formula 10 is condensed with N,N-dimethylformamide dialkyl acetal to form an enaminone derivative of formula 22, which in steps "b" and "e" is condensed with an appropriate hydrazine to form a pyrazole compound. With a substituted hydrazine the latter reaction may yield a mixture of regioisomers from which the compound of formula 24 can be separated and purified by silica gel chromatography or preparative HPLC. When hydrazine is used (m is 0 and R1 is hydrogen), an N-unsubstituted pyrazole of formula 23 is obtained. In the latter case in step "g" the introduction of the —$(CH_2)_m$R1 group to form a compound of formula 24 is accomplished through N-alkylation with a suitable alkylating agent of formula L-$(CH_2)_m$R1. In steps "c" and "f" pyrazoles of formula 23 and 24 are then respectively transformed into halogenated compounds of formula 25 and 26 respectively by reaction with a N-halosuccinimide, for instance, N-iodosuccinimide.

Alternatively, a compound of general formula 25 can be obtained starting from an organometal reagent of formula 21, such as a boron-pyrazolo derivative, which, in step "q", is cross-coupled with a suitable electrophile, such as an heteroaryl halide of formula 35, to form a compound of formula 36, which in step "r" is halogenated to form a compound of formula 37. The latter in step "s" is deprotected to give a compound of general formula 25. In step "d" a compound of formula 25 is transformed into a compound of formula 26 through N-alkylation with a suitable alkylating agent of formula L-$(CH_2)_m$R1 analogously to step "g".

A compound of formula 26 makes up a key intermediate that can be transformed into a compound of formula (II) following a number of synthetic routes.

For instance, in step "h" a compound of formula 26 is transformed directly into a compound of formula (II) by exploiting any of the cross-coupling reactions suitable for the formation of carbon-carbon bonds. Said reactions, which are well known in the art, imply coupling with a suitable organometal reagent, such as, for instance, an organoboron compound (Suzuki reaction).

Alternatively, in step "o" a compound of formula 26 is transformed in an organometal derivative, such as a boron-pyrazolo derivative which in step "p" is cross-coupled to a suitable electrophile, such as an heteroaryl halide of formula 29, to form a compound of formula (II).

Alternatively, in step "k" a compound of formula 26 is cross-coupled with a suitable enol ether to give a compound of formula 32 by a two-step sequence involving cross-coupling with a suitable enol ether organometal derivative followed by hydrolysis of the enol ether intermediate.

Alternatively, in step "i" a compound of formula 26 is subjected to a Sonogashira type reaction with trimethylsilylacetylene to form an intermediate of formula 30. In step "j" desilylation of the latter following hydration of the intermediate alkyne that is carried out in step "l", yields a compound of formula 32. In step "m" the transformation of a compound of formula 32 into a compound of formula (II) is accomplished by forming the enaminone derivative of formula 33, which, in step "n" is condensed with an appropriate guanidine derivative or an S-alkyl isothiourea derivative to give a compound of formula (II) wherein X is a Nitrogen atom.

According to step "a" of method C, synthesis of the enaminone derivative of formula 22 is accomplished as described for step "f" of method A.

According to step "e" of method C, the conversion of the compound of formula 22 into the compound of formula 24 is accomplished as described under step "g" of method A.

According to step "b" of method C, wherein hydrazine is used (m is 0 and R1 is hydrogen), an N-unsubstituted pyrazole of formula 23 is obtained. The reaction is conducted as described under step "g1" of method A.

According to steps "d" and "g" of method C, conversion of a compound of formula 23 or 25 in another compound of formula 24 or 26 respectively is accomplished as described under step "h" of method A.

According to steps "c" and "f" of method C, transformation of a compound of formula 23 or 24 in a compound of formula 25 or 26 respectively can be accomplished using a number of halogenating agents. Preferred is the iodination, which can be accomplished using iodine, iodine monochloride, or N-Iodo succinimide. Reaction with iodine is carried out for instance using solvents such as acetonitrile, toluene dichloromethane or water and the like, optionally in the presence of KI or of a base such as triethylamine, $K_2CO_3$, NaOH and the like, at temperatures ranging from −20° C. to reflux and for a time ranging from 30 minutes to about 48 hours. Reaction with iodine monochloride is carried out using solvents such as acetic acid, dichloromethane or the like at temperatures ranging from −20° C. to reflux and for a time ranging from 30 minutes to about 48 hours. Preferably said reaction is carried out using N-Iodo succinimide in solvents such as N,N-dimethylformamide or N,N-dimethylacetamide at temperatures ranging from −20° C. to reflux and for a time ranging from 30 minutes to about 48 hours.

According to step "q" of method C, an organometal reagent of formula 21 is coupled with a suitable electrophile as described under step "h" of Method B.

According to step "r" of method C, a protected arylpyrazole of formula 36 is transformed into an halogenated derivative of formula 37 as described for steps "c" and "f" of method C.

According to step "s" of method C, the removal of the protecting group $PG_3$ can be accomplished in a number of ways depending on the nature of said protecting group. For instance, when $PG_3$ is a tetrahydropyranyl group, a trimethylsilylethoxymethyl group (SEM) or a methoxyethoxymethyl (MEM) a transformation of a compound of formula 37 to a compound of formula 25 can be accomplished using hydrochloric acid in methanol or ethanol. When $PG_3$ is a benzyloxymethyl group, deprotection can also be achieved by catalytic hydrogenation.

According to step "h" of method C, the intermediate of formula 26 can be cross-coupled with a suitable oragnometal, such as, for instance, an organoboron compound (Suzuki reaction), an organotin compound (Stille reaction), an organozinc, organoalluminium or organozirconium compound (Negishi reaction), and the like. Said reactions well known among those with ordinary skills in the art are accomplished as described under step "f" of method B.

According to step "o" of method C, a compound of formula (II) can alternatively be obtained by transforming a compound of formula 26 into a suitable organometal derivative, such as an organoboron, an organotin or the like as described under step "g" of method B.

According to step "p" of method C, said organometal derivative is reacted with an appropriate electrophile as described under step "h" of method B.

According to step "k" of method C, a compound of formula 26 is cross-coupled with a suitable enol ether organometal derivative, such as 1-ethoxyvinyltri-n-butyltin following hydrolysis of the enol ether intermediate.

According to step "i" of method C, a compound of formula 26 is reacted with trimethylsilylacetylene in the presence of a suitable palladium catalyst such as PdCl2(PPh$_3$)$_2$, Pd(PPh$_3$)$_4$, and the like, and of a suitable copper catalyst, such as CuI. Said reaction is carried out in the presence of a suitable base, such as triethylamine, diethylamine, diisopropylamine and the like, optionally in the presence of a phosphine ligand, such as triphenylphosphine. The reaction is normally carried out at temperatures ranging from −20° C. to reflux and for a time ranging from 30 minutes to about 48 hours.

According to step "j" of method C, the trimethylsilyl group is removed using a base such as KOH, NaOH, K$_2$CO$_3$, in a solvent such as methanol, ethanol or the like or using a suitable fluoride salt, such as KF, n-Bu$_4$NF in solvents such as tetrahydrofuran, dimethoxyethane, N,N-dimethylformamide or the like.

According to step "l" of method C, the hydration of the alkyne of formula 31 to give a compound of formula 32 is accomplished using, for instance acetic acid, trifluoroacetic acid, trifluoromethansulfonic acid, Hg(OTf)$_2$, NaHSO$_3$, and the like in a suitable aqueous solvent such as acetonitrile, dioxane, ethanol or the like.

According to step "m" of method C, the synthesis of the enaminone derivative of formula 33 is accomplished as described under step "f" of method A.

According to step "n" of method C, the condensation of the compound of formula 33 with a compound of formula 34 to form a compound of formula (II) is accomplished using solvents such as N,N-dimethylformamide, N,N-dimethylacetamide, water, tetrahydrofuran, dioxane, dimethoxyethane, acetonitrile, ethanol, isopropanol or mixture thereof, optionally in the presence of a suitable base such as sodium ethoxide, sodium methoxide, K$_2$CO$_3$, NaOH, DBU, or the like at temperatures ranging from 20° C. to reflux and for a time ranging from 30 minutes to about 48 hours.

Method D

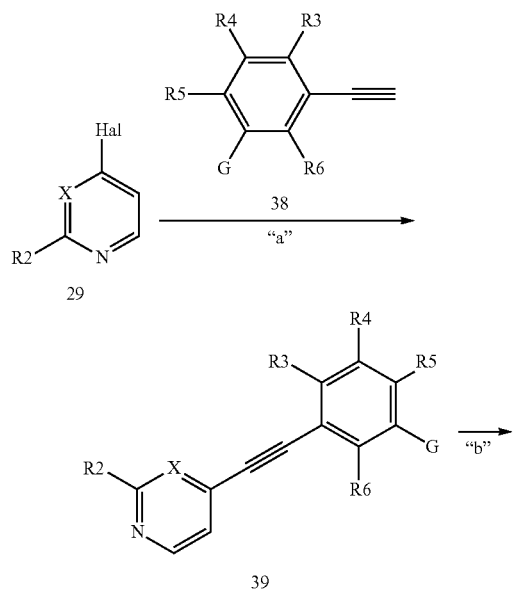

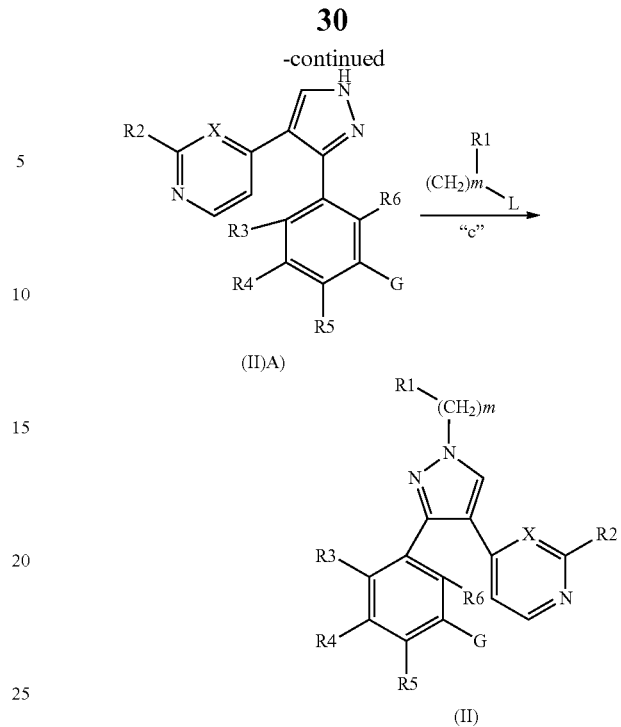

In the above scheme, m, R1, R2, R3, R4, R5, R6, G, L and Hal are as defined above.

In a further synthetic process for the preparation of a compound of formula (II), which is described in method D, in step "a" a suitable heteroaryl halide of formula 29 is subjected to a Sonogashira reaction in the presence of a suitable aryl alkyne of formula 38 to form a compound of formula 39. In step "b" the latter compound is reacted with a diazoalkane derivative, such as trimethylsilyl diazomethane, to form a compound of formula (II)A. In step "c" the introduction of the —(CH$_2$)mR1 group to form a compound of formula (II) is accomplished through N-alkylation of the suitable alkylating agent of formula L-(CH$_2$)mR1. The latter reaction could yield a mixture of regioisomers from which the desired isomer is purified by known methods such as silica gel chromatography or preparative HPLC.

According to step "a" of method D, a compound of formula 29 is coupled to an alkyne of formula 38 by means of a Sonogashira reaction, in the presence of a suitable palladium catalyst such as PdCl2(PPh$_3$)$_2$, Pd(PPh$_3$)$_4$, and the like, and of a suitable copper catalyst, such as CuI. Said reaction is carried out in the presence of a suitable base, such as triethylamine, diethylamine, diisopropylethylamine and the like, optionally in the presence of a phosphine ligand, such as triphenylphosphine. The reaction is normally carried out at temperatures ranging from −20° C. to reflux and for a time ranging from 30 minutes to about 48 hours.

According to step "b" of method D, the reaction of a compound of formula 39 with trimethylsilyl diazomethane is carried out in solvents such as dichloromethane, diethyl ether, tetrahydrofuran, acetonitrile, toluene or the like at temperatures ranging from −20° C. to reflux and for a time ranging from 30 minutes to about 48 hours. Aqueous work up, optionally in the presence of an acid such as for instance hydrochloric acid, yields a compound of formula (II)A.

According to step "c" of method D, a compound of formula (II)A is converted into another compound of formula (II) by reaction with a compound of formula L-(CH$_2$)mR1, as described under step "h" of method A.

A compounds of formula (II) prepared according to method A, method B, method C and method D may be further transformed in another compound of formula (II) following procedures well known to those skilled in the art. For instance, a compound of formula (II)B, i.e. a compound of formula (II) wherein X is CH group and R2 is hydrogen, or a compound of formula (II)K, i.e. a compound of formula (II) wherein X is CH group and R2 is halogen, said compound can further be transformed in another compound of formula (II)C, (II)D, (II)E and (II)F wherein R2 is respectively NR14R15, NHR14, NH$_2$ or NHCOR16, according to method E described below.

Method E

In the above scheme, m, R1, R3, R4, R5, R6, G, R14, R15, R16 and Hal are as defined above.

In a synthetic process for the preparation of a compound of formula (II)C, (II)D, (II)E and (II)F which is described in method E, in step "a" the pyridine nitrogen of a compound of formula (II)B is oxidized to form a N-oxide derivative of formula 40. In step "b", and "c" respectively, the reaction of the latter with a suitable electrophilic species such as tosyl anhydride in the presence or followed by treatment with a suitable nucleophile such as a secondary (NHR14R15) or a primary (NH$_2$R14) amine yields a compound of formula (II)C and (II)D respectively. Alternatively, in step "b1" and "c1" respectively, a compound of formula (II)K is reacted

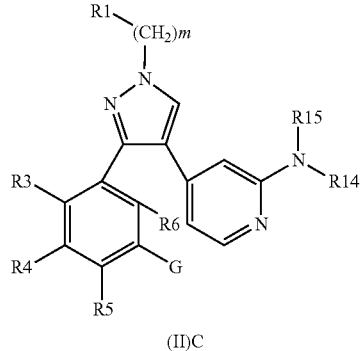

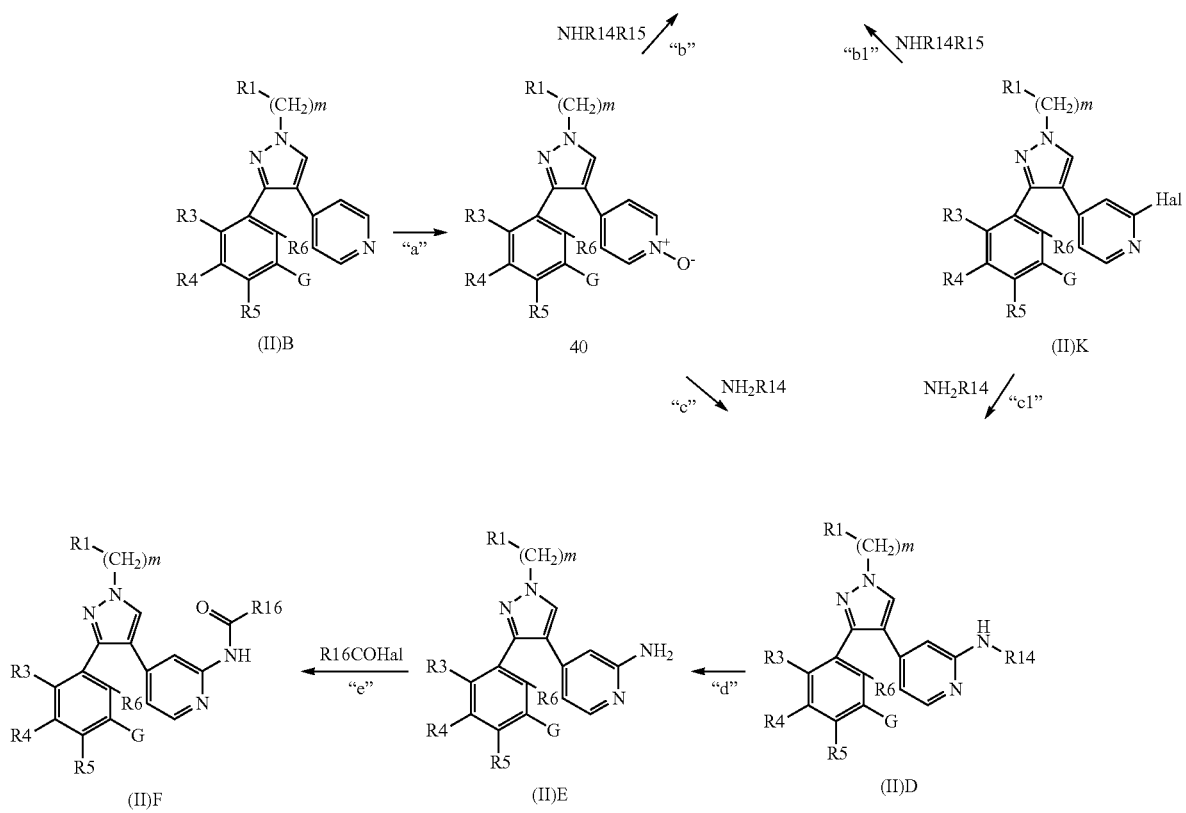

with a suitable nucleophile such as a secondary (NHR14R15) or a primary (NH₂R14) amine to yield a compound of formula (II)C and (II)D respectively. Optionally in step "d", when R14 is represented by a t-Butyl group, a benzyl group or the like, said groups may be removed for instance by treatment with acid or under reductive conditions to yield a compound of formula (II)E. In step "e" the latter may optionally be acylated using a suitable electrophile such as an acyl halide to form a compound of formula (II)F.

According to step "a" of method E, the oxidation of the pyridine nitrogen is carried out using oxidizing agents well-known to those skilled in the art, such as, for instance, hydrogen peroxide in a solvent such as acetic acid or m-chloroperbenzoic acid in solvents such as dichloromethane, acetone, tetrahydrofuran or the like at temperatures ranging from 0° C. to reflux and for a time ranging from 30 minutes to about 48 hours.

According to step "b" and "c" of method E, the transformation of a compound of formula 40 into a compound of formula (II)C and (II)D is accomplished by activating the pyridine N-oxide and reacting it with a secondary or primary amine. Activation is normally carried using a suitable electrophilic reagent, such as oxalyl chloride, trifluoromethanesulfonyl chloride, tosyl chloride, phosphoryl chloride (POCl₃), benzoyl chloride, acetic anhydride, tosyl anhydride and the like, in a solvent such as dichloromethane, tetrahydrofuran, acetonitrile, toluene, trifluoromethyl benzene and the like. Preferred is the use of tosyl anhydride in trifluoromethyl benzene. The reaction is normally carried out in the presence of the secondary or primary amine, and may be carried out at temperatures ranging from 20° C. to reflux and for a time ranging from 30 minutes to about 48 hours.

According to steps "b1" and "c1" of method E, the transformation of a compound of formula (II)K into a compound of formula (II)C and (II)D is accomplished by reacting it with a secondary or primary amine in solvents such as N,N-dimethylformamide, N,N-dimethylacetamide, N-methylpyrrolidone, dimethylsulfoxide, dichloromethane, tetrandrofuran, dioxane, ethanol and the like, optionally in the presence of a suitable base such as, for instance, K₂CO₃, NaOH, triethylamine at temperatures ranging from 20° C. to reflux and for a time ranging from 30 minutes to about 48 hours.

According to step "d" of method E, when a primary amine such as t-butylamine or benzylamine has been used in step b, the alkylic residue of such amine may be removed. The reaction, is normally carried out using strong acids, such as trifluoroacetic acid, optionally in the presence of suitable co-solvent, such as dichloromethane, at temperatures ranging from 20° C. to reflux and for a time ranging from 30 minutes to about 48 hours. Alternatively, said reaction is carried out using reductive conditions, such H₂ in the presence of a suitable hydrogenation catalyst. The hydrogenation catalyst is usually a metal, most often palladium, which can be used as such or supported on carbon, in a suitable solvent such as, for instance, tetrahydrofuran, 1,4-dioxane, N,N-dimethylformamide, methanol, ethyl acetate, or a mixture thereof.

According to step "e" of method E, compounds of formula (II)E are converted in a carboxamide of formula (II)F. It is clear to the skilled person that this reaction can be accomplished in a variety of ways and operative conditions, which are widely known in the art for the preparation of carboxamides. As an example, a compound of formula (II)E is acylated with a compound of formula R16COHal, wherein Hal is an halogen, such as chloride; the reaction is performed in a suitable solvent such as, for instance, dichloromethane, chloroform, tetrahydrofuran, diethyl ether, 1,4-dioxane, acetonitrile, toluene, or N,N-dimethylformamide, in the presence of a suitable base such as triethylamine, diisopropyl ethylamine, DBU and the like at a temperature ranging from about −10° C. to reflux and for a suitable time, for instance from about 30 minutes to about 96 hours.

A compound of formula (II) prepared according to method A, method B, method C and method D may be further transformed in another compound of formula (II) following procedures well known to those skilled in the art. For instance, a compound of formula (II)G, i.e. a compound of formula (II) wherein X is nitrogen and R2 is thiomethyl, or a compound of formula (II)L, i.e. a compound of formula (II) wherein X is nitrogen and R2 is halogen, said compound can further be transformed in other compounds of formula (II)H, (11)1 and (II)J wherein R2 is respectively NR14R15, NH₂ or NHCOR16, according to method F described below.

Method F

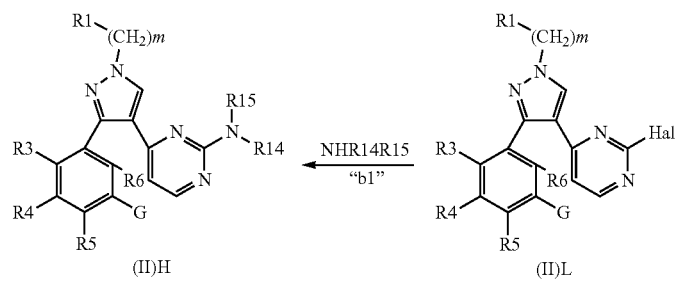

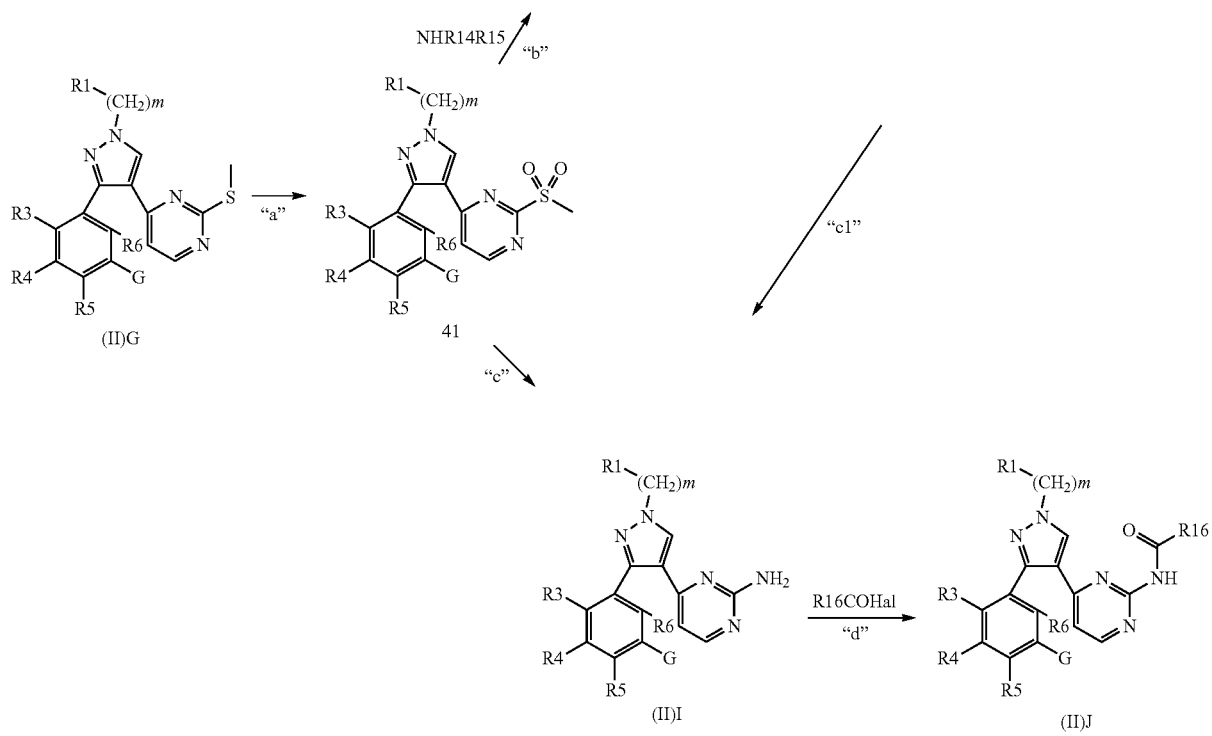

In the above scheme, m, R1, R3, R4, R5, R6, G, R14, R15, R16 and Hal are as defined above.

In a synthetic process for the preparation of a compound of formula (II)H, (II)I and (II)J which is described in method F, in step "a" the reaction of a compound of formula (II)G with an oxidizing agent yields a sulfonyl derivative of formula 41. In step "b" the latter is treated with a suitable nucleophile such as a primary or secondary amine of formula NHR14R15 to give a compound of formula (II)H. In step "c" the sulfonyl derivative of formula 41 is treated with ammonium chloride to form a compound of formula (II)1. Alternatively, in step "b1" and "c1", a compound of formula (II)L is reacted with a suitable nucleophile such as a primary or secondary amine of formula (NHR14R15) or with ammonium chloride to yield a compound of formula (II)H and (II)I respectively. A compound of formula (II)I may optionally be acylated using a suitable electrophile of formula R16COHal, wherein Hal is an halide, such as chloride or the like to form a compound of formula (II)J.

According to step "a" of method F, the oxidation of the thiomethyl group is carried out using oxidizing agents well-known to those skilled in the art, such as, for instance, oxone in a suitable solvent such as tetrahydrofuran, dioxane, acetone, optionally in the presence of water as a cosolvent, or m-chloroperbenzoic acid in solvents such as dichloromethane, acetone, tetrahydrofuran or the like at temperatures ranging from 0° C. to reflux and for a time ranging from 30 minutes to about 48 hours.

According to step "b" and "b1" of method F, the transformation of a compound of formula 41 in a compound of formula (II)H is carried out using a primary or secondary amine of formula R14R15NH in solvents such as N,N-dimethylformamide, N,N-dimethylacetamide, N-methylpyrrolidone, dimethylsulfoxide, dichloromethane, tetrandrofuran, dioxane, ethanol and the like, optionally in the presence of a suitable base such as, for instance, $K_2CO_3$, NaOH, triethylamine at temperatures ranging from 20° C. to reflux and for a time ranging from 30 minutes to about 48 hours.

According to step "c" and "c1" of method F, the formation of a compound (II)I from a compound of formula 41 is accomplished using a solution of ammonia in a suitable solvent, such as, dichloromethane, ethanol and the like, or ammonium salts, such as, for instance ammonium acetate in solvents such as N,N-dimethylformamide, N,N-dimethylacetamide, N-methylpyrrolidone, dimethylsulfoxide and the like at temperatures ranging from 20° C. to reflux and for a time ranging from 30 minutes to about 48 hours.

According to step "d" of method F, a compound of formula (II)I may be converted in a carboxamide of formula (II)J. It is clear to the skilled person that this reaction can be accomplished in a variety of ways and operative conditions, which are widely known in the art for the preparation of carboxamides. As an example, a compound of formula (II)I is acylated with a compound of formula R16COHal, wherein Hal is an halogen, such as chloride; the reaction is performed as described under step "e" of method E.

The compound of formula (I) can be prepared according to any of the methods G, H, I, J and M described below, provided that the interfering amino groups are protected by the introduction of suitable protecting groups, as can be understood by those skilled in the art.

According to method G described below, starting from a compound of formula (II)1, i.e. a compound of formula (II) wherein G is nitro, or from a compound of formula (II)2, i.e. a compound of formula (II) wherein G is a protected amino group, a compound of formula (I)C, (I)D, (I)E (I)F, (I)G or (I)H wherein A is respectively $NHSO_2$, NHCOO, NHCON (Y), NHCSNH, NHCO or $SO_2N(Y)$ is prepared.

Method G

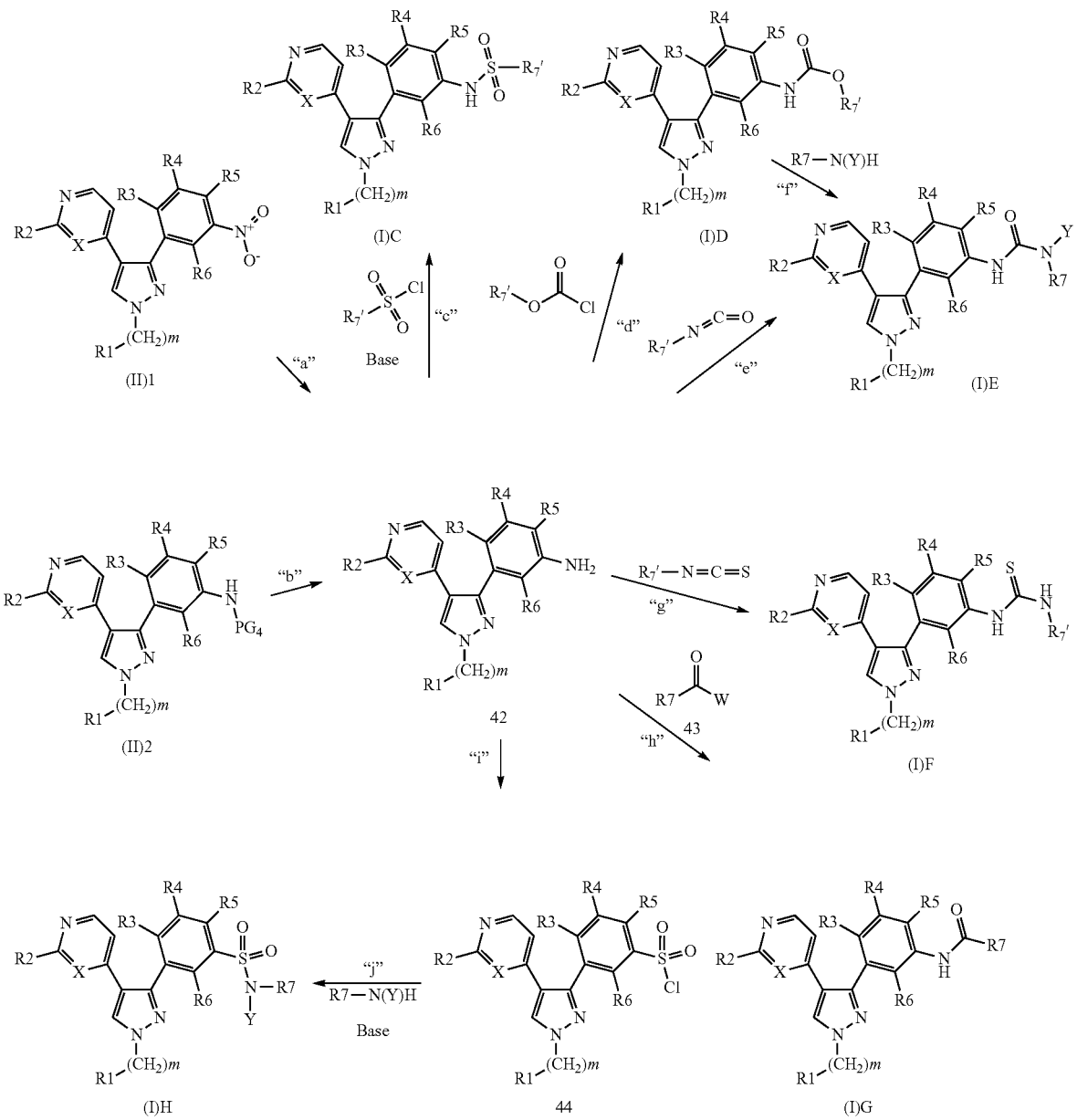

In the above scheme, X, m, R1, R2, R3, R4, R5, R6, R7 and Y are as defined above, R7' is as R7 described above but not hydrogen and W is a suitable leaving group such as hydroxy or halogen, and $PG_4$ is a suitable protecting group of the amino moiety such as benzyl, bis-benzyl, p-methoxybenzyl, trityl, phtaloyl, benzyloxycarbonyl, p-nitrobenzyloxycarbonyl, and the like.

In a synthetic process for the preparation of a compound of formula from (I)C to (I)H which is described in method G, in step "a" a compound of formula (II)1 is converted into a compound of formula 42 by reducing the nitro group to amino group. In step "b", said compound of formula 42 is obtained by removal of a suitable protecting group of the amino moiety from a compound of formula II(2).

In step "c", "d", "e", "g" and h" said compound of formula 42 is then reacted with different types of electrophile to provide respectively a compound of formula (I)C, (I)D, (I)E, (I)F and (I)G. In step "f", a compound of formula (I)D is converted into a compound of formula (I)E by reaction with a suitable primary or secondary amine. In step "i" a compound of formula 42 is subjected to a diazotation reaction under the Sandmeier conditions following reaction with $SO_2$ in the presence of hydrochloric acid and a suitable copper catalyst to form a sulfonyl chloride of formula 44. In step "j" the latter compound is reacted with a suitable primary amine to yield a compound of formula (I)H.

According to step "a" of method G, the nitro group of a compound of formula (II)1 is reduced to amino group to yield a compound of formula 42. The reaction may be carried out in a variety of way and operative conditions, which are widely known in the art for reducing a nitro to an amino group.

Preferably, this reaction is carried out in a suitable solvent such as, for instance, water, methanol, tetrahydrofuran, 1,4-dioxane, N,N-dimethylformamide, ethyl acetate, or a mixture thereof, in the presence of a suitable reducing agent, such as, for instance, hydrogen and a hydrogenation catalyst, or by treatment with cyclohexene or cyclohexadiene and a hydrogenation catalyst, or by treatment with tin (II) chloride, or by treatment with zinc or zinc (II) chloride and aqueous hydrochloric acid or acetic acid or ammonium chloride, at a temperature ranging from 0° C. to reflux and for a time varying from about 1 hour to about 96 hours. The hydrogenation catalyst is usually a metal, most often palladium, which can be used as such or supported on carbon.

According to step "b" of method G, when the $PG_4$ is a protecting group such as benzyl ($NHCH_2Ph$), bisbenzyl ($N(CH_2Ph)_2$), p-methoxybenzyl, p-methoxyphenyl, trityl, benzyloxycarbonyl, or p-nitrobenzyloxycarbonyl group, deprotection can be accomplished using $H_2$ in the presence of a suitable hydrogenation catalyst. The hydrogenation catalyst is usually a metal, most often palladium, or a metal derivative, such as $Pd(OH)_2$, which can be used as such or supported on carbon, in a suitable solvent such as, for instance, tetrahydrofuran, 1,4-dioxane, N,N-dimethylformamide, methanol, ethyl acetate, or a mixture thereof. Alternatively, said deprotection can be accomplished using strong acids, such as, for instance, sulphuric acid, hydrochloric acid, trifluoroacetic acid, trifluoromethanesulfonic acid or the like in the presence of a suitable solvent such as toluene, acetonitrile, dichloromethane or the like at a temperature ranging from 0° C. to reflux and for a time varying from about 1 hour to about 96 hours. In addition, when such a protecting group is a p-methoxyphenyl group, deprotection can be accomplished also under oxidative conditions, using for instance cerium ammonium nitrate (CAN) in a suitable solvent such as acetonitrile, dioxane, water methylethylketone or mixture thereof, at a temperature ranging from 0° C. to reflux and for a time varying from about 1 hour to about 24 hours. When said protecting group is represented by a phtaloyl group removal of the protecting group can be accomplished using hydrazine in a suitable solvent such as ethanol, water, dioxane, tetrahydrofuran and the like at a temperature ranging from 0° C. to reflux and for a time varying from about 1 hour to about 96 hours.

According to step "c" of method G, a compound of formula 42 is reacted with a sulfonyl chloride in the presence of a suitable base, such as for instance, pyridine, N-methyl morpholine, diisopropyl ethylamine, in the appropriate solvent such as pyridine, dichloromethane or tetrahydrofuran, at a temperature ranging from 0° C. to reflux and for a time varying from about 1 hour to about 7 days.

According to step "d" of method G, a compound of formula 42 is preferably reacted with a chloroformate in the appropriate solvent such as tetrahydrofuran, N,N-dimethylformamide, dichloromethane, chloroform, acetonitrile, toluene or mixtures thereof, at a temperature ranging from about −10° C. to reflux and for a time varying from about 30 minutes to about 96 hours. The reaction is normally carried out in the presence of an opportune proton scavenger such as triethylamine, N,N-diisopropylethylamine or pyridine.

According to step "e" of method G, a compound of formula 42 is reacted with the appropriate isocyanate in a suitable solvent such as a dichloromethane or tetrahydrofuran to yield an urea of formula (I)E. The reaction is normally carried out at a temperature ranging from about −10° C. to reflux and for a time varying from about 30 minutes to about 96 hours.

According to step "f" of method G, a compound of formula (I)E is obtained also from a compound of formula (I)D by reaction with an appropriate amine of formula R7N(Y)H. Said reaction is typically carried out in the appropriate solvent such as dimethylsulfoxide, tetrahydrofuran, N,N-dimethylformamide, N,N-dimethylacetamide, acetonitrile, toluene or mixtures thereof, optionally in the presence of a further base such as TEA, DIPEA DBU or an organometallic reagent such as a Grignard reagent or trimethyl aluminium, at a temperature ranging from about −10° C. to reflux and for a time varying from about 30 minutes to about 96 hours.

According to step "g" of method G, a compound of formula 42 is reacted with an appropriate thioisocyanate in a suitable solvent such as dichloromethane or tetrahydrofuran to yield a thiourea of formula (I)F. The reaction is normally carried out at a temperature ranging from about −10° C. to reflux and for a time varying from about 30 minutes to about 96 hours.

According to step "h" of method G, a compound of formula 42 is transformed into an amide of formula (I)G by condensation with any derivative of formula 43. It is clear to the skilled person that this reaction can be accomplished in a variety of ways and operative conditions, which are widely known in the art for the preparation of carboxamides.

As an example, when W is an halogen such as chloride, the reaction is performed in a suitable solvent such as, for instance, dichloromethane, chloroform, tetrahydrofuran, diethyl ether, 1,4-dioxane, acetonitrile, toluene, or N,N-dimethylformamide or the like at a temperature ranging from about −10° C. to reflux and for a suitable time, for instance from about 30 minutes to about 96 hours. The reaction is carried out in the presence of an opportune proton scavenger such as triethylamine, N,N-diisopropylethylamine or pyridine. When W is an hydroxy group, the reaction is carried out in the presence of a coupling agent such as, for instance, 2-(1H-benzotriazol-1-yl)-1,1,3,3-tetramethyluronium tetrafluoroborate (TBTU), 1,3-dicyclohexylcarbodiimide, 1,3-diisopropylcarbodiimide, 1-(3-dimethylaminopropyl)-3-ethylcarbodiimide, N-cyclohexylcarbodiimide-N'-propyloxymethyl polystyrene or N-cyclohexylcarbodiimide-N'-methyl polystyrene, in a suitable solvent such as, for instance, dichloromethane, chloroform, tetrahydrofuran, diethyl ether, 1,4-dioxane, acetonitrile, toluene, or N,N-dimethylformamide at a temperature ranging from about −10° C. to reflux and for a suitable time, for instance from about 30 minutes to about 96 hours. The said reaction is optionally carried out in the presence of a suitable catalyst, for instance 4-dimethylaminopyridine, or in the presence of a further coupling reagent such as N-hydroxybenzotriazole. Alternatively, this same reaction is also carried out, for example, through a mixed anhydride method, by using an alkyl chloroformate such as ethyl, iso-butyl, or iso-propyl chloroformate, in the presence of a tertiary base such as triethylamine, N,N-diisopropylethylamine or pyridine, in a suitable solvent such as, for instance, toluene, dichloromethane, chloroform, tetrahydrofuran, acetonitrile, diethyl ether, 1,4-dioxane, or N,N-dimethylformamide, at a temperature ranging from about −30° C. to room temperature.

According to step "i" of method G, the amino group of a compound of formula 42 is subjected to a diazotation reaction under the Sandmeier conditions following reaction with SO₂ in the presence of hydrochloric acid and a suitable copper catalyst to form a sulfonyl chloride of formula 44. The diazotation reaction is performed using sodium nitrite in water or aqueous solvents, in the presence of a mineral acid, such as hydrochloric acid, sulphuric acid and the like, or using isoamyl nitrite in a suitable solvent such as dichloromethane, dimethoxyethane, tetrahydrofuran and the like at a temperature ranging from 0° C. to reflux and for a time ranging from 30 minutes to about 24 hours. Next the diazonium salt is typically reacted with SO₂ in the presence of CuCl2 in the suitable solvent such as water, acetic acid or mixtures thereof at a temperature ranging from 0° C. to about 50° C. and for a time ranging from 30 minutes to about 6 hours.

According to step "j" of method G, a compound of formula 44 is reacted with a suitable amine to yield a compound of formula (I)H. Said reaction is normally carried out in a suitable solvent such as, for instance, dichloromethane, chloroform, tetrahydrofuran, diethyl ether, 1,4-dioxane, acetonitrile, toluene, or N,N-dimethylformamide or the like at a temperature ranging from about −10° C. to reflux and for a suitable time, for instance from about 30 minutes to about 96 hours. The reaction may be carried out in the presence of an opportune proton scavenger such as triethylamine, N,N-diisopropylethylamine or pyridine.

According to method H described below, starting from a compound of formula (II)3, i.e. a compound of formula (II) wherein G is bromine, a compound of formula (I)I or (I)J wherein A is respectively CH₂SO₂N(Y) or CH₂CON(Y) is prepared.

Method H

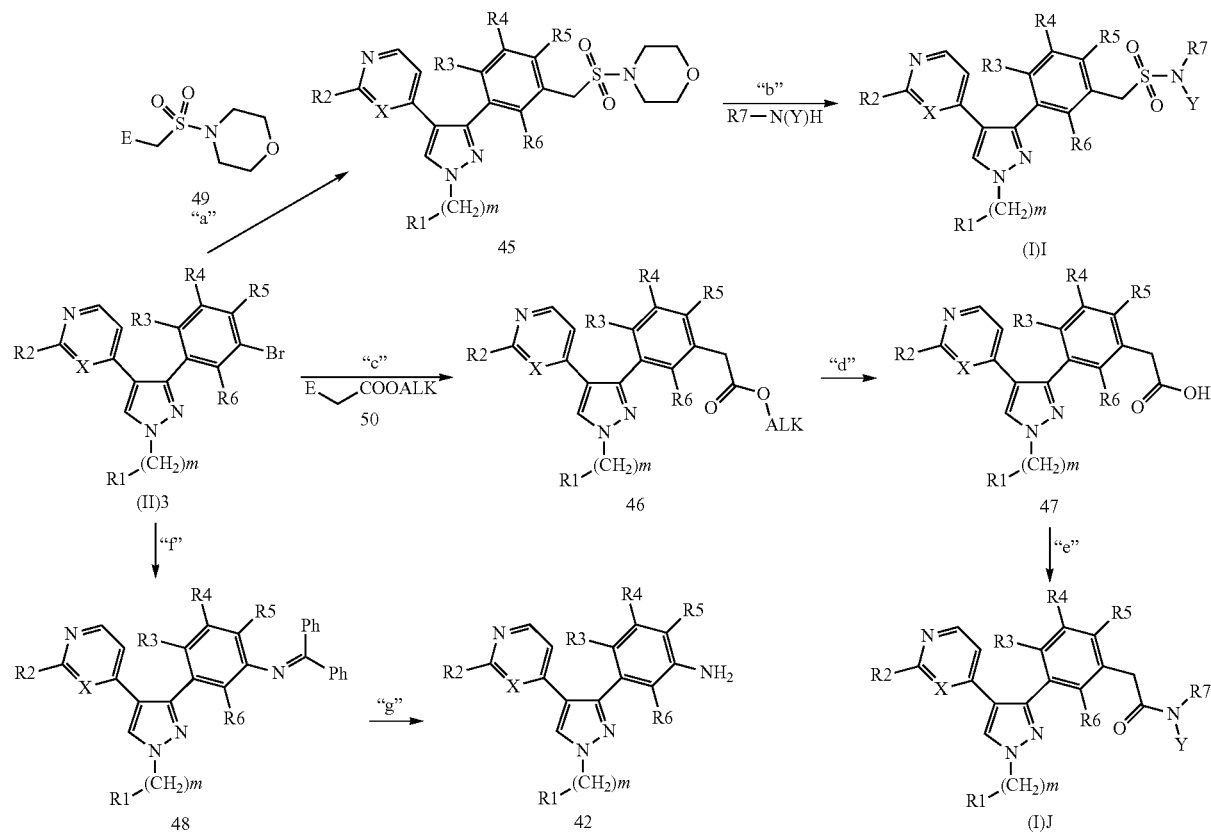

In the above scheme, X, m, R1, R2, R3, R4, R5, R6, E, R7, Alk, and Y are as defined above.

In a synthetic process for the preparation of a compound of formula (I)I and (I)J which is described in method H, in step "a" a compound of formula (II)3 is transformed in a compound of formula 45 by reaction with a suitable methanesulfonamide or alkylsulfonylamidoacetate of formula 49, in the presence of a suitable base, palladium-based catalyst and ligand. In step "b" the latter compound is than reacted with a suitable amine to form a compound of formula (I)I.

In step "c" a compound of formula (II)3 is reacted with an alkyl malonate salt in the presence of a suitable copper catalyst to form a compound of formula 46 which in step "d" is then hydrolyzed to the corresponding carboxylic acid of formula 47 by means of any of methods known in the art, for instance by using lithium hydroxide in the presence of suitable solvents such as mixtures of tetrahydrofuran, methanol and water. Said compound of formula 47 in step "e" is then condensed with a suitable amine to form a compound of formula (I)J. Alternatively, a compound of formula (II)3 is aminated under the Buchwald-Hartwig reaction conditions using benzophenone imine, a suitable base and a palladium catalyst to form a compound of formula 48. In step "g" the latter is hydrolyzed under acidic conditions, for instance using hydrochloric acid to form a compound of formula 42 that is subjected to any of the reactions reported in method G shown above.

According to step "a" of method H, the reaction between a compound of formula (II)3 and a suitable methylsulfonamide or alkylsulfonylamido acetate such as 4-methanesulfonylmorpholine of formula 49, is carried out following the conditions reported by Gimm, J. B.; Katcher, M. H.; Witter, D. J.; Northrup, A. B.; (J. Org. Chem. 2007, 72 (21), 8135-8138), using a base such as, for instance, sodium tertbutoxide, a suitable palladium catalyst, such as $Pd(OAc)_2$, a ligand, such as triphenylphosphine or tri tertbutylphosphonium tetrafluoroborate. Said reaction is normally carried out in solvents such as dioxane, dimethoxyethane and the like at a temperature ranging from about 0° C. to reflux and for a suitable time, for instance from about 30 minutes to about 96 hours. In case an alkylsulfonylamido acetate is used (compounds 48 where E is an alkyloxycarbonyl group) said reaction is followed by treatment with a variety of bases, such as, for instance $K_2CO_3$ or sodium amide in a suitable solvent such as 1,4-dioxane, dimethyl sulfoxide N,N-dimethylformamide or the like at a temperature ranging from about 20° C. to reflux and for a suitable time, for instance from about 30 minutes to about 96 hours.

According to step "b" of method H, the reaction between a compound of formula 45 and an amine is normally carried out in a suitable solvent, such as 1,4-dioxane, acetonitrile, toluene, or N,N-dimethylformamide or the like at a temperature ranging from about 20° C. to reflux and for a suitable time, for instance from about 30 minutes to about 96 hours.

According to step "c" of method H, the reaction between a compound of formula (II)3 and a suitable alkyl acetate or alkyl malonate of formula 50, is carried out using a base such as, for instance, sodium hydride, a suitable catalyst, such as CuBr, $Pd(OAc)_2$ or $PdCl_2$ a ligand, such as, for instance triphenylphosphine. Said reaction is normally carried out in solvents such as dioxane, dimethoxyethane and the like at a temperature ranging from about 0° C. to reflux and for a suitable time, for instance from about 30 minutes to about 96 hours. In case an alkyl malonate is used (i.e. a compound of formula 50 where E is an alkyloxycarbonyl group) said reaction is followed by treatment with a base, such as, for instance $K_2CO_3$ or sodium amide in a suitable solvent such as 1,4-dioxane, dimethyl sulfoxide N,N-dimethylformamide or the like at a temperature ranging from about 20° C. to reflux and for a suitable time, for instance from about 30 minutes to about 96 hours.

According to step "d" of method H, the hydrolysis of the alkyl ester of formula 46 is carried out according to well-known methods, for instance in the presence of aqueous alkaline solutions such as aqueous sodium hydroxide or lithium hydroxide in solvents such as tetrahydrofuran, methanol water and mixtures thereof. Said reaction typically requires from 30 minutes to 96 hours and is carried out at a temperature ranging from 0° C. to reflux.

According to step "e" of method H, a compound of formula 47 is transformed in an amide of formula (I)J by the condensation with a suitable amine. It is clear to the skilled person that this reaction can be accomplished in a variety of ways and operative conditions, which are widely known in the art for the preparation of carboxamides. As an example, the reaction is carried out in the presence of a coupling agent such as, for instance, 2-(1H-benzotriazol-1-yl)-1,1,3,3-tetramethyluronium tetrafluoroborate (TBTU), 1,3-dicyclohexylcarbodiimide, 1,3-diisopropylcarbodiimide, 1-(3-dimethylaminopropyl)-3-ethylcarbodiimide, N-cyclohexylcarbodiimide-N'-propyloxymethyl polystyrene or N-cyclohexylcarbodiimide-N'-methyl polystyrene, in a suitable solvent such as, for instance, dichloromethane, chloroform, tetrahydrofuran, diethyl ether, 1,4-dioxane, acetonitrile, toluene, or N,N-dimethylformamide at a temperature ranging from about −10° C. to reflux and for a suitable time, for instance from about 30 minutes to about 96 hours. Said reaction is optionally carried out in the presence of a suitable catalyst, for instance 4-dimethylaminopyridine, or in the presence of a further coupling reagent such as N-hydroxybenzotriazole. Alternatively, this same reaction is also carried out, for example, through a mixed anhydride method, by using an alkyl chloroformate such as ethyl, iso-butyl, or iso-propyl chloroformate, in the presence of a tertiary base such as triethylamine, N,N-diisopropylethylamine or pyridine, in a suitable solvent such as, for instance, toluene, dichloromethane, chloroform, tetrahydrofuran, acetonitrile, diethyl ether, 1,4-dioxane, or N,N-dimethylformamide, at a temperature ranging from about −30° C. to room temperature.

According to step "f" of method H, a compound of formula (II)3 is converted into a compound of formula 48 by reaction with benzophenone imine in the presence of a suitable base, such as sodium tert-buthoxide, a suitable catalyst, such as tris dibenzylidenacetone dipalladium, $Pd_2(dba)_3$, and optionally an additional ligand, such as 2,2'-bis(diphenylphosphino)-1,1'-binaphthyl (BINAP), in a suitable solvent, such as toluene, dimethoxyethane, dioxane and the like at a temperature ranging from about 20° C. to reflux and for a suitable time, for instance from about 30 minutes to about 96 hours.

According to step "g" of method H, the hydrolysis of a compound of formula 48 is accomplished using an acid such as hydrochloric acid in dioxane. Said reaction is normally carried out at a temperature ranging from about 0° C. to 40° C. and for a suitable time, for instance from about 30 minutes to about 96 hours.

Further elaboration of a compound of formula 42 is carried out according to method G.

According to method I described below, starting from a compound of formula (II)4, i.e. a compound of formula (II) wherein G is a cyano group, a compound of formula (I)K, (I)L, (I)M, (I)N, (I)O or (I)P wherein A is respectively CON (Y), $CH_2NHSO_2$, $CH_2NHCOO$, $CH_2NHCONH$, $CH_2NHCSNH$, or $CH_2NHCO$ is prepared.

45
Method I
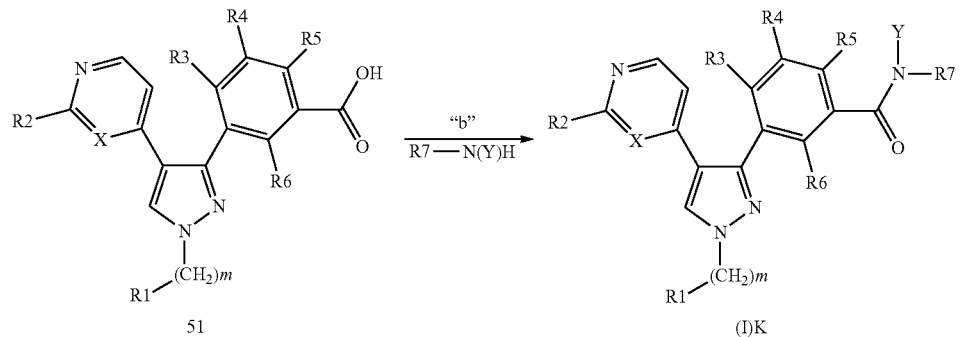
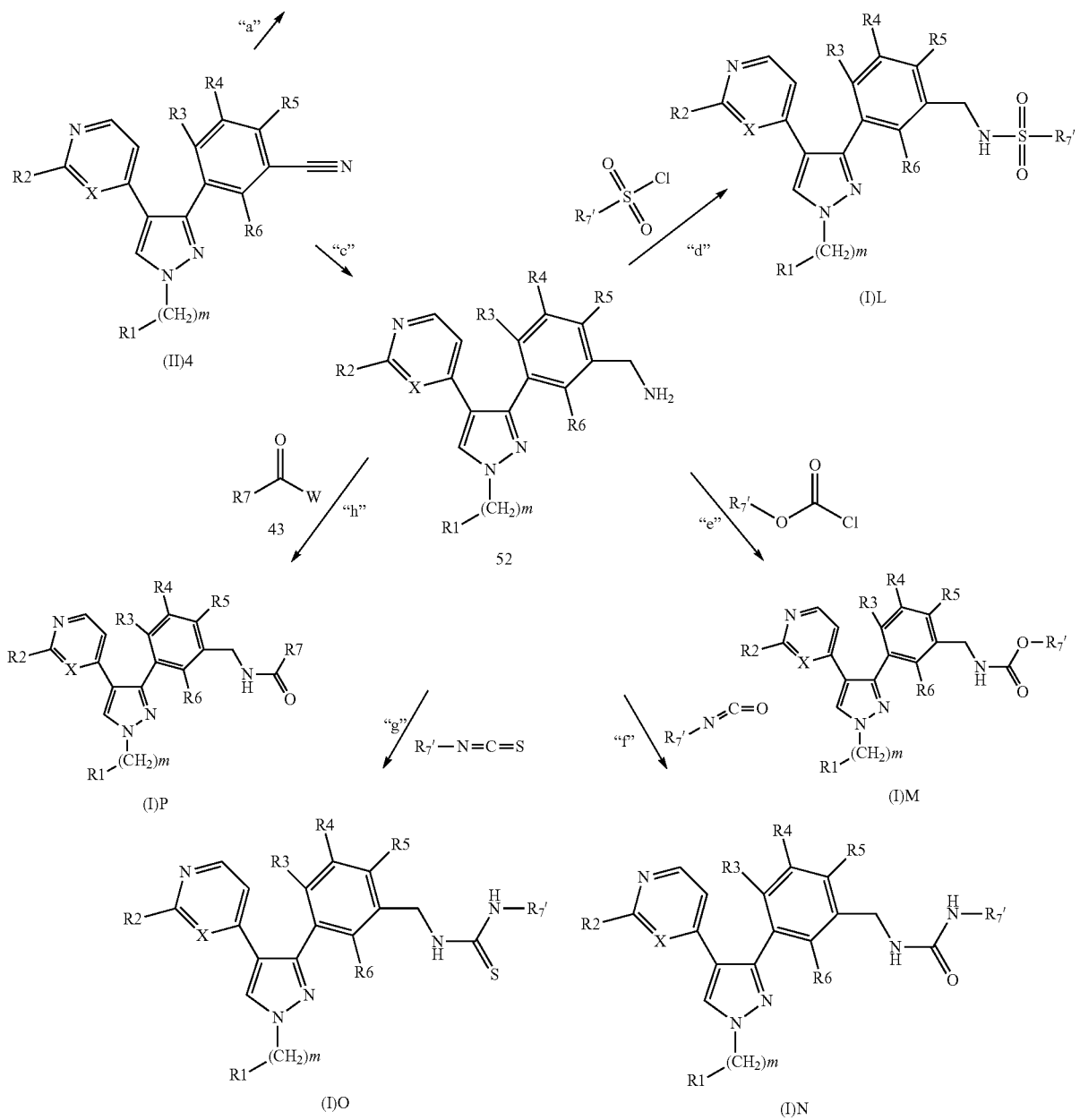

In the above scheme, X, m, R1, R2, R3, R4, R5, R6, R7, R7', Y and W are as defined above.

In a synthetic process for the preparation of a compound of formula from (I)K to (I)P which is described in method I, in step "a" the cyano group of a compound of formula (II)4 is hydrolized to form a compound of formula 51, and the latter in step "b" is then condensed with a suitable amine to form a compound of formula (I)K. Alternatively in step "c" the cyano group of a compound of formula (II)4 is reduced to form a compound of formula 52. In step "d", "e", "f, "g" and "h" said compound of formula 52 is then reacted with different types of electrophile to provide respectively a compound of formula (I)L, (I)M, (I)N, (I)O and (I)P.

According to step "a" of method I, the hydrolysis of the cyano group is accomplished by using any of the method known in the art, preferably by using aqueous hydrochloric acid under microwave heating at temperature ranging between 80 and 200° C. for a time between 3 and 120 minutes.

According to step "b" of method I, a compound of formula 51 is transformed in an amide of formula (I)K by the condensation with a suitable amine. It is clear to the skilled person that this reaction can be accomplished in a variety of ways and operative conditions, which are widely known in the art for the preparation of carboxamides. As an example, the reaction is carried out in the presence of a coupling agent such as, for instance, 2-(1H-benzotriazol-1-yl)-1,1,3,3-tetramethyluronium tetrafluoroborate (TBTU), 1,3-dicyclohexylcarbodiimide, 1,3-diisopropylcarbodiimide, 1-(3-dimethylaminopropyl)-3-ethylcarbodiimide, N-cyclohexylcarbodiimide-N'-propyloxymethyl polystyrene or N-cyclohexylcarbodiimide-N'-methyl polystyrene, in a suitable solvent such as, for instance, dichloromethane, chloroform, tetrahydrofuran, diethyl ether, 1,4-dioxane, acetonitrile, toluene, or N,N-dimethylformamide at a temperature ranging from about –10° C. to reflux and for a suitable time, for instance from about 30 minutes to about 96 hours. Said reaction is optionally carried out in the presence of a suitable catalyst, for instance 4-dimethylaminopyridine, or in the presence of a further coupling reagent such as N-hydroxybenzotriazole. Alternatively, this same reaction is also carried out, for example, through a mixed anhydride method, by using an alkyl chloroformate such as ethyl, iso-butyl, or iso-propyl chloroformate, in the presence of a tertiary base such as triethylamine, N,N-diisopropylethylamine or pyridine, in a suitable solvent such as, for instance, toluene, dichloromethane, chloroform, tetrahydrofuran, acetonitrile, diethyl ether, 1,4-dioxane, or N,N-dimethylformamide, at a temperature ranging from about –30° C. to room temperature.

According to step "c" of method I, a compound of formula (II)4 is transformed in a compound of formula 52 by using a suitable reducing agent, for instance lithium alluminium hydride, lithium boron hydride, borane dimethylsulfide complex, borane or the like, in a suitable solvent such as tetrahydrofuran, diethyl ether, toluene, dichloromethane, diglyme and the like, at temperature ranging from –50° to reflux, for a suitable reaction time, for instance, between 30 minutes and 48 hours.

Steps from "d" to "h" of method I are respectively carried out as described under step "c", "d", "e", "g" and "h" of method G.

According to method J described below, starting from a compound of formula (II)5, i.e. a compound of formula (II) wherein G is G is a suitable carboxylic ester, a compound of formula (I)Q wherein A is CH$_2$SO$_2$N(Y) is prepared.

Method J

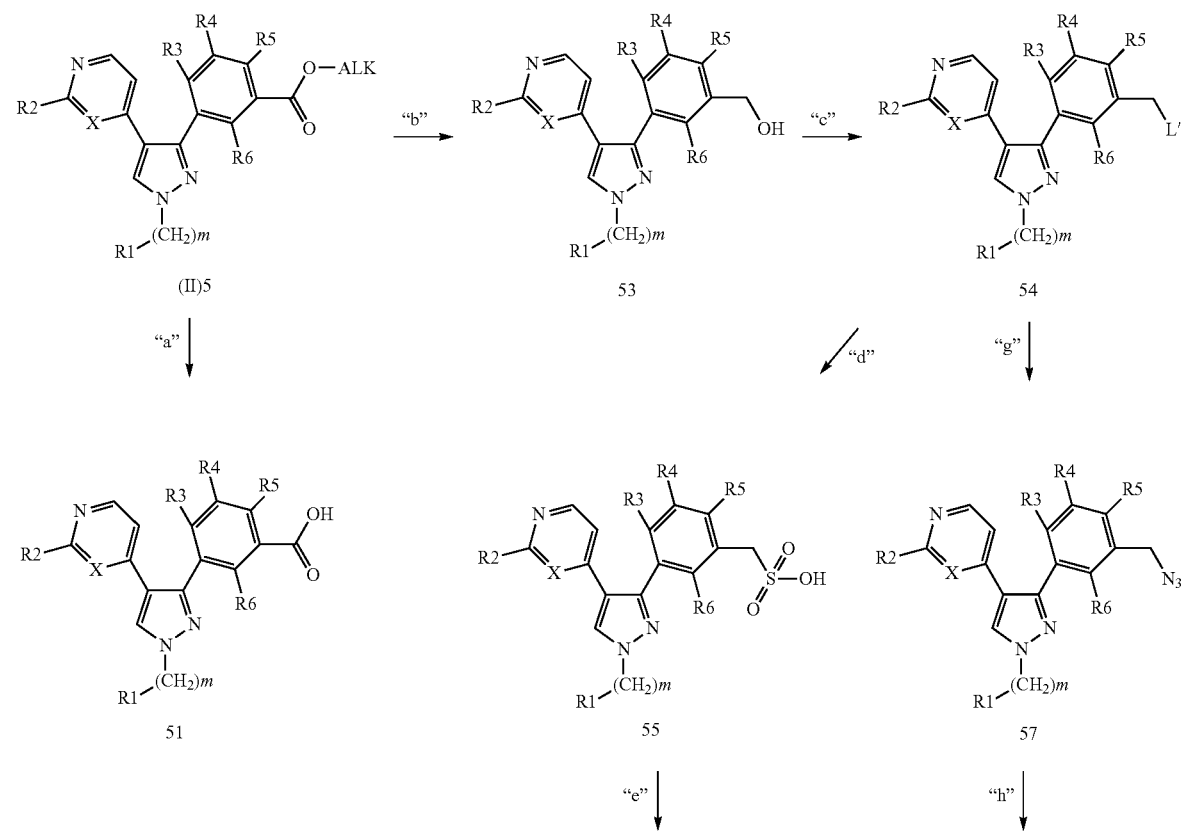

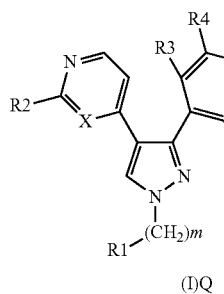

(I)Q

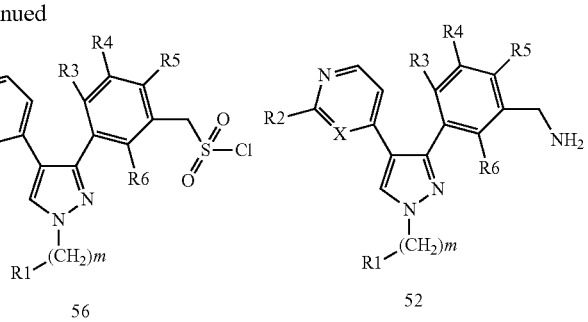

56    52

In the above scheme, X, m, R1, R2, R3, R4, R5, R6, R7, Y, Alk and L' are as defined above.

In a synthetic process described in method J, a compound of formula 51 is obtained in step "a" by the hydrolysis of the alkoxycarbonyl group of a compound of formula (II)5. The compound of formula 51 is then subjected to an amidation reaction according to what described in method I, step "b". In step "b" the alkoxycarbonyl group of compounds (II)5 is reduced to form a compound of formula 53. In step "c" the hydroxy group of the latter is then replaced by a more suitable leaving group, for instance bromine, a tosylate, mesylate or triflate. In step "d" a compound of formula 54 so obtained is reacted with a suitable nucleophile such as sodium sulfite, to form a compound of formula 55. Alternatively in step "g", a compound of formula 54 is reacted with sodium azide and then, in step "h", the intermediate alkyl azide is reduced to form a compound of formula 52 that is further functionalized following treatment with the appropriate electrophile as reported in method I shown above. In step "e" a compound of formula 55 is then transformed in the corresponding chloride derivative and then in step "f" treated with a suitable amine to give a compound of formula (I)Q.

According to step "a" of method J, the hydrolysis of the alkyl ester is carried out according to well-known methods, for instance in the presence of aqueous alkaline solutions such as aqueous sodium hydroxide or lithium hydroxide in solvents such as tetrahydrofuran, methanol water and mixtures thereof. Said reaction typically requires from 30 minutes to 96 hours and is carried out at a temperature ranging from 0° C. to reflux.

According to step "b" of method J, the reduction of a compound of formula (II)5 is carried out by using a suitable reducing agent, for instance lithium alluminium hydride, lithium boron hydride, borane or the like, in a suitable solvent such as tetrahydrofuran, diethyl ether, toluene, dichloromethane and the like, at temperature ranging from −50 to reflux, for a suitable reaction time, for instance, between 30 minutes and 48 hours. According to step "c" of method J, the hydroxy group of a compound of formula 53 is transformed in a more suitable leaving group following procedures well known in the art. For instance, its transformation in a bromine atom can be accomplished using an appropriate brominating agent such as $Ph_3PBr_2$, $PBr_3$, $SOBr_2$ or the like in a suitable solvent such as dichloromethane, tetrahydrofuran, diethyl ether, toluene, and the like, for a time ranging between 30 minutes to 24 hours and is carried out at a temperature ranging from 0° C. to reflux. The transformation of the hydroxy group in a tosylate, mesylate or triflate group is usually carried out using suitable reagents such as, for instance, tosyl chloride, mesyl chloride, trifluoromethanesulfonyl chloride respectively.

According to step "d" of method J, a compound of formula 54 is reacted with reagents such as sodium sulfite in solvents such as water, N,N-dimethylformamide, acetone or mixture thereof, optionally in the additional presence of a compound such as tetrabutyl ammonium bromide or the like, at a temperature ranging from 20° C. to reflux and for a time ranging from 30 minutes to about 24 hours.

According to step "e" of method J, a compound of formula 54 is reacted with reagents such as $PCl_5$, $POCl_3$, $SOCl_2$, $(COCl)_2$ or the like, in a suitable solvent such as tetrahydrofuran, dichloromethane or the like at a temperature ranging from 20° C. to reflux and for a time ranging from 30 minutes to about 24 hours to form compounds of formula 56.

According to step "f" of method J, a compound of formula 56 is reacted with a suitable amine to yield a compound of formula (I)Q. Said reaction is normally carried out in a suitable solvent such as, for instance, dichloromethane, chloroform, tetrahydrofuran, diethyl ether, 1,4-dioxane, acetonitrile, toluene, or N,N-dimethylformamide or the like at a temperature ranging from about −10° C. to reflux and for a suitable time, for instance from about 30 minutes to about 96 hours. The reaction may be carried out in the presence of an opportune proton scavenger such as triethylamine, N,N-diisopropylethylamine or pyridine.

Conversion of a compound of formula 54 into a compound of formula 52 can be accomplished in a number of ways and operative conditions well established among those skilled in the art. Just as an example a two-step sequence involving the formation of an alkyl azide of formula 57 and its reduction to an amino compound of formula 52 is reported here.

Accordingly, in step "g" of method J, a compound of formula 54 is reacted with a compound such as sodium azide in a solvent such as N,N-dimethylformamide, acetone, tetrahydrofuran, ethanol at a temperature ranging from about 20° C. to reflux and for a suitable time, for instance from about 30 minutes to about 96 hours.

According to step "h" of method J, a compound of formula 57 is reduced to form a compound of formula 52. Said reduction is accomplished using any suitable reducing agent such as, for instance, $PPh_3$, $SnCl_2$, $BH_3$ or the like in suitable solvent such as tetrahydrofuran, ethanol N,N-dimethylformamide or the like at a temperature ranging from about 20° C. to reflux and for a suitable time, for instance from about 30 minutes to about 96 hours.

A compound of formula (I) prepared according to method G, method H, method I, or method J may be further converted into another compound of formula (I) following procedures well known to those skilled in the art.

For instance, a compound of formula (I)R, i.e. a compound of formula (I) wherein X is a CH group and R2 is hydrogen or a compound of formula (I)AA, i.e. a compound of formula (I) wherein X is a CH group and R2 is halogen, said compound can further be transformed into another compound of formula (I)S, (I)T, (I)U or (I)V wherein R2 is respectively NR14R15, NHR14, NH$_2$ or NHCOR16, according to method K described below.

Method K sented by a t-butyl group, a benzyl group or the like, said groups is removed for instance by treatment with acid or under reductive conditions to yield a compound of formula (I)U. In step "e" the latter is optionally acylated using a suitable electrophile such as an acyl chloride to form a compound of formula (I)V.

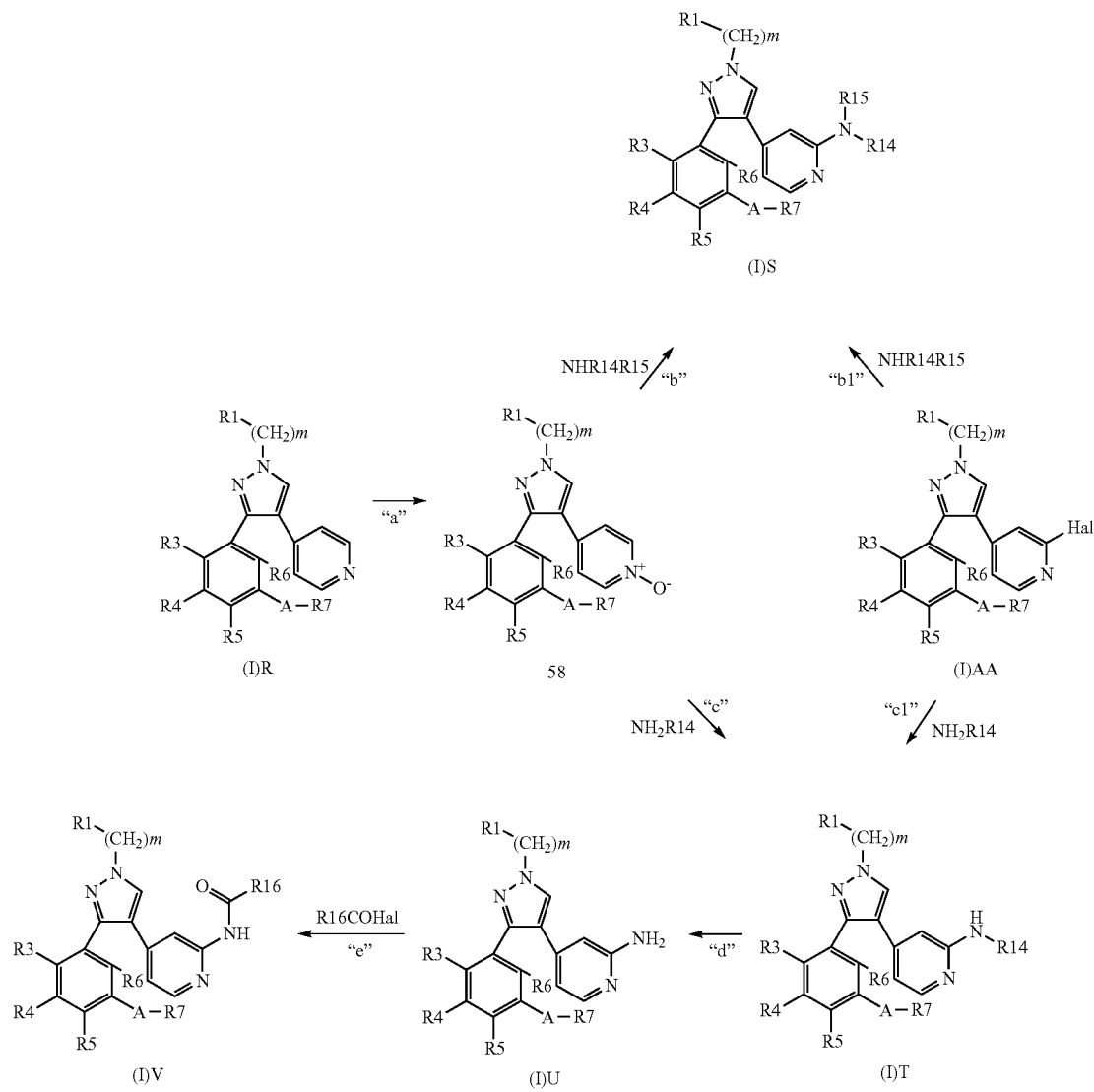

In the above scheme, m, R1, R3, R4, R5, R6, A, R7, R14, R15, R16 and Hal are as defined above.

In a synthetic process for the preparation of a compound of formula (I)S, (I)T, (I)U and (I)V which is described in method K, in step "a" the pyridine nitrogen of a compound of formula (I)R is oxidized to form a N-oxide derivative of formula 58. In step "b" and "c" respectively, the reaction of the latter with a suitable electrophilic species such as tosyl anhydride in the presence or followed by treatment with a suitable nucleophile such as a secondary (NHR14R15) or a primary (NH$_2$R14) amine yields a compound of formula (I)S and (I)T respectively. Alternatively, in step "b1" and "c1" respectively, a compound of formula (I)AA is reacted with a suitable nucleophile such as a secondary (NHR14R15) or a primary (NH$_2$R14) amine to yield a compound of formula (I)S and (I)T respectively. Optionally in step "d", when R14 is repre- The reactions of steps "a", "b", "c", "d", "c1", "d1" and "e" of method K are accomplished analogously to those of to steps "a", "b", "c", "d", "c1", "d1" and "e" of method E shown above.

A compound of formula (I) prepared according to method G, method H, method I, or method J may be further converted into another compound of formula (I) following procedures well known to those skilled in the art.

For instance, a compound of formula (I)W, i.e. a compound of formula (I) wherein X is nitrogen and R2 is thiomethyl or a compound of formula (I)AB, i.e. a compound of formula (I) wherein X is nitrogen and R2 is halogen, said compound can further be transformed into another compound of formula (I)X, (I)Y or (I)Z wherein R2 is respectively NR14R15, NH$_2$ or NHCOR16, according to method L described below.

Method L

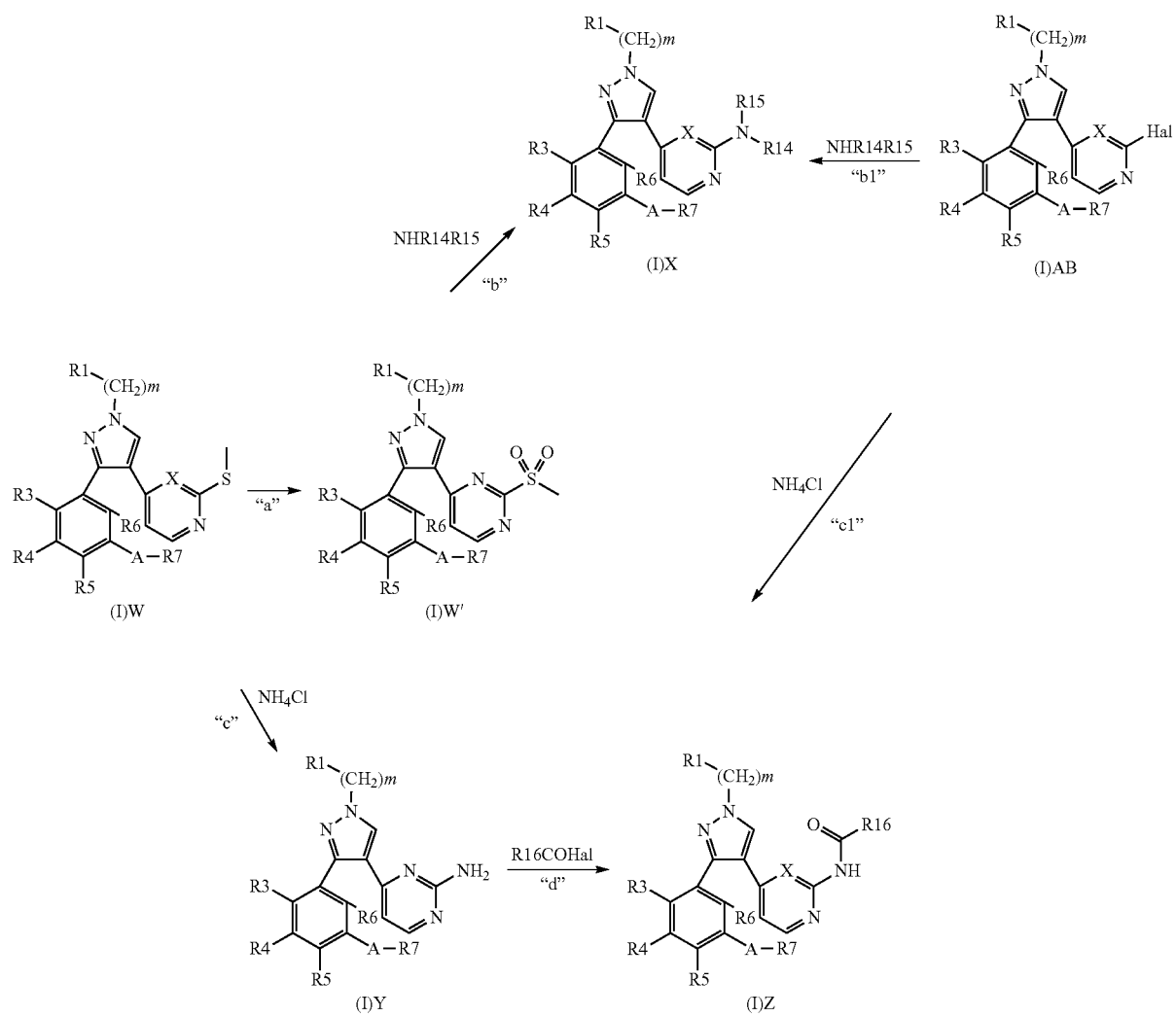

In the above scheme, m, R1, R3, R4, R5, R6, A, R7, R14, R15 and R16 and Hal are as defined.

In a synthetic process for the preparation of compounds of formula (I)X, (I)Y and (I)Z which is described in method L, in step "a" the reaction of a compound of formula (I)W with an oxidizing agent yields a sulfonyl derivative of formula (I)W'. In step "b" the latter is treated with a suitable nucleophile such as a primary or secondary amine of formula NHR14R15 to give a compound of formula (I)X. In step "c" the sulfonyl derivative of formula (I)W' is treated with ammonium chloride to form a compound of formula (I)Y. Alternatively, in step "b1" and "c1", a compound of formula (I)AB is reacted with a suitable nucleophile such as a primary or secondary amine of formula (NHR14R15) or with ammonium chloride to yield a compound of formula (I)X and (I)Y respectively. A compound of formula (I)Y is optionally acylated using a suitable electrophile of formula R16COHal, wherein Hal is an halide, such as chlorid or the like to form a compound of formula (I)Z.

The reactions of steps "a", "b", "c", "b1", "c1" and "d" of method L are accomplished analogously to those of steps "a", "b", "c", b1", "c1" and "d" of method F shown above.

In a further process, a compound of formula 60 is transformed into a compound of formula (I)A, according to method M shown below.

Method M

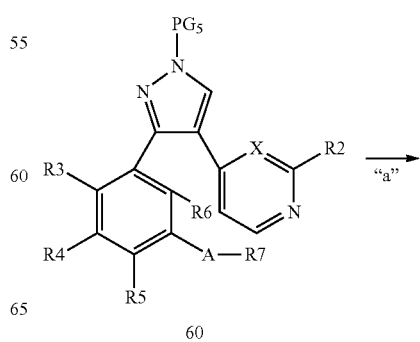

60

-continued

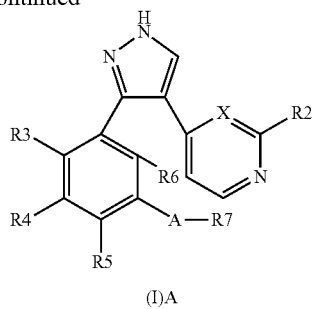

(I)A

In the above scheme, X, R2, R3, R4, R5, R6, A, R7 are as defined above, m is 0, R1 is hydrogen and PG$_5$ is a protecting group or a resin for solid phase synthesis.

It is readily understood by those skilled in the art, that when PG$_5$ represents a suitable protecting group or a resin for solid phase synthesis, a variety of methods, which are well known in the art, can be used to remove such a protecting group or resin depending on the nature of the PG$_5$.

According to step "a" of method M, when the PG$_5$ is a protecting group such as a silyl group or a derivative thereof such as 2-trimethylsilylethanesulfonyl (SEM), 2-trimethylsilylethanesulfonyl (SES) and the like, deprotection can be accomplished using tetrabutyl ammonium fluoride, cesium fluoride, as well as trifluoroacetic acid, perchloric acid, hydrochloric acid, hydrofluoric acid, and derivatives thereof, in a suitable solvent such as tetrahydrofuran, 1,4-dioxane, 1,2-dimethoxyethane, methanol, ethanol, acetonitrile, dichloromethane, N,N-dimethylformamide or the like at a temperature ranging from 0° C. to reflux and for a time ranging from 30 minutes to about 24 hours. When such a protecting group is represented by a tetrahydropyranyl group, the transformation of a compound of formula 60 into a compound of formula (I) is accomplished using hydrochloric acid in methanol or ethanol. When said protecting group is, for instance, benzyl, p-methoxybenzyl or trityl, transformation of a compound of formula 60 into a compound of formula (I) is accomplished using strong acids such as for instance trifluoroacetic acid in a suitable cosolvent such as dichloromethane at temperature ranging from 20° C. to reflux or above, provided that the reaction is carried out in a sealed vial heating for instance with a microwave oven, for a time ranging from 30 minutes to about 24 hours. When said protecting group is, for instance, tert-butoxycarbonyl the transformation of a compound of formula 60 into a compound of formula (I) is accomplished using strong acids such as for instance trifluoroacetic acid in a suitable cosolvent such as dichloromethane or hydrochloric acid in dioxane at temperature ranging from 20° C. to reflux or above, provided that the reaction is carried out in a sealed vial heating for instance with a microwave oven, for a time ranging from 30 minutes to about 24 hours. When said protecting group is, for instance, ethoxycarbonyl the transformation of a compound of formula 60 into a compound of formula (I)A is accomplished using, for instance, triethylamine in the presence of methanol or the like at temperature ranging from 20° C. to reflux for a suitable time usually between 30 minutes and 48 hours.

When the PG$_5$ group represents a resin for solid phase synthesis, removal of such a resin is accomplished according to methods well known to those skilled in the art, which depend on the nature of such a resin. Typically when trityl chloride resin, 2-chlorotrityl chloride resin, 4-(bromomethyl)phenoxymethyl resin, 4-(bromomethyl)phenoxyethyl resin, Bromo-(4-methoxyphenyl)methyl polystyrene resin/Bromo MAMP resin), p-nitrophenyl carbonate Wang resin, p-nitrophenyl carbonate Merrifield resin, 3,4-dihydro-2H-pyran-2-ylmethyoxymethyl resin, p-nitrophenyl carbonate buthyloxymethyl resin, and the like are used, removal is accomplished using trifluoroacetic acid in a suitable solvent such as dichloromethane at room temperature for a suitable time, usually between 5 minutes and 24 hours.

In a further process, a compound of formula (II)A obtained by method A, method B, method C and method D is transformed into a compound of formula 61 according to method N shown below.

Method N

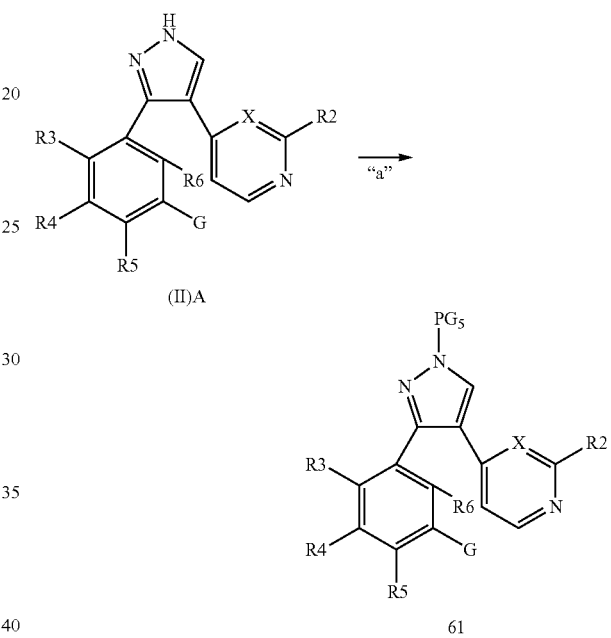

In the above scheme, X, R2, R3, R4, R5, R6, G and PG$_5$ are as defined above.

It is readily understood by those skilled in the art, that the installation of PG$_5$ may be accomplished in a number of ways and following a variety of methods, which are well known in the art, depending on the nature of the PG$_5$.

According to step "a'" of method N, when PG$_5$ is a silyl deriv, tetrahydropiranyl, p-methoxybenzyl or trityl the transformation of a compound of formula (II)A in a compound of formula 61 is accomplished as described under step "e", of method B. When PG$_5$ is an alkoxycarbonyl group the transformation of a compound of formula (II)A in a compound of formula 61 is accomplished using the appropriate dialkyl carbonate, such as for instance di-tert-butyl dicarbonate, an alkyl chlororformate, such as for instance ethyl chloroformate, optionally in the presence of a suitable base, such as triethylamine, N,N-diisopropyl ethylamine or the like in a suitable solvent, such as, for instance dichloromethane, tetrahydrofuran, at a temperature ranging from 0° C. to reflux and for a time ranging from 30 minutes to about 48 hours.

When PG$_5$ is a resin for solid-phase synthesis the loading can be accomplished using any suitable resin such as a plystyrene or polyethylenglycol grafted polystyrene resin provided that they bear a suitable linker. A non-limiting list of such resins include trityl chloride resin, 2-chlorotrityl chloride resin, 4-(bromomethyl)phenoxymethyl resin, 4-(bromomethyl)phenoxyethyl resin, Bromo MAMP resin, p-nitrophenyl carbonate Wang resin, p-nitrophenyl carbonate Merrifield resin, 3,4-dihydro-2H-pyran-2-ylmethyoxymethyl resin, p-nitrophenyl carbonate buthyloxymethyl resin, and the like. Said resins are typically reacted with compounds of general formula (II)A in a suitable solvent such as dichloromethane, tetrahydrofuran, toluene, 1,2-dimethoxyethane, N,N-dimethylformamide, methanol, or mixtures thereof, optionally in the presence of an opportune proton scavenger such as triethylamine, $K_2CO_3$, N,N-diisopropylethylamine, pyridine or the like, at a temperature ranging from 0° C. to 40° C. and for a time ranging from 30 minutes to about 48 hours. It is clearly understood by those skilled in the art, that when in said compounds of formula (II) m is 0 and R1 is a protective group as described above, any or even a mixture of the regioisomeric compounds of formula (II) and 10 can be used for the forthcoming transformation as said protective group will be removed at the end of transformation by using any of the procedure known in the art, providing compounds of general formula (I) wherein m is 0 and R1 is hydrogen.

When preparing the compounds of formula (I) according to any variant of the process, which are all to be intended as within the scope of the invention, optional functional groups within the starting materials, the reagents or the intermediates thereof, and which could give rise to unwanted side reactions, need to be properly protected according to conventional techniques.

The starting materials of the process object of the present invention, comprehensive of any possible variant, as well as any reactant thereof, are known compounds and if not commercially available per se may be prepared according to well-known methods.

Pharmacology

Assays
In Vitro Cell Proliferation Assay
Exponentially growing human melanoma cells A375 (with a mutated B-RAF) and human melanoma cells Mewo (with wild-type B-Raf) were seeded and incubated at 37° C. in a humidified 5% $CO_2$ atmosphere. After 24 hours, scalar doses of the compound were added to the medium and cells oncubated for 72 hours. At the end of treatment, cells were washed and counted. Cell number was determined by a cellular adenosine triphosphate monitoring system. Cell proliferation was compared to control cells and the concentration inhibiting cell growth by 50% was calculated.

p-MAPK (T202/Y204) ArrayScan Assay
A375 human melanoma cells, having a mutated B-RAF, are seeded in 384-well poly-lysine coated plates (Matrix) at a density of 1000 cells/well with appropriate medium supplemented with 10% FCS and incubated for 16-24 hours. Cells are treated for 1.5 or 2 hours with increasing doses of compounds (starting dose 10 µM, dilution factor 2.5). At the end of the treatment cells are fixed with p-formaldehyde 3.7% for 15-30 min, then washed twice with D-PBS (80 l/well) and permeabilized with D-PBS containing 0.1% Triton X-100 and 1% BSA (Sigma-Aldrich) for 15 minutes at room temperature (staining solution). Anti-phospho-MAPK (T202/Y204) monoclonal antibody E10 (Cell Signaling, cat. #9106) diluted 1:100 is added in staining solution and incubated for 1 hour at 37° C. After removal of the primary antibody solution, the anti-mouse Cy™2-conjugated (Green) secondary antibody (Amersham) diluted 1:500 in staining solution containing 2 µg/ml DAPI is added. The plate is incubated for 1 hour at 37° C., washed twice and then red with Cellomics' ArrayScan VTI (4 fields/well, CytoNucTrans algorithm).

The parameter "MEAN_RingAvgIntenCh2", which measures the mean cytoplasmatic fluorescence intensity associated to p-MAPK staining, is reported as the final result.

B-RAF mutations, that constitutively activate the kinase, have been identified in the majority of melanoma and a large fraction of colorectal and papillary thyroid carcinoma. The growth of cells with activated B-RAF strictly depends on B-RAF activity.

Given the above assays, the compounds of formula (I) result to posses a remarkable activity in inhibiting cell proliferation, with $IC_{50}$ values lower than 10 µM on the cell line with mutated B-Raf (A375), and higher on the cell line with wild-type B-Raf (Mewo), as reported in the following table.

In the same table the data obtained with compounds of formula (I) in the ArrayScan assay are also reported and demonstrate the ability of the compounds of formula (I) to inhibit the signal transduction pathway controlled by B-RAF activation in A375 cell line with mutated B-RAF. The $IC_{50}$ values are always lower than 10 µM and are in agreement with the $IC_{50}$ values obtained in the proliferation assay on the same cell line, confirming that the antiproliferative activity of the compounds is due to the inhibition of B-RAF activity.

TABLE 1

Proliferation and Array Scan data

| Cmpd. N° | Name | Proliferation | | Array Scan |
| --- | --- | --- | --- | --- |
| | | A375 $IC_{50}$ (µM) | Mewo $IC_{50}$ (µM) | A375 $IC_{50}$ (µM) |
| 1 | 1-[3-(4-Pyridin-4-yl-1H-pyrazol-3-yl)-phenyl]-3-(4-trifluoromethyl-phenyl)-urea | 1.02 | 8.60 | 0.93 |
| 2 | 2,5-Difluoro-N-[3-(4-pyridin-4-yl-1H-pyrazol-3-yl)-phenyl]-benzenesulfonamide | 1.40 | >10 | 0.64 |
| 4 | N-(4-tert-Butyl-phenyl)-3-(4-pyridin-4-yl-1H-pyrazol-3-yl)-benzamide | 2.31 | 5.84 | 1.26 |
| 5 | 1-(4-Chloro-3-trifluoromethyl-phenyl)-3-{3-[1-(2-fluoro-ethyl)-4-pyridin-4-yl-1H-pyrazol-3-yl]-phenyl}-urea | 4.31 | 6.76 | 2.09 |
| 6 | Furan-2-sulfonic acid [3-(4-pyridin-4-yl-1H-pyrazol-3-yl)-phenyl]-amide | 7.52 | >10 | 5.47 |

TABLE 1-continued

Proliferation and Array Scan data

| Cmpd. N° | Name | Proliferation | | Array Scan |
|---|---|---|---|---|
| | | A375 IC$_{50}$ (μM) | Mewo IC$_{50}$ (μM) | A375 IC$_{50}$ (μM) |
| 7 | Thiophene-3-sulfonic acid [3-(4-pyridin-4-yl-1H-pyrazol-3-yl)-phenyl]-amide | 7.38 | >10 | 5.52 |
| 8 | 1-[3-(4-Pyridin-4-yl-1H-pyrazol-3-yl)-phenyl]-3-p-tolyl-urea | 4.48 | >10 | 1.45 |
| 9 | 1-(4-Chloro-phenyl)-3-[3-(4-pyridin-4-yl-1H-pyrazol-3-yl)-phenyl]-urea | 4.10 | >10 | 4.80 |
| 10 | 1-[3-(1-Ethyl-4-pyridin-4-yl-1H-pyrazol-3-yl)-phenyl]-3-(4-trifluoromethyl-phenyl)-urea | 1.63 | 7.5 | 0.54 |
| 11 | 1-[3-(1-Cyanomethyl-4-pyridin-4-yl-1H-pyrazol-3-yl)-phenyl]-3-(4-trifluoromethyl-phenyl)-urea | 1.13 | 7.69 | 0.23 |
| 12 | 1-{3-[4-(2-aminopyridin-4-yl)-1H-pyrazol-3-yl]phenyl}-3-[4(trifluoromethyl)-phenyl]urea | 5.96 | >10 | 4.65 |
| 13 | 1-{3-[1-(2-Fluoro-ethyl)-4-pyridin-4-yl-1H-pyrazol-3-yl]-phenyl}-3-(4-trifluoromethyl-phenyl)-urea | 1.38 | 8.11 | 0.56 |
| 14 | 1-{3-[1-(2-Hydroxy-ethyl)-4-pyridin-4-yl-1H-pyrazol-3-yl]-phenyl}-3-(4-trifluoromethyl-phenyl)-urea | 6.94 | >10 | 2.63 |
| 16 | N-[3-(4-Pyridin-4-yl-1H-pyrazol-3-yl)-phenyl]-2-(4-trifluoromethyl-phenyl)-acetamide | 2.89 | >10 | 1.34 |
| 17 | N-[4-(3-{3-[3-(4-Trifluoromethyl-phenyl)-ureido]-phenyl}-1H-pyrazol-4-yl)-pyridin-2-yl]-acetamide | 0.25 | 9.40 | <0.04 |
| 18 | N-[2,4-Difluoro-3-(4-pyridin-4-yl-1H-pyrazol-3-yl)-phenyl]-2,5-difluoro-benzenesulfonamide | 0.72 | >10 | 0.36 |
| 19 | Thiophene-3-sulfonic acid [2,4-difluoro-3-(4-pyridin-4-yl-1H-pyrazol-3-yl)-phenyl]-amide | 3.17 | >10 | 0.83 |
| 20 | Furan-2-sulfonic acid [2,4-difluoro-3-(4-pyridin-4-yl-1H-pyrazol-3-yl)-phenyl]-amide | 9.14 | >10 | 5.48 |
| 21 | Propane-1-sulfonic acid [2,4-difluoro-3-(4-pyridin-4-yl-1H-pyrazol-3-yl)-phenyl]-amide | 4.28 | >10 | 1.79 |
| 31 | 1-{3-[4-(2-Amino-pyrimidin-4-yl)-1H-pyrazol-3-yl]-phenyl}-3-(4-trifluoromethyl-phenyl)-urea | 2.70 | >10 | 0.73 |
| 32 | N-[4-(3-{3-[3-(4-Trifluoromethyl-phenyl)-ureido]-phenyl}-1H-pyrazol-4-yl)-pyrimidin-2-yl]-acetamide | 5.32 | >10 | 2.51 |
| 34 | N-{3-[4-(2-Amino-pyrimidin-4-yl)-1H-pyrazol-3-yl]-phenyl}-2,5-difluoro-benzenesulfonamide | 3.18 | >10 | 0.34 |
| 39 | N-[4-(3-{3-[3-(4-Trifluoromethyl-phenyl)-ureido]-phenyl}-1H-pyrazol-4-yl)-pyridin-2-yl]-propionamide | 1.14 | >10 | 2.32 |
| 40 | N-[4-(3-{3-[3-(4-Trifluoromethyl-phenyl)-ureido]-phenyl}-1H-pyrazol-4-yl)-pyridin-2-yl]-isobutyramide | 3.63 | >10 | 1.75 |
| 43 | 4-Hydroxy-N-[4-(3-{3-[3-(4-trifluoromethyl-phenyl)-ureido]-phenyl}-1H-pyrazol-4-yl)-pyridin-2-yl]-butyramide | 3.5 | >10 | 0.41 |
| 47 | 4-Pyridin-4-yl-3-{3-[3-(4-trifluoromethyl-phenyl)-ureido]-phenyl}-pyrazole-1-carboxylic acid ethyl ester | 2.66 | >10 | 0.75 |

TABLE 1-continued

Proliferation and Array Scan data

| Cmpd. N° | Name | Proliferation | | Array Scan |
|---|---|---|---|---|
| | | A375 IC$_{50}$ (µM) | Mewo IC$_{50}$ (µM) | A375 IC$_{50}$ (µM) |
| 48 | 1-[3-(1-Methyl-4-pyridin-4-yl-1H-pyrazol-3-yl)-phenyl]-3-(4-trifluoromethyl-phenyl)-urea | 3.86 | >10 | 1.79 |
| 49 | 1-[3-(1-Butyl-4-pyridin-4-yl-1H-pyrazol-3-yl)-phenyl]-3-(4-trifluoromethyl-phenyl)-urea | 2.61 | 4.54 | 1.59 |
| 50 | 1-[3-(1-Isobutyl-4-pyridin-4-yl-1H-pyrazol-3-yl)-phenyl]-3-(4-trifluoromethyl-phenyl)-urea | 1.9 | 5.09 | 1.12 |
| 51 | N-[3-(1-Ethyl-4-pyridin-4-yl-1H-pyrazol-3-yl)-2,4-difluoro-phenyl]-2,5-difluoro-benzenesulfonamide | <0.02 | >10 | <0.01 |
| 52 | N-[2,4-Difluoro-3-(1-methyl-4-pyridin-4-yl-1H-pyrazol-3-yl)-phenyl]-2,5-difluoro-benzenesulfonamide | 0.16 | >10 | <0.01 |
| 53 | N-{2,4-Difluoro-3-[4-(2-methylamino-pyridin-4-yl)-1H-pyrazol-3-yl]-phenyl}-2,5-difluoro-benzenesulfonamide | 1.75 | >10 | 0.87 |
| 54 | N-{3-[4-(2-Ethylamino-pyridin-4-yl)-1H-pyrazol-3-yl]-2,4-difluoro-phenyl}-2,5-difluoro-benzenesulfonamide | 0.97 | >10 | 0.31 |
| 55 | N-{3-[4-(2-Ethylamino-pyrimidin-4-yl)-1H-pyrazol-3-yl]-phenyl}-2,5-difluoro-benzenesulfonamide | 1.25 | >10 | 0.17 |
| 56 | N-[2,4-Difluoro-3-(1-isobutyl-4-pyridin-4-yl-1H-pyrazol-3-yl)-phenyl]-2,5-difluoro-benzenesulfonamide | <0.02 | >10 | <0.01 |
| 57 | N-[3-(1-Ethyl-4-pyridin-4-yl-1H-pyrazol-3-yl)-2,4-difluoro-phenyl]-2-fluoro-benzenesulfonamide | 0.33 | >10 | 0.02 |
| 58 | N-[3-(1-Ethyl-4-pyridin-4-yl-1H-pyrazol-3-yl)-2,4-difluoro-phenyl]-3-fluoro-benzenesulfonamide | 0.29 | >10 | 0.04 |

From all of the above, the novel compounds of formula (I) of the invention appear to be particularly advantageous in the therapy of diseases caused by deregulated protein kinase activity such as cancer.

The compounds of the present invention can be administered either as single agents or, alternatively, in combination with known anticancer treatments such as radiation therapy or chemotherapy regimen in combination with, for example, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

If formulated as a fixed dose, such combination products employ the compounds of this invention within the dosage range described below and the other pharmaceutically active agent within the approved dosage range. Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, and conditions of the patient and administration route.

For example, a suitable dosage adopted for oral administration of a compound of formula (I) may range from about 10 to about 1 g per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form.

For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium to starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions.

As an example the syrups may contain, as a carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier. The suppositories may contain, together with the active compound, a pharmaceutically acceptable carrier, e.g., cocoa butter, polyethylene glycol, a polyoxyethylene sorbitan fatty acid ester surfactant or lecithin.

EXPERIMENTAL SECTION

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

The short forms and abbreviations used herein have the following meaning:

| g | (grams) | mg | (milligrams) |
|---|---|---|---|
| ml | (milliliters) | mM | (millimolar) |
| μM | (micromolar) | mmol | (millimoles) |
| h | (hours) | MHz | (Mega-Hertz) |
| mm | (millimeters) | Hz | (Hertz) |
| M | (molar) | min | (minutes) |
| mol | (moles) | TLC | (thin layer chromatography) |
| r.t. | (room temperature) | TEA | (triethylamine) |
| TFA | (trifluoroacetic acid) | DMF | (N,N-dimethyl formamide) |
| DIPEA | (N,N-diisopropyl-N-ethylamine) | DCM | (dichloromethane) |
| THF | (tetrahydrofuran) | Hex | (hexane) |
| MeOH | (Methanol) | DMSO | (dimethylsulfoxide) |
| TIPS | (triisopropylsilyl) | bs | (broad singlet) |
| TBDMS | (dimethyl-tert-butylsilyl) | BOC | (tert-butyloxycarbonyl) |
| NaH = | sodium hydride, 60% in mineral oil | $Ac_2O$ | acetic anhydride |
| Dppf | (1,1'-bis(diphenyl-phosphino)ferrocene) | ESI = | electrospray ionization |

-continued

| mCPBA | (m-chloroperbenzoic acid) | Ac | (acetyl) |
|---|---|---|---|
| TBTU | (2-(1H-benzotriazol-1-yl)-1,1,3,3-tetramethyluronium tetrafluoroborate | | |
| RP-HPLC | (reverse phase high performance liquid chromatography) | | |

With the aim to better illustrate the present invention, without posing any limitation to it, the following examples are now given.

As used herein the symbols and conventions used in the processes, schemes and examples are consistent with those used in the contemporary scientific literature, for example, the *Journal of the American Chemical Society* or the *Journal of Biological Chemistry*.

Unless otherwise noted, all materials were obtained from commercial suppliers, of the best grade and used without further purification. Anhydrous solvent such as DMF, THF, $CH_2Cl_2$ and toluene were obtained from the Aldrich Chemical Company. All reactions involving air- or moisture-sensitive compounds were performed under nitrogen or argon atmosphere.

General Purification and Analytical Methods

Flash Chromatography was performed on silica gel (Merck grade 9395, 60A). HPLC was performed on Waters X Terra RP 18 (4.6×50 mm, 3.5 μm) column using a Waters 2790 HPLC system equipped with a 996 Waters PDA detector and Micromass mod. ZQ single quadrupole mass spectrometer, equipped with an electrospray (ESI) ion source. Mobile phase A was ammonium acetate 5 mM buffer (pH 5.5 with acetic acid-acetonitrile 95:5), and Mobile phase B was water-acetonitrile (5:95). Gradient from 10 to 90% B in 8 minutes, hold 90% B 2 minutes. UV detection at 220 nm and 254 nm. Flow rate 1 mL/min. Injection volume 10 microL. Full scan, mass range from 100 to 800 amu. Capillary voltage was 2.5 KV; source temperature was 120° C.; cone was 10 V. Retention times (HPLC r.t.) are given in minutes at 220 nm or at 254 nm. Mass are given as m/z ratio.

When necessary, compounds were purified by preparative HPLC on a Waters Symmetry C18 (19×50 mm, 5 μm) column or on a Waters X Terra RP 18 (30×150 mm, 5 μm) column using a Waters preparative HPLC 600 equipped with a 996 Waters PDA detector and a Micromass mod. ZMD single quadrupole mass spectrometer, electron spray ionization, positive mode. Mobile phase A was water-0.01% trifluoroacetic acid, and mobile phase B was acetonitrile. Gradient from 10 to 90% B in 8 min, hold 90% B 2 min. Flow rate 20 mL/min. In alternative, mobile phase A was water-0.1% $NH_3$, and mobile phase B was acetonitrile. Gradient from 10 to 100% B in 8 min, hold 100% B 2 min.

Flow rate 20 mL/min.

1H-NMR spectrometry was performed on a Mercury VX 400 operating at 400.45 MHz equipped with a 5 mm double resonance probe [1H (15N-31P) ID_PFG Varian].

Preparation of 4-[3-(3-nitro-phenyl)-1H-pyrazol-4-yl]-pyridine

[(II)A, X=CH; R2, R3, R4, R5, R6=H; G=$NO_2$]
Method A

Step a:
[Hydroxy-(3-nitro-phenyl)methyl]-phosphonic acid dimethyl ester

3-Nitrobenzaldehyde (20 g, 0.132 mol) was dissolved in 100 mL of ethyl acetate. Triethylamine (22 mL, 0.158 mol, 1.2 eq) was added, followed by dimethylphosphite (15.7 mL, 0.171 mmol, 1.3 eq) and the mixture was stirred at room temperature. After 2 hours the mixture was diluted with 150 mL of ethyl acetate and washed with saturated aqueous ammonium chloride (2×50 mL) and water (50 mL). The organic layer was dried over $Na_2SO_4$ and concentrated under reduced pressure. The residue was treated with ethyl ether to obtain a beige solid, which was filtered and dried under vacuum at 40° C. for 1 h (26.7 g, 77% yield).

HPLC (254 nm): $R_t$: 3.15 min.

$^1$H NMR (401 MHz, DMSO-$d_6$) δ=8.30 (q, J=1.8 Hz, 1 H), 8.14-8.20 (m, 1 H), 7.89 (d, J=7.6 Hz, 1 H), 7.68 (t, J=7.6 Hz, 1 H), 6.62 (dd, J=5.9, 14.1 Hz, 1 H), 5.30 (dd, J=5.9, 14.0 Hz, 1 H), 3.67 (d, J=7.4 Hz, 3 H), 3.64 (d, J=7.4 Hz, 3 H). HRMS (ESI) calcd for C9H12NO6P [M+H]$^+$ 262.0475, found 262.0478.

Step b: [(3-Nitro-phenyl)-(tetrahydro-pyran-2-yloxy)-methyl]-phosphonic acid dimethyl ester

[Hydroxy-(3-nitro-phenyl)-methyl]-phosphonic acid dimethyl ester (26.7 g, 0.102 mol) was suspended in dry toluene (340 mL) under nitrogen atmosphere. 3,4-Dihydro-2H-pyrane (20.6 mL, 0.228 mol, 2.2 eq) was added, followed by p-toluenesulfonic acid (590 mg, 0.003 mol, 0.03 eq) and the mixture was stirred at 60° C. for 1 h. the reaction mixture was then concentrated under reduced pressure, taken up with ethyl acetate (300 mL) and washed with saturated aqueous $NaHCO_3$ and water. The organic layer was dried over $Na_2SO_4$ and concentrated to dryness. The desired product was obtained in quantitative yield as a yellow solid (mixture of 2 diastereoisomers).

HPLC (254 nm): $R_t$: 4.88 min.

$^1$H NMR (401 MHz, DMSO-$d_6$) (major diastereoisomer) δ=8.25 (q, J=2.2 Hz, 1 H), 8.23 (dt, J=2.5, 8.2 Hz, 1 H), 7.88 (d, J=8.3 Hz, 1 H), 7.70 (t, J=7.9 Hz, 1 H), 5.38 (d, J=17.3 Hz, 1 H), 4.43 (t, J=2.7 Hz, 1 H), 3.85-3.97 (m, 1 H), 3.73 (d, J=10.5 Hz, 3 H), 3.65 (d, J=10.5 Hz, 3 H), 3.48-3.56 (m, 1 H), 1.49-1.82 (3 m, 6 H). HRMS (ESI) calcd for C14H20NO7P [M+H]$^+$ 346.105, found 346.1043.

Step c: 4-[2-(3-Nitro-phenyl)-2-(tetrahydro-pyran-2-yloxy)-vinyl]-pyridine

[(3-Nitro-phenyl)-(tetrahydro-pyran-2-yloxy)-methyl]-phosphonic acid dimethyl ester (40.7 g, 0.105 mol) was dissolved in dry THF (1 L) under nitrogen. Sodium hydride (60% suspension in mineral oil) (6.3 g, 0.158 mol, 1.5 eq) was added and the mixture was stirred for 10 minutes at room temperature. Neat 4-picolinaldehyde (10 mL, 0.105 mol, 1 eq) was then added dropwise and the mixture was heated to 60° C. and stirred at this temperature for 2.5 hours. The reaction mixture was concentrated under reduced pressure to ⅓ of the original volume and then diluted with water (500 mL). pH was adjusted to 7-8 by adding a saturated solution of $NaHCO_3$ and the mixture was extracted with ethyl acetate (4×300 mL). The organic layer was dried over $Na_2SO_4$ and concentrated to dryness. An oil (37.7 g) was obtained, which was used without further purification in the following step.

Step d: 1-(3-Nitro-phenyl)-2-pyridin-4-yl-ethanone

The oil obtained in the previous step was dissolved in methanol (570 mL). 1N HCl (57 mL) was added and the mixture was stirred at 50° C. for 2 hours. The mixture was then concentrated under reduced pressure and diluted with water (200 mL). pH was adjusted to 7-8 by addition of $NaHCO_3$. The precipitated product was collected by filtration, washed with water and dried under vacuum at 60° C. for 1 h obtaining 23.7 g of brown solid. The solid was purified by flash chromatography on silica gel (ethyl acetate) and then treated with ethyl ether to obtain an off-white solid, which was dried under vacuum at 40° C. for 1 h (15 g, 59% yield over three steps).

HPLC (254 nm): $R_t$: 4.29 min.

$^1$H NMR (401 MHz, DMSO-$d_6$) δ=8.74 (t, J=1.8 Hz, 1 H), 8.52-8.55 (m, 2 H), 8.52 (m, 1 H), 8.49 (m, 1 H), 7.89 (t, J=7.8 Hz, 1 H), 7.30-7.34 (m, 2 H), 4.63 (s, 2 H).

HRMS (ESI) calcd for C13H10N2O3 [M+H]$^+$ 243.0764, found 243.0772.

Step f: (E)-3-Dimethylamino-1-(3-nitro-phenyl)-2-pyridin-4-yl-propenone 1-(3-Nitro-phenyl)-2-pyridin-4-yl-ethanone (6 g, 24.77 mmol) was dissolved in dry toluene (240 mL) under nitrogen atmosphere, dimethylformamidedimethylacetal (13.2 mL, 99.36 mmol, 4 eq) was added and the mixture was heated to 80° C. and stirred for 2 hours. The reaction mixture was then evaporated to dryness and kept under high vacuum for 2 hours. The crude (7.44 g) was obtained as oil and was used as is in the following step.

HPLC (254 nm): $R_t$: 3.57 min.

$^1$H NMR (401 MHz, DMSO-$d_6$) δ=8.44 (br. s., 2 H), 8.26 (ddd, J=1.0, 2.3, 8.2 Hz, 1 H), 8.14 (br. s., 1 H), 7.80 (d, J=7.4 Hz, 1 H), 7.66 (t, J=7.9 Hz, 1 H), 7.36 (s, 1 H), 7.16 (br. s., 2 H), 2.75 (br. s., 6 H).

HRMS (ESI) calcd for C16H15N3O3 [M+H]$^+$ 298.1186, found 298.1188.

Step g: 4-[3-(3-Nitro-phenyl)-1H-pyrazol-4-yl]-pyridine [(II)A, X=CH, R', R3, R4, R5, R6=H, G=NO$_2$]

Crude (E)-3-Dimethylamino-1-(3-nitro-phenyl)-2-pyridin-4-yl-propenone (24.77 mmol) was dissolved in a hydrazine solution 1M in THF (100 mL, 100 mmol, 4 eq) under nitrogen atmosphere and the mixture was heated to 70° C. and stirred at this temperature for 2 hours. The mixture was then allowed to cool to room temperature and then kept at 4° C. for 2 hours. The crystallized solid was collected by filtration and dried at 40° C. under vacuum for 2 hours. 4.88 g (74% yield over two steps) of 4-[3-(3-nitro-phenyl)-1H-pyrazol-4-yl]-pyridine were obtained as off-white solid.

HPLC (254 nm): $R_t$: 3.88 min.

$^1$H NMR (401 MHz, DMSO-$d_6$) δ=13.53 (br. s., 1 H), 8.50 (d, J=5.9 Hz, 2 H), 8.29 (s, 1 H), 8.25 (s, 1 H), 8.23 (m, 1 H), 7.86 (dd, J=2.0, 7.2 Hz, 1 H), 7.70 (t, J=7.9 Hz, 1 H), 7.29 (d, J=6.1 Hz, 2 H). HRMS (ESI) calcd for C14H10N4O2 [M+H]+267.0877, found 267.0883.

Example 1

1-(2,4-Difluoro-phenyl)-3-[3-(4-pyridin-4-yl-1H-pyrazol-3-yl)-phenyl]-urea

[(I)E, X=CH; R1, R2, R3, R4, R5, R6=H; m=0; Y=H; R7=2,4-difluorophenyl]

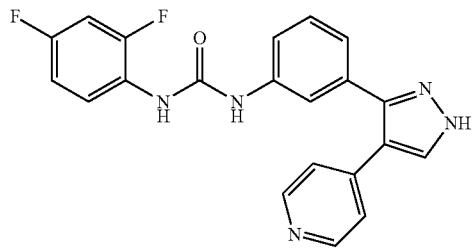 [SMILES: O=C(Nc1cccc(-c2n[nH]cc2-c2ccncc2)c1)Nc1ccc(F)cc1F]

Method N
Step a

4-[3-(3-Nitro-phenyl)-1H-pyrazol-4-yl]-pyridine (9.5 mmol) and DIPEA (3.26 ml, 19.5 mmol) and were added to a slurry of trityl chloride resin (5 g, 1.27 mmol/g loading, 6.35 mmol) in DCM (50 ml). The mixture was gently stirred at rt for 24 h and then filtered under reduced pressure. The resin was suspended in a mixture of DCM/MeOH/DIPEA 85:10:5 (100 ml), stirred for 20 min and filtered. After washing consecutively with DCM, DMF and MeOH, it was dried overnight in the oven at 35° C. under reduced pressure. The resin gave rise to a loading of 1 mmol/g measured by weight increase.

Method G
Step a

A solution of $SnCl_2 \cdot H_2O$ (6.6 g, 30 mmol) in DMF (10 ml) was added to a slurry of the resin obtained in the previous step (2 g, 2 mmol) in DMF (10 ml). The suspension was stirred at r.t. for 48 h. After filtering under reduced pressure the resin was washed with DMF (3×), DCM (3×), MeOH (3×) and Et2O (3×) and dried at 35° C. under vacuum.

Step e

The appropriate isocyanate (0.04 mmol) was added to the resin obtained in Step a (100 mg, 0.01 mmol), swelled in DCM (3 ml) in the Quest vessel. The resulting suspension was stirred for 20 h at r.t., filtered, washed with DCM, DMF and MeOH, dried under nitrogen flux and used in the next step.

Method M
Step a

A solution of 2 ml of TFA 20% in DCM was added to 100 mg of the resin obtained in Step d in the Quest vessels. The red suspension was stirred for 1 h then filtered and the resin washed twice with 1 ml of DCM. The filtered solution was evaporated under nitrogen flux to give the product as an oil, which was purified by preparative HPLC.

HPLC (254 nm): $R_t$: 4.43 min $^1$H NMR (401 MHz, DMSO-$d_6$), δ=13.55 (br s, 1 H), 9.15 (s, 1 H), 8.63 (d, J=6.5 Hz, 2 H), 8.51 (s, 1 H), 8.41 (br. s., 1 H), 8.03 (td, J=6.2, 9.2 Hz, 1 H), 7.66 (d, J=6.5 Hz, 2 H), 7.61 (t, J=1.8 Hz, 1 H), 7.49-7.55 (m, 1 H), 7.37-7.44 (m, 1 H), 7.31 (ddd, J=2.9, 8.9, 11.6 Hz, 1 H), 6.99-7.10 (m, 2 H). HRMS (ESI) calcd for $C_{21}H_{16}F_2N_5O$ [M+H]$^+$ 392.1318, found 392.1308.

Operating in an analogous way the following compounds were obtained:

1-Naphthalen-1-yl-3-[3-(4-pyridin-4-yl-1H-pyrazol-3-yl)-phenyl]-urea

[(I)E, X=CH; R1, R2, R3, R4, R5, R6=H; m=0; Y=H; R7=naphthalene-1-yl]

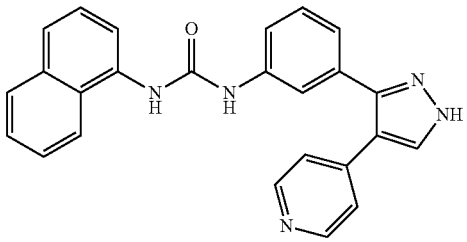 [SMILES: O=C(Nc1cccc(-c2n[nH]cc2-c2ccncc2)c1)Nc1cccc2ccccc12]

HPLC (254 nm): $R_t$: 4.64 min $^1$H NMR (401 MHz, DMSO-$d_6$), δ=13.41 and 13.26 (2br s, 1 H, tautomers), 9.15 (br s, 1 H), 8.75 (br s, 1H), 8.47 (d, J=6.1 Hz, 2 H), 8.27 (br s, 1 H), 8.11 (d, J=8.2 Hz, 1 H), 7.93-7.93 (m, 3 H), 7.56-7.66 (m, 6 H), 7.45-7.50 (m, 1 H), 7.31 (br. s., 2 H).

HRMS (ESI) calcd for $C_{25}H_{19}N_5O$ [M+H]$^+$ 406.1663, found 406.1655.

1-(3-Chloro-phenyl)-3-[3-(4-pyridin-4-yl-1H-pyrazol-3-yl)-phenyl]-urea

[(I)E, X=CH; R1, R2, R3, R4, R5, R6=H; m=0; Y=H; R7=3-chloro-phenyl]

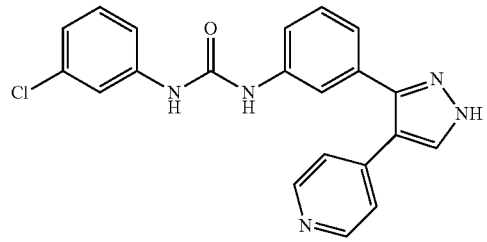 [SMILES: O=C(Nc1cccc(Cl)c1)Nc1cccc(-c2n[nH]cc2-c2ccncc2)c1]

HPLC (254 nm): $R_t$: 4.72 min.

$^1$H NMR (401 MHz, DMSO-$d_6$), δ=13.45 and 13.31 (2br s, 1 H, tautomers), 8.86 (br s, 2 H), 8.47 (d, J=6.0 Hz, 2 H), 8.27 and 7.96 (2br s, 1 H, tautomers), 7.69 (t, J=2.0 Hz, 1 H), 7.24-7.53 (m, 8 H), 7.00-7.04 (m, 1 H). HRMS (ESI) calcd for $C_{21}H_{16}ClN_5O$ [M+H]$^+$ 390.1116, found 390.1104.

1-(3-Methoxy-phenyl)-3-[3-(4-pyridin-4-yl-1H-pyrazol-3-yl)-phenyl]-urea

[(I)E, X=CH; R1, R2, R3, R4, R5, R6=H; m=0; Y=H; R7=3-methoxy-phenyl]

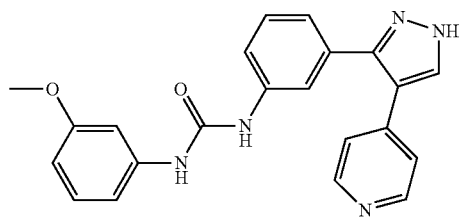 [SMILES: COc1cccc(NC(=O)Nc2cccc(-c3n[nH]cc3-c3ccncc3)c2)c1]

HPLC (254 nm): $R_t$: 4.22 min.

$^1$H NMR (401 MHz, DMSO-d$_6$), δ=13.39 and 13.28 (2br s, 1 H, tautomers), 8.68 (m, 2 H), 8.43-8.48 (m, 2 H), 8.25 and 7.96 (2br s, 1 H, tautomers), 7.39-7.53 (m, 4 H), 7.29 (br s, 2 H), 7.14-7.20 (m, 2 H), 6.91 (ddd, J=0.9, 1.2, 7.2 Hz, 1 H), 6.56 (dd, J=1.9, 8.2 Hz, 1 H), 3.73 (s, 3 H). HRMS (ESI) calcd for C$_{22}$H$_{19}$N$_5$O$_2$ [M+H]$^+$ 386.1612, found 386.1604.

1-(3-Fluoro-phenyl)-3-[3-(4-pyridin-4-yl-1H-pyrazol-3-yl)-phenyl]-urea

[(I)E, X═CH; R1, R2, R3, R4, R5, R6═H; m=0; Y═H; R7=3-fluoro-phenyl]

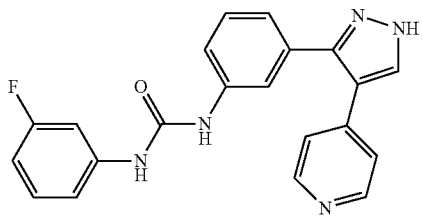 [SMILES: O=C(Nc1cccc(F)c1)Nc1cccc(-c2n[nH]cc2-c2ccncc2)c1]

HPLC (254 nm): R$_t$: 4.40 min.
$^1$H NMR (401 MHz, DMSO-d$_6$), δ=13.40 and 13.28 (2br s, 1 H, tautomers), 8.86 (br s, 2 H), 8.47 (d, J=6.0 Hz, 2 H), 8.25 and 7.96 (2br s, 1 H, tautomers), 7.48-7.52 (m, 1 H), 7.47 (dt, J=2.2, 12.2 Hz, 1 H), 7.27-7.33 (m, 5 H), 7.11 (dd, J=1.2, 8.3 Hz, 1 H), 6.75-6.83 (m, 2 H). HRMS (ESI) calcd for C$_{21}$H$_{16}$FN$_6$O [M+H]$^+$ 374.1412, found 374.1407.

1-(4-Fluoro-phenyl)-3-[3-(4-pyridin-4-yl-1H-pyrazol-3-yl)-phenyl]-urea

[(I)E, X═CH; R1, R2, R3, R4, R5, R6═H; m=0; Y═H; R7=4-fluoro-phenyl]

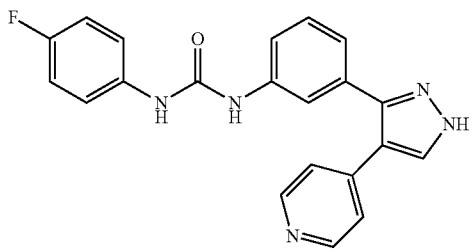 [SMILES: O=C(Nc1ccc(F)cc1)Nc1cccc(-c2n[nH]cc2-c2ccncc2)c1]

HPLC (254 nm): R$_t$: 4.30 min.
$^1$H NMR (401 MHz, DMSO-d$_6$), δ=13.44 (br s, 1 H), 8.79 (br s, 1 H), 8.71 (br s, 1 H), 8.53 (d, J=6.1 Hz, 2 H), 8.26 (br s, 1 H), 7.56 (s, 1 H), 7.37-7.48 (m, 6 H), 7.07-7.16 (m, 2 H), 7.03 (d, J=6.2 Hz, 1 H). HRMS (ESI) calcd for C$_{21}$H$_{16}$FN$_5$O [M+H]$^+$ 374.1412, found 374.1407.

1-(2,6-Dimethyl-phenyl)-3-[3-(4-pyridin-4-yl-1H-pyrazol-3-yl)-phenyl]-urea

[(I)E, X═CH; R1, R2, R3, R4, R5, R6═H; m=0; Y═H; R7=2,6-dimethyl-phenyl]

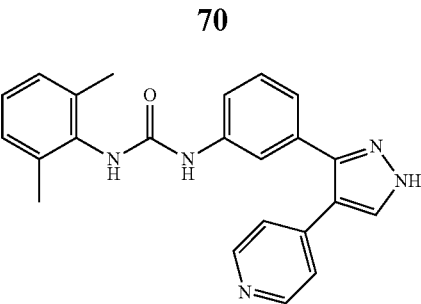

HPLC (254 nm): R$_t$: 4.54 min.
$^1$H NMR (401 MHz, DMSO-d$_6$), δ=13.40 (br. s., 1 H), 8.86 (br s, 2 H), 8.52 (d, J=6.0 Hz, 2 H), 8.28 (br. s., 1 H), 7.37-7.77 (m, 4 H), 7.44 (d, J=6.0 Hz, 2 H), 6.97-7.09 (m, 3 H), 2.20 (s, 6 H). HRMS (ESI) calcd for C$_{23}$H$_{21}$N$_5$O [M+H]$^+$ 384.1819, found 384.1810.

1-(2-Methoxy-phenyl)-3-[3-(4-pyridin-4-yl-1H-pyrazol-3-yl)-phenyl]-urea

[(I)E, X═CH; R1, R2, R3, R4, R5, R6═H; m=0; Y═H; R7=2-methoxy-phenyl]

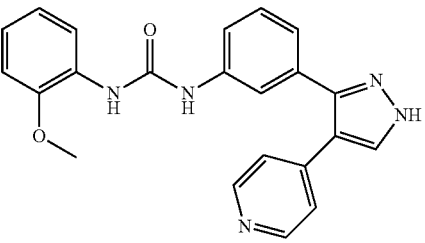 [SMILES: COc1ccccc1NC(=O)Nc1cccc(-c2n[nH]cc2-c2ccncc2)c1]

HPLC (254 nm): R$_t$: 4.76 min.
$^1$H NMR (401 MHz, DMSO-d$_6$), δ=13.48 (s, 1 H), 9.42 (br. s., 1 H), 8.52-8.59 (m, 2 H), 8.22 (s, 1 H), 8.09 (dd, J=1.7, 7.9 Hz, 1 H), 7.58 (d, J=1.6 Hz, 1 H), 7.38-7.53 (m, 4 H), 7.04 (d, J=7.8 Hz, 1 H), 7.02 (dd, J=1.5, 8.0 Hz, 1 H), 6.95 (td, J=1.7, 7.7 Hz, 1 H), 6.85-6.92 (m, 1 H), 3.88 (s, 3 H). HRMS (ESI) calcd for C$_{22}$H$_{19}$N$_5$O$_2$ [M+H]$^+$ 386.1612, found 386.1608.

1-[3-(4-Pyridin-4-yl-1H-pyrazol-3-yl)-phenyl]-3-(4-trifluoromethoxy-phenyl)-urea

[(I)E, X═CH; R1, R2, R3, R4, R5, R6═H; m=0; Y═H; R7=4-trifluoromethoxy-phenyl]

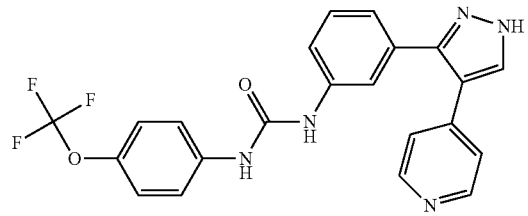 [SMILES: O=C(Nc1ccc(OC(F)(F)F)cc1)Nc1cccc(-c2n[nH]cc2-c2ccncc2)c1]

HPLC (254 nm): R$_t$: 4.24 min.
$^1$H NMR (401 MHz, DMSO-d$_6$), δ=13.39 and 13.28 (2br s, 1 H, tautomers), 8.83 (br s, 2 H), 8.44-8.49 (m, 2 H), 8.25 and 7.96 (2br s, 1 H, tautomers), 7.50-7.56 (m, 5 H), 7.26-7.31 (m, 4 H), 7.02 (m, 1 H). HRMS (ESI) calcd for C$_{22}$H$_{16}$F$_3$N$_5$O$_2$ [M+H]$^+$ 440.1329, found 440.1318.

1-(3,4-Difluoro-phenyl)-3-[3-(4-pyridin-4-yl-1H-pyrazol-3-yl)-phenyl]-urea

[(I)E, X=CH; R1, R2, R3, R4, R5, R6=H; m=0; Y=H; R7=3,4-difluoro-phenyl]

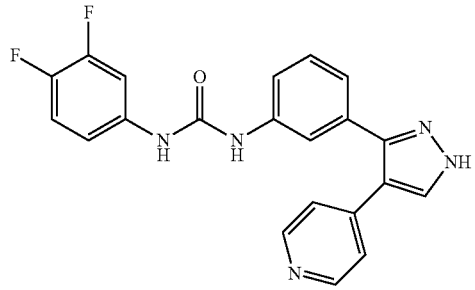 [SMILES: O=C(Nc1cccc(-c2n[nH]cc2-c2ccncc2)c1)Nc1ccc(F)c(F)c1]

HPLC (254 nm): $R_t$: 4.54 min $^1$H NMR (401 MHz, DMSO-$d_6$), δ=13.39 and 13.28 (2br s, 1 H, tautomers), 8.84 (br s, 2 H), 8.44-8.49 (m, 2 H), 8.25 and 7.96 (2br s, 1 H, tautomers), 7.64 (m, 1 H), 7.28-7.50 (m, 6H), 7.09-7.13 (m, 1 H), 7.02 (m, 1 H). HRMS (ESI) calcd for $C_{21}H_{16}F_2N_5O$ [M+H]$^+$ 392.1318, found 392.1312.

1-(2,6-Diethyl-phenyl)-3-[3-(4-pyridin-4-yl-1H-pyrazol-3-yl)-phenyl]-urea

[(I)E, X=CH; R1, R2, R3, R4, R5, R6=H; m=0; Y=H; R7=2,6-diethyl-phenyl]

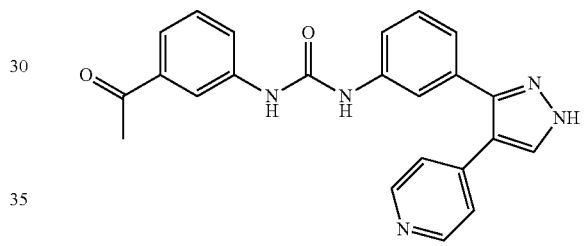

HPLC (254 nm): $R_t$: 4.76 min.

$^1$H NMR (401 MHz, DMSO-$d_6$), δ=13.36 and 13.25 (2br s, 1 H, tautomers), 8.78 (br s, 2 H), 8.42-8.46 (m, 2 H), 8.23 and 7.95 (2br s, 1 H, tautomers), 7.28-7.50 (m, 5H), 7.13-7.22 (m, 1 H), 7.07-7.13 (m, 2 H), 6.95 (m, 1 H), 2.53-2.61 (m, 4 H), 1.13 (t, J=7.6 Hz, 6 H). HRMS (ESI) calcd for $C_{25}H_{25}N_5O$ [M+H]$^+$ 412.2132, found 412.2121.

3-{3-[3-(4-Pyridin-4-yl-1H-pyrazol-3-yl)-phenyl]-ureido}-benzoic acid methyl ester

[(I)E, X=CH; R1, R2, R3, R4, R5, R6=H; m=0; Y=H; R7=3-carbomethoxy-phenyl]

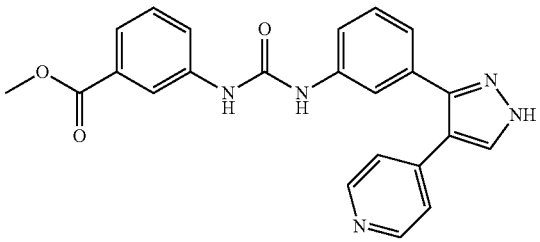 [SMILES: COC(=O)c1cccc(NC(=O)Nc2cccc(-c3n[nH]cc3-c3ccncc3)c2)c1]

HPLC (254 nm): $R_t$: 4.24 min.

$^1$H NMR (401 MHz, DMSO-$d_6$), δ=13.40 and 13.28 (2br s, 1 H, tautomers), 8.76-8.91 (m, 2 H), 8.44-8.48 (m, 2 H), 8.25 and 7.96 (2br s, 1 H, tautomers), 8.19 (t, J=1.8 Hz, 1 H), 7.61 (ddd, J=1.1, 2.2, 8.1 Hz, 1 H), 7.55-7.59 (m, 1 H), 7.50-7.55 (m, 3 H), 7.43 (t, J=7.9 Hz, 1 H), 7.29 (br. s., 2 H), 7.02 (m, 1 H), 3.86 (s, 3 H). HRMS (ESI) calcd for $C_{23}F_{19}N_5O_3$ [M+H]$^+$ 414.1561, found 414.1549.

1-(3-Acetyl-phenyl)-3-[3-(4-pyridin-4-yl-1H-pyrazol-3-yl)-phenyl]-urea

[(I)E, X=CH; R1, R2, R3, R4, R5, R6=H; m=0; Y=H; R7=3-acetyl-phenyl]

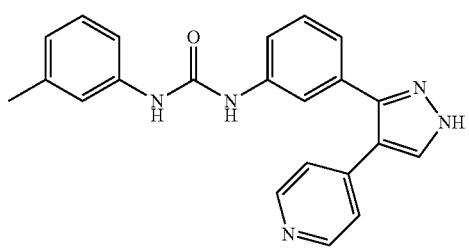 [SMILES: Cc1cccc(NC(=O)Nc2cccc(-c3n[nH]cc3-c3ccncc3)c2)c1]

HPLC (254 nm): $R_t$: 3.95 min.

$^1$H NMR (401 MHz, DMSO-$d_6$), δ=13.41 and 13.28 (2br s, 1 H, tautomers), 8.75-8.95 (m, 2 H), 8.43-8.49 (m, 2 H), 8.27 and 7.97 (2br s, 1 H, tautomers), 8.06 (t, J=1.8 Hz, 1 H), 7.63-7.69 (m, 1 H), 7.59 (d, J=7.8 Hz, 1 H), 7.50-7.56 (m, 3 H), 7.44 (t, J=7.9 Hz, 1 H), 7.28 (br. s., 2 H), 7.02 (m, 1 H), 2.57 (s, 3 H). HRMS (ESI) calcd for $C_{23}H_{19}N_5O_2$ [M+H]$^+$ 398.1612, found 398.1601.

1-[3-(4-Pyridin-4-yl-1H-pyrazol-3-yl)-phenyl]-3-m-tolyl-urea

[(I)E, X=CH; R1, R2, R3, R4, R5, R6=H; m=0; Y=H; R7=3-methyl-phenyl]

HPLC (254 nm): $R_t$: 4.47 min.

$^1$H NMR (401 MHz, DMSO-$d_6$), δ=13.38 and 13.27 (2br s, 1 H, tautomers), 8.53-8.77 (m, 2 H), 8.42-8.49 (m, 2 H), 8.24 and 7.96 (2br s, 1 H, tautomers), 7.48-7.56 (m, 4 H), 7.28 (br. s., 2 H), 7.21 (d, J=7.8 Hz, 1 H), 7.15 (t, J=7.9 Hz, 1 H), 7.02 (m, 1 H), 6.79 (d, J=7.6 Hz, 1 H), 2.28 (s, 3 H). HRMS (ESI) calcd for $C_{22}H_{16}N_5O$ [M+H]$^+$ 370.1663, found 370.1660.

1-[3-(4-Pyridin-4-yl-1H-pyrazol-3-yl)-phenyl]-3-o-tolyl-urea

[(I)E, X=CH; R1, R2, R3, R4, R5, R6=H; m=0; Y=H; R7=2-methyl-phenyl]

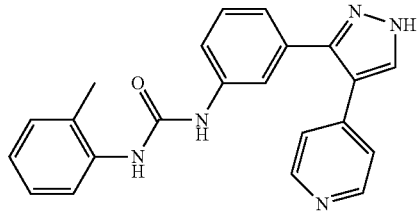 [SMILES: Cc1ccccc1NC(=O)Nc1cccc(-c2n[nH]cc2-c2ccncc2)c1]

HPLC (254 nm): R$_t$: 4.26 min.

$^1$H NMR (401 MHz, DMSO-d$_6$), δ=13.39 and 13.28 (2br s, 1 H, tautomers), 8.95-9.18 (m, 1 H), 8.43-8.49 (m, 2 H), 8.25 and 7.98 (2br s, 1 H, tautomers), 7.90-7.99 (m, 1 H), 7.80 (d, J=7.9 Hz, 1 H), 7.35-7.61 (m, 3 H), 7.29 (br. s., 2 H), 7.18 (d, J=7.4 Hz, 1 H), 7.14 (t, J=7.8 Hz, 1 H), 6.96-7.05 (m, 1 H), 6.92-6.98 (m, 1 H), 2.23 (s, 3 H). HRMS (ESI) calcd for $C_{22}H_{19}N_5O$ [M+H]$^+$ 370.1663, found 370.1656.

1-[3-(4-Pyridin-4-yl-1H-pyrazol-3-yl)-phenyl]-3-(3-trifluoromethyl-phenyl)-urea

[(I)E, X=CH; R1, R2, R3, R4, R5, R6=H; m=0; Y=H; R7=3-trifluoromethyl-phenyl]

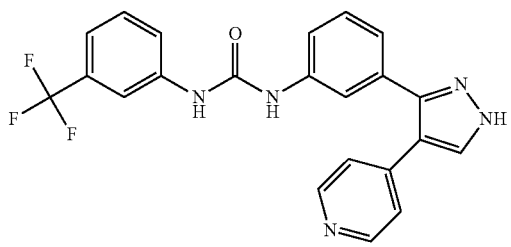 [SMILES: O=C(Nc1cccc(-c2n[nH]cc2-c2ccncc2)c1)Nc1cccc(C(F)(F)F)c1]

HPLC (254 nm): R$_t$: 5.03 min $^1$H NMR (401 MHz, DMSO-d$_6$), δ=13.40 and 13.29 (2br s, 1 H, tautomers), 8.83-9.04 (m, 2 H), 8.46 (d, J=6.0 Hz, 2 H), 8.25 and 7.96 (2br s, 1 H, tautomers), 8.00 (s, 1 H), 7.48-7.57 (m, 5 H), 7.26-7.33 (m, 3 H), 6.99-7.07 (m, 1 H). HRMS (ESI) calcd for $C_{22}H_{16}F_3N_5O$ [M+H]$^+$ 424.1380, found 424.1369.

1-(2-Fluoro-5-trifluoromethyl-phenyl)-3-[3-(4-pyridin-4-yl-1H-pyrazol-3-yl)-phenyl]-urea

[(I)E, X=CH; R1, R2, R3, R4, R5, R6=H; m=0; Y=H; R7=2-fluoro-5-trifluoromethyl-phenyl]

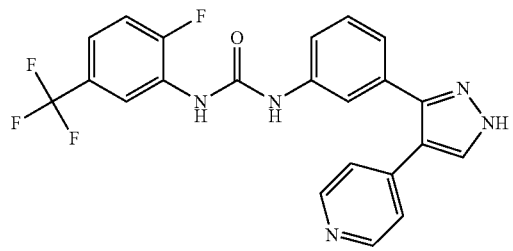 [SMILES: O=C(Nc1cccc(-c2n[nH]cc2-c2ccncc2)c1)Nc1cc(C(F)(F)F)ccc1F]

HPLC (254 nm): R$_t$: 6.03 min.

$^1$H NMR (401 MHz, DMSO-d$_6$), δ=13.41 and 13.29 (2br s, 1 H, tautomers), 9.27 and 9.19 (2br s, 1 H, tautomers), 8.89 and 8.84 (2br s, 1 H, tautomers), 8.58 (d, J=6.7 Hz, 1 H), 8.45 (d, J=6.1 Hz, 2 H), 8.24 and 7.95 (2br s, 1 H, tautomers), 7.25-7.62 (m, 7 H), 7.01-7.10 (m, 1 H). HRMS (ESI) calcd for $C_{22}H_{15}F_4N_5O$ [M+H]$^+$ 442.1286, found 442.1267.

1-(3-Phenoxy-phenyl)-3-[3-(4-pyridin-4-yl-1H-pyrazol-3-yl)-phenyl]-urea

[(I)E, X=CH; R1, R2, R3, R4, R5, R6=H; m=0; Y=H; R7=3-phenoxy-phenyl]

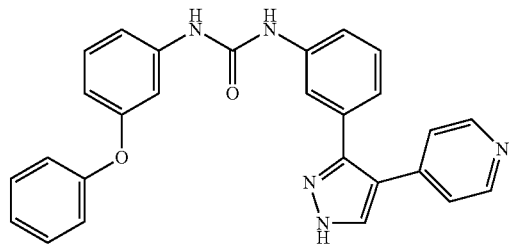 [SMILES: O=C(Nc1cccc(Oc2ccccc2)c1)Nc1cccc(-c2n[nH]cc2-c2ccncc2)c1]

HPLC (254 nm): R$_t$: 6.16 min.

$^1$H NMR (401 MHz, DMSO-d$_6$), δ=13.38 and 13.27 (2br s, 1 H, tautomers), 8.65-8.81 (m, 2 H), 8.45 (d, J=6.0 Hz, 2 H), 8.24 and 7.95 (2br s, 1 H, tautomers), 7.37-7.44 (m, 2 H), 7.24-7.30 (m, 3 H), 7.22 (t, J=2.1 Hz, 1 H), 7.10-7.18 (m, 2 H), 6.96-7.06 (m, 4 H), 6.59-6.64 (m, 1 H). HRMS (ESI) calcd for $C_{27}H_{21}N_5O_2$ [M+H]$^+$ 448.1768, found 448.1752.

1-(3,5-Difluoro-phenyl)-3-[3-(4-pyridin-4-yl-1H-pyrazol-3-yl)-phenyl]-urea

[(I)E, X=CH; R1, R2, R3, R4, R5, R6=H; m=0; Y=H; R7=3,5-difluoro-phenyl]

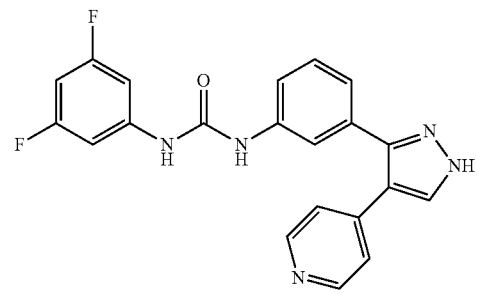 [SMILES: O=C(Nc1cc(F)cc(F)c1)Nc1cccc(-c2n[nH]cc2-c2ccncc2)c1]

HPLC (254 nm): R$_t$: 5.56 min.

$^1$H NMR (401 MHz, DMSO-d$_6$), δ=13.40 and 13.29 (2br s, 1 H, tautomers), 9.09 and 9.04 (2br s, 1 H, tautomers), 8.97 and 8.88 (2br s, 1 H, tautomers), 8.43-8.47 (m, 2 H), 8.25 and 7.96 (2br s, 1 H, tautomers), 7.25-7.62 (m, 5 H), 7.14-7.21 (m, 2 H), 7.01-7.10 (m, 1 H), 6.75-6.83 (m, 2 H). HRMS (ESI) calcd for $C_{21}H_{16}F_2N_5O$ [M+H]$^+$ 392.1318, found 392.1315.

1-(4-Cyano-phenyl)-3-[3-(4-pyridin-4-yl-1H-pyrazol-3-yl)-phenyl]-urea

[(I)E, X=CH; R1, R2, R3, R4, R5, R6=H; m=0; Y=H; R7=4-cyano-phenyl]

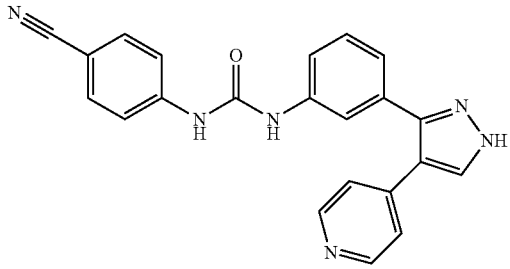 [SMILES: N#Cc1ccc(NC(=O)Nc2cccc(-c3n[nH]cc3-c3ccncc3)c2)cc1]

HPLC (254 nm): R$_t$: 5.05 min.

$^1$H NMR (401 MHz, DMSO-d$_6$), δ=13.40 and 13.29 (2br s, 1 H, tautomers), 9.20 and 9.15 (2br s, 1 H, tautomers), 8.99 and 8.90 (2br s, 1 H, tautomers), 8.44-8.48 (m, 2 H), 8.25 and 7.96 (2br s, 1 H, tautomers), 7.70-7.75 (m, 2 H), 7.59-7.64 (m, 2 H), 7.25-7.56 (m, 5 H), 7.01-7.10 (m, 1 H). HRMS (ESI) calcd for $C_{22}H_{16}N_6O$ [M+H]$^+$ 381.1459, found 381.1452.

1-[3-(4-Pyridin-4-yl-1H-pyrazol-3-yl)-phenyl]-3-p-tolyl-urea (Cpnd. 8)

[(I)E, X=CH; R1, R2, R3, R4, R5, R6=H; m=0; Y=H; R7=4-methyl-phenyl]

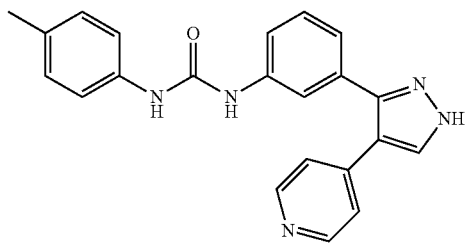 [SMILES: Cc1ccc(NC(=O)Nc2cccc(-c3n[nH]cc3-c3ccncc3)c2)cc1]

HPLC (254 nm): R$_t$: 5.35 min.

$^1$H NMR (401 MHz, DMSO-d$_6$), δ=13.39 and 13.28 (2br s, 1 H, tautomers), 8.48-8.64 (m, 2 H), 8.44-8.48 (m, 2 H), 8.25 and 7.97 (2s, 1 H, tautomers), 7.26-7.70 (m, 7 H), 7.08 (d, J=8.0 Hz, 2 H), 6.95-7.05 (m, 1 H), 2.25 (s, 3 H). HRMS (ESI) calcd for $C_{22}H_{19}N_5O$ [M+H]$^+$ 370.1663, found 370.1680.

1-(4-Chloro-phenyl)-3-[3-(4-pyridin-4-yl-1H-pyrazol-3-yl)-phenyl]-urea (Cpnd. 9)

[(I)E, X=CH, R1, R2, R3, R4, R5, R6=H, m=0, Y=H; R7=4-chloro-phenyl]

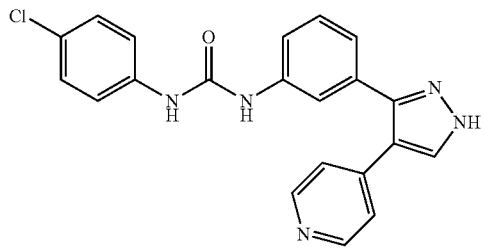 [SMILES: O=C(Nc1ccc(Cl)cc1)Nc1cccc(-c2n[nH]cc2-c2ccncc2)c1]

HPLC (254 nm): R$_t$: 5.57 min.

$^1$H NMR (401 MHz, DMSO-d$_6$), δ=13.40 and 13.29 (2br s, 1 H, tautomers), 8.71-8.85 (m, 2 H), 8.45-8.50 (m, 2 H), 8.26 and 7.97 (2s, 1 H, tautomers), 7.25-7.63 (m, 9 H), 6.97-7.08 (m, 1 H). HRMS (ESI) calcd for $C_{21}H_{16}ClN_5O$ [M+H]$^+$ 390.1116, found 390.1131.

1-Biphenyl-4-yl-3-[3-(4-pyridin-4-yl-1H-pyrazol-3-yl)-phenyl]-urea

[(I)E, X=CH; R1, R2, R3, R4, R5, R6=H; m=0; Y=H; R7=4-phenyl-phenyl]

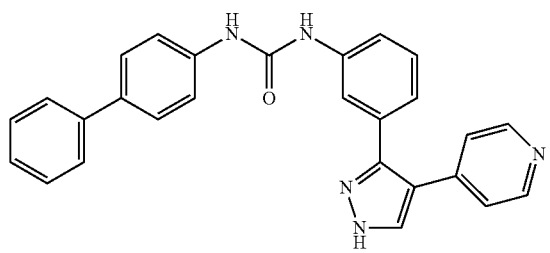 [SMILES: O=C(Nc1ccc(-c2ccccc2)cc1)Nc1cccc(-c2n[nH]cc2-c2ccncc2)c1]

HPLC (254 nm): R$_t$: 6.10 min.

$^1$H NMR (401 MHz, DMSO-d$_6$), δ=13.40 and 13.28 (2br s, 1 H, tautomers), 8.72-8.86 (m, 2 H), 8.46 (d, J=6.0 Hz, 2 H), 8.26 and 7.97 (2s, 1 H, tautomers), 7.57-7.66 (m, 4 H), 7.51-7.56 (m, 2 H), 7.41-7.47 (m, 3 H), 7.27-7.35 (m, 3 H), 6.97-7.06 (m, 1 H). HRMS (ESI) calcd for $C_{27}H_{21}N_5O$ [M+H]$^+$ 432.1819, found 432.1833.

1-Benzyl-3-[3-(4-pyridin-4-yl-1H-pyrazol-3-yl)-phenyl]-urea

[(I)E, X=CH; R1, R2, R3, R4, R5, R6=H; m=0; Y=H; R7=benzyl]

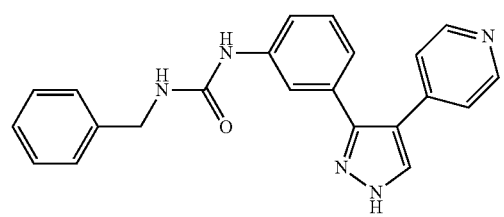 [SMILES: O=C(NCc1ccccc1)Nc1cccc(-c2n[nH]cc2-c2ccncc2)c1]

HPLC (254 nm): R$_t$: 4.93 min.

$^1$H NMR (401 MHz, DMSO-d$_6$), δ=13.35 and 13.25 (2br s, 1 H, tautomers), 8.54-8.76 (m, 1 H), 8.40-8.50 (m, 2 H), 8.24 and 7.95 (2s, 1 H, tautomers), 7.20-7.57 (m, 10 H), 6.88-6.97

1-(4-Dimethylamino-phenyl)-3-[3-(4-pyridin-4-yl-1H-pyrazol-3-yl)-phenyl]-urea

[(I)E, X=CH; R1, R2, R3, R4, R5, R6=H; m=0; Y=H; R7=4-dimethylamino-phenyl]

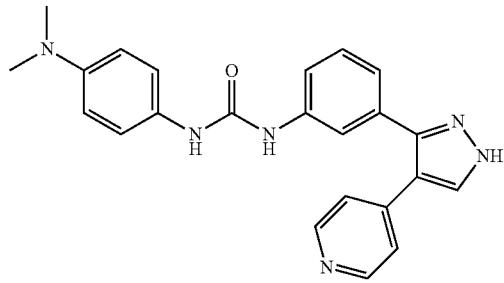 [SMILES: CN(C)c1ccc(NC(=O)Nc2cccc(-c3n[nH]cc3-c3ccncc3)c2)cc1]

HPLC (254 nm): R$_t$: 5.03 min.
$^1$H NMR (401 MHz, DMSO-d$_6$), δ=8.73 (br s, 1 H), 8.60 (d, J=6.6 Hz, 2 H), 8.43 (br s, 1 H), 7.56-7.61 (m, 3 H), 7.50-7.54 (m, 1 H), 7.33-7.40 (m, 1 H), 7.28 (d, J=8.9 Hz, 2 H), 7.02 (d, J=7.8 Hz, 1 H), 6.79 (d, J=7.0 Hz, 2 H), 2.87 (s, 6 H). HRMS (ESI) calcd for C$_{23}$H$_{22}$N$_5$O [M+H]$^+$ 399.1928, found 399.1931.

1-(2-Fluoro-phenyl)-3-[3-(4-pyridin-4-yl-1H-pyrazol-3-yl)-phenyl]-urea

[(I)E, X=CH; R1, R2, R3, R4, R5, R6=H; m=0; Y=H; R7=2-fluoro-phenyl]

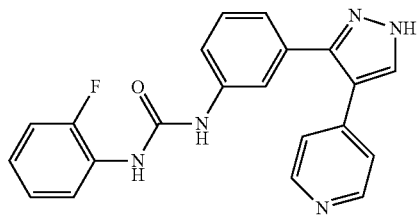 [SMILES: O=C(Nc1cccc(-c2n[nH]cc2-c2ccncc2)c1)Nc1ccccc1F]

HPLC (254 nm): R$_t$: 5.21 min.
$^1$H NMR (401 MHz, DMSO-d$_6$), δ=13.41 and 13.29 (2br s, 1 H, tautomers), 9.10 (br s, 1 H), 8.45-8.52 (m, 3 H), 8.25 and 7.96 (2br s, 1 H, tautomers), 7.50-7.62 (m, 1 H), 7.27-7.33 (m, 2 H), 7.21-7.26 (m, 1 H), 7.11-7.17 (m, 1 H), 6.97-7.07 (m, 5 H). HRMS (ESI) calcd for C$_{21}$H$_{16}$FN$_5$O [M+H]$^+$ 374.1412, found 374.1419.

1-(4-Phenoxy-phenyl)-3-[3-(4-pyridin-4-yl-1H-pyrazol-3-yl)-phenyl]-urea

[(I)E, X=CH; R1, R2, R3, R4, R5, R6=H; m=0; Y=H; R7=4-phenoxy-phenyl]

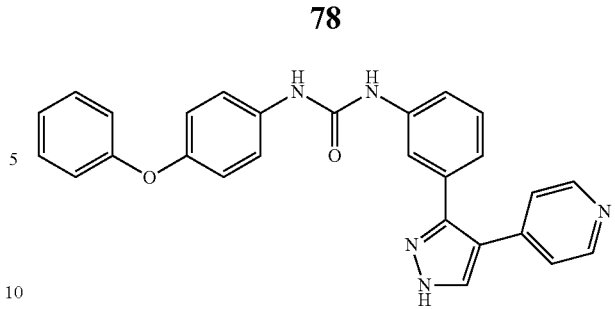

HPLC (254 nm): R$_t$: 6.08 min.
$^1$H NMR (401 MHz, DMSO-d$_6$), δ=13.40 and 13.28 (2br s, 1 H, tautomers), 8.60-8.80 (m, 2 H), 8.43-8.47 (m, 2 H), 8.25 and 7.96 (2br s, 1 H, tautomers), 7.49-7.55 (m, 2 H), 7.46 (d, J=9.0 Hz, 2 H), 7.37 (dd, J=7.4, 8.7 Hz, 1 H), 7.27-7.32 (m, 2 H), 7.05-7.14 (m, 1 H), 6.89-7.01 (m, 5 H). HRMS (ESI) calcd for C$_{27}$H$_{21}$N$_5$O$_2$ [M+H]$^+$ 448.1768, found 448.1772.

1-Benzo[1,3]dioxol-5-yl-3-[3-(4-pyridin-4-yl-1H-pyrazol-3-yl)-phenyl]-urea

[(I)E, X=CH; R1, R2, R3, R4, R5, R6=H; m=0; Y=H; R7=1-benzo[1,3]dioxol-5-yl]

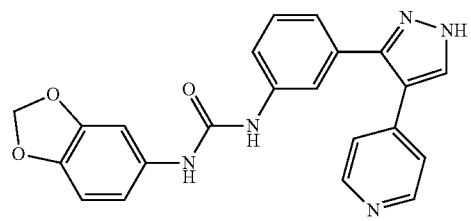 [SMILES: O=C(Nc1cccc(-c2n[nH]cc2-c2ccncc2)c1)Nc1ccc2c(c1)OCO2]

HPLC (254 nm): R$_t$: 4.94 min.
$^1$H NMR (401 MHz, DMSO-d$_6$), δ=13.40 and 13.28 (2br s, 1 H, tautomers), 8.50-8.76 (m, 2 H), 8.43-8.48 (m, 2 H), 8.28 and 7.97 (2br s, 1 H, tautomers), 7.25-7.60 (m, 5 H), 7.18 (d, J=2.0 Hz, 1 H), 6.96-7.05 (m, 1 H), 6.81-6.86 (m, 1 H), 6.72-6.79 (m, 1 H), 5.97 (s, 2 H). HRMS (ESI) calcd for C$_{22}$H$_{17}$N$_5$O$_3$ [M+H]$^+$ 400.1404, found 400.1412.

1-Phenyl-3-[3-(4-pyridin-4-yl-1H-pyrazol-3-yl)-phenyl]-urea

[(I)E, X=CH; R1, R2, R3, R4, R5, R6=H; m=0; Y=H; R7=phenyl]

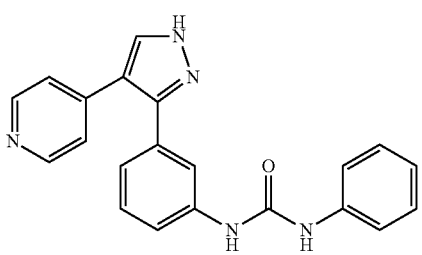 [SMILES: O=C(Nc1ccccc1)Nc1cccc(-c2n[nH]cc2-c2ccncc2)c1]

HPLC (254 nm): R$_t$: 4.18 min.
1H NMR (401 MHz, DMSO-d6) δ=13.38 and 13.27 (2br. s., 1 H, tautomers), 8.60-8.85 (m, 2 H), 8.45 (dd, J=1.5, 4.6 Hz, 2 H), 8.24 and 7.95 (2br. s., 1 H, tautomers), 7.33-7.60 (m, 4 H), 7.22-7.33 (m, 6 H), 6.97 (q, J=7.3 Hz, 1 H). HRMS (ESI) calcd for $C_{21}H_{17}N_5O$ [M+H]$^+$ 356.1506, found 356.1516

1-Isopropyl-3-[3-(4-pyridin-4-yl-1H-pyrazol-3-yl)-phenyl]-urea

[(I)E, X═CH; R1, R2, R3, R4, R5, R6═H; m═0; Y═H; R7═isopropyl]

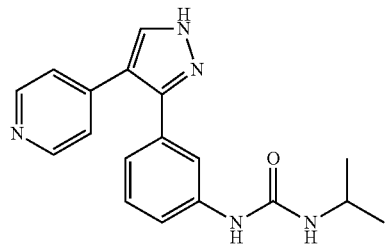 [SMILES: CC(C)NC(=O)Nc1cccc(-c2n[nH]cc2-c2ccncc2)c1]

HPLC (254 nm): R$_t$: 3.84 min.
$^1$H NMR (401 MHz, DMSO-d6) δ=13.27 (br. s., 1 H), 8.43 (d, J=6.0 Hz, 2 H), 8.28 (br.s., 1 H), 8.20 and 7.95 (2br. s., 1 H, tautomers), 7.47 (br. s., 1 H), 7.42 (t, J=1.7 Hz, 1 H), 7.26 (d, J=5.7 Hz, 2 H), 6.90 (d, J=6.8 Hz, 1 H), 6.00 (br. s., 1 H), 3.66-3.79 (m, 1 H), 1.08 (d, J=6.5 Hz, 6 H). HRMS (ESI) calcd for $C_{18}H_{19}N_5O$ [M+H]$^+$ 322.1663, found 322.1666

1-(4-Methoxy-phenyl)-3-[3-(4-pyridin-4-yl-1H-pyrazol-3-yl)-phenyl]-urea

[(I)E, X═CH; R1, R2, R3, R4, R5, R6═H; m═0; Y═H; R7═4-methoxyphenyl]

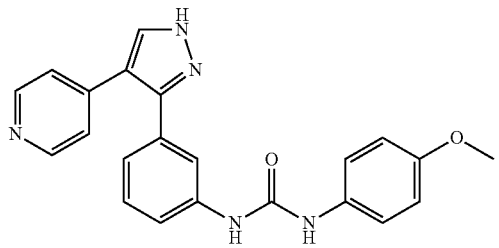 [SMILES: COc1ccc(NC(=O)Nc2cccc(-c3n[nH]cc3-c3ccncc3)c2)cc1]

HPLC (254 nm): R$_t$: 4.12 min.
$^1$H NMR (401 MHz, DMSO-d6) δ=13.37 and 13.26 (2br. s., 1 H, tautomers), 8.48-8.85 (m, 2 H), 8.44 (d, J=6.1 Hz, 2 H), 8.23 and 7.95 (2br. s., 1 H, tautomers), 7.33 (d, J=9.0 Hz, 2 H), 7.27 (d, J=3.8 Hz, 2 H), 6.98 (br. s., 1 H), 6.84-6.87 (m, 2 H), 3.71 (s, 3 H). HRMS (ESI) calcd for $C_{22}H_{19}N_5O_2$ [M+H]$^+$ 386.1612, found 386.1615

4-{3-[3-(4-Pyridin-4-yl-1H-pyrazol-3-yl)-phenyl]-ureido}-benzoic acid ethyl ester

[(I)E, X═CH; R1, R2, R3, R4, R5, R6═H; m═0; Y═H; R7═4-carbethoxyphenyl]

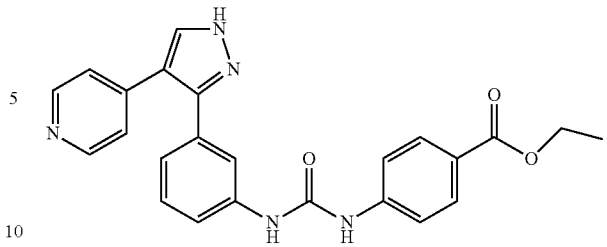

HPLC (254 nm): R$_t$: 4.69 min.
$^1$H NMR (401 MHz, DMSO-d6) δ=13.40 and 13.28 (2br. s., 1 H, tautomers), 9.08 (br. s., 1 H), 8.86 (br. s., 1 H), 8.46 (d, J=6.0 Hz, 2 H), 8.25 and 7.92 (2br. s., 1 H, tautomers), 7.89 (d, J=8.9 Hz, 2 H), 7.57 (d, J=8.9 Hz, 2 H), 7.25-7.35 (m, 2 H), 6.93-7.11 (m, 1 H), 4.28 (q, J=7.2 Hz, 2 H), 1.32 (t, J=7.2 Hz, 3 H). HRMS (ESI) calcd for $C_{24}H_{21}N_5O_3$ [M+H]$^+$ 428.1717, found 428.1723

1-(4-Chloro-3-trifluoromethyl-phenyl)-3-[3-(4-pyridin-4-yl-1H-pyrazol-3-yl)-phenyl]-urea

[(I)E, X═CH; R1, R2, R3, R4, R5, R6═H; m═0; Y═H; R7═4-chloro-3-trifluoromethyl-phenyl]

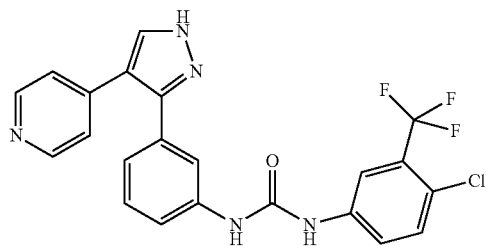 [SMILES: O=C(Nc1cccc(-c2n[nH]cc2-c2ccncc2)c1)Nc1ccc(Cl)c(C(F)(F)F)c1]

HPLC (254 nm): R$_t$: 5.44 min.
$^1$H NMR (401 MHz, DMSO-d6) δ=13.42 and 13.30 (2br. s., 1 H, tautomers), 9.03-9.28 (m, 1 H), 8.93 (d, J=20.0 Hz, 1 H), 8.46 (d, J=6.1 Hz, 2 H), 8.06-8.12 (m, 1 H), 7.54-7.68 (m, 2 H), 7.31 (d, J=4.9 Hz, 2 H), 7.05 (br. s., 1 H). HRMS (ESI) calcd for $C_{22}H_{15}ClF_3N_5O$ [M+H]$^+$ 458.0990, found 428. 458.0991.

Example 2

4-Methoxy-N-[3-(4-pyridin-4-yl-1H-pyrazol-3-yl)-phenyl]-benzenesulfonamide

[(I)C, X═CH; R1, R2, R3, R4, R5, R6═H; m═0; R7'═4-methoxy-phenyl]

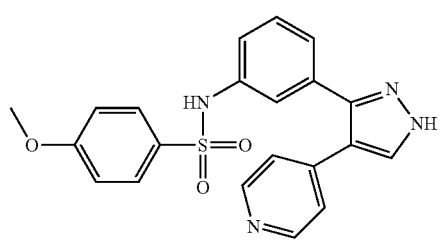 [SMILES: COc1ccc(S(=O)(=O)Nc2cccc(-c3n[nH]cc3-c3ccncc3)c2)cc1]

The above sulfonamide was prepared in an analogous way according to Methods G and M using a solid phase approach.

The amino derivative immobilized on the resin obtained as described in Example 1 was derivatized and then cleaved from the resin as described below.

Method G

Step c

A solution of DIPEA (103 μL, 0.06 mmol) and the appropriate sulfonyl chlorides (0.06 mmol) in 2 ml of DCM was added to a suspension of the resin obtained in Step a (Method G) (Example 2) (100 mg, 0.01 mmol) in DCM (1 ml).

The obtained suspension was stirred for 20 h at r.t., filtered, washed with DCM, DMF and MeOH, dried under nitrogen flux and used in the next step.

Method M

Step a

A solution of 2 mL of TFA 20% in DCM were added to 100 mg of the resins obtained in Step b in the Quest vessels. The red suspension was stirred for 1 h then filtered and the resin washed twice with 1 ml of DCM. The filtered solution was evaporated under nitrogen flux to give the product as a crude solid, which was purified by preparative HPLC.

HPLC (254 nm): $R_t$: 4.01 min.

$^1$H NMR (401 MHz, DMSO-$d_6$), δ=13.27 (br s., 1 H), 10.25 (br s., 1 H), 8.40 (d, J=6.0 Hz, 2 H), 8.17 (br s., 1 H), 7.62 (d, J=8.8 Hz, 2 H), 7.17-7.30 (m, 1 H), 7.15 (d, J=6.0 Hz, 2 H), 6.60-7.12 (m, 5 H), 3.79 (s, 3 H). HRMS (ESI) calcd for $C_{21}H_{18}N_4O_3S$ [M+H]$^+$ 407.1173, found 407.1159.

Operating in an analogous way the following compounds were obtained:

4-Methyl-N-[3-(4-pyridin-4-yl-1H-pyrazol-3-yl)-phenyl]-benzenesulfonamide

[(I)C, X=CH; R1, R2, R3, R4, R5, R6=H; m=0; R7'=4-methyl-phenyl]

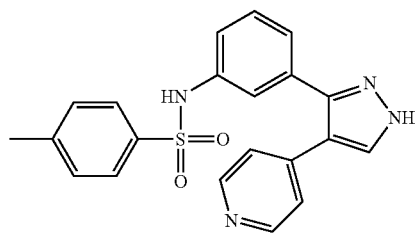 [SMILES: Cc1ccc(S(=O)(=O)Nc2cccc(-c3n[nH]cc3-c3ccncc3)c2)cc1]

HPLC (254 nm): $R_t$: 4.20 min.

$^1$H NMR (401 MHz, DMSO-$d_6$), δ=13.27 (br s., 1 H), 10.26 (br s., 1 H), 8.39 (d, J=6.1 Hz, 2 H), 8.19 (br s., 1 H), 7.58 (d, J=8.2 Hz, 2 H), 7.26-7.32 (m, 2 H), 7.19-7.25 (m, 1 H), 7.15 (d, J=6.1 Hz, 2 H), 6.60-7.12 (m, 3 H), 2.33 (s, 3 H).

HRMS (ESI) calcd for $C_{21}H_{18}N_4O_3S$ [M+H]$^+$ 391.1223, found 391.1215

3-Methyl-N-[3-(4-pyridin-4-yl-1H-pyrazol-3-yl)-phenyl]-benzenesulfonamide

[(I)C, X=CH; R1, R2, R3, R4, R5, R6=H; m=0; R7'=3-methyl-phenyl]

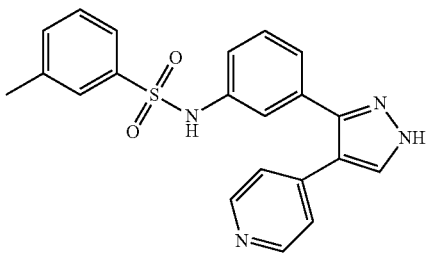 [SMILES: Cc1cccc(S(=O)(=O)Nc2cccc(-c3n[nH]cc3-c3ccncc3)c2)c1]

HPLC (254 nm): $R_t$: 4.17 min.

$^1$H NMR (401 MHz, DMSO-$d_6$), δ=13.27 (br s., 1H), 13.27 (br s., 1 H), 10.31 (s, 1 H), 8.37-8.42 (m, 2 H), 8.20 (br. s., 1 H), 7.53 (s, 1 H), 7.46-7.51 (m, 1 H), 7.33-7.41 (br s., 2 H), 7.19-7.29 (m, 1 H), 7.14-7.18 (m, 2 H), 6.90-7.12 (m, 3 H), 2.32 (s, 3 H). HRMS (ESI) calcd for $C_{21}H_{18}N_4O_2S$ [M+H]$^+$ 391.1223, found 391.1211.

3-Methoxy-N-[3-(4-pyridin-4-yl-1H-pyrazol-3-yl)-phenyl]-benzenesulfonamide

[(I)C, X=CH; R1, R2, R3, R4, R5, R6=H; m=0; R7'=3-methoxy-phenyl]

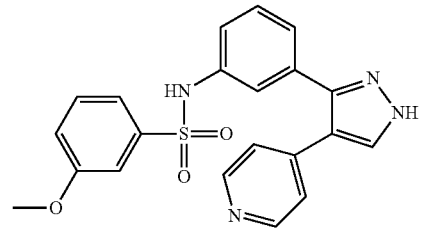 [SMILES: COc1cccc(S(=O)(=O)Nc2cccc(-c3n[nH]cc3-c3ccncc3)c2)c1]

HPLC (254 nm): $R_t$: 4.04 min.

$^1$H NMR (401 MHz, DMSO-$d_6$), δ=13.28 (br. s., 1 H), 10.34 (br. s., 1 H), 8.38-8.41 (m, 2 H), 8.20 (br. s., 1 H), 7.40-7.45 (m, 1 H), 7.20-7.29 (m, 3 H), 7.14-7.17 (m, 3 H), 6.97-7.05 (m, 2 H), 3.75 (s, 3 H). HRMS (ESI) calcd for $C_{21}H_{18}N_4O_3S$ [M+H]$^+$ 407.1173, found 407.1157.

5-Isoxazol-3-yl-thiophene-2-sulfonic acid [3-(4-pyridin-4-yl-1H-pyrazol-3-yl)-phenyl]-amide

[(I)C, X=CH; R1, R2, R3, R4, R5, R6=H; m=0; R7'=5-isoxazol-3-yl-thiophen-2-yl]

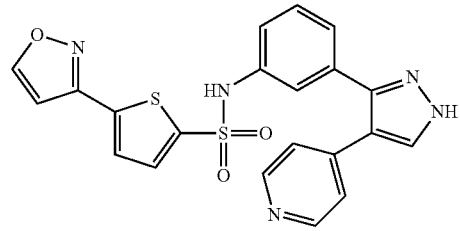 [SMILES: O=S(=O)(Nc1cccc(-c2n[nH]cc2-c2ccncc2)c1)c1ccc(-c2ccon2)s1]

HPLC (254 nm): $R_t$: 4.50 min.

$^1$H NMR (401 MHz, DMSO-$d_6$), δ=13.39 and 13.30 (2br s, 1 H, tautomers), 10.72 (br. s., 1 H), 8.71 (d, J=2.0 Hz, 1 H), 8.35-8.46 (m, 2 H), 8.21 and 7.92 (2br s, 1 H, tautomers), 7.68 (d, J=3.9 Hz, 1 H), 7.56 (d, J=3.9 Hz, 1 H), 7.21-7.45 (m, 4 H), 7.14-7.20 (m, 2 H), 7.07 (d, J=2.0 Hz, 1 H). HRMS (ESI) calcd for $C_{21}H_{15}N_5O_3S_2$ [M+H]$^+$ 450.0689, found 450.0677.

4-Fluoro-N-[3-(4-pyridin-4-yl-1H-pyrazol-3-yl)-phenyl]-benzenesulfonamide

[(I)C, X=CH; R1, R2, R3, R4, R5, R6=H; m=0; R7'=4-fluoro-phenyl]

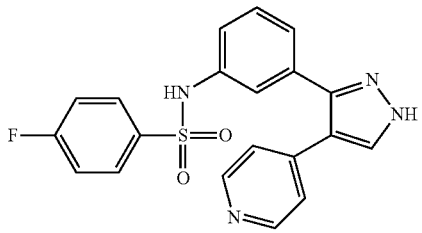

HPLC (254 nm): $R_t$: 4.13 min.

$^1$H NMR (401 MHz, DMSO-d$_6$), δ=13.28 (br. s., 1 H), 10.39 (br. s., 1 H), 8.41 (d, J=5.8 Hz, 2 H), 8.20 (br. s., 1 H), 7.73-7.79 (m, 2 H), 7.36-7.40 (m, 2 H), 7.07-7.30 (m, 6 H). HRMS (ESI) calcd for $C_{20}H_{15}FN_4O_2S$ [M+H]$^+$ 395.0973, found 395.0969.

4-Nitro-N-[3-(4-pyridin-4-yl-1H-pyrazol-3-yl)-phenyl]-benzenesulfonamide

[(I)C, X=CH; R1, R2, R3, R4, R5, R6=H; m=0; R7'=4-nitro-phenyl]

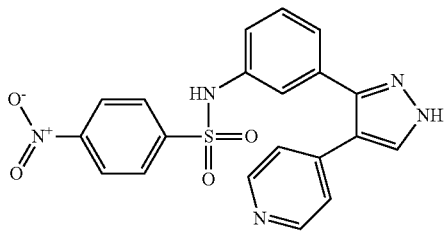 [SMILES: O=[N+]([O-])c1ccc(S(=O)(=O)Nc2cccc(-c3n[nH]cc3-c3ccncc3)c2)cc1]

HPLC (254 nm): $R_t$: 4.11 min.

$^1$H NMR (401 MHz, DMSO-d$_6$), δ=13.28 (br. s., 1 H), 10.70 (br. s., 1 H), 8.32-8.41 (m, 4 H), 8.20 (br. s., 1 H), 7.93-7.96 (m, 2 H), 7.05-7.31 (m, 6 H). HRMS (ESI) calcd for $C_{20}H_{15}N_5O_4S$ [M+H]$^+$ 422.0918, found 422.0914.

3-Fluoro-N-[3-(4-pyridin-4-yl-1H-pyrazol-3-yl)-phenyl]-benzenesulfonamide

[(I)C, X=CH; R1, R2, R3, R4, R5, R6=H; m=0; R7'=3-fluoro-phenyl]

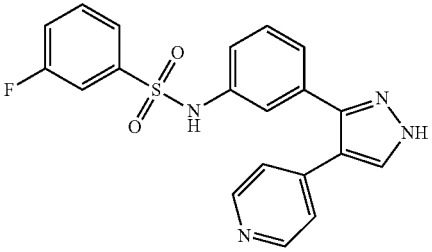

HPLC (254 nm): $R_t$: 4.37 min.

$^1$H NMR (401 MHz, DMSO-d$_6$), δ=13.28 (br. s., 1 H), 10.48 (br. s., 1 H), 8.39-8.42 (m, 2 H), 8.21 (br. s., 1 H), 7.46-7.64 (m, 4 H), 7.06-7.31 (m, 6 H). HRMS (ESI) calcd for $C_{20}H_{15}FN_4O_2S$ [M+H]$^+$ 395.0973, found 395.0961.

2-Fluoro-N-[3-(4-pyridin-4-yl-1H-pyrazol-3-yl)-phenyl]-benzenesulfonamide

[(I)C, X=CH; R1, R2, R3, R4, R5, R6=H; m=0; R7'=2-fluoro-phenyl]

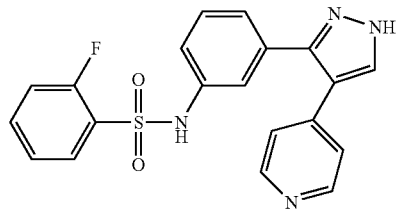 [SMILES: O=S(=O)(Nc1cccc(-c2n[nH]cc2-c2ccncc2)c1)c1ccccc1F]

HPLC (254 nm): $R_t$: 3.98 min.

$^1$H NMR (401 MHz, DMSO-d$_6$), δ=13.27 (br. s., 1 H), 10.69 (br. s., 1 H), 8.38-8.42 (m, 2 H), 8.38-8.42 (m, 2 H), 8.20 (br. s., 1 H), 7.60-7.80 (m, 2 H), 7.00-7.41 (m, 8 H). HRMS (ESI) calcd for $C_{20}H_{15}FN_4O_2S$ [M+H]$^+$ 395.0973, found 395.0955.

4-Cyano-N-[3-(4-pyridin-4-yl-1H-pyrazol-3-yl)-phenyl]-benzenesulfonamide

[(I)C, X=CH; R1, R2, R3, R4, R5, R6=H; m=0; R7'=4-cyano-phenyl]

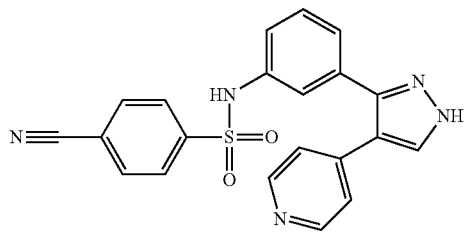 [SMILES: N#Cc1ccc(S(=O)(=O)Nc2cccc(-c3n[nH]cc3-c3ccncc3)c2)cc1]

HPLC (254 nm): $R_t$: 4.20 min.

$^1$H NMR (401 MHz, DMSO-d$_6$), δ=13.29 (br. s., 1 H), 10.63 (br. s., 1 H), 8.40-8.44 (m, 2 H), 8.20 (br. s., 1 H), 8.03 (d, J=8.3 Hz, 2 H), 7.85 (d, J=8.3 Hz, 2 H), 7.06-7.40 (m, 6 H). HRMS (ESI) calcd for $C_{21}H_{16}N_5O_2S$ [M+H]$^+$ 402.1019, found 402.1015.

1,2-Dimethyl-1H-imidazole-4-sulfonic acid [3-(4-pyridin-4-yl-1H-pyrazol-3-yl)-phenyl]-amide

[(I)C, X=CH; R1, R2, R3, R4, R5, R6=H; m=; R7'=1,2-dimethyl-1H-imidazol-4-yl]

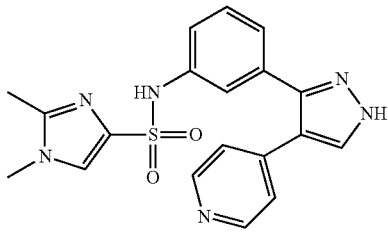 [SMILES: Cc1nc(S(=O)(=O)Nc2cccc(-c3n[nH]cc3-c3ccncc3)c2)cn1C]

HPLC (254 nm): $R_t$: 3.06 min.
$^1$H NMR (401 MHz, DMSO-d$_6$), δ=13.27 (br. s., 1 H), 10.19 (br. s., 1 H), 8.41 (d, J=5.9 Hz, 2 H), 8.22 (br. s., 1 H), 7.63 (s, 1 H), 6.95-7.40 (m, 6 H), 3.53 (s, 3 H), 2.25 (s, 3 H). HRMS (ESI) calcd for C$_{19}$H$_{18}$N$_6$O$_2$S [M+H]$^+$ 395.1285, found 395.1274.

6-Chloro-imidazo[2,1-b]thiazole-5-sulfonic acid [3-(4-pyridin-4-yl-1H-pyrazol-3-yl)-phenyl]-amide

[(I)C, X=CH; R1, R2, R3, R4, R5, R6=H; m=0; R7'=6-chloro-imidazo[2,1-b]thiazol-5-yl]

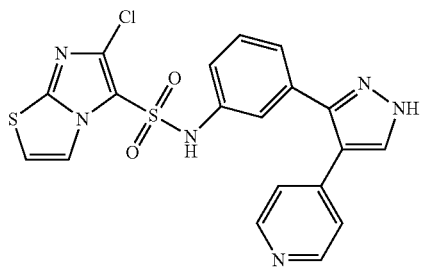 [SMILES: O=S(=O)(Nc1cccc(-c2n[nH]cc2-c2ccncc2)c1)c1c(Cl)nc2sccn12]

HPLC (254 nm): $R_t$: 3.82 min.
$^1$H NMR (401 MHz, DMSO-d$_6$), δ=13.26 (br. s., 1 H), 8.38-8.40 (m, 2 H), 8.20 (br. s., 1 H), 7.88-7.92 (m, 1 H), 7.55-7.60 (m, 1 H), 6.88-7.30 (m, 5 H). HRMS (ESI) calcd for C$_{19}$H$_{13}$ClN$_6$O$_2$S$_2$ [M+H]$^+$ 457.0303, found 457.0295.

4-Acetyl-N-[3-(4-pyridin-4-yl-1H-pyrazol-3-yl)-phenyl]-benzenesulfonamide

[(I)C, X=CH; R1, R2, R3, R4, R5, R6=H; m=0; R7'=4-acetyl-phenyl]

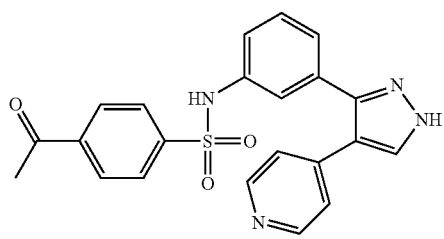 [SMILES: CC(=O)c1ccc(S(=O)(=O)Nc2cccc(-c3n[nH]cc3-c3ccncc3)c2)cc1]

HPLC (254 nm): $R_t$: 4.15 min $^1$H NMR (401 MHz, DMSO-d$_6$), δ=13.28 (br. s., 1 H), 10.55 (br. s., 1 H), 8.36-8.45 (m, 2 H), 8.20 (br. s., 1 H), 8.09-8.09 (m, 2 H), 7.83 (d, J=8.4 Hz, 2 H), 7.05-7.39 (m, 6 H), 2.60 (s, 3 H). HRMS (ESI) calcd for C$_{22}$H$_{18}$N$_4$O$_3$S [M+H]$^+$ 419.1173, found 419.1163.

5-Bromo-thiophene-2-sulfonic acid [3-(4-pyridin-4-yl-1H-pyrazol-3-yl)-phenyl]-amide

[(I)C, X=CH; R1, R2, R3, R4, R5, R6=H; m=0; R7'=5-bromo-thiophen-2-yl]

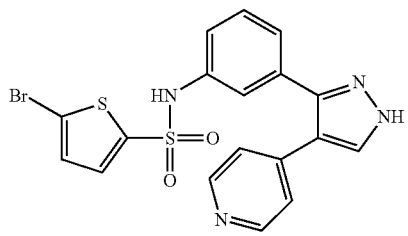 [SMILES: O=S(=O)(Nc1cccc(-c2n[nH]cc2-c2ccncc2)c1)c1ccc(Br)s1]

HPLC (254 nm): $R_t$: 5.07 min.
$^1$H NMR (401 MHz, DMSO-d$_6$), δ=13.31 (br. s., 1 H), 10.62 (br. s., 1 H), 8.41-8.45 (m, 2 H), 8.22 (br. s., 1 H), 7.12-7.45 (m, 8 H). HRMS (ESI) calcd for C$_{18}$H$_{13}$BrN$_4$O$_2$S$_2$ [M+H]$^+$ 460.9736, found 460.9728.

N-[3-(4-Pyridin-4-yl-1H-pyrazol-3-yl)-phenyl]-4-trifluoromethoxy-benzenesulfonamide

[(I)C, X=CH; R1, R2, R3, R4, R5, R6=H; m=0; R7'=4-trifluoromethoxyphenyl]

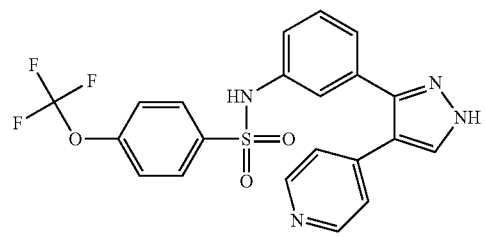 [SMILES: O=S(=O)(Nc1cccc(-c2n[nH]cc2-c2ccncc2)c1)c1ccc(OC(F)(F)F)cc1]

HPLC (254 nm): $R_t$: 4.84 min.
$^1$H NMR (401 MHz, DMSO-d$_6$), δ=13.28 (br. s., 1 H), 10.49 (br. s., 1 H), 8.39-8.43 (m, 2 H), 8.20 (br. s., 1 H), 7.81-7.85 (m, 2 H), 7.51-7.57 (m, 2 H), 7.05-7.39 (m, 6 H). HRMS (ESI) calcd for C$_{21}$H$_{15}$F$_3$N$_4$O$_3$S [M+H]$^+$ 461.089, found 461.0881.

3,5-Difluoro-N-3-(4-pyridin-4-yl-1H-pyrazol-3-yl)-phenyl]-benzenesulfonamide

[(I)C, X=CH; R1, R2, R3, R4, R5, R6=H; m=0; R7'=3,5-difluoro-phenyl]

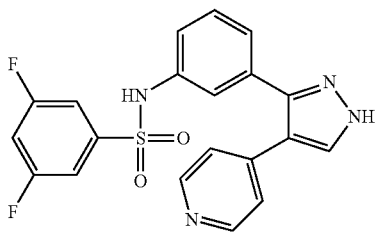 [SMILES: O=S(=O)(Nc1cccc(-c2n[nH]cc2-c2ccncc2)c1)c1cc(F)cc(F)c1]

HPLC (254 nm): R$_t$: 5.25 min.
$^1$H NMR (401 MHz, DMSO-d$_6$), δ=13.30 (br. s., 1 H), 10.58 (br. s., 1 H), 8.38-8.43 (m, 2 H), 8.21 (br. s., 1 H), 7.55-7.65 (m, 1 H), 7.35-7.42 (m, 3 H), 7.26-7.33 (m, 1 H), 7.07-7.20 (m, 4 H). HRMS (ESI) calcd for C$_{20}$H$_{14}$F$_2$N$_4$O$_2$S [M+H]$^+$ 413.0879, found 413.0870.

2,5-Difluoro-N-[3-(4-pyridin-4-yl-1H-pyrazol-3-yl)-phenyl]-benzenesulfonamide (Cmpd. 2)

[(I)C, X=CH; R1, R2, R3, R4, R5, R6=H; m=0; R7'=2,5-difluoro-phenyl]

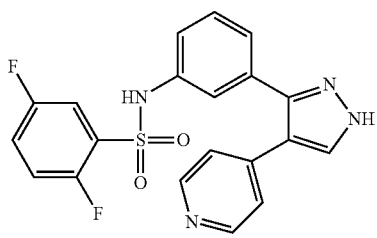 [SMILES: O=S(=O)(Nc1cccc(-c2n[nH]cc2-c2ccncc2)c1)c1cc(F)ccc1F]

HPLC (254 nm): R$_t$: 5.06 min.
$^1$H NMR (401 MHz, DMSO-d$_6$), δ=13.29 (br. s., 1 H), 10.83 (br. s., 1 H), 8.38-8.44 (m, 2 H), 8.21 (br. s., 1 H), 7.45-7.61 (m, 3 H), 7.06-7.40 (m, 6 H). HRMS (ESI) calcd for C$_{20}$H$_{14}$F$_2$N$_4$O$_2$S [M+H]$^+$ 413.0879, found 413.0864.

Pyridine-3-sulfonic acid [3-(4-pyridin-4-yl-1H-pyrazol-3-yl)-phenyl]-amide

[(I)C, X=CH; R1, R2, R3, R4, R5, R6=H; m=0; R7'=pyridin-3-yl]

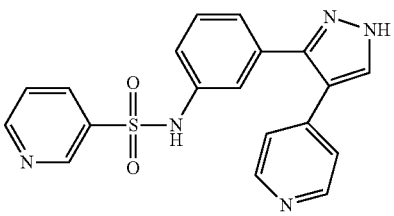 [SMILES: O=S(=O)(Nc1cccc(-c2n[nH]cc2-c2ccncc2)c1)c1cccnc1]

HPLC (254 nm): R$_t$: 4.28 min.
$^1$H NMR (401 MHz, DMSO-d$_6$), δ=13.29 (br. s., 1 H), 10.57 (br. s., 1 H), 8.85 (d, J=2.0 Hz, 1 H), 8.79 (dd, J=1.5, 4.8 Hz, 1 H), 8.42 (d, J=3.7 Hz, 2 H), 8.21 (br. s., 1 H), 8.05-8.10 (m, 1 H), 7.60 (dd, J=5.1, 7.6 Hz, 1 H), 7.07-7.40 (m, 6 H). HRMS (ESI) calcd for C$_{19}$H$_{15}$N$_5$O$_2$S [M+H]$^+$ 378.1019, found 378.1010.

2-Methyl-N-[3-(4-pyridin-4-yl-1H-pyrazol-3-yl)-phenyl]-benzenesulfonamide

[(I)C, X=CH; R1, R2, R3, R4, R5, R6=H; m=0; R7'=2-methyl-phenyl]

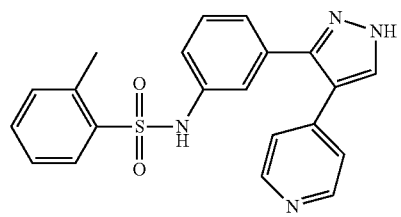 [SMILES: Cc1ccccc1S(=O)(=O)Nc1cccc(-c2n[nH]cc2-c2ccncc2)c1]

HPLC (254 nm): R$_t$: 5.07 min.
$^1$H NMR (401 MHz, DMSO-d$_6$), δ=13.26 (br. s., 1 H), 10.47 (br. s., 1 H), 8.41 (d, J=5.9 Hz, 2 H), 8.19 (br. s., 1 H), 7.75 (s, 1 H), 7.43-7.53 (m, 1 H), 6.98-7.40 (m, 8 H), 2.55 (s, 3 H). HRMS (ESI) calcd for C$_{21}$H$_{18}$N$_4$O$_2$S [M+H]$^+$ 391.1223, found 391.1221.

4-Pyrazol-1-yl-N-[3-(4-pyridin-4-yl-1H-pyrazol-3-yl)-phenyl]-benzenesulfonamide

[(I)C, X=CH; R1, R2, R3, R4, R5, R6=H; m=0; R7'=4-pyrazol-1-yl-phenyl]

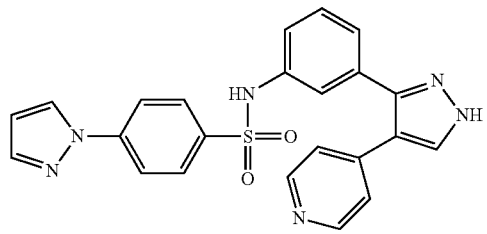 [SMILES: O=S(=O)(Nc1cccc(-c2n[nH]cc2-c2ccncc2)c1)c1ccc(-n2cccn2)cc1]

HPLC (254 nm): R$_t$: 5.03 min.
$^1$H NMR (401 MHz, DMSO-d$_6$), δ=13.27 (br. s., 1 H), 10.39 (br. s., 1 H), 8.58 (d, J=2.4 Hz, 1 H), 8.37 (br. s., 2 H), 7.89-8.25 (m, 4 H), 7.77-7.83 (m, 2 H), 6.90-7.35 (m, 6 H), 6.60 (dd, J=1.7, 2.6 Hz, 1 H). HRMS (ESI) calcd for C$_{23}$H$_{18}$N$_6$O$_2$S [M+H]$^+$ 443.1285, found 443.1270.

4-Chloro-N-[3-(4-pyridin-4-yl-1H-pyrazol-3-yl)-phenyl]-benzenesulfonamide

[(I)C, X=CH; R1, R2, R3, R4, R5, R6=H; m=0; R7'=4-chloro-phenyl]

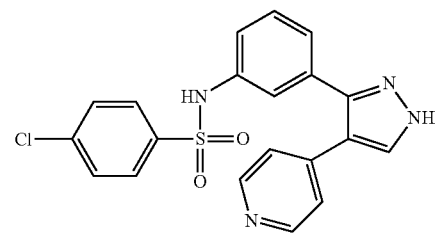 [SMILES: O=S(=O)(Nc1cccc(-c2n[nH]cc2-c2ccncc2)c1)c1ccc(Cl)cc1]

HPLC (254 nm): R$_t$: 5.31 min.
$^1$H NMR (401 MHz, DMSO-d$_6$), δ=13.28 (br. s., 1 H), 10.44 (br. s., 1 H), 8.42 (d, J=5.6 Hz, 2 H), 8.20 (br. s., 1 H), 7.68-7.74 (m, 2 H), 7.58-7.66 (m, 2 H), 7.05-7.40 (m, 6 H). HRMS (ESI) calcd for $C_{20}H_{16}ClN_4O_2S$ [M+H]$^+$ 411.0677, found 411.0691.

3,4-Dichloro-N-[3-(4-pyridin-4-yl-1H-pyrazol-3-yl)-phenyl]-benzenesulfonamide

[(I)C, X=CH; R1, R2, R3, R4, R5, R6=H; m=0; R7'=3,4-dichloro-phenyl]

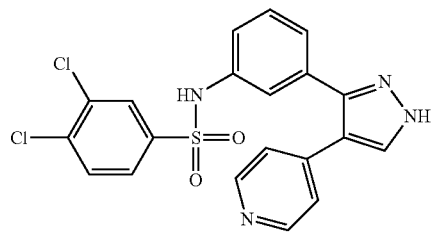 [SMILES: O=S(=O)(Nc1cccc(-c2n[nH]cc2-c2ccncc2)c1)c1ccc(Cl)c(Cl)c1]

HPLC (254 nm): R$_t$: 5.68 min.

$^1$H NMR (401 MHz, DMSO-d$_6$), δ=13.30 (br. s., 1 H), 10.52 (br. s., 1 H), 8.40-8.44 (m, 2 H), 8.21 (br. s., 1 H), 7.82-7.90 (m, 2 H), 7.61-7.68 (m, 1 H), 7.08-7.44 (m, 6 H). HRMS (ESI) calcd for $C_{20}H_{14}Cl_2N_4O_2S$ [M+H]$^+$ 445.0288, found 445.0293.

N-[3-(4-Pyridin-4-yl-1H-pyrazol-3-yl)-phenyl]-3-trifluoromethyl-benzenesulfonamide

[(I)C, X=CH; R1, R2, R3, R4, R5, R6=H; m=0; R7'=3-trifluoromethyl-phenyl]

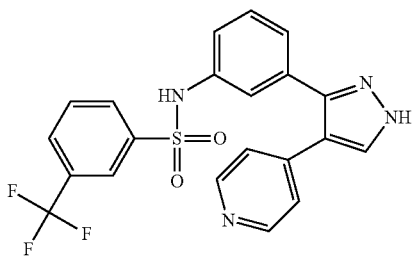 [SMILES: O=S(=O)(Nc1cccc(-c2n[nH]cc2-c2ccncc2)c1)c1cccc(C(F)(F)F)c1]

HPLC (254 nm): R$_t$: 5.54 min.

$^1$H NMR (401 MHz, DMSO-d$_6$), δ=13.21 (br. s., 1 H), 10.51 (br. s., 1 H), 8.86 (br. s., 2 H), 7.60-7.99 (m, 5 H), 6.68-7.22 (m, 6 H). HRMS (ESI) calcd for $C_{21}H_{15}F_3N_4O_2S$ [M+H]$^+$ 445.0941, found 445.0958.

N-[3-(4-Pyridin-4-yl-1H-pyrazol-3-yl)-phenyl]-4-trifluoromethyl-benzenesulfonamide

[(I)C, X=CH; R1, R2, R3, R4, R5, R6=H; m=0; R7'=4-trifluoromethyl-phenyl]

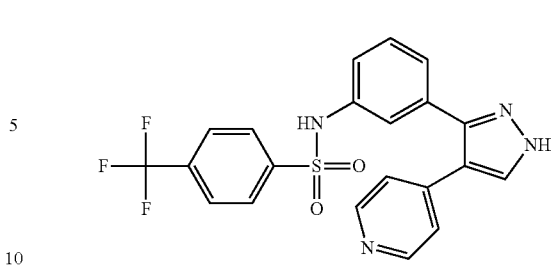

HPLC (254 nm): R$_t$: 5.60 min.

$^1$H NMR (401 MHz, DMSO-d$_6$), δ=13.40 (br. s., 1 H), 10.62 (br. s., 1 H), 8.49 (d, J=6.3 Hz, 2 H), 8.27 (br. s., 1 H), 7.88-8.01 (m, 4 H), 7.30 (d, J=6.0 Hz, 2 H), 7.07-7.25 (m, 4 H). HRMS (ESI) calcd for $C_{21}H_{16}F_3N_4O_2S$ [M+H]$^+$ 445.0941, found 445.0949.

2-Methoxy-N-[3-(4-pyridin-4-yl-1H-pyrazol-3-yl)-phenyl]-benzenesulfonamide

[(I)C, X=CH; R1, R2, R3, R4, R5, R6=H; m=0; R7'=2-methoxy-phenyl]

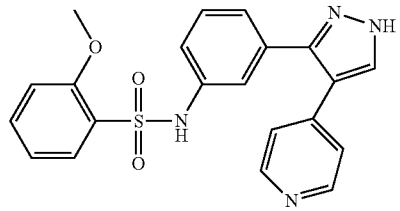 [SMILES: COc1ccccc1S(=O)(=O)Nc1cccc(-c2n[nH]cc2-c2ccncc2)c1]

HPLC (254 nm): R$_t$: 4.81 min.

$^1$H NMR (401 MHz, DMSO-d$_6$), δ=13.26 (br. s., 1 H), 10.05 (br. s, 1 H), 8.39 (d, J=5.6 Hz, 2 H), 8.21 (br. s., 1 H), 7.67 (dd, J=1.6, 7.8 Hz, 1 H), 7.57 (t, J=8.4 Hz, 1 H), 7.05-7.37 (m, 7 H), 7.01 (t, J=7.7 Hz, 1 H), 3.82 (s, 3 H). HRMS (ESI) calcd for $C_{21}H_{18}N_4O_3S$ [M+H]$^+$ 407.1173, found 407.1176.

Furan-2-sulfonic acid [3-(4-pyridin-4-yl-1H-pyrazol-3-yl)-phenyl]amide (Cmpd. 6)

[(I)C, X=CH; R1, R2, R3, R4, R5, R6=H; m=0; R7'=2-furyl]

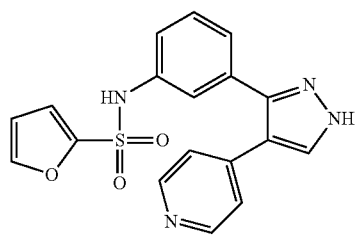 [SMILES: O=S(=O)(Nc1cccc(-c2n[nH]cc2-c2ccncc2)c1)c1ccco1]

HPLC (254 nm): R$_t$: 4.58 min.

$^1$H NMR (401 MHz, DMSO-d$_6$), δ=13.34 (br. s., 1 H), 10.70 (br. s., 1 H), 8.42-8.52 (m, 2 H), 8.26 (br. s., 1 H), 7.94 (dd, J=0.9, 1.8 Hz, 1 H), 6.95-7.45 (m, 7 H), 6.62 (dd, J=1.7, 3.5 Hz, 1 H). HRMS (ESI) calcd for $C_{18}H_{14}N_4O_3S$ [M+H]$^+$ 367.0860, found 367.0870.

Benzo[b]thiophene-3-sulfonic acid [3-(4-pyridin-4-yl-1H-pyrazol-3-yl)-phenyl]amide

[(I)C, X=CH; R1, R2, R3, R4, R5, R6=H; m=0; R7'=benzo[b]thiophen-3-yl]

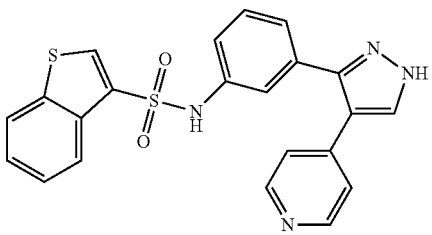 [SMILES: O=S(=O)(Nc1cccc(-c2n[nH]cc2-c2ccncc2)c1)c1csc2ccccc12]

HPLC (254 nm): $R_t$: 5.34 min.
$^1$H NMR (401 MHz, DMSO-$d_6$), δ=13.21 (br. s., 1 H), 10.69 (br. s., 1 H), 8.35 (br. s., 2 H), 7.86-8.26 (m, 3 H), 6.80-7.52 (m, 9 H). HRMS (ESI) calcd for $C_{22}H_{16}N_4O_2S_2$ [M+H]$^+$ 433.0788, found 433.0788.

Thiophene-3-sulfonic acid [3-(4-pyridin-4-yl-1H-pyrazol-3-yl)-phenyl]-amide (Cmpd. 7)

[(I)C, X=CH; R1, R2, R3, R4, R5, R6=H; m=0; R7'=3-thiophen-3-yl]

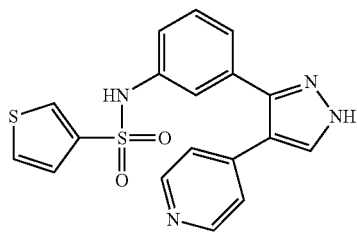 [SMILES: O=S(=O)(Nc1cccc(-c2n[nH]cc2-c2ccncc2)c1)c1ccsc1]

HPLC (254 nm): $R_t$: 4.71 min.
$^1$H NMR (401 MHz, DMSO-$d_6$), δ=13.28 (br. s., 1 H), 10.27 (br. s., 1 H), 8.43 (dd, J=1.3, 4.6 Hz, 2 H), 7.91-8.24 (m, 2 H), 7.71 (dd, J=3.0, 5.2 Hz, 1 H), 7.05-7.40 (m, 7 H). HRMS (ESI) calcd for $C_{18}H_{14}N_4O_2S_2$ [M+H]$^+$ 383.0631, found 383.0648.

Benzothiazole-6-sulfonic acid [3-(4-pyridin-4-yl-1H-pyrazol-3-yl)-phenyl]-amide

[(I)C, X=CH; R1, R2, R3, R4, R5, R6=H; m=0; R7'=benzothiazol-6-yl]

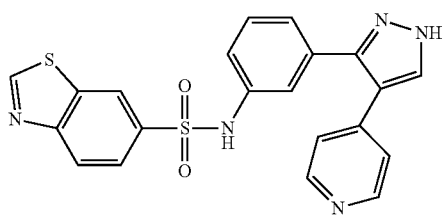 [SMILES: O=S(=O)(Nc1cccc(-c2n[nH]cc2-c2ccncc2)c1)c1ccc2ncsc2c1]

HPLC (254 nm): $R_t$: 4.63 min.
$^1$H NMR (401 MHz, DMSO-$d_6$), δ=13.26 (br. s., 1 H), 10.46 (br. s., 1 H), 9.61 (s, 1 H), 8.64 (br. s., 1 H), 8.33 (br. s., 2 H), 8.23 (d, J=8.7 Hz, 1 H), 8.19 (s, 1 H), 7.84 (dd, J=2.0, 8.7 Hz, 1 H), 7.00-7.41 (m, 6 H). HRMS (ESI) calcd for $C_{21}H_{15}N_5O_2S_2$ [M+H]$^+$ 434.0740, found 434.0755.

N-[3-(4-Pyridin-4-yl-1H-pyrazol-3-yl)-phenyl]-methanesulfonamide

[(I)C, X=CH; R1, R2, R3, R4, R5, R6=H; m=0; R7'=methyl]

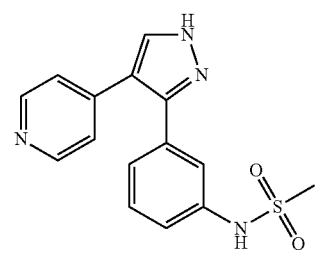 [SMILES: CS(=O)(=O)Nc1cccc(-c2n[nH]cc2-c2ccncc2)c1]

HPLC (254 nm): $R_t$: 3.14 min.
$^1$H NMR (401 MHz, DMSO-$d_6$) δ=13.39 (br. s., 1 H), 9.82 (br. s., 1 H), 8.51 (d, J=5.4 Hz, 2 H), 7.39 (d, J=5.2 Hz, 2 H), 7.24 (m, 2 H), 7.11 (m, 2 H), 6.98 (m, 2 H). HRMS (ESI) calcd for C15H14N4O2S [M+H]+ 315.091, found 315.0916.

N-[3-(4-Pyridin-4-yl-1H-pyrazol-3-yl)-phenyl]-benzenesulfonamide

[(I)C, X=CH; R1, R2, R3, R4, R5, R6=H; m=0; R7'=phenyl]

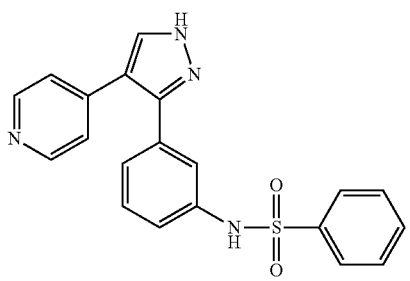 [SMILES: O=S(=O)(Nc1cccc(-c2n[nH]cc2-c2ccncc2)c1)c1ccccc1]

HPLC (254 nm): $R_t$: 4.02 min.
$^1$H NMR (401 MHz, DMSO-$d_6$) δ=13.27 (br. s., 1 H), 10.35 (br. s., 1 H), 8.40 (d, J=5.9 Hz, 2 H), 8.19 (br. s., 1 H), 7.68-7.72 (m, 2 H), 7.60 (t, J=7.2 Hz, 1 H), 7.52 (t, J=7.7 Hz, 2 H), 7.26 (br. s., 1 H), 7.13 (d, J=6.1 Hz, 2 H), 7.04 (d, J=7.2 Hz, 1 H). HRMS (ESI) calcd for C20H16N4O2S [M+H]+ 377.1067, found 377.1075

N-{4-[3-(4-Pyridin-4-yl-1H-pyrazol-3-yl)-phenylsulfamoyl]-phenyl}-acetamide

[(I)C, X=CH; R1, R2, R3, R4, R5, R6=H; m=0; R7'=4-acetylamino-phenyl]

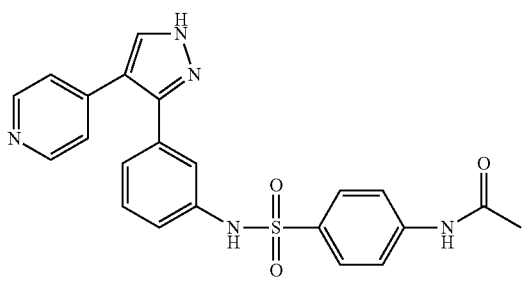 [SMILES: CC(=O)Nc1ccc(S(=O)(=O)Nc2cccc(-c3n[nH]cc3-c3ccncc3)c2)cc1]

HPLC (254 nm): $R_t$: 3.54 min.
$^1$H NMR (401 MHz, DMSO-d6) δ=13.29 (br. s., 1 H), 10.28 (s, 1 H), 8.38-8.41 (m, 2 H), 8.31 (s, 1 H), 8.11 (br. s., 1 H), 7.67-7.71 (m, 2 H), 7.61-7.64 (m, 2 H), 7.26 (t, J=7.0 Hz, 1 H), 7.11-7.14 (m, 2 H), 7.03 (d, J=7.6 Hz, 1 H), 2.05 (s, 3H). HRMS (ESI) calcd for C22H19N5O3S [M+H]+ 434.1282, found 434.1295

Thiophene-2-sulfonic acid [3-(4-pyridin-4-yl-1H-pyrazol-3-yl)-phenyl]-amide

[(I)C, X=CH; R1, R2, R3, R4, R5, R6=H; m=0; R7'=thiophen-2-yl]

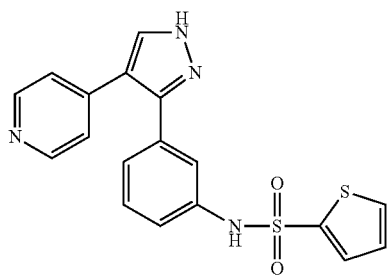 [SMILES: O=S(=O)(Nc1cccc(-c2n[nH]cc2-c2ccncc2)c1)c1cccs1]

HPLC (254 nm): $R_t$: 3.93 min.
$^1$H NMR (401 MHz, DMSO-d$_6$) δ=13.28 (br. s., 1 H), 8.41 (d, J=5.7 Hz, 2 H), 8.05-8.33 (m, 1 H), 7.83 (br. s., 1 H), 7.42 (br. s., 1 H), 7.22-7.35 (m, 1 H), 7.17 (d, J=5.2 Hz, 3 H), 6.91-7.12 (m, 2 H). HRMS (ESI) calcd for C18H14N4O2S2 [M+H]+ 383.0631, found 383.0633.

4-Methyl-isoxazole-5-sulfonic acid [3-(4-pyridin-4-yl-1H-pyrazol-3-yl)-phenyl]-amide

[(I)C, X=CH; R1, R2, R3, R4, R5, R6=H; m=0; R7'=4-methyl-isoxazole-5-yl]

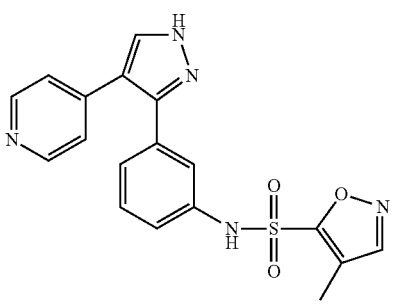 [SMILES: Cc1cnoc1S(=O)(=O)Nc1cccc(-c2n[nH]cc2-c2ccncc2)c1]

HPLC (254 nm): $R_t$: 3.93 min.

$^1$H NMR (401 MHz, DMSO-d$_6$) δ=13.44 (br. s., 1 H), 7.30 (br. s., 1 H), 7.12-7.25 (m, 2 H), 7.07 (s, 1 H), 6.86-7.04 (m, 1 H), 1.93 (d, J=6.2 Hz, 1 H), 1.76 (s, 3 H). HRMS (ESI) calcd for C18H15N5O3S [M+H]+ 382.0969, found 382.0976.

3-Methyl-3H-imidazole-4-sulfonic acid [3-(4-pyridin-4-yl-1H-pyrazol-3-yl)-phenyl]-amide

[(I)C, X=CH; R1, R2, R3, R4, R5, R6=H; m=0; R7'=3-methyl-3H-imidazole-4-yl]

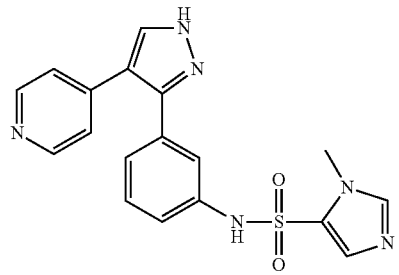 [SMILES: Cn1cncc1S(=O)(=O)Nc1cccc(-c2n[nH]cc2-c2ccncc2)c1]

HPLC (254 nm): $R_t$: 3.00 min.
$^1$H NMR (401 MHz, DMSO-d$_6$) δ=13.26 (br. s., 1 H), 10.25 (br. s., 1 H), 8.34-8.47 (m, 2 H), 7.72 (s, 2 H), 7.09-7.39 (m, 4 H), 7.01 (br. s., 1 H), 3.63 (s, 3 H). HRMS (ESI) calcd for C18H16N6O2S [M+H]+ 381.1128, found 381.1143.

3H-Imidazole-4-sulfonic acid [3-(4-pyridin-4-yl-1H-pyrazol-3-yl)-phenyl]-amide

[(I)C, X=CH; R1, R2, R3, R4, R5, R6=H; m=0; R7'=3H-imidazole-4-yl]

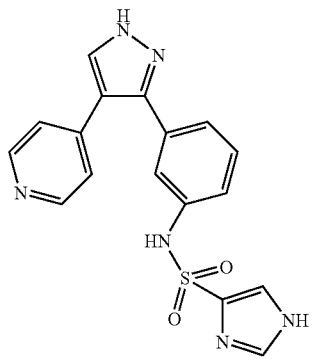 [SMILES: O=S(=O)(Nc1cccc(-c2n[nH]cc2-c2ccncc2)c1)c1c[nH]cn1]

HPLC (254 nm): $R_t$: 3.76 min.
$^1$H NMR (401 MHz, DMSO-d$_6$) δ=13.25 (s, 1H), 10.12 (s, 1H), 8.38 (dd, J=1.5, 4.6 Hz, 2 H), 8.07 (br. s., 1 H), 7.74 (d, J=1.1 Hz, 1 H), 7.63 (s, 1 H), 7.17-7.29 (m, 3H), 7.10-7.16 (m, 2 H), 6.95 (d, J=7.2 Hz, 1 H).

HRMS (ESI) calcd for C17H14N6O2S [M+H]+ 367.0972, found 367.0965.

1H-Pyrazole-4-sulfonic acid [3-(4-pyridin-4-yl-1H-pyrazol-3-yl)-phenyl]-amide

[(I)C, X=CH; R1, R2, R3, R4, R5, R6=H; m=0; R7'=pyrazol-4-yl]

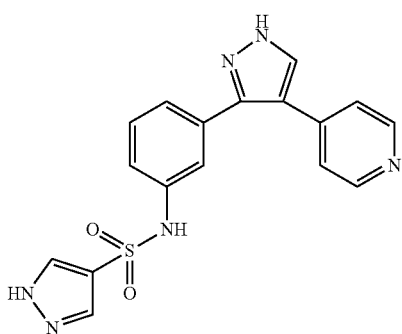 [SMILES: O=S(=O)(Nc1cccc(-c2n[nH]cc2-c2ccncc2)c1)c1cn[nH]c1]

HPLC (254 nm): R$_t$: 3.97 min.
$^1$H NMR (401 MHz, DMSO-d$_6$) δ=13.56 (br. s, 1H), 13.27 (br. s, 1H), 10.08 (s, 1H), 8.39-8.45 (m, 2H), 7.70-8.20 (m, 3H), 7.20-7.40 (m, 3H), 7.10-7.18 (m, 2H), 7-7.08 (m, 1H). HRMS (ESI) calcd for C17H14N6O2S [M+H]+ 367.0972, found 367.0962.

Example 3

3-(4-Pyridin-4-yl-1H-pyrazol-3-yl)-phenyl]-carbamic acid methyl ester

[(I)D, X=CH; R1, R2, R3, R4, R5, R6=H; m=0; R7'=methyl]

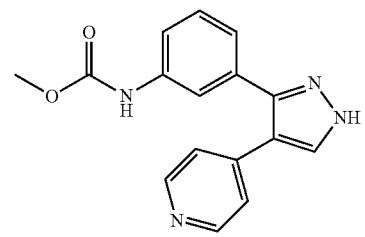 [SMILES: COC(=O)Nc1cccc(-c2n[nH]cc2-c2ccncc2)c1]

The above carbamate was prepared in an analogous way according to Methods G and M using a solid phase approach. The amino derivative immobilized on the resin obtained as described in Example 1 was derivatized and then cleaved from the resin as described below.
Method G
Step d
A solution of DIPEA (103 μL, 0.06 mmol) and the appropriate chloroformate (0.06 mmol) in 2 ml of DCM was added to a suspension of the resin obtained in Step a (Example 1) (100 mg, 0.01 mmol) in DCM (1 ml). The obtained suspension was stirred for 20 h at rt, filtered, washed with DCM, DMF and MeOH, dried under nitrogen flux and used in the next step.
Method M
Step a
A solution of 2 ml of TFA 20% in DCM were added to 100 mg of the resins obtained in Step c in the Quest vessels. The red suspension was stirred for 1 h then filtered and the resin washed twice with 1 ml of DCM. The filtered solution was evaporated under nitrogen flux to give the product as a crude solid, which was purified by preparative HPLC.
HPLC (254 nm): R$_t$: 3.25 min
$^1$H NMR (401 MHz, DMSO-d$_6$), δ=13.28 (br. s., 1 H), 9.72 (s, 1 H), 8.40-8.47 (m, 2 H), 8.11 (br. s., 1 H), 7.51-7.57 (m, 2 H), 7.34 (t, J=7.8 Hz, 1 H), 7.23-7.27 (m, 2 H), 7.02 (d, J=7.7 Hz, 1 H), 3.65 (s, 3 H). HRMS (ESI) calcd for C$_{16}$H$_{14}$N$_4$O$_2$ [M+H]$^+$ 295.1190, found 295.1184.

Operating in an analogous way the following carbamate was prepared:

[3-(4-Pyridin-4-yl-1H-pyrazol-3-yl)-phenyl]-carbamic acid 4-methoxy-phenyl ester

[(I)D, X=CH; R1, R2, R3, R4, R5, R6=H; m=0; R7'=4-methoxyphenyl]

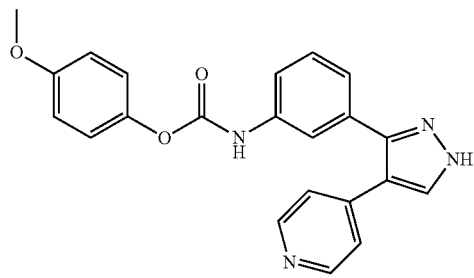 [SMILES: COc1ccc(OC(=O)Nc2cccc(-c3n[nH]cc3-c3ccncc3)c2)cc1]

HPLC (254 nm): R$_t$: 5.31 min.
$^1$H NMR (401 MHz, DMSO-d$_6$), δ=13.32 (br. s., 1 H), 8.86 (s., 1 H), 8.47 (d, J=6.0 Hz, 2 H), 7.61 (br. s., 1 H), 7.30-7.36 (m, 3 H), 7.10-7.16 (m, 3 H), 6.92-6.99 (m, 3 H), 6.88 (s, 1 H), 3.66 (s, 1 H). HRMS (ESI) calcd for C$_{22}$H$_{18}$N$_4$O$_3$ [M+H]$^+$ 387.1452, found 387.1470.

Example 4

1-Methyl-3-[3-(4-pyridin-4-yl-1H-pyrazol-3-yl)-phenyl]-urea

[(I)E, X=CH; R1, R2, R3, R4, R5, R6=H; m=0; Y=H; R7=methyl]

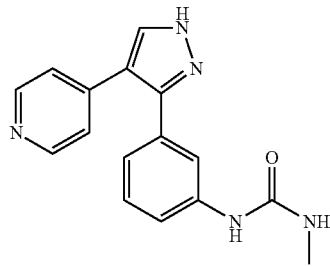 [SMILES: CNC(=O)Nc1cccc(-c2n[nH]cc2-c2ccncc2)c1]

The above urea was prepared according to Methods G and M using a solid phase approach, by substitution of an appropriate carbamate. The amino derivative immobilized on the resin obtained as described in Example 1 was derivatized and then cleaved from the resin as described below.
Method G
Step f
The resin obtained in Step c (Example 3) (0.125 mmol, 1 eq.) was suspended in dry DCM (2.5 ml) and methylamine (1.25 mmol, 10 eq.) was added. The final suspension was shaken for 24-48 h at room temperature in a sealed reactor. The resin was rinsed with dioxane (×2), DMF (×2), DCM (×2), DMF (×2), MeOH (×2) and DCM (×2). A solution of TFA 20% in DCM (2 ml) was added to the resin in the Quest vessels. The red suspension was shaken for 1 h then filtered and the resin washed twice with 1 ml of DCM. The filtered solution was evaporated under nitrogen flux to give the products as a an oil, which was purified by preparative HPLC.

Method M

Step a

A solution of TFA 20% in DCM (2 mL) was added to 100 mg of the resins obtained in Step i in the Quest vessels. The red suspension was stirred for 1 h then filtered and the resin washed twice with 1 ml of DCM. The filtered solution was evaporated under nitrogen flux to give the product as a crude solid, which was purified by preparative HPLC.

HPLC (254 nm): $R_t$: 2.91 min.

$^1$H NMR (401 MHz, DMSO-d6) δ=13.33 and 13.24 (2br. s., 1 H, tautomers), 8.62 and 8.52 (2br. s., 1 H, tautomers), 8.42-8.45 (m, 2 H), 8.23 and 7.95 (2br. s., 1 H, tautomers), 7.39-7.51 (m, 1 H), 7.18-7.37 (m, 3 H), 6.78-7.07 (m, 1 H), 5.98 (d, J=14.5 Hz, 1 H), 2.62 (d, J=4.6 Hz, 3 H). HRMS (ESI) calcd for C16H15N5O [M+H]+ 294.135, found 294.1346.

Operating in an analogous way the following urea was prepared:

[3-(4-Pyridin-4-yl-1H-pyrazol-3-yl)-phenyl]-urea

[(I)E, X=CH; R1, R2, R3, R4, R5, R6=H; m=0; Y=H; R7=H]

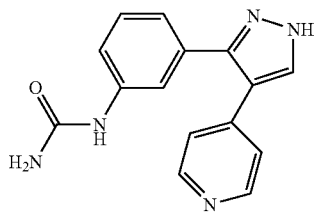 [SMILES: NC(=O)Nc1cccc(-c2n[nH]cc2-c2ccncc2)c1]

HPLC (254 nm): $R_t$: 2.54 min.

$^1$H NMR (401 MHz, DMSO-d$_6$), δ=13.23 (br. s., 1 H), 8.61 (s, 1 H), 8.42-8.45 (m, 2 H), 8.09 (br. s., 1 H), 7.46-7.50 (m, 2 H), 7.24-7.29 (m, 3 H), 6.89-6.96 (m, 1 H), 5.84 (s, 2 H). HRMS (ESI) calcd for C$_{15}$H$_{13}$N$_5$O [M+H]$^+$ 280.1193, found 280.1201.

Example 5

N-[3-(4-Pyridin-4-yl-1H-pyrazol-3-yl)-phenyl]-acetamide

[(I)G, X=CH; R1, R2, R3, R4, R5, R6=H; m=0; R7=methyl]

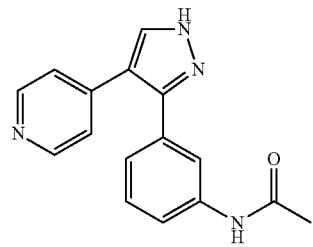 [SMILES: CC(=O)Nc1cccc(-c2n[nH]cc2-c2ccncc2)c1]

The above amide was prepared according to Methods G and M using a solid phase approach, the amino derivative immobilized on the resin obtained as described in Example 1 was derivatized and then cleaved from the resin as described below.

Method G

Step h

Acetic acid (0.5 mmol, 5 eq.) was added to a solution of DIPEA (0.6 mmol, 6 eq.) and PyBOP (0.5 mmol, 5 eq.) in dry DCM (2.5 ml) and the solution was stirred for 30 min, then the mixture was added to resin (0.1 mmol, 1 eq.) and shaken at 25° C. in a reactor (Quest 210™ or Miniblocks™). The resin was rinsed with DCM (×2), DMF (×2), MeOH (×2), DMF (×2) and DCM (×2) and then dried in nitrogen flux. A solution of TFA 20% in DCM (2 mL) was added to the resin in the Quest vessels. The red suspension was shaken for 1 h then filtered and the resin washed twice with 1 ml of DCM. The filtered solution was evaporated under nitrogen flux to give the products as an oil, which was purified by preparative HPLC.

Method M

Step a

A solution of TFA 20% in DCM (2 mL) was added to 100 mg of the resins obtained in Step g in the Quest vessels. The red suspension was stirred for 1 h then filtered and the resin washed twice with 1 ml of DCM. The filtered solution was evaporated under nitrogen flux to give the product as a crude solid, which was purified by preparative HPLC.

HPLC (254 nm): $R_t$: 2.98 min.

$^1$H NMR (401 MHz, DMSO-d$_6$) δ=13.41 and 13.31 (2br. s., 1 H, tautomers), 10.06 and 9.97 (2br. s., 1 H, tautomers), 8.46 (d, J=4.02 Hz, 2 H), 8.27 and 7.99 (2br. s., 1 H, tautomers), 7.69 (br. s., 1 H), 7.31 (br. s., 2 H), 7.05 (br. s., 1 H), 2.03 (s, 3 H). HRMS (ESI) calcd for C16H14N4O [M+H]+ 279.1241, found 279.1240

Operating in an analogous way the following amides were prepared:

5-Oxo-pyrrolidine-2-carboxylic acid [3-(4-pyridin-4-yl-1H-pyrazol-3-yl)-phenyl]-amide

[(I)G, X=CH; R1, R2, R3, R4, R5, R6=H; m=0; R7=5-oxo-pyrrolidin-2-yl]

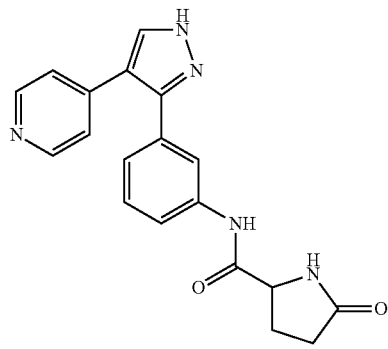 [SMILES: O=C1CCC(C(=O)Nc2cccc(-c3n[nH]cc3-c3ccncc3)c2)N1]

HPLC (254 nm): $R_t$: 5.50 min.

$^1$H NMR (401 MHz, DMSO-d$_6$) δ=13.31 (br. s., 1 H), 10.11 (br. s., 1 H), 8.42-8.44 (m, 2 H), 8.30 (s, 1 H), 7.86 (s, 1 H), 7.25 (d, J=6.1 Hz, 2 H), 7.08 (br. s., 1 H), 4.17 (dd, J=4.3, 8.6 Hz, 1 H), 2.26-2.40 (m, 1 H), 2.08-2.25 (m, 2 H), 1.91-2.03 (m, 1 H). HRMS (ESI) calcd for C19H17N5O2 [M+H]+ 348.1455, found 348.1462.

Cyclopropanecarboxylic acid [3-(4-pyridin-4-yl-1H-pyrazol-3-yl)-phenyl]-amide

[(I)G, X=CH; R1, R2, R3, R4, R5, R6=H; m=0; R7=cyclopropyl]

99

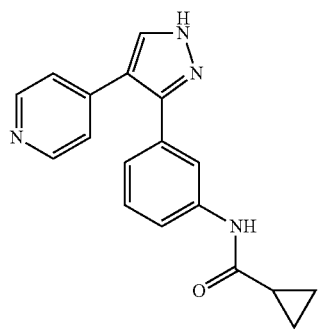 [SMILES: O=C(Nc1cccc(-c2n[nH]cc2-c2ccncc2)c1)C1CC1]

HPLC (254 nm): R$_t$: 3.43 min.

$^1$H NMR (401 MHz, DMSO-d6) δ=13.36 and 13.27 (2br. s., 1 H, tautomers), 10.29 and 10.20 (2br. s., 1 H, tautomers), 8.43 (d, J=6.1 Hz, 2 H), 8.23 (s, 1 H), 7.68 (br. s., 1 H), 7.25 (d, J=5.0 Hz, 2 H), 1.76 (quin, J=6.2 Hz, 1 H), 0.69-0.84 (m, 4 H). HRMS (ESI) calcd for C18H16N4O [M+H]+ 305.1397, found 305.1403.

Pyridine-2-carboxylic acid [3-(4-pyridin-4-yl-1H-pyrazol-3-yl)-phenyl]-amide

[(I)G, X=CH; R1, R2, R3, R4, R5, R6=H; m=0; R7=2-pyridyl]

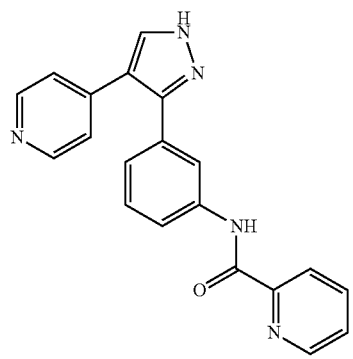 [SMILES: O=C(Nc1cccc(-c2n[nH]cc2-c2ccncc2)c1)c1ccccn1]

HPLC (254 nm): R$_t$: 4.01 min.

$^1$H NMR (401 MHz, DMSO-d$_6$) δ=13.41 and 13.31 (2br. s., 1 H, tautomers), 10.77 and 10.68 (2br. s., 1 H, tautomers), 8.74 (dt, J=0.8, 4.0 Hz, 1 H), 8.42-8.48 (m, 2 H), 8.27 (br. s., 1 H), 8.13-8.16 (m, 1 H), 8.10 (br. s., 1 H), 8.04-8.10 (m, 1 H), 7.99 (br. s., 1 H), 7.90 (br. s., 1 H), 7.68 (ddd, J=1.2, 4.9, 7.4 Hz, 1 H), 7.29 (d, J=3.5 Hz, 2 H), 7.14 (br. s., 1 H). HRMS (ESI) calcd for C20H15N5O [M+H]+ 342.135, found 342.1349

Thiophene-2-carboxylic acid [3-(4-pyridin-4-yl-1H-pyrazol-3-yl)-phenyl]-amide

[(I)G, X=CH; R1, R2, R3, R4, R5, R6=H; m=0; R7=2-thiofenyl]

100

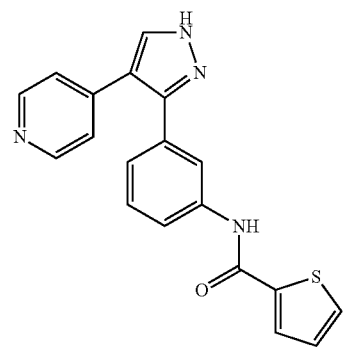 [SMILES: O=C(Nc1cccc(-c2n[nH]cc2-c2ccncc2)c1)c1cccs1]

HPLC (254 nm): R$_t$: 3.99 min $^1$H NMR (401 MHz, DMSO-d6) δ=13.41 and 13.32 (2br. s., 1 H, tautomers), 10.32 and 10.28 (2br. s., 1 H, tautomers), 8.45 (dd, J=1.4, 4.7 Hz, 2 H), 8.26 (br.s., 1 H), 8.02 (d, J=3.2 Hz, 1 H), 7.87 (d, J=4.9 Hz, 2 H), 7.36 (br. s., 1 H), 7.28 (br. s., 2 H), 7.23 (dd, J=3.8, 4.9 Hz, 1 H), 7.09 (br. s., 1 H). HRMS (ESI) calcd for C19H14N4O S [M+H]+ 347.0961, found 347.0969.

N-[3-(4-Pyridin-4-yl-1H-pyrazol-3-yl)-phenyl]-2-ureido-acetamide

[(I)G, X=CH; R1, R2, R3, R4, R5, R6=H; m=0; R7=ureidomethyl]

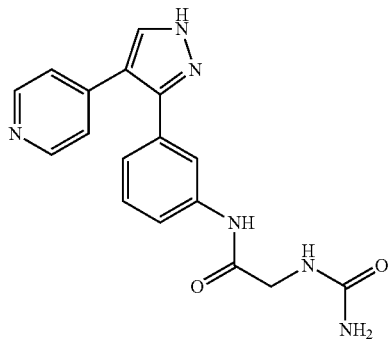 [SMILES: NC(=O)NCC(=O)Nc1cccc(-c2n[nH]cc2-c2ccncc2)c1]

HPLC (254 nm): R$_t$: 2.48 min.

$^1$H NMR (401 MHz, DMSO-d6) δ=13.39 and 13.29 (2br. s., 1 H, tautomers), 9.98 (br.s., 1 H), 8.37-8.52 (m, 1 H), 8.24 and 7.97 (2br. s., 1 H, tautomers), 7.70 (s, 1 H), 7.26 (d, J=5.9 Hz, 1 H), 5.67 (s, 1 H), 4.08 (br. s., 1 H), 3.80 (d, J=5.7 Hz, 1 H), 3.18 (s, 2 H). HRMS (ESI) calcd for C17H16N6O2 [M+H]$^+$ 337.1408, found 337.1417.

Example 6

1-[3-(4-Pyridin-4-yl-1H-pyrazol-3-yl)-phenyl]-3-(4-trifluoromethyl-phenyl)-urea (Cmpd. 1)

[(I)E, X=CH; R1, R2, R3, R4, R5, R6=H; m=0; Y=H; R7=4-trifluoromethyl-phenyl]

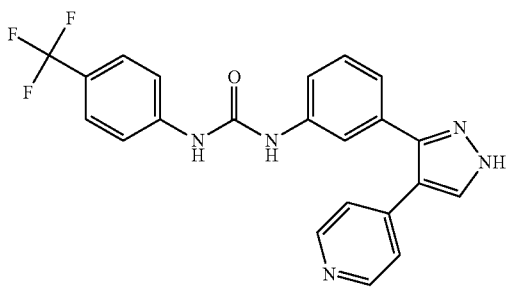 [SMILES: O=C(Nc1ccc(C(F)(F)F)cc1)Nc1cccc(-c2n[nH]cc2-c2ccncc2)c1]

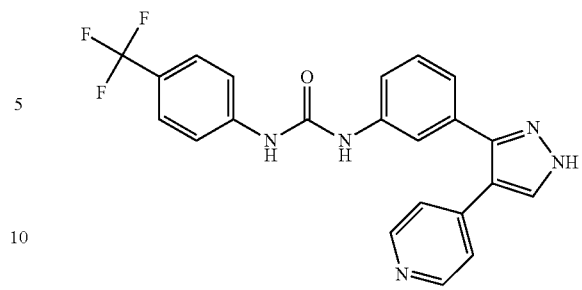

Ureas can also be prepared in solution, according to Method G, as described below.

Method G

Step a 3-(4-Pyridin-4-yl-1H-pyrazol-3-yl)-phenylamine

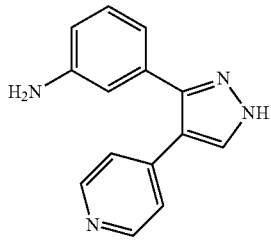 [SMILES: Nc1cccc(-c2n[nH]cc2-c2ccncc2)c1]

1.27 g (4.77 mmol) of 4-[3-(3-nitro-phenyl)-1H-pyrazol-4-yl]-pyridine was suspended in methanol (200 mL). Pd/C 10% (250 mg) was added and the mixture was agitated under hydrogen pressure (50 psi) in a Parr apparatus at room temperature for 4 hours. The catalyst was then filtered on a Celite pad and washed with methanol. The filtrate was concentrated to dryness to obtain 1.1 g (98% yield) of 3-(4-pyridin-4-yl-1H-pyrazol-3-yl)-phenylamine as an off-white solid.

HPLC (254 nm): $R_t$: 2.91 min.

$^1$H NMR (401 MHz, DMSO-d$_6$) (selected signals) δ=8.67 (d, J=6.6 Hz, 2 H), 8.40 (br. s., 1 H), 7.77 (d, J=6.3 Hz, 2 H), 7.19 (t, J=7.7 Hz, 1 H), 6.76 (m, 1 H), 6.75 (m, 1 H), 6.65 (d, J=6.6 Hz, 1 H).

HRMS (ESI) calcd for C14H12N4 [M+H]+ 237.1135, found 237.1134.

Step e

1-[3-(4-Pyridin-4-yl-1H-pyrazol-3-yl)-phenyl]-3-(4-trifluoromethyl-phenyl)-urea

[(I)E, X=CH; R1, R2, R3, R4, R5, R6=H; m=0; Y=H; R7=4-trifluoromethyl-phenyl]

To 3-(4-Pyridin-4-yl-1H-pyrazol-3-yl)-phenylamine (700 mg, 3 mmol) in anhydrous pyridine (15 mL) at 0° C. 4-trifluoromethylphenylisocyanate (420 μL, 3 mmol) was added. The reaction was stirred for 2 hours at 0° C. under nitrogen atmosphere to give a mixture of monourea and bis-urea as regioisomeric mixture. Solvent was removed under reduced pressure. The residue was dissolved in methanol (15 mL) and triethylamine (1 mL, 7.8 mmol) was added and the reaction was stirred at room temperature overnight. After this time only the monourea could be detected by HPLC/MS. The solvent was removed under reduced pressure and the residue was dissolved in ethyl acetate (100 mL) and washed successively with water (3×50 mL). The crude was purified by silica gel column chromatography (DCM/methanol 9:1) to give the desired product as a white solid (75%).

HPLC (254 nm): $R_t$: 5.92 min.

$^1$H NMR (401 MHz, DMSO-d$_6$), δ=13.40 and 13.29 (2br s, 1 H, tautomers), 9.10 and 9.05 (2br s, 1 H, tautomers), 8.93 and 8.84 (2br s, 1 H, tautomers), 8.44-8.48 (m, 2 H), 8.25 and 7.96 (2br s, 1 H, tautomers), 7.60-7.67 (m, 4 H), 7.26-7.56 (m, 5 H), 7.00-7.09 (m, 1 H). HRMS (ESI) calcd for C$_{22}$H$_{16}$F$_3$N$_5$O [M+H]+ 424.1380, found 424.1367.

Operating in an analogous way the following product was prepared:

1-[3-(4-Pyridin-4-yl-1H-pyrazol-3-yl)-phenyl]-3-thiophen-3-yl-urea

[(I)E, X=CH; R1, R2, R3, R4, R5, R6=H; m=0; Y=H; R7=thiophen-3-yl]

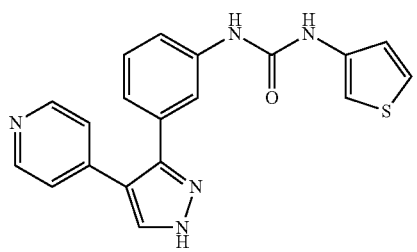 [SMILES: O=C(Nc1ccsc1)Nc1cccc(-c2n[nH]cc2-c2ccncc2)c1]

HPLC (254 nm): $R_t$: 4.90 min.

$^1$H NMR (401 MHz, DMSO-d$_6$) (selected signals) δ=13.39 and 13.27 (2br s, 1 H, tautomers), 8.94 and 8.88 (2br s, 1 H, tautomers), 8.76 and 8.66 (2br s, 1 H, tautomers), 8.45 and 8.42 (2 m, 2 H, tautomers), 7.96 and 7.92 (2br s, 1 H, tautomers), 7.43 (dd, J=5.12, 3.29 Hz, 1H), 7.26 (dd, J=3.29, 1.34 Hz, 1H), 7.25-7.32 (m, 2 H), 7.28 (br s, 1 H), 7.05 (dd, J=5.12, 1.34 Hz, 1H). HRMS (ESI) calcd for C19H15N5OS [M+H]+ 362.107, found 362.1066.

Example 7

1-[3-(4-Pyridin-4-yl-1H-pyrazol-3-yl)-phenyl]-3-(4-trifluoromethyl-phenyl)-thiourea

[(I)F, X=CH; R1, R2, R3, R4, R5, R6=H; m=0; R7'=4-trifluoromethylphenyl]

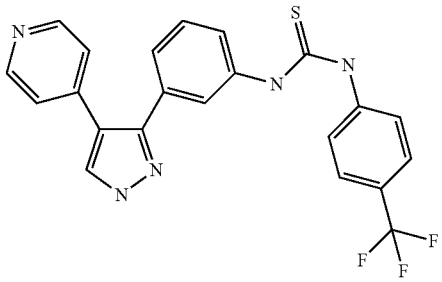 [SMILES: FC(F)(F)c1ccc(NC(=S)Nc2cccc(-c3n[nH]cc3-c3ccncc3)c2)cc1]

The above compound was prepared according to Method G (Step g) as described below:

To a solution of 3-(4-pyridin-4-yl-1H-pyrazol-3-yl)-phenylamine (31 mg, 0.131 mmol) (prepared as described in Example 6) in a dichloromethane/acetone (1:1,5 mL) (4-trifluoromethyl-phenyl)-thioisocyanate (32 mg, 0.157 mmol) was added. The mixture was stirred at room temperature overnight and then evaporated to dryness. The residue taken up with methanol (5 mL), TEA (2 mL) was added, and the solution was stirred at room temperature overnight. After evaporation to dryness the compound was purified by flash chromatography, over silica gel, using dichloromethane-methanol (98:2) as the eluant system. 1-[3-(4-Pyridin-4-yl-1H-pyrazol-3-yl)-phenyl]-3-(4-trifluoromethyl-phenyl)-thiourea was obtained as a colorless solid (15 mg, 87%)

$^1$H NMR (401 MHz, DMSO-d6) δ=13.41, 13.29 (ds, 1H), 10.10 (br. s., 2 H), 8.43 (d, J=6.1 Hz, 2 H), 8.24, 7.94 (ds, 1H), 7.76-7.73 (m, 4 H), 7.58-7.20 (m, 6 H). HRMS (ESI) calcd for C22H17F3N5S [M+H]+ 440.1151, found 440.1146.

Example 8

N-[3-(4-Pyridin-4-yl-1H-pyrazol-3-yl)-phenyl]-2-(4-trifluoromethyl-phenyl)-acetamide (Cmpd. 16)

[(I)G, X=CH; R1, R2, R3, R4, R5, R6=H; m=0; R7=4-trifluoromethylphen-1-ylmethyl]

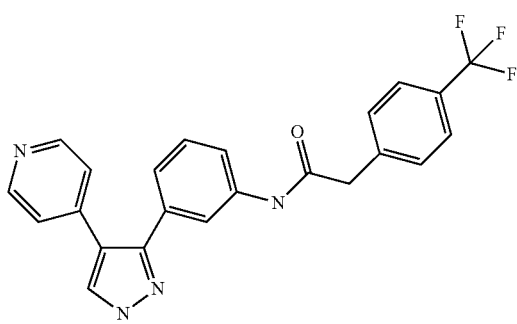 [SMILES: O=C(Cc1ccc(C(F)(F)F)cc1)Nc1cccc(-c2n[nH]cc2-c2ccncc2)c1]

Method G
Step h

To a suspension of 3-(4-pyridin-4-yl-1H-pyrazol-3-yl)-phenylamine (80 mg, 0.339 mmol) (prepared as described in Example 6) in dichloromethane (8 mL), were added in the following order: (4-trifluoromethyl-phenyl)-acetic acid (138 mg, 0.678 mmol), DIPEA (131 mg, 174 uL, 1.017 mol) and TBTU (326 mg, 1.017 mol). The reaction mixture was stirred at room temperature for 4 hours. Then it was poured into a solution of saturated NaHCO$_3$, the phases separated, and the organic phase was washed twice with saturated NaHCO$_3$, and twice with water. The organic solvent was evaporated, and the residue taken up with methanol (5 mL). TEA (2 mL) was added, and the solution was stirred at room temperature overnight. After evaporation to dryness the compound was purified by flash chromatography, over silica gel, using dichloromethane-methanol (97:3) as the eluant system. N-[3-(4-Pyridin-4-yl-1H-pyrazol-3-yl)-phenyl]-2-(4-trifluoromethyl-phenyl)-acetamide was obtained as a colorless solid (125 mg, 87%).

$^1$H NMR (401 MHz, DMSO-d$_6$) δ=13.37, 13.27 (ds, 1H), 10.36, 10.27 (ds, 1H), 8.43 (d, J=5.9 Hz, 2 H), 8.23, 7.94 (ds, 1H), 7.72-7.02 (m, 8H), 3.76 (s, 2 H). HRMS (ESI) calcd for C23H17F3N4O [M+H]+ 423.1427, found 423.1427.

Operating in analogous way the following compounds were prepared:

1-(4-Trifluoromethyl-phenyl)-cyclopropanecarboxylic acid [3-(4-pyridin-4-yl-1H-pyrazol-3-yl)-phenyl]-amide

[(I)G, X=CH; R1, R2, R3, R4, R5, R6=H; m=0; R7=1-(4-trifluoromethylphenyl)-cycloprop-1-yl]

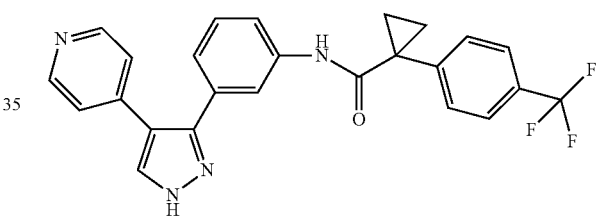

$^1$H-NMR (401 MHz, DMSO-d$_6$) δ=13.25 (s, 1H), 9.5 (s, 1H), 8.42 (dd, J=1.4, 4.7 Hz, 2 H), 8.23 (s, 1H), 7.65-7.70 (m, 4 H), 7.52-7.58 (m, 4 H), 7.20-7.26 (m, 2 H), 1.46-1.53 (m, 2 H), 1.15-1.22 (m, 2 H).

N-[3-(4-Pyridin-4-yl-1H-pyrazol-3-yl)-phenyl]-2-(4-trifluoromethyl-phenyl)-propionamide

[(I)G, X=CH; R1, R2, R3, R4, R5, R6=H; m=0; R7=1-(4-trifluoromethylphenyl)-ethyl]

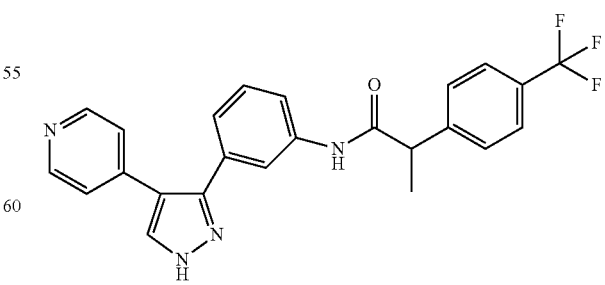

HPLC (254 nm): R$_t$: 6.07 min
$^1$H NMR (401 MHz, DMSO-d6) δ=13.27 (s, 1 H), 10.18 (s, 1 H), 8.39-8.45 (m, 2 H), 8.22 (s, 1 H), 7.53-7.79 (m, 6 H), 7.27-7.46 (m, 1 H), 7.20-7.26 (m, 2 H), 6.90-7.12 (m, 1 H), 3.94 (q, J=7.1 Hz, 1 H), 1.43 (d, J=7.0 Hz, 3 H).

HRMS (ESI) calcd for [M+H]+ 437.1584, found 4370.5588

Example 9

1-(4-Chloro-3-trifluoromethyl-phenyl)-3-{3-[1-(2-fluoro-ethyl)-4-pyridin-4-yl-1H-pyrazol-3-yl]-phenyl}-urea (Cmpd. 5)

[(I)E, X=CH; R2, R3, R4, R5, R6=H; m=2, R1=F; Y=H; R7=4-chloro-3-trifluoromethyl-1-phenyl]

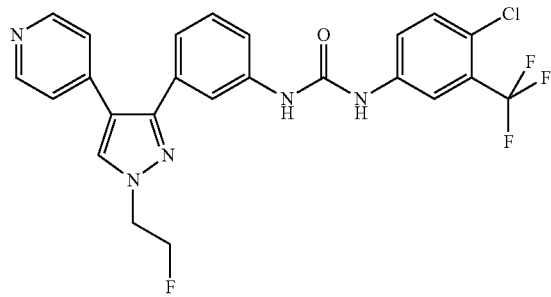 [SMILES: O=C(Nc1cccc(-c2nn(CCF)cc2-c2ccncc2)c1)Nc1ccc(Cl)c(C(F)(F)F)c1]

Method A

Step h

4-[1-(2-fluoroethyl)-3-(3-nitrophenyl)-1H-pyrazol-4-yl]pyridine

To 4-[3-(3-nitrophenyl)-1H-pyrazol-4-yl]pyridine (100 mg, 0.37 mmol) in N,N-dimethylformamide (3.7 mL) 1-iodo-2-fluoroethane (128 mg, 0.75 mmol) and cesium carbonate (240 mg, 0.74 mmol) were added. The mixture was stirred at 50° C. for 3 hours to give the alkylated product as a 5:1 regiosomeric mixture (at 254 nm). Solvent was removed under reduced pressure and the residue was dissolved in ethyl acetate (100 mL) and washed successively with saturated NaHCO$_3$ solution (3×50 mL), and brine (1×50 mL). The organic solution was dried over Na$_2$SO$_4$ and filtered, and the solvent was evaporated under reduced pressure. The major regioisomer was isolated by reverse phase column chromatography in 72% yield.

Method G

Step a

3-[1-(2-fluoroethyl)-4-(pyridin-4-yl)-1H-pyrazol-3-yl]aniline

To 4-[1-(2-fluoroethyl)-3-(3-nitrophenyl)-1H-pyrazol-4-yl]pyridine in a solution of dioxane/water (5:1) ammonium chloride (144 mg, 2.7 mmol) and zinc (70 mg, 1.08 mmol) were added. The reaction was stirred at 80° C. After two hours the reaction was allowed to cool to room temperature and it was poured into Na$_2$HPO$_4$ (pH=8) solution and extracted with ethyl acetate. The organic layer was washed with brine (1×50 mL), dried over Na$_2$SO$_4$ and filtered. The filtrate was concentrated under reduced pressure and it was used in the next step without further purification.

Step e 1-(4-Chloro-3-trifluoromethyl-phenyl)-3-{3-[1-(2-fluoro-ethyl)-4-pyridin-4-yl-1H-pyrazol-3-yl]-phenyl}-urea

[(I)E, X=CH; R2, R3, R4, R5, R6=H; m=2; R1=F; Y=H; R7=4-chloro-3-trifluoromethyl-1-phenyl]

To 3-[1-(2-fluoroethyl)-4-(pyridin-4-yl)-1H-pyrazol-3-yl] aniline (80 mg, 0.28 mmol) in anhydrous methylene chloride (1.5 mL) 4-chloro-3-(trifluoromethyl)phenyl isocyanate (81.5 mg, 0.37 mmol) was added. The reaction was stirred at room temperature under nitrogen atmosphere for two hours. The solvent was removed under reduced pressure and the crude was purified by silica gel column chromatography (7:3 ethyl acetate/hexane, grading to 100% acetate) to give the desired product as white solid in 64% yield over two steps.

HPLC (254 nm): R$_t$: 6.66 min.

$^1$H NMR (401 MHz, DMSO-d$_6$) δ=9.10 (s, 1 H), 8.91 (s, 1 H), 8.48 (d, J=5.9 Hz, 2 H), 8.28 (s, 1 H), 8.09 (d, J=1.8 Hz, 1 H), 7.61-7.63 (m, 2 H), 7.58 (t, J=1.8 Hz, 1 H), 7.46-7.54 (m, 1 H), 7.31 (t, J=7.9 Hz, 1 H), 7.23-7.28 (m, 2 H), 7.01 (dt, J=1.3, 7.6 Hz, 1 H), 4.75-4.99 (m, 2 H), 4.32-4.61 (m, 2 H). HRMS (ESI) calcd for C24H18ClF4N5O [M+H]+ 504.1209, found 504.1195.

Operating in an analogous way the following compounds were prepared:

1-(4-Chloro-3-trifluoromethyl-phenyl)-3-{3-[4-pyridin-4-yl-1-(2,2,2-trifluoro-ethyl)-1H-pyrazol-3-yl]-phenyl}-urea

[(I)E, X=CH; R2, R3, R4, R5, R6=H; m=1; R1=CF3; Y=H; R7=4-chloro-3-trifluoromethyl-1-phenyl]

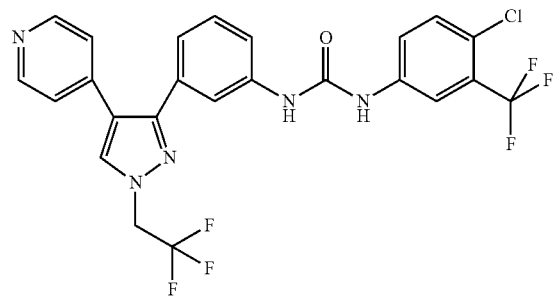 [SMILES: O=C(Nc1cccc(-c2nn(CC(F)(F)F)cc2-c2ccncc2)c1)Nc1ccc(Cl)c(C(F)(F)F)c1]

HPLC (254 nm): R$_t$: 7.06 min.

$^1$H NMR (401 MHz, DMSO-d$_6$) δ=9.11 (s, 1 H), 8.94 (s, 1 H), 8.48-8.56 (m, 2 H), 8.35 (s, 1 H), 8.09 (d, J=1.7 Hz, 1 H), 7.58-7.64 (m, 3 H), 7.48-7.55 (m, 1 H), 7.32 (t, J=7.9 Hz, 1 H), 7.26-7.29 (m, 2 H), 6.99 (ddd, J=1.0, 1.3, 7.9 Hz, 1 H), 5.18-5.32 (m, 2 H). HRMS (ESI) calcd for C24H16ClF6N5O [M+H]+ 540.1021, found 540.101.

1-(4-Chloro-3-trifluoromethyl-phenyl)-3-[3-(1-cyclobutyl-4-pyridin-4-yl-1H-pyrazol-3-yl)-phenyl]-urea

[(I)E, X=CH; R2, R3, R4, R5, R6=H; m=0; R1=cyclobutyl; Y=H; R7=4-chloro-3-trifluoromethyl-1-phenyl]

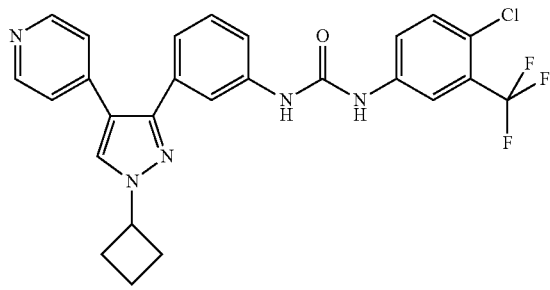 [SMILES: O=C(Nc1cccc(-c2nn(C3CCC3)cc2-c2ccncc2)c1)Nc1ccc(Cl)c(C(F)(F)F)c1]

HPLC (254 nm): $R_t$: 7.31 min.

$^1$H NMR (401 MHz, DMSO-d6) δ=9.10 (s, 1 H), 8.92 (s, 1 H), 8.46 (d, J=6.0 Hz, 2 H), 8.34 (s, 1 H), 8.09 (d, J=2.0 Hz, 1 H), 7.59-7.64 (m, 2 H), 7.51-7.56 (m, 2 H), 7.31 (t, J=7.9 Hz, 1 H), 7.24-7.28 (m, 2 H), 7.01 (dt, J=1.2, 7.7 Hz, 1 H), 4.91 (quin, J=8.4 Hz, 1 H), 2.55-2.63 (m, 2 H), 2.38-2.49 (m, 2 H), 1.77-1.90 (m, 2 H). HRMS (ESI) calcd for C26H21ClF3N5O [M+H]+ 512.146, found 512.1453.

1-[3-(1-But-3-enyl-4-pyridin-4-yl-1H-pyrazol-3-yl)-phenyl]-3-(4-chloro-3-trifluoromethyl-phenyl)-urea

[(I)E, X=CH; R2, R3, R4, R5, R6=H; m=2; R1=vinyl; Y=H; R7=4-chloro-3-trifluoromethyl-phenyl]

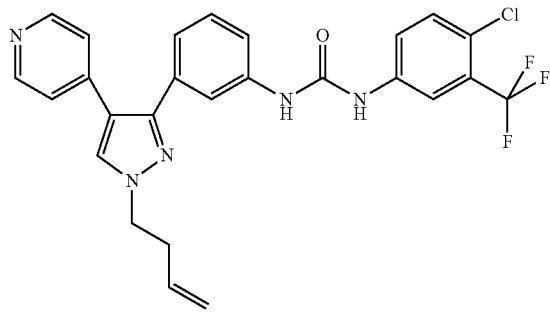 [SMILES: C=CCCn1cc(-c2ccncc2)c(-c2cccc(NC(=O)Nc3ccc(Cl)c(C(F)(F)F)c3)c2)n1]

HPLC (254 nm): $R_t$: 7.14 min.

$^1$H NMR (401 MHz, DMSO-d6) δ=9.10 (s, 1 H), 8.90 (s, 1 H), 8.51 (br. s., 2 H), 8.25 (s, 1 H), 8.09 (d, J=1.8 Hz, 1 H), 7.59-7.67 (m, 2 H), 7.56 (t, J=1.7 Hz, 1 H), 7.47-7.53 (m, 1 H), 7.31 (t, J=7.9 Hz, 1 H), 7.27 (br. s., 2 H), 6.99-7.02 (m, 1 H), 5.79-5.93 (m, J=17.1, 10.3, 6.7, 6.7 Hz, 1 H), 5.11-5.19 (m, J=17.3, 1.7, 1.7, 1.5 Hz, 1 H), 5.05-5.10 (m, 1 H), 4.26 (t, J=7.1 Hz, 2 H), 2.60-2.71 (m, 2 H). HRMS (ESI) calcd for C26H21ClF3N5O [M+H]+ 512.146, found 512.1453.

Example 10

1-[3-(1-Isobutyl-4-pyridin-4-yl-1H-pyrazol-3-yl)-phenyl]-3-(4-trifluoromethyl-phenyl)-urea (Cmpd. 50)

[(I)E, X=CH; R2, R3, R4, R5, R6=H; m=1; R1=i-propyl; Y=H; R7=4-trifluoromethyl-phenyl]

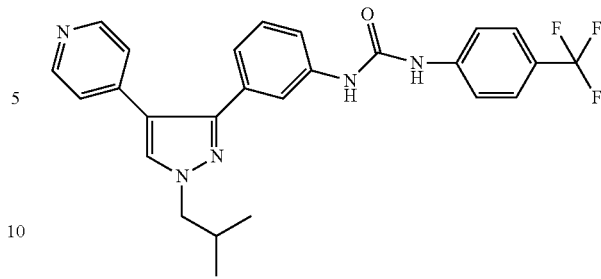

To 1-[3-(4-pyridin-4-yl-1H-pyrazol-3-yl)-phenyl]-3-(4-trifluoromethyl-phenyl)-urea (prepared as described in Example 6) (100 mg, 0.24 mmol) in N,N-dimethylformamide (1 mL) were added 1-iodo-2-methyl-propane (54μL, 0.47 mmol) and cesium carbonate (152 mg, 0.47 mmol). The reaction was stirred at 50° C. for three hours then poured into water and extracted with ethyl acetate (50 mL). The organic layer was washed with brine, dried over anhydrous sodium sulphate, filtered and concentrated. The two regioisomers of the pyrazole were isolated by silica gel column chromatography (DCM/ethanol 98:2).

HPLC (254 nm): $R_t$: 6.14 min.

$^1$H NMR (401 MHz, DMSO-$d_6$) δ=9.03 (s, 1 H), 8.85 (s, 1 H), 8.46 (d, J=6.1 Hz, 2 H), 8.22 (s, 1 H), 7.59-7.67 (m, 4 H), 7.56 (t, J=1.8 Hz, 1 H), 7.45-7.55 (m, 1 H), 7.30 (t, J=7.9 Hz, 1 H), 7.25 (d, J=6.1 Hz, 2 H), 6.99 (ddd, J=1.0, 1.5, 7.6 Hz, 1 H), 3.99 (d, J=7.1 Hz, 2 H), 2.20 (spt, J=6.8 Hz, 1 H), 0.92 (d, J=6.7 Hz, 6 H). HRMS (ESI) calcd for C26H24F3N5O [M+H]+ 480.2006, found 480.2007.

Operating in an analogous way the following compounds were prepared:

1-[3-(1-Ethyl-4-pyridin-4-yl-1H-pyrazol-3-yl)-phenyl]-3-(4-trifluoromethyl-phenyl)-urea (Cmpd. n° 10)

[(I)E, X=CH; R1, R2, R3, R4, R5, R6=H; m=2; Y=H; R7=4-trifluoromethyl-phenyl]

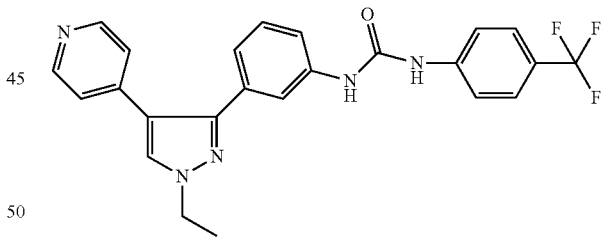

HPLC (254 nm): $R_t$: 5.56 min.

$^1$H NMR (401 MHz, DMSO-$d_6$) δ=9.03 (s, 1 H), 8.85 (s, 1 H), 8.46 (d, J=6.2 Hz, 2 H), 8.24 (s, 1 H), 7.59-7.68 (m, 4 H), 7.56 (t, J=1.8 Hz, 1 H), 7.49-7.51 (m, 1 H), 7.30 (t, J=7.9 Hz, 1 H), 7.24 (d, J=6.1 Hz, 2 H), 6.99 (ddd, J=1.0, 1.5, 7.6 Hz, 1 H), 4.22 (q, J=7.3 Hz, 2 H), 1.47 (t, J=7.3 Hz, 3 H). HRMS (ESI) calcd for C24H20F3N5O [M+H]$^+$ 452.1693, found 452.1704.

1-[3-(1-Butyl-4-pyridin-4-yl-1H-pyrazol-3-yl)-phenyl]-3-(4-trifluoromethyl-phenyl)-urea (Cmpd. n° 49)

[(I)E, X=CH; R1, R2, R3, R4, R5, R6=H; m=4; Y=H; R7=4-trifluoromethyl-phenyl]

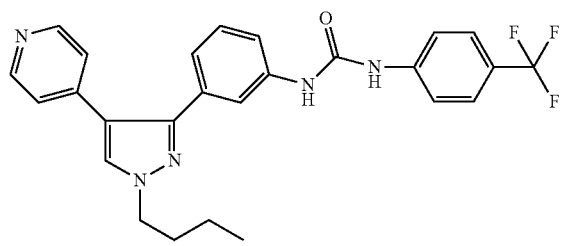 [SMILES: CCCCn1cc(-c2ccncc2)c(-c2cccc(NC(=O)Nc3ccc(C(F)(F)F)cc3)c2)n1]

HPLC (254 nm): R$_t$: 5.56 min.

$^1$H NMR (401 MHz, DMSO-d$_6$) δ=9.03 (s, 1 H), 8.85 (s, 1 H), 8.45 (d, J=6.1 Hz, 2 H), 8.23 (s, 1 H), 7.59-7.67 (m, 4 H), 7.55 (t, J=1.8 Hz, 1 H), 7.47-7.51 (m, 1 H), 7.30 (t, J=7.9 Hz, 1 H), 7.24 (d, J=6.1 Hz, 2 H), 6.99 (dt, J=1.2, 7.8 Hz, 1 H), 4.18 (t, J=7.1 Hz, 2 H), 1.85 (quin, J=7.3 Hz, 2 H), 1.34 (dq, J=7.4, 14.9 Hz, 2 H), 0.93 (t, J=7.4 Hz, 3 H). HRMS (ESI) calcd for C26H24F3N5O [M+H]+ 480.2006, found 480.199.

1-[3-(1-Methyl-4-pyridin-4-yl-1H-pyrazol-3-yl)-phenyl]-3-(4-trifluoromethyl-phenyl)-urea (Cmpd. 48)

[(I)E, X=CH; R1, R2, R3, R4, R5, R6=H; m=1; Y=H; R7=4-trifluoromethyl-phenyl]

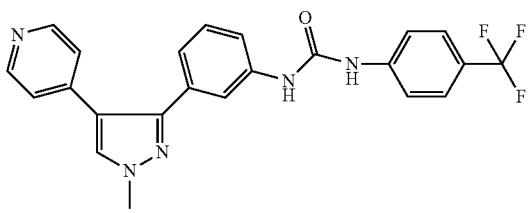 [SMILES: Cn1cc(-c2ccncc2)c(-c2cccc(NC(=O)Nc3ccc(C(F)(F)F)cc3)c2)n1]

HPLC (254 nm): R$_t$: 5.15 min.

$^1$H NMR (401 MHz, DMSO-d$_6$) δ=9.04 (s, 1 H), 8.85 (s, 1 H), 8.46 (d, J=6.1 Hz, 2 H), 8.18 (s, 1 H), 7.59-7.67 (m, 4 H), 7.56 (t, J=1.8 Hz, 1 H), 7.45-7.48 (m, 1 H), 7.30 (t, J=7.9 Hz, 1 H), 7.23 (d, J=6.1 Hz, 2 H), 6.99 (dt, J=1.2, 7.7 Hz, 1 H), 3.90-3.96 (m, 3 H). HRMS (ESI) calcd for C23H18F3N5O [M+H]$^+$ 438.1536, found 438.155.

1-[3-(1-Cyanomethyl-4-pyridin-4-yl-1H-pyrazol-3-yl)-phenyl]-3-(4-trifluoromethyl-phenyl)-urea (Cmpd. n° 11)

[(I)E, X=CH; R2, R3, R4, R5, R6=H; m=1; R1=cyano; Y=H; R7=4-trifluoromethyl-phenyl]

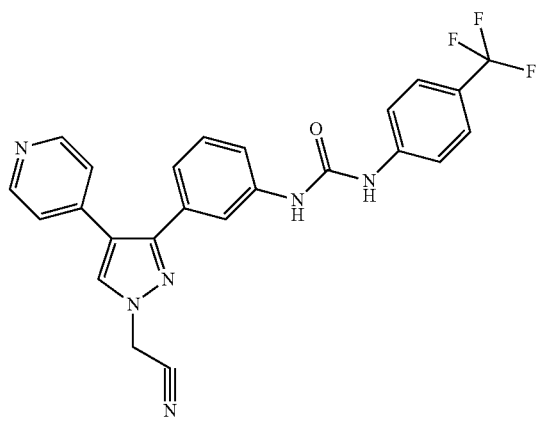 [SMILES: N#CCn1cc(-c2ccncc2)c(-c2cccc(NC(=O)Nc3ccc(C(F)(F)F)cc3)c2)n1]

HPLC (254 nm): R$_t$: 6.3 min.

$^1$H NMR (401 MHz, DMSO-d$_6$) δ=9.16 (s, 1 H), 9.01 (s, 1 H), 8.46-8.52 (m, 2 H), 8.32 (s, 1 H), 7.59-7.69 (m, 4 H), 7.60-7.65 (m, 1H), 7.50-7.54 (m, 1 H), 7.32 (t, J=7.9 Hz, 1 H), 7.24-7.29 (m, 2 H), 7.00-6.95 (m, 1H), 5.61 (s, 2 H). HRMS (ESI) calcd for C24H17F3N5O [M+H]+ 463.1489, found 463.1497.

2-(4-Pyridin-4-yl-3-{3-[3-(4-trifluoromethyl-phenyl)-ureido]-phenyl}-pyrazol-1-yl)-acetamide

[(I)E, X=CH; R2, R3, R4, R5, R6=H; m=0; R1=aminocarbonylmethyl; Y=H; R7=4-trifluoromethyl-phenyl]

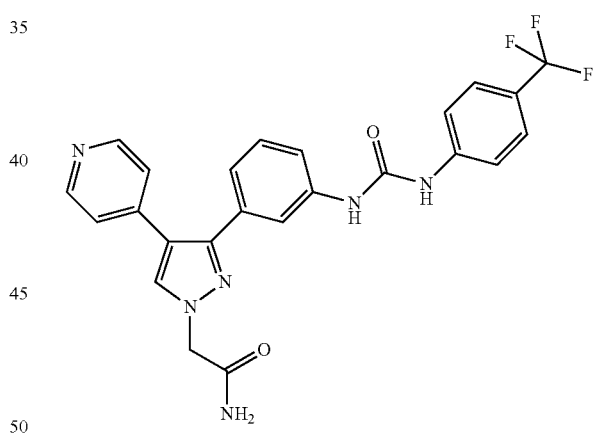

HPLC (254 nm): R$_t$: 5.58 min.

$^1$H NMR (401 MHz, DMSO-d$_6$) δ=9.04 (s, 1 H), 8.87 (s, 1 H), 8.35-8.54 (m, 2 H), 8.19 (s, 1 H), 7.59-7.68 (m, 4 H), 7.58 (t, J=1.8 Hz, 1 H), 7.48-7.51 (m, 1 H), 7.33 (s, 2 H), 7.30 (t, J=7.9 Hz, 1 H), 7.22-7.27 (m, 2 H), 6.99 (dt, J=1.2, 7.7 Hz, 1 H), 4.85 (s, 2 H). HRMS (ESI) calcd for C24H19F3N6O2 [M+H]+ 481.1595, found 481.1596.

Example 11

1-{3-[1-(2-Hydroxy-ethyl)-4-pyridin-4-yl-1H-pyrazol-3-yl]-phenyl}-3-(4-trifluoromethyl-phenyl)-urea (Cmpd. 14)

[(I)E, X=CH; R2, R3, R4, R5, R6=H; m=2; R1=hydroxy; Y=H; R7=4-trifluoromethyl-phenyl]

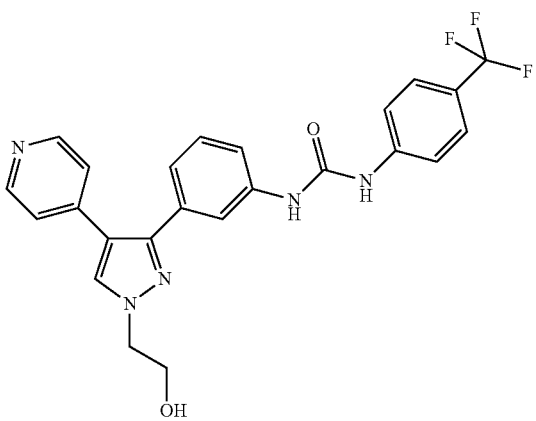 [SMILES: O=C(Nc1ccc(C(F)(F)F)cc1)Nc1cccc(-c2nn(CCO)cc2-c2ccncc2)c1]

The above compound was prepared as described in Example 10 using 2-(2-bromo-ethoxy)-tetrahydro-pyran as alkylating agent. The protective group was then removed as described below.

To 1-(3-{4-pyridin-4-yl-1-[2-(tetrahydro-pyran-2-yloxy)-ethyl]-1H-pyrazol-3-yl}-phenyl)-3-(4-trifluoromethyl-phenyl)-urea (50 mg, 0.09 mmol) in methylene chloride (1 mL) p-toluenesulfonic acid (PTSA) (25.8 mg, 0.13 mmol) was added, the reaction was stirred at room temperature for two days. The solvent was removed under reduced pressure and the product was isolated by silica gel column chromatography (DCM/methanol 93:7).

HPLC (254 nm): $R_t$: 5.8 min.
$^1$H NMR (401 MHz, DMSO-$d_6$) δ=9.09 (s, 1 H), 8.92 (s, 1 H), 8.55 (d, J=5.6 Hz, 2 H), 8.34 (s, 1 H), 7.59-7.68 (m, 5 H), 7.49 (m, 1 H), 7.33 (t, J=7.9 Hz, 1 H), 7.11 (m, 2 H), 7.03 (m, 1 H), 5.02 (s, 1 H), 4.25 (t, J=5.5 Hz, 2 H), 3.85 (t, J=5.4 Hz, 2 H). HRMS (ESI) calcd for C24H20F3N5O2 [M+H]+ 468.1642, found 468.1624.

Example 12

(4-Pyridin-4-yl-3-{3-[3-(4-trifluoromethyl-phenyl)-ureido]-phenyl}-pyrazol-1-yl)-acetic acid

[(I)E, X=CH; R2, R3, R4, R5, R6=H; m=1; R1=carboxyl; Y=H; R7=4-trifluoromethyl-phenyl]

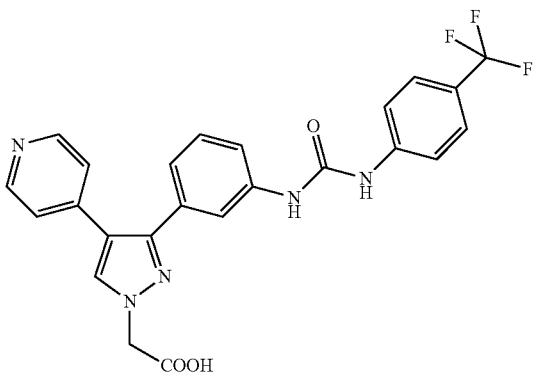 [SMILES: O=C(O)Cn1cc(-c2ccncc2)c(-c2cccc(NC(=O)Nc3ccc(C(F)(F)F)cc3)c2)n1]

The above compound was prepared as described in Example 10 using bromoacetic acid ethyl ester as alkylating agent. The ester was then hydrolized as described below.

To (4-pyridin-4-yl-3-{3-[3-(4-trifluoromethyl-phenyl)-ureido]-phenyl}-pyrazol-1-yl)-acetic acid ethyl ester in tetrahydrofuran (2 mL) and water (0.5 mL) lithium hydroxide (7.2 mg, 0.17 mmol) was added and the reaction was stirred at room temperature overnight. Ethyl acetate (50 mL) and 5% potassium hydrogen carbonate solution (20 mL) were then added. The organic layer was washed with brine, dried over anhydrous sodium sulphate, filtered and concentrated to yield the desired product.

HPLC (254 nm): Rt: 6.38 min.
1H NMR (401 MHz, DMSO-$d_6$) δ=9.24 (s, 1 H), 9.07 (s, 1 H), 8.57 (dd, J=1.3, 5.0 Hz, 2 H), 8.36 (s, 1 H), 7.58-7.68 (m, 5 H), 7.48-7.53 (m, 1 H), 7.42-7.46 (m, 2 H), 7.33 (t, J=7.9 Hz, 1 H), 6.99-7.04 (m, 1 H), 5.09 (s, 2 H).

HRMS (ESI) calcd for C24H18F3N5O3 [M+H]+ 482.1435, found 482.1445.

Example 13

1-[3-(1-Piperidin-4-yl-4-pyridin-4-yl-1H-pyrazol-3-yl)-phenyl]-3-(4-trifluoromethyl-phenyl)-urea
(Cmpd. 15)

[(I)E, X=CH; R2, R3, R4, R5, R6=H; m=0; R1=piperidin-4-yl; Y=H; R7=4-trifluoromethyl-phenyl]

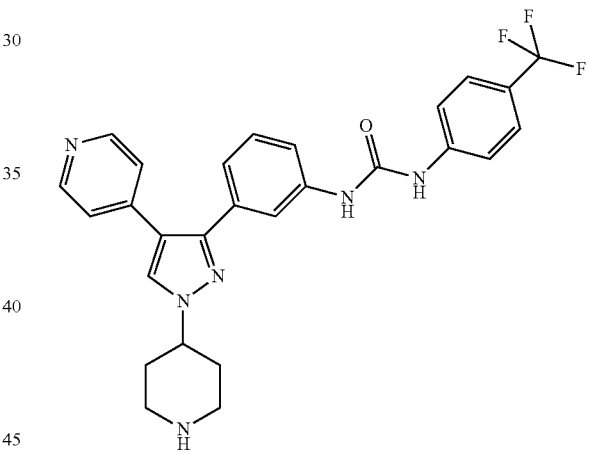

Method A
Step h

4-[3-(3-Nitro-phenyl)-4-pyridin-4-yl-pyrazol-1-yl]-piperidine-1-carboxylic acid tert-butyl ester To a suspension of 4-[3-(3-nitro-phenyl)-1H-pyrazol-4-yl]-pyridine (200 mg, 0.750 mmol) in anhydrous tetrahydrofuran (3 mL) at 0° C. triphenylphosphine (293 mg, 1.12 mmol, 1.5 eq), 4-hydroxy-piperidine-1-carboxylic acid tert-butyl ester (150 mg, 0.750 mmol, 1 eq) and DEAD (176 μL, 1.12 mmol, 1.5 eq) were added. The reaction was allowed to warm to room temperature and stirred under nitrogen atmosphere overnight. The regioisomeric ratio was 1:4 at 254 nm in favor of the N1-alkylated product. The solvent was removed under reduced pressure and the residue was purified by silica gel column chromatography (DCM/ethanol 97:3) to give 950 mg of major regioisomer contaminated with triphenylphosphinoxide.

Method G

Step a

Synthesis of 4-[3-(3-Amino-phenyl)-4-pyridin-4-yl-pyrazol-1-yl]-piperidine-1-carboxylic acid tert-butyl ester To crude 4-[3-(3-nitro-phenyl)-4-pyridin-4-yl-pyrazol-1-yl]-piperidine-1-carboxylic acid tert-butyl ester (0.75 mmol) in methanol (20 mL) Pd/C 10% (190 mg) was added. The reaction was stirred under hydrogen atmosphere (45 psi) at room temperature for six hours. The suspension was filtered to remove the catalyst, and then concentrated to give the crude product that was used in the next step without further purification.

Step e

1-[3-(1-piperidin-4-yl-4-pyridin-4-yl-1H-pyrazol-3-yl)-phenyl]-3-(4-trifluoromethyl-phenyl)-urea To 4-[3-(3-amino-phenyl)-4-pyridin-4-yl-pyrazol-1-yl]-piperidine-1-carboxylic acid tert-butyl ester (0.75 mmol) in anhydrous N,N-dimethylformamide (5 mL) 4-trifluoromethylphenylisocyanate (104 μL, 0.75 mmol) was added at 0° C. The reaction was allowed to warm to room temperature and it was stirred under nitrogen atmosphere overnight. The crude product was purified by silica gel column chromatography (DCM/methanol 93:7) to give 4-(4-pyridin-4-yl-3-{3-[3-(4-trifluoromethyl-phenyl)-ureido]-phenyl}-pyrazol-1-yl)-piperidine-1-carboxylic acid tert-butyl ester.

To 4-(4-pyridin-4-yl-3-{3-[3-(4-trifluoromethyl-phenyl)-ureido]-phenyl}-pyrazol-1-yl)-piperidine-1-carboxylic acid tert-butyl ester (100 mg, 0.16 mmol) in dioxane (2 mL) HCl 4M in dioxane (1 mL, 3.30 mmol) was added. After one hour the reaction was diluted with ethyl acetate (50 mL) and washed with saturated NaHCO$_3$ solution (3×50 mL) and brine (1×50 mL). The organic phase was dried over Na$_2$SO$_4$, filtered and the solvent was evaporated under reduced pressure. The deprotected urea was isolated by reverse phase chromatography.

HPLC (254 nm): Rt: 5.08 min.

$^1$H NMR (401 MHz, DMSO-d6) δ=10.08 (s, 1 H), 9.85 (s, 1 H), 8.45 (d, J=5.7 Hz, 2 H), 8.30 (br. s., 2 H), 8.28 (s, 1 H), 7.64-7.71 (m, 3 H), 7.60 (d, J=8.9 Hz, 2 H), 7.50-7.55 (m, 1 H), 7.22-7.31 (m, 3 H), 6.90-6.95 (m, 1 H), 4.35-4.42 (m, 1 H), 2.73-2.86 (m, 2 H), 2.08-2.21 (m, 2 H), 1.94-2.05 (m, 2 H). HRMS (ESI) calcd for C27H26F3N5O [M+H]+ 507.2115, found 507.2108.

Operating in an analogous way the following compounds were prepared:

1-{3-[1-(2-Fluoro-ethyl)-4-pyridin-4-yl-1H-pyrazol-3-yl]-phenyl}-3-(4-trifluoromethyl-phenyl)-urea (Cmpd. 13)

[(I)E, X=CH; R2, R3, R4, R5, R6=H; m=2; R1=F; Y=H; R7=4-trifluoromethyl-phenyl]

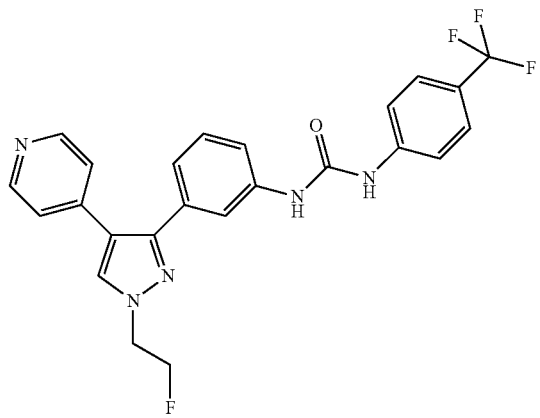 [SMILES: O=C(Nc1ccc(C(F)(F)F)cc1)Nc1cccc(-c2nn(CCF)cc2-c2ccncc2)c1]

HPLC (254 nm): Rt: 6.38 min.

$^1$H NMR (401 MHz, DMSO-d6) δ=9.04 (s, 1 H), 8.87 (s, 1 H), 8.48 (d, J=6.1 Hz, 2 H), 8.29 (s, 1 H), 7.60-7.69 (m, 4 H), 7.58 (t, J=1.8 Hz, 1 H), 7.47-7.53 (m, 1 H), 7.31 (t, J=7.9 Hz, 1 H), 7.26-7.29 (m, 2 H), 7.01 (m, 1 H), 4.79-4.95 (m, 2 H), 4.47-4.59 (m, 2 H). HRMS (ESI) calcd for C24H20F4N5O [M+H]+ 470.1599, found 470.1595.

1-(4-Chloro-3-trifluoromethyl-phenyl)-3-[3-(1-isopropyl-4-pyridin-4-yl-1H-pyrazol-3-yl)-phenyl]-urea

[(I)E, X=CH; R2, R3, R4, R5, R6=H; m=0; R1=i-propyl; Y=H; R7=4-chloro-3-trifluoromethyl-phenyl]

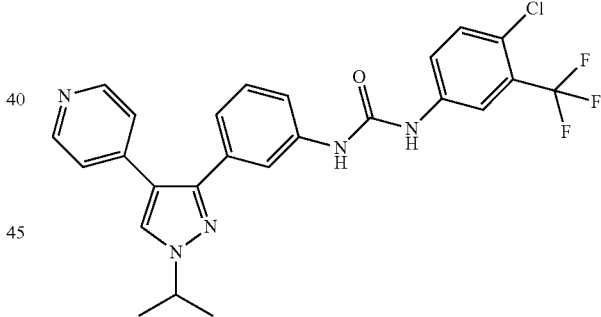

HPLC (254 nm): Rt: 7.11 min.

$^1$H NMR (401 MHz, DMSO-d$_6$) δ=9.10 (s, 1 H), 8.92 (s, 1 H), 8.47 (d, J=5.6 Hz, 2 H), 8.31 (s, 1 H), 8.09 (d, J=2.1 Hz, 1 H), 7.58-7.66 (m, 2 H), 7.49-7.57 (m, 3 H), 7.26-7.34 (m, 3 H), 7.01 (dt, J=1.1, 7.7 Hz, 1 H), 4.55-4.62 (m, 1 H), 1.52 (d, J=6.6 Hz, 6 H)HRMS (ESI) calcd for C25H22ClF3N5O [M+H]+ 500.1460, found 500.1465.

Example 14

1-(4-Chloro-3-trifluoromethyl-phenyl)-3-[3-(1-phenyl-4-pyridin-4-yl-1H-pyrazol-3-yl)-phenyl]-urea

[(I)E, X=CH; R2, R3, R4, R5, R6=H; m=0; R1=phenyl; Y=H; R7=4-chloro-3-trifluoromethyl-phenyl]

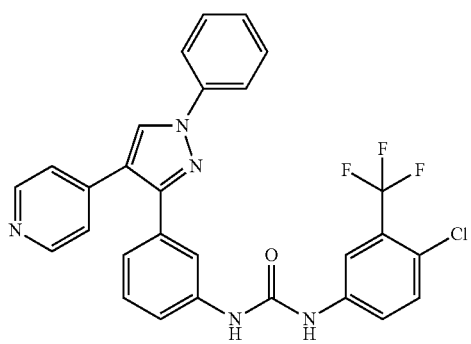 [SMILES: O=C(Nc1cccc(-c2nn(-c3ccccc3)cc2-c2ccncc2)c1)Nc1ccc(Cl)c(C(F)(F)F)c1]

Method A
Step g

4-[3-(3-nitro-phenyl)-1-phenyl-1H-pyrazol-4-yl]-pyridine

3-Dimethylamino-1-(3-nitro-phenyl)-2-pyridin-4-yl-propenone (150 mg, 0.505 mmol) was dissolved in dry THF (2 mL) under nitrogen atmosphere. Phenylhydrazine (0.2 mL, 2.02 mmol, 4 eq) was added and the mixture was heated to 70° C. and stirred at this temperature for 1.5 hours. The mixture was concentrated to dryness. A 77:23 mixture (A % at 254 nm) of two regioisomers was obtained in favour of 4-[5-(3-nitro-phenyl)-1-phenyl-1H-pyrazol-4-yl]-pyridine (regiochemistry determined at the end of the synthesis). The crude product was purified by reverse phase chromatography to give 100 mg (58% yield) of phenylpyrazole still as regioisomer mixture.

Method G
Step a

3-(1-phenyl-4-pyridin-4-yl-1H-pyrazol-3-yl)-phenylamine

The nitroderivative (100 mg, 0.292 mmol) was suspended in a 5:1 dioxane/water mixture (2 mL). Zinc powder (77 mg, 1.18 mmol, 4 eq) was added, followed by ammonium chloride (157 mg, 2.94 mmol, 10 eq) and the mixture was heated at 100° C. for 4 hours. The reaction mixture was then diluted with water and ethyl acetate, pH was adjusted to 8 with NaHCO₃ and the aqueous phase was extracted with ethylacetate. The organic layer was dried over Na₂SO₄ and concentrated to dryness to obtain 65 mg (66% yield) of crude product. Regioisomeric ratio is 86:14 by HPLC (254 nm) and 2:1 by ¹H-NMR in favour of 3-(2-phenyl-4-pyridin-4-yl-2H-pyrazol-3-yl)-phenylamine.

Step e

1-(4-Chloro-3-trifluoromethyl-phenyl)-3-[3-(1-phenyl-4-pyridin-4-yl-1H-pyrazol-3-yl)-phenyl]-urea 3-(1-Phenyl-4-pyridin-4-yl-1H-pyrazol-3-yl)-phenylamine (as regioisomeric mixture) was dissolved in dry dichloromethane (1 mL) under nitrogen atmosphere, 4-chloro-3-trifluoromethylphenylisocyanate (61 mg, 0.275 mmol, 1.4 eq) was added and the reaction mixture was stirred at room temperature for 3 hours. The solution was concentrated to dryness and purified by chromatography on silica gel (SP1, gradient n-hexane/ethyl acetate 1:1 to pure ethyl acetate). Two pools of fractions containing the two separated regioisomers were obtained, together with some mixed fractions (total yield 78%). 55 mg of 1-(4-Chloro-3-trifluoromethyl-phenyl)-3-[3-(2-phenyl-4-pyridin-4-yl-2H-pyrazol-3-yl)-phenyl]-urea were obtained as colourless oil.

HPLC (254 nm): Rt: 7.68 min.
¹H NMR (401 MHz, DMSO-d₆) δ=9.14 (s, 1 H), 9.04 (s, 1 H), 8.96 (s, 1 H), 8.55 (d, J=6.0 Hz, 2 H), 8.09 (d, J=2.3 Hz, 1 H), 7.96 (d, J=7.6 Hz, 2 H), 7.65 (m, 1 H), 7.61-7.64 (m, 2 H), 7.55-7.61 (m, 3 H), 7.34-7.42 (m, 4 H), 7.12 (dt, J=1.1, 7.7 Hz, 1 H).
HRMS (ESI) calcd for C28H20ClF3N5O [M+H]+ 534.1303, found 534.1305.

Example 15

4-Pyridin-4-yl-3-{3-[3-(4-trifluoromethyl-phenyl)-ureido]-phenyl}-pyrazole-1-carboxylic acid ethyl ester (Cmpd. 47)

[(I)E, X═CH; R2, R3, R4, R5, R6═H; m═0; R1═ethoxycarbonyl; Y═H; R7═4-trifluoromethyl-phenyl]

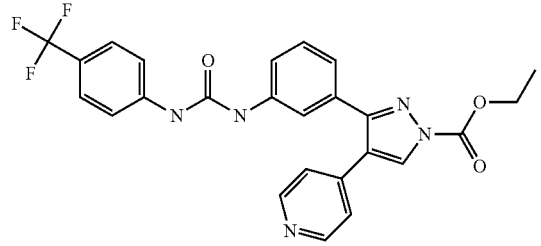 [SMILES: CCOC(=O)n1cc(-c2ccncc2)c(-c2cccc(NC(=O)Nc3ccc(C(F)(F)F)cc3)c2)n1]

To a suspension of 1-[3-(4-pyridin-4-yl-1H-pyrazol-3-yl)-phenyl]-3-(4-trifluoromethyl-phenyl)-urea (100 mg, 0.236 mmol) (prepared as described in Example 6) in THF (10 mL) DIPEA (61 mg, 81 uL, 0.427 mmol) was added. The mixture was stirred for 5 minutes before adding ethyl chloroformate (31 mg, 27 uL, 0.283 mmol). After 2 hours the mixture was evaporated to dryness, taken up with ethyl acetate and washed three times with water. The organic phase was dried over Na₂SO₄, evaporated to dryness and triturated with diisopropyl ether to yield 4-pyridin-4-yl-3-{3-[3-(4-trifluoromethyl-phenyl)-ureido]-phenyl}-pyrazole-1-carboxylic acid ethyl ester (90 mg, 77%).
¹H NMR (401 MHz, DMSO-d6) δ=9.11 (s, 1 H), 8.98 (s, 1 H), 8.84 (s, 1 H), 8.50-8.57 (m, 2 H), 7.61-7.68 (m, 5 H), 7.56 (ddd, J=0.9, 2.2, 8.2 Hz, 1 H), 7.32-7.39 (m, 3 H), 7.01 (ddd, J=1.0, 1.3, 7.8 Hz, 1 H), 4.52 (q, J=7.2 Hz, 2 H), 1.41 (t, J=7.1 Hz, 3 H). HRMS (ESI) calcd for C25H20F3N5O3 [M+H]+ 496.1591, found 496.1587.

Preparation of -(4-pyridin-4-yl-1H-pyrazol-3-yl)-benzonitrile

[(II)A, X═CH; R2, R3, R4, R5, R6═H; G═CN]
Method A

Step a:
[(3-cyano-phenyl-hydroxy-methyl]-phosphonic acid dimethyl ester

A mixture of 3-formyl-benzonitrile (10 g, 76.26 mmol), triethylamine (9.26 g, 91.05 mmol) and dimethyl-phosphite (10.91 g, 99.14 mmol) was stirred in ethyl acetate at room temperature for 2 hours. The solvent was evaporated and the residue was dissolved in ethyl acetate (50 ml), washed with a saturated ammonium chloride solution (1×50 ml), dried (Na$_2$SO$_4$) and the filtrate was evaporated affording the crude [(3-cyanophenyl-hydroxymethyl]-phosphonic acid dimethyl ester as a yellow solid (13.60 g, 56.43 mmol, 74%).

$^1$H NMR (401 MHz, DMSO-d6) δ=7.81 (q, J=1.8 Hz, 1 H), 7.77 (dt, J=1.8, 7.8 Hz, 2 H), 7.58 (t, J=7.7 Hz, 1 H), 6.51 (dd, J=5.9, 14.4 Hz, 1 H), 5.16 (dd, J=5.9, 13.9 Hz, 1 H), 3.64 (d, J=10.2 Hz, 3 H), 3.62 (d, J=10.2 Hz, 3 H).

MS ESI (M+H) calc 242.0577; found. 242.0576 (C10H12NO4P).

Step b: [(3-cyano-phenyl)-(tetrahydro-pyran-2-yloxy)-methyl]phosphonic acid dimethyl ester 3,4-Dihydro-2H-pyran (10.83 g, 128.70 mmol) and p-toluenesulfonic acid (0.34 g, 1.75 mmol) were added to a solution of [(3-cyanophenyl-hydroxy-methyl]-phosphonic acid dimethyl ester (14.10 g, 58.50 mmol) in dry toluene (195 ml) and the reaction mixture was stirred under nitrogen atmosphere at 50° C. for 3 h. The solvent was then removed under vacuum and the residue was taken up with ethyl acetate (100 ml). The organic layer was washed with a saturated NaHCO$_3$ solution (1×100 ml), brine (1×100 ml) and dried over Na$_2$SO$_4$. The filtrate was evaporated to dryness to give the crude [(3-cyanophenyl)-(tetrahydro-pyran-2-yloxy)-methyl]phosphonic acid dimethyl ester as a yellow oil (19 g, 58.46 mmol, 100%).

$^1$H NMR (401 MHz, DMSO-d6) δ=7.85-7.74 (m, 3 H), 7.63-7.58 (m, 1 H), 5.24 (d, J=17.4 Hz, 1 H), 5.24 (d, J=12.7 Hz, 1 H), 4.96 (t, J=3.0 Hz, 1 H), 4.39 (t, J=2.5 Hz, 1 H), 3.89 (dt, J=6.0, 11.7 Hz, 1 H), 3.71 (d, J=10.5 Hz, 3 H), 3.64 (d, J=10.5 Hz, 3 H), 3.64 (td, J=7.6, 10.4 Hz, 2 H), 3.51 (d, J=12.2 Hz, 1 H), 1.87-1.31 (m, 6 H). MS ESI (M+H) calc 326.1152; found. 326.1158 (C15H20NO5P).

Step c: 3-[(E)-2-pyridin-4-yl-1-(tetrahydro-pyran-2-yloxy)-vinyl]-benzonitrile Sodium hydride (2.28 g, 94.98 mmol) was added to a solution of [(3-cyano-phenyl)-(tetrahydro-pyran-2-yloxy)-methyl]phosphonic acid dimethyl ester (20.58 g, 63.3 mmol) in dry THF and the mixture was stirred at room temperature for 15'. Pyridine-4-carbaldehyde (6.78 g, 63.3 mmol) was then added and the reaction mixture was stirred at 50° C. for 3 h under nitrogen atmosphere. In order to affect completion a further addition of pyridine-4-carbaldehyde (0.68 g, 6.33 mmol) was required. Distilled water (40 ml) was slowly poured into the reaction mixture and the solvent (THF) was removed under reduced pressure. The water layer was extracted with EtOAc (3×100 ml), DCM (1×100 ml) and the organic layers were dried over Na$_2$SO$_4$. The filtrate was evaporated to dryness to give the crude product 3-[(E)-2-Pyridin-4-yl-1-(tetrahydro-pyran-2-yloxy)-vinyl]-benzonitrile as a brown oil (19.0 g, 62.10 mmol, 98%).

MS ESI (M+H) calc 307.1441; found. 307.1436 (C19H18N2O2).

Step d: 3-(pyridin-4-yl-acetyl)-benzonitrile

3-[(E)-2-Pyridin-4-yl-1-(tetrahydro-pyran-2-yloxy)-vinyl]-benzonitrile (19.0 g, 62.1 mmol) was dissolved into methanol (0.4 ml) and a solution of HCl 1N (0.04 ml) was added. The mixture was stirred at 50° C. for 1 h. Upon reaction completion, the solvent was evaporated and a saturated NaHCO$_3$ solution was added dropwise to the left water layer leading to the precipitation of 3-(pyridin-4-yl-acetyl)-benzonitrile (4) as a yellow solid (9.65 g, 43.4 mmol, 70%).

$^1$H NMR (401 MHz, DMSO-d$_6$) δ=8.49-8.57 (m, 3 H), 8.32 (dt, J=1.2, 8.6 Hz, 1 H), 8.15 (ddd, J=1.2, 1.4, 7.9 Hz, 1 H), 7.79 (dd, J=0.5, 15.6 Hz, 1 H), 7.28-7.35 (m, 2 H), 4.57 (s, 2 H). MS ESI (M+H) calc 223.0866; found. 223.0864 (C14H10N2O).

Step f: 3-((E)-3-dimethylamino-2-pyridin-4-yl-acryloyl)benzonitrile 3-(Pyridin-4-yl-acetyl)-benzonitrile (4.91 g, 22.1 mmol) was dissolved into dry toluene (0.2 ml) and dimethoxymethyl-dimethyl-amine (10.6 g, 88.5 mmol) was added. The reaction mixture was stirred at 80° C. for 2 h under nitrogen atmosphere. The solvent was removed under vacuum and crude 3-((E)-3-Dimethylamino-2-pyridin-4-yl-acryloyl)benzonitrile was used in the next step without further purification.

Step g: 3-(4-pyridin-4-yl-1H-pyrazol-3-yl)-benzonitrile

A 1 M solution of hydrazine in THF (0.090 ml, 88.5 mmol) was added to 3-((E)-3-dimethylamino-2-pyridin-4-yl-acryloyl)benzonitrile (6.13 g, 22.1 mmol) and the mixture was stirred at 60° C. for 1 h. The product 3-(4-pyridin-4-yl-1H-pyrazol-3-yl)-benzonitrile (4.89 g, 19.8 mmol, 90%) was isolated as a white solid by filtration from the reaction mixture.

HPLC (254 nm): R$_t$: 3.50 min $^1$H NMR (401 MHz, DMSO-d6) δ=13.48 (br. s., 1 H), 8.49 (d, J=5.9 Hz, 2 H), 8.28 (d, J=1.3 Hz, 1 H), 7.84-7.81 (m, 1 H), 7.99-7.90 (m, 1 H), 7.84 (d, J=1.1 Hz, 2 H), 7.74-7.70 (m, 1 H), 7.61 (t, J=8.1 Hz, 1 H), 7.25 (d, J=5.9 Hz, 2 H). MS ESI (M+H) calc 247.0978; found. 247.0973 (C15H10N4).

Example 16

N-Benzyl-3-(4-pyridin-4-yl-1H-pyrazol-3-yl)-benzamide

[(I)K, X=CH; R1, R2, R3, R4, R5, R6=H; m=0; Y=H; R7=benzyl]

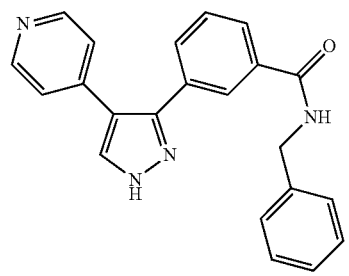 [SMILES: O=C(NCc1ccccc1)c1cccc(-c2n[nH]cc2-c2ccncc2)c1]

Method I

Step a: 3-(4-pyridin-4-yl-1H-pyrazol-3-yl)-benzoic acid hydrochloride

A solution of 3-(4-pyridin-4-yl-1H-pyrazol-3-yl)-benzonitrile (1.2 g, 4.87 mmol) in 3M HCl (24 ml) was heated to 150° C. for 30 minutes in a microwave vessel. The product 3-(4-pyridin-4-yl-1H-pyrazol-3-yl)-benzoic acid hydrochloride was isolated as a white solid by filtration from the reaction mixture (1.03 g, 4.3 mmol, 89%).

HPLC (254 nm): R$_t$: 3.18 min $^1$H-NMR (401 MHz, DMSO-d6) δ=13.13 (br.s., 1H), 8.68 (d, J=6.6 Hz, 2 H), 8.50 (br. s., 1 H), 8.10-8.00 (m, 2 H), 7.76-7.68 (m, 3 H), 7.62 (t, J=8.0 Hz, 1 H). MS ESI (M+H) calc 266.0924; found. 266.0927 (C15H11N3O2).

Step b: N-benzyl-3-(4-pyridin-4-yl-1H-pyrazol-3-yl)-benzamide

A solution of 1-ethyl-3-(3-dimethylaminopropyl)-carbodiimide hydrochloride (0.029 g, 0.15 mmol, 1.5 eq) in dry DCM (1 mL) and a solution of 1-hydroxybenzotriazole (0.020 g, 0.15 mmol, 1.5 eq) and DIPEA (0.064 g, 0.50 mmol, 5 eq) in dry DMF (0.1 mL) were added to 3-(4-pyridin-4-yl-1H-pyrazol-3-yl)-benzoic acid hydrochloride (0.030 g, 0.10 mmol, 1 eq) in dry DMF (0.200 ml). Benzylamine (2 eq) was added to the reaction mixture, which was stirred at room temperature for 24 h. Distilled water (1.5 mL) was poured into the suspension that was stirred for 1 h at room temperature and the organic layer was separated by filtration through Alltech Separator Tube. The solvent was evaporated and reverse phase purification of the crude afforded the final product as a solid.

HPLC (254 nm): $R_t$: 4.88 min
$^1$H-NMR (401 MHz, DMSO-d6) δ=13.3 (br.s., 1 H), 9.08 (t, J=5.4 Hz, 1 H), 8.46 (d, J=6.0 Hz, 2 H), 8.28 (d, J=0.5 Hz, 1 H), 8.06-7.85 (m, 2 H), 7.65-7.44 (m, 2 H), 7.39-7.18 (m, 7 H), 4.48 (t, J=5.1 Hz, 2 H). MS ESI (M+H) calc 355.1554; found. 355.1568 (C22H18N4O).

Operating in an analogous way the following amides were prepared:

3-(4-Pyridin-4-yl-1H-pyrazol-3-yl)-benzamide

[(I)K, X=CH; R1, R2, R3, R4, R5, R6, R7=H; m=0; Y=H]

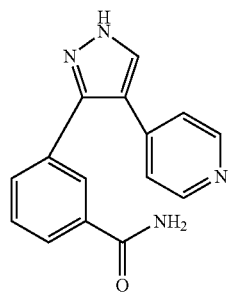 [SMILES: NC(=O)c1cccc(-c2n[nH]cc2-c2ccncc2)c1]

HPLC (254 nm): $R_t$: 3.42 min
$^1$H-NMR (401 MHz, DMSO-d6 δ=13.36 (s, 1 H), 8.50-8.44 (m, 2 H), 8.28 (s, 1 H), 8.0-7.84 (m, 2 H), 7.66-7.42 (m, 4 H), 7.30-7.21 (m, 2 H). MS ESI (M+H) calc 265.1084; found. 265.1080 (C15H12N4O)

N-Propyl-3-(4-pyridin-4-yl-1H-pyrazol-3-yl)benzamide

[(I)K, X=CH; R1, R2, R3, R4, R5, R6=H; m=0; Y=H; R7=propyl]

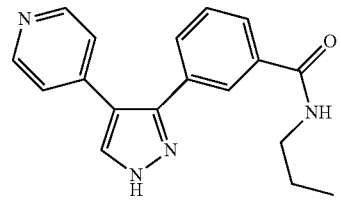 [SMILES: CCCNC(=O)c1cccc(-c2n[nH]cc2-c2ccncc2)c1]

HPLC (254 nm): $R_t$: 4.29 min
$^1$H NMR (401 MHz, DMSO-d6) δ=13.3 (br.s., 1 H), 8.53-8.46 (m, 1 H), 8.45 (dd, J=1.4, 4.7 Hz, 2 H), 8.28 (br.s., 1 H), 7.98 (s, 1 H), 7.83 (m, 1 H), 7.52-7.40 (m, 2 H), 7.50-7.30 (m, 2 H), 3.25-3.16 (m, 2 H), 1.58-1.46 (m, 2 H), 0.88 (t, J=7.4 Hz, 3 H). MS ESI (M+H) calc 307.1554; found. 307.1555 (C18H18N4O).

N-(2-Hydroxy-ethyl)-N-methyl-3-(4-pyridin-4-yl-1H-pyrazol-3-yl)-benzamide [(I)K, X=CH; R1, R2, R3, R4, R5, R6=H; m=0; R7=2-hydroxy-ethyl; Y=methyl]

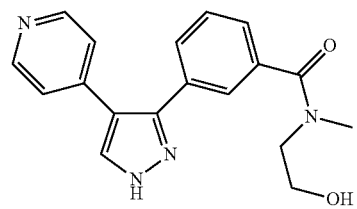 [SMILES: CN(CCO)C(=O)c1cccc(-c2n[nH]cc2-c2ccncc2)c1]

HPLC (254 nm): $R_t$: 3.51 min
$^1$H NMR (401 MHz, DMSO-d6) δ=13.35 (br.s. 1 H), 8.46 (d, J=6.0 Hz, 2 H), 8.25 (br.s., 1 H), 7.57-7.35 (m, 4 H), 7.26 (br. s., 2 H), 4.75 (t, J=5.5 Hz, 1 H), 3.65-3.40 (m, 4 H), 2.93 (m, 3 H). MS ESI (M+H) calc 323.1503; found. 323.1515 (C18H18N4O2).

N,N-Dimethyl-3-(4-pyridin-4-yl-1H-pyrazole-3-yl)-benzamide

[(I)K, X=CH; R1, R2, R3, R4, R5, R6=H; m=0; R7, Y=methyl]

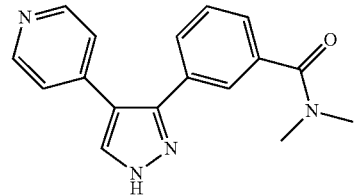 [SMILES: CN(C)C(=O)c1cccc(-c2n[nH]cc2-c2ccncc2)c1]

HPLC (254 nm): $R_t$: 3.87 min
$^1$H NMR (401 MHz, DMSO-d6) δ=13.35 (br.s. 1 H), 8.46 (d, J=5.9 Hz, 2 H), 8.25 (br.s., 1 H), 7.57-7.44 (m, 4 H), 7.30-7.23 (m, 2 H), 2.96 (br.s. 3H), 2.87 (br.s., 3H). MS ESI (M+H) calc 293.1397; found. 293.1387 (C17H16N4O).

N-(4-Acetylamino-phenyl)-3-(4-pyridin-4-yl-1H-pyrazol-3-yl)-benzamide

[(I)K, X=CH; R1, R2, R3, R4, R5, R6=H; m=0; Y=H; R7=4-acetylaminophenyl]

121

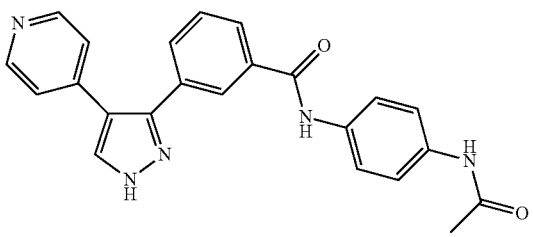 [SMILES: CC(=O)Nc1ccc(NC(=O)c2cccc(-c3n[nH]cc3-c3ccncc3)c2)cc1]

HPLC (254 nm): R$_t$: 4.24 min
$^1$H NMR (401 MHz, DMSO-d6) δ=13.41 (br.s, 1 H), 10.23 (s, 1 H), 9.90 (s, 1 H), 8.48 (dd, J=1.5, 4.6 Hz, 2 H), 8.31 (br.s, 1 H), 8.10-7.92 (m, 2 H), 7.69-7.48 (m, 6 H), 7.30 (d, J=4.3 Hz, 2 H), 2.04 (s, 3 H). MS ESI (M+H) calc 398.1612; found. 398.1617 (C23H19N5O2).

N-(1-Phenyl-ethyl)-3-(4-pyridin-4-yl-1H-pyrazol-3-yl)-benzamide

[(I)K, X=CH; R1, R2, R3, R4, R5, R6=H; m=0; Y=H; R7=1-phenylethyl]

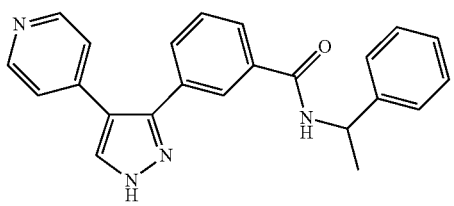 [SMILES: CC(NC(=O)c1cccc(-c2n[nH]cc2-c2ccncc2)c1)c1ccccc1]

HPLC (254 nm): R$_t$: 5.13 min
$^1$H NMR (401 MHz, DMSO-d6) δ=13.36 (br.s, 1 H), 8.85 (d, J=7.9 Hz, 1 H), 8.45 (d, J=6.1 Hz, 2 H), 8.28 (br.s, 1 H), 8.00-7.21 (m, 11 H), 5.16 (quin, J=7.6 Hz, 1 H), 1.46 (d, J=7.1 Hz, 3 H). MS ESI (M+H) calc 369.1710; found. 369.1724 (C23H20N4O).

3-(4-Pyridin-4-yl-1H-pyrazole-3-yl)-N-(3-trifluoromethyl-phenyl)-benzamide

[(I)K, X=CH; R1, R2, R3, R4, R5, R6=H; m=0; Y=H; R7=3-trifluoromethylphenyl]

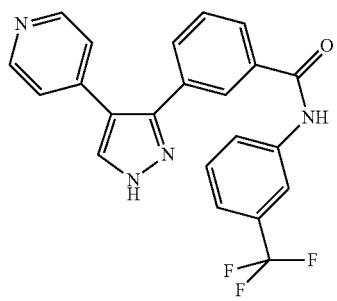 [SMILES: O=C(Nc1cccc(C(F)(F)F)c1)c1cccc(-c2n[nH]cc2-c2ccncc2)c1]

HPLC (254 nm): R$_t$: 5.89 min
$^1$H NMR (401 MHz, DMSO-d6) δ=13.41 (br.s, 1 H), 10.59 (br.s, 1H), 8.46 (d, J=6.1 Hz, 2 H), 8.29 (br.s, 1H), 8.00-7.45 (m, 8 H), 7.30-7.23 (m, 2 H). MS ESI (M+H) calc 409.1271; found. 409.1282 (C22H15F3N4O).

122

N-(2-fluoro-phenyl)-3-(4-pyridin-4-yl-1H-pyrazol-3-yl)-benzamide

[(I)K, X=CH; R1, R2, R3, R4, R5, R6=H; m=0; Y=H; R7=2-fluorophenyl]

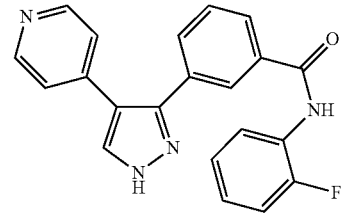 [SMILES: O=C(Nc1ccccc1F)c1cccc(-c2n[nH]cc2-c2ccncc2)c1]

HPLC (254 nm): R$_t$: 5.00 min
$^1$H NMR (401 MHz, DMSO-d6) δ=13.34 (br.s, 1 H), 10.18 (br.s, 1H), 8.46 (m, 2 H), 8.17 (br.s, 1 H), 8.12 (br.s, 1H), 8.0 (m, 1 H), 7.60-7.56 (m, 3 H), 7.31-7.19 (m, 5 H). MS ESI (M+H) calc 359.1303; found. 359.1308 (C21H15FN4O).

N-Ethyl-3-(4-pyridin-4-yl-1H-pyrazol-3-yl)-benzamide

[(I)K, X=CH; R1, R2, R3, R4, R5, R6=H; m=0; Y=H; R7=ethyl]

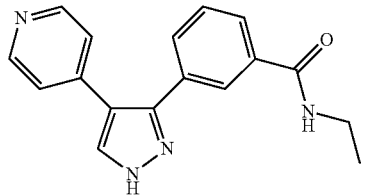 [SMILES: CCNC(=O)c1cccc(-c2n[nH]cc2-c2ccncc2)c1]

HPLC (254 nm): R$_t$: 3.96 min
$^1$H NMR (401 MHz, DMSO-d6) δ=13.34 (s, 1 H), 8.51 (br.s, 1 H), 8.46 (d, J=6.1 Hz, 2 H), 8.30 (s, 1 H), 7.98 (s, 1 H), 7.85 (br.s, 1 H), 7.60-7.45 (m, 2 H), 7.27 (d, J=5.1 Hz, 2 H), 1.12 (t, J=7.2 Hz, 3 H), 8.46 (d, J=6.1 Hz, 2 H), 7.27 (d, J=5.1 Hz, 2 H), 3.29 (m, 2 H), 1.12 (t, J=7.2 Hz, 3 H). MS ESI (M+H) calc 293.1397; found. 293.1392 (C17H16N4O)

N-Methyl-3-(4-pyridin-4-yl-1H-pyrazol-3-yl)-benzamide

[(I)K, X=CH; R1, R2, R3, R4, R5, R6=H; m=0; Y=H; R7=methyl]

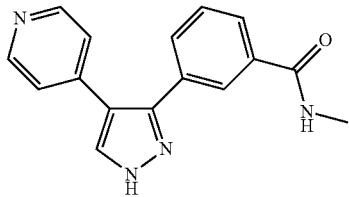 [SMILES: CNC(=O)c1cccc(-c2n[nH]cc2-c2ccncc2)c1]

HPLC (254 nm): R$_t$: 3.62 min
$^1$H NMR (401 MHz, DMSO-d6) δ=13.36 (s, 1 H), 8.53-8.42 (m, 3 H), 8.28 (s, 1 H), 7.97 (br.s. 1 H), 7.86-7.81 (br.s, 1 H), 7.62-7.44 (m, 2 H), 7.27-7.21 (m, 2 H), 2.78 (m, 3 H). MS ESI (M+H) calc 279.1241; found. 279.1241 (C16H14N4O)

123

N-Hydroxy-3-(4-Pyridin-4-Yl-1H-Pyrazol-3-Yl)-Benzamide

[(I)K, X=CH; R1, R2, R3, R4, R5, R6=H; m=0; Y=H; R7=hydroxy]

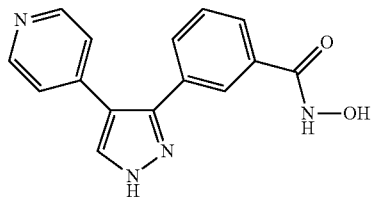 [SMILES: O=C(NO)c1cccc(-c2n[nH]cc2-c2ccncc2)c1]

HPLC (254 nm): R$_t$: 3.33 min
$^1$H NMR (401 MHz, DMSO-d6) δ=13.37 (s, 1 H), 11.24 (s, 1 H), 9.04 (s, 1 H), 8.50-8.44 (m, 2 H), 8.25 (s, 1 H), 8.10-7.45 (m, 4 H), 7.29-7.22 (m, 2 H). MS ESI (M+H) calc 281.1033; found. 281.1022 (C15H12N4O2)

3-(4-pyridin-4-yl-1H-pyrazol-3-yl)-N-(4-trifluoromethyl-phenyl)-benzamide (Cmpd. 46)

[(I)K, X=CH; R1, R2, R3, R4, R5, R6=H; m=0; Y=H; R7=4-trifluoromethylphenyl]

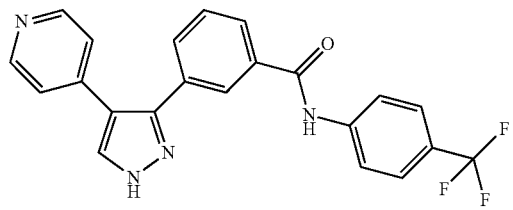 [SMILES: O=C(Nc1ccc(C(F)(F)F)cc1)c1cccc(-c2n[nH]cc2-c2ccncc2)c1]

HPLC (254 nm): R$_t$: 5.95 min
MS ESI (M+H) calc 409.1271; found. 409.1281 (C22H15F3N4O).

N-tert-Butyl-3-(4-pyridin-4-yl-1H-pyrazol-3-yl)-benzamide

[(I)K, X=CH; R1, R2, R3, R4, R5, R6=H; m=0; Y=H; R7=tert-butyl]

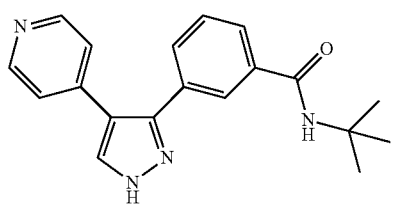 [SMILES: CC(C)(C)NC(=O)c1cccc(-c2n[nH]cc2-c2ccncc2)c1]

HPLC (254 nm): R$_t$: 4.82 min
$^1$H NMR (401 MHz, DMSO-d6) δ=13.33 (s, 1 H), 8.47-8.43 (m, 2 H), 8.26 (s, 1 H), 8.03-7.39 (m, 5 H), 7.19-7.19 (m, 2 H), 1.36 (s, 9 H). MS ESI (M+H) calc 321.1710; found. 321.1716 (C19H20N4O)

N-Isothiazol-3-yl-3-(4-pyridin-4-yl-1H-pyrazol-3-yl)-benzamide

[(I)K, X=CH; R1, R2, R3, R4, R5, R6=H; m=0; Y=H; R7=isothiazol-3-yl]

124

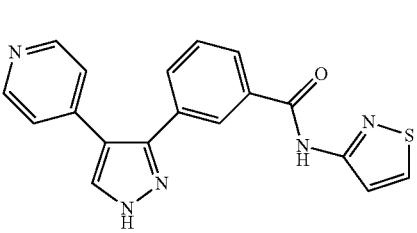 [SMILES: O=C(Nc1ccsn1)c1cccc(-c2n[nH]cc2-c2ccncc2)c1]

HPLC (254 nm): R$_t$: 4.58 min
$^1$H NMR (401 MHz, DMSO-d6) δ=13.45 (s, 1 H), 8.52-8.44 (m, 2 H), 8.22 (s, 1 H), 8.02-7.56 (m, 5 H), 7.53 (d, J=3.5 Hz, 1 H), 7.30-7.25 (m, 2 H), 7.24 (d, J=3.4 Hz, 1 H). MS ESI (M+H) calc 348.0914; found. 348.0915 (C18H13N5OS)

N-Benzyl-N-methyl-3-(4-pyridin-4-yl-1H-pyrazol-3-yl)-benzamide

[(I)K, X=CH; R1, R2, R3, R4, R5, R6=H; m=0; R7=benzyl, Y=methyl]

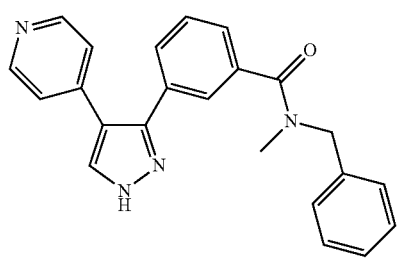 [SMILES: CN(Cc1ccccc1)C(=O)c1cccc(-c2n[nH]cc2-c2ccncc2)c1]

HPLC (254 nm): R$_t$: 5.01 min
$^1$H NMR (401 MHz, DMSO-d6) δ=13.39 (s, 1 H), 8.55-8.40 (m, 2 H), 8.27 (s, 1 H), 7.66-7.04 (m, 11 H), 4.65 (br.s, 2 H), 2.79 (s, 3 H). MS ESI (M+H) calc 369.1710; found. 369.1714 (C23H20N4O)

N-(3-Methoxy-phenyl)-3-(4-pyridin-4-yl-1H-pyrazol-3-yl)benzamide

[(I)K, X=CH; R1, R2, R3, R4, R5, R6=H; m=0; Y=H; R7=3-methoxyphenyl]

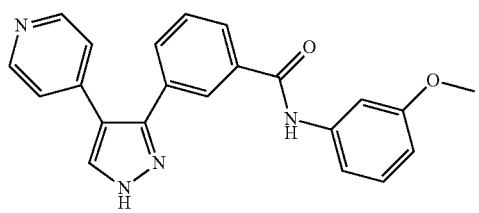 [SMILES: COc1cccc(NC(=O)c2cccc(-c3n[nH]cc3-c3ccncc3)c2)c1]

HPLC (254 nm): R$_t$: 5.12 min
$^1$H NMR (401 MHz, DMSO-d6) δ=13.39 (s, 1 H), 10.24 (s, 1 H), 8.46 (d, J=5.6 Hz, 2 H), 8.29 (s, 1 H), 8.02-7.18 (m, 9 H), 6.68 (d, J=8.4 Hz, 1 H), 3.75 (s, 3 H). MS ESI (M+H) calc 371.1503; found. 371.1513 (C22H18N4O2)

N-Furan-2-yl-methyl-3-(4-pyridin-4-yl-1H-pyrazol-3-yl)-benzamide

[(I)K, X=CH; R1, R2, R3, R4, R5, R6=H; m=0; Y=H; R7=furan-2-yl]

125

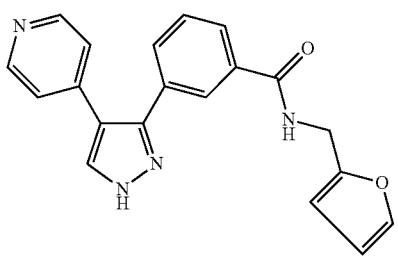 [SMILES: O=C(NCc1ccco1)c1cccc(-c2n[nH]cc2-c2ccncc2)c1]

HPLC (254 nm): $R_t$: 4.53 min
$^1$H NMR (401 MHz, DMSO-d6) δ=13.36 (s, 1 H), 9.00 (t, J=5.7 Hz, 1 H), 8.44 (d, J=6.0 Hz, 2 H), 8.27 (s, 1 H), 8.07-7.43 (m, 5 H), 7.28-7.19 (m, 2 H), 6.40-6.38 (m, 1 H), 6.28-6.21 (m, 1 H), 4.45 (d, J=4.9 Hz, 2 H). MS ESI (M+H) calc 345.1346; found. 345.1351 (C20H16N4O2)

N-Cyclohexyl-3-(4-pyridin-4-yl-1H-pyrazol-3-yl) benzamide

[(I)K, X=CH; R1, R2, R3, R4, R5, R6=H; m=0; Y=H; R7=cyclohexyl]

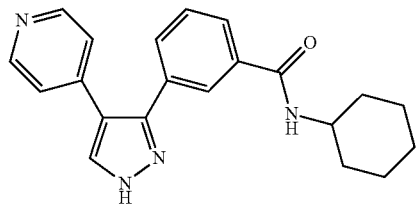 [SMILES: O=C(NC1CCCCC1)c1cccc(-c2n[nH]cc2-c2ccncc2)c1]

HPLC (254 nm): $R_t$: 5.10 min
$^1$H NMR (401 MHz, DMSO-d6) δ=13.35 (s, 1 H), 8.48-8.41 (m, 2 H), 8.30-8.18 (m, 2 H), 7.98 (br.s, 1 H), 7.88-7.79 (m, 1 H), 7.61-7.37 (m, 2 H), 7.29-7.18 (m, 2 H), 3.76 (m, 1 H), 1.94-1.00 (m, 10 H). MS ESI (M+H) calc 347.1867; found. 347.1874 (C21H22N4O)

N-(4-Chloro-phenyl)-3-(4-pyridin-4-yl-1H-pyrazol-3-yl)-benzamide (Cpnd. 3)

[(I)K, X=CH; R1, R2, R3, R4, R5, R6=H; m=0; Y=H; R7=4-chlorophenyl]

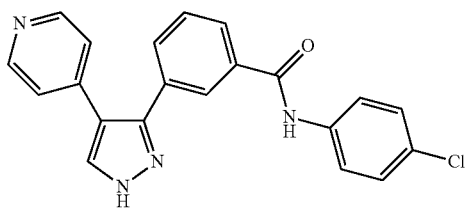 [SMILES: O=C(Nc1ccc(Cl)cc1)c1cccc(-c2n[nH]cc2-c2ccncc2)c1]

HPLC (254 nm): $R_t$: 5.60 min
$^1$H NMR (401 MHz, DMSO-d6) δ=13.40 (s, 1 H), 10.42 (s, 1 H), 8.50-8.44 (m, 2 H), 8.29 (s, 1 H), 8.09 (s, 1 H), 8.10-7.94 (m, 1 H), 7.84-7.78 (m, 2 H), 7.68-7.52 (m, 2 H), 7.44-7.38 (m, 2 H), 7.31-7.22 (m, 2 H). MS ESI (M+H) calc 375.1007; found. 375.1020 (C21H15ClN4O)

126

N-(4-Methoxy-phenyl)-3-(4-pyridin-4-yl-1H-pyrazol-3-yl)-benzamide

[(I)K, X=CH; R1, R2, R3, R4, R5, R6=H; m=0; Y=H; R7=4-methoxyphenyl]

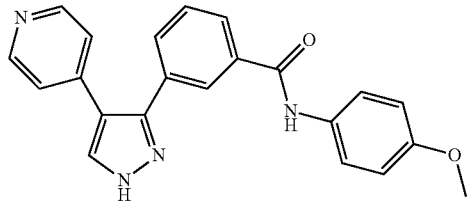 [SMILES: COc1ccc(NC(=O)c2cccc(-c3n[nH]cc3-c3ccncc3)c2)cc1]

HPLC (254 nm): $R_t$: 4.97 min
$^1$H NMR (401 MHz, DMSO-d6) δ=13.43 (s, 1 H), 10.17 (s, 1 H), 8.49-8.45 (m, 2 H), 8.23 (br. s., 1 H), 8.08 (s, 1 H), 7.98 (br. s., 1 H), 7.70-7.64 (m, 2 H), 7.60-7.53 (m, 2 H), 7.29-7.25 (m, 2 H), 6.97-6.89 (m, 2 H), 3.75 (s, 3 H). MS ESI (M+H) calc 371.1503; found. 371.1512 (C22H18N4O2).

N-Butyl-3-(4-pyridin-4-yl-1H-pyrazol-3-yl)-benzamide

[(I)K, X=CH; R1, R2, R3, R4, R5, R6=H; m=0; Y=H; R7=butyl]

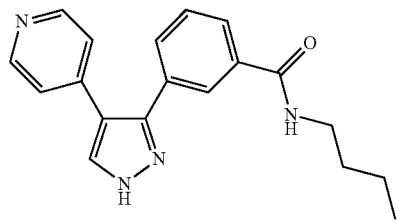 [SMILES: CCCCNC(=O)c1cccc(-c2n[nH]cc2-c2ccncc2)c1]

HPLC (254 nm): $R_t$: 4.73 min
$^1$H NMR (401 MHz, DMSO-d6) δ=13.43 (s, 1 H), 8.47 (br. s., 1 H), 8.46-8.43 (m, 2 H), 8.28 (s, 1 H), 8.03-7.7 (m, 2H), 7.60-7.42 (m, 2 H), 7.24 (d, J=4.0 Hz, 2 H), 3.28-3.20 (m, 2 H), 1.55-1.44 (m, 2 H), 1.36-1.26 (m, 2 H), 0.90 (t, J=7.3 Hz, 3 H). MS ESI (M+H) calc 321.1710; found. 321.1709 (C19H20N4O).

N-(4-Fluoro-phenyl)-3-(4-pyridin-4-yl-1H-pyrazol-3-yl)-benzamide

[(I)K, X=CH; R1, R2, R3, R4, R5, R6=H; m=0; Y=H; R7=4-fluorophenyl]

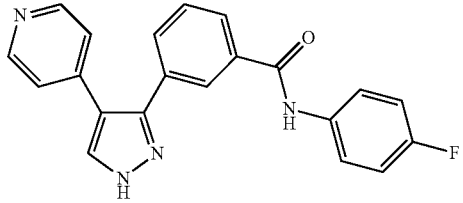 [SMILES: O=C(Nc1ccc(F)cc1)c1cccc(-c2n[nH]cc2-c2ccncc2)c1]

HPLC (254 nm): $R_t$: 5.17 min
$^1$H NMR (401 MHz, DMSO-d6) δ=13.40 (s, 1 H), 10.35 (s, 1 H), 8.48-8.44 (m, 2 H), 8.29 (s, 1 H), 8.13-7.92 (m, 2 H), 7.82-7.73 (m, 2 H), 7.67-7.51 (m, 2 H), 7.31-7.23 (m, 2 H), 7.22-7.15 (m, 2 H). MS ESI (M+H) calc 359.1303; found. 359.1305 (C21H15FN4O)

N-(4-Fluoro-phenyl)-3-(4-pyridin-4-yl-1H-pyrazol-3-yl)-benzamide

[(I)K, X=CH; R1, R2, R3, R4, R5, R6=H; m=0; Y=H; R7=3-fluorophenyl]

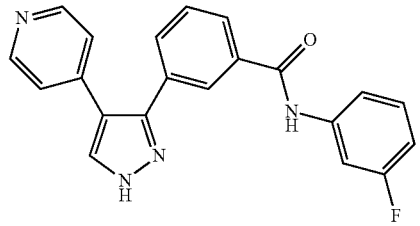 [SMILES: O=C(Nc1cccc(F)c1)c1cccc(-c2n[nH]cc2-c2ccncc2)c1]

HPLC (254 nm): $R_t$: 5.31 min $^1$H NMR (401 MHz, DMSO-d6) δ=13.41 (s, 1 H), 10.48 (s, 1 H), 8.47 (dd, J=1.5, 4.6 Hz, 2 H), 8.30 (s, 1 H), 8.11-7.92 (m, 2 H), 7.74 (dt, J=2.3, 11.8 Hz, 1 H), 7.68-7.53 (m, 3 H), 7.39 (q, J=7.9 Hz, 1 H), 7.30-7.24 (m, 2 H), 6.98-6.90 (m, 1 H). MS ESI (M+H) calc 359.1303; found. 359.1311 (C21H15FN4O)

N-Phenyl-3-(4-pyridin-4-yl-1H-pyrazol-3-yl)-benzamide

[(I)K, X=CH; R1, R2, R3, R4, R5, R6=H; m=0; Y=H; R7=phenyl]

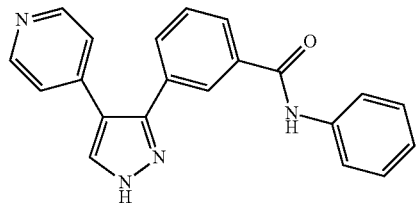 [SMILES: O=C(Nc1ccccc1)c1cccc(-c2n[nH]cc2-c2ccncc2)c1]

HPLC (254 nm): $R_t$: 5.03 min $^1$H NMR (401 MHz, DMSO-d6) δ=13.40 (s, 1 H), 10.29 (s, 1 H), 8.47 (d, J=6.0 Hz, 2 H), 8.29 (s, 1 H), 8.09 (s, 1 H), 8.08-7.92 (m, 1 H), 7.80-7.73 (m, 1 H), 7.70-7.53 (m, 2 H), 7.40-7.31 (m, 2 H), 7.30-7.23 (m, 1 H), 7.29 (br. s., 2 H), 7.15-7.07 (m, 1 H). MS ESI (M+H) calc 341.1397; found. 341.1399 (C21H16N4O).

N-Isobutyl-3-(4-pyridin-4-yl-1H-pyrazol-3-yl)-benzamide

[(I)K, X=CH; R1, R2, R3, R4, R5, R6=H; m=0; Y=H; R7=i-butyl]

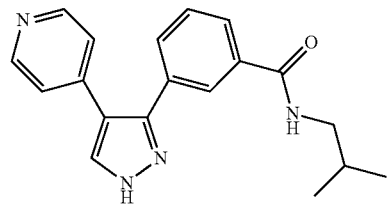 [SMILES: CC(C)CNC(=O)c1cccc(-c2n[nH]cc2-c2ccncc2)c1]

HPLC (254 nm): $R_t$: 4.67 min $^1$H NMR (401 MHz, DMSO-d6) δ=13.36 (s, 1 H), 8.49 (br. s., 1 H), 8.45 (d, J=5.9 Hz, 2 H), 8.27 (s, 1 H), 7.97 (s, 1 H), 7.88-7.80 (m, 1 H), 7.58-7.42 (m, 2 H), 7.28-7.22 (m, 2 H), 3.07 (t, J=6.1 Hz, 2 H), 1.83 (dt, J=6.8, 13.4 Hz, 1 H), 0.87 (d, J=6.7 Hz, 6 H). MS ESI (M+H) calc 321.1710; found. 321.1707 (C19H20N4O)

N-Isopropyl-3-(4-pyridin-4-yl-1H-pyrazol-3-yl)-benzamide

[(I)K, X=CH; R1, R2, R3, R4, R5, R6=H; m=0; Y=H; R7=i-propyl]

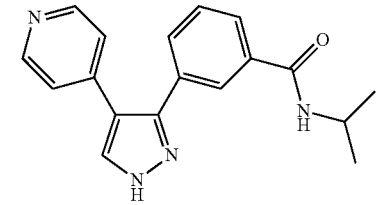 [SMILES: CC(C)NC(=O)c1cccc(-c2n[nH]cc2-c2ccncc2)c1]

HPLC (254 nm): $R_t$: 4.32 min $^1$H NMR (401 MHz, DMSO-d6) δ=13.36 (s, 1 H), 8.45 (d, J=6.0 Hz, 2 H), 8.28 (s, 1 H), 8.25 (s, 1 H), 8.01-7.96 (m, 1 H), 7.95-7.81 (m, 1 H), 7.60-7.40 (m, 2 H), 7.29-7.24 (br.s. 2 H), 4.04-4.16 (m, 1 H), 1.16 (d, J=6.6 Hz, 6 H). MS ESI (M+H) calc 307.1554; found. 307.1543 (C18H18N4O)

N-Allyl-3-(4-pyridin-4-yl-1H-pyrazol-3-yl)-benzamide

[(I)K, X=CH; R1, R2, R3, R4, R5, R6=H; m=0; Y=H; R7=allyl]

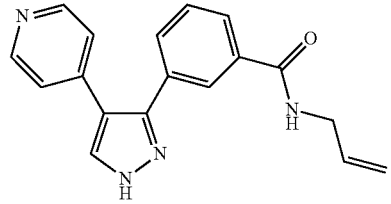 [SMILES: C=CCNC(=O)c1cccc(-c2n[nH]cc2-c2ccncc2)c1]

HPLC (254 nm): $R_t$: 4.18 min $^1$H NMR (401 MHz, DMSO-d6) δ=13.36 (s, 1 H), 8.70 (br. s., 1 H), 8.47-8.42 (m, 2 H), 8.28 (s, 1 H), 8.00 (s, 1 H), 7.90-7.84 (m, 1 H), 7.62-7.41 (m, 2 H), 7.28-7.20 (br. s., 2 H), 5.89 (dddd, J=5.2, 5.4, 10.3, 17.2 Hz, 1 H), 5.04-5.20 (m, 2 H), 3.89 (br. s., 2 H). MS ESI (M+H) calc 305.1397; found. 305.1383 (C18H16N4O)

N-(3-Chloro-phenyl)-3-(4-pyridin-4-yl-1H-pyrazol-3-yl)-benzamide

[(I)K, X=CH; R1, R2, R3, R4, R5, R6=H; m=0; Y=H; R7=3-chlorophenyl]

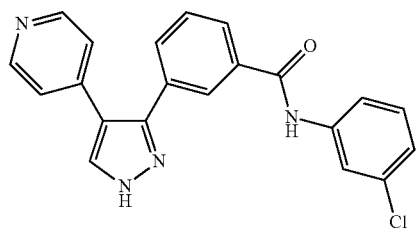 [SMILES: O=C(Nc1cccc(Cl)c1)c1cccc(-c2n[nH]cc2-c2ccncc2)c1]

HPLC (254 nm): $R_t$: 5.62 min
$^1$H NMR (401 MHz, DMSO-d6) δ=13.36 (s, 1 H), 10.45 (s, 1 H), 8.47 (d, J=6.0 Hz, 2 H), 8.30 (s, 1 H), 8.09 (s, 1 H), 8.07-7.97 (m, 1 H), 7.96 (t, J=2.0 Hz, 1 H), 7.71 (dd, J=1.1, 8.2 Hz, 1 H), 7.67-7.52 (m, 2 H), 7.39 (t, J=8.0 Hz, 1 H), 7.26 (d, J=4.6 Hz, 2 H), 7.17 (d, J=7.6 Hz, 1 H). MS ESI (M+H) calc 375.1007; found. 375.1007 (C21H15ClN4O)

3-(4-pyridin-4-yl-1H-pyrazol-3-yl)-N-o-tolyl-benzamide

[(I)K, X=CH; R1, R2, R3, R4, R5, R6=H; m=0; Y=H; R7=2-methylphenyl]

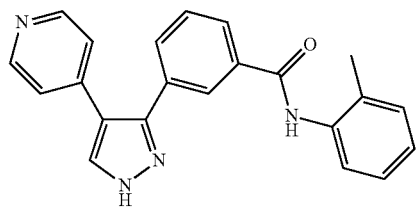 [SMILES: Cc1ccccc1NC(=O)c1cccc(-c2n[nH]cc2-c2ccncc2)c1]

HPLC (254 nm): $R_t$: 4.99 min
$^1$H-NMR (401 MHz, DMSO-d$_6$ δ=13.36 (s, 1 H), 9.89 (s, 1 H), 8.51-8.40 (m, 2 H), 8.27 (s, 1 H), 8.08-7.92 (m, 1 H), 7.69-7.11 (m, 9 H), 2.19 (s, 3 H). MS ESI (M+H) calc 355.1554; found. 355.1563 (C22H18N4O)

3-(4-pyridin-4-yl-1H-pyrazol-3-yl)-N-p-tolyl-benzamide

[(I)K, X=CH; R1, R2, R3, R4, R5, R6=H; m=0; Y=H; R7=4-methylphenyl]

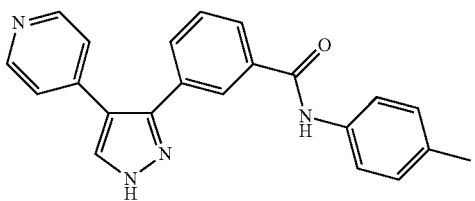 [SMILES: Cc1ccc(NC(=O)c2cccc(-c3n[nH]cc3-c3ccncc3)c2)cc1]

HPLC (254 nm): $R_t$: 5.35 min
$^1$H NMR (401 MHz, DMSO-d6)) δ=13.39 (s, 1 H), 10.21 (s, 1 H), 8.46 (dd, J=1.4, 4.6 Hz, 2 H), 8.29 (s, 1 H), 8.08 (s, 1 H), 8.06-7.92 (m, 1 H), 7.64 (d, J=8.4 Hz, 2 H), 7.62-7.52 (m, 2 H), 7.30-7.23 (br. s., 2 H), 7.16 (d, J=8.3 Hz, 2 H), 2.29 (s, 3 H). MS ESI (M+H) calc 355.1554; found. 355.1566 (C22H18N4O)

N-(2-Methoxy-phenyl)-3-(4-pyridin-4-yl-1H-pyrazol-3-yl)-benzamide

[(I)K, X=CH; R1, R2, R3, R4, R5, R6=H; m=0; Y=H; R7=2-methoxyphenyl]

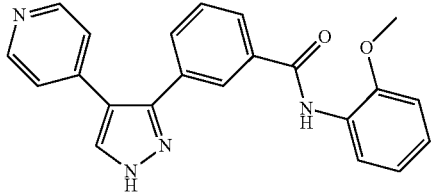 [SMILES: COc1ccccc1NC(=O)c1cccc(-c2n[nH]cc2-c2ccncc2)c1]

HPLC (254 nm): $R_t$: 5.24 min
$^1$H NMR (401 MHz, DMSO-d6)) δ=13.39 (s, 1 H), 9.42 (s, 1 H), 8.47 (d, J=6.0 Hz, 2 H), 8.29 (s, 1 H), 8.06 (br. s., 1 H), 8.04-7.92 (m, 1 H), 7.76 (d, J=7.7 Hz, 1 H), 7.67-7.51 (m, 2 H), 7.28 (br. s., 2 H), 7.22-7.15 (m, 1 H), 7.12-7.06 (m, 1 H), 6.97 (t, 1 H), 3.82 (s, 3 H). MS ESI (M+H) calc 371.1503; found. 371.1508 (C22H18N4O2)

N-(4-Methoxy-phenyl)-N-methyl-3-(4-pyridin-4-yl-1H-pyrazol-3-yl)-benzamide [(I)K, X=CH; R1, R2, R3, R4, R5, R6=H; m=0; R7=4-methoxyphenyl, Y=methyl]

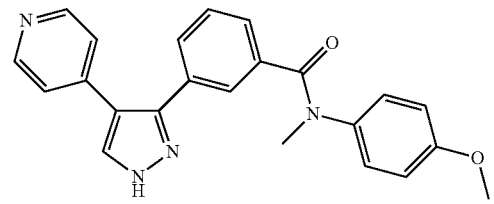 [SMILES: COc1ccc(N(C)C(=O)c2cccc(-c3n[nH]cc3-c3ccncc3)c2)cc1]

HPLC (254 nm): $R_t$: 4.85 min
$^1$H NMR (401 MHz, DMSO-d6)) δ=13.29 (s, 1 H), 8.48-8.41 (m, 2 H), 8.21 (s, 1 H), 7.35 (br.s., 1 H), 7.30-7.17 (m, 3 H), 7.14-7.02 (m, 4 H), 6.87-6.78 (m, 2 H), 3.67 (s, 3 H), 3.31 (s, 3 H). MS ESI (M+H) calc 385.1659; found. 385.1674 (C23H20N4O2).

N-(4-tert-Butyl-phenyl)-3-(4-pyridin-4-yl-1H-pyrazol-3-yl)-benzamide (Cpnd. 4) [(I)K, X=CH R1, R2, R3, R4, R5, R6=H; m=0; Y=H; R7=4-tert-butylphenyl]

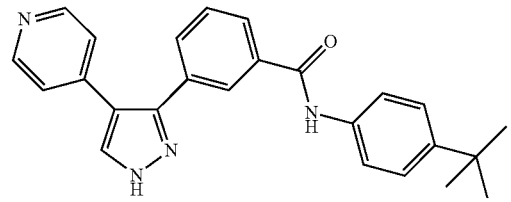 [SMILES: CC(C)(C)c1ccc(NC(=O)c2cccc(-c3n[nH]cc3-c3ccncc3)c2)cc1]

HPLC (254 nm): R$_t$: 6.27 min $^1$H NMR (401 MHz, DMSO-d6) δ=13.40 (s, 1 H), 10.22 (s, 1 H), 8.49-8.44 (m, 2 H), 8.29 (br.s, 1 H), 8.09 (s, 1 H), 8.07-7.93 (br.s, 1 H), 7.71-7.65 (m, 2 H), 7.64-7.41 (m, 3 H), 7.37 (d, J=8.7 Hz, 2 H), 7.27 (d, J=4.8 Hz, 1 H), 1.29 (s, 9 H). MS ESI (M+H) calc 397.2023; found. 397.2035 (C25H24N4O)

3-(4-pyridin-4-yl-1H-pyrazol-3-yl)-N-m-tolyl-benzamide

[(I)K, X=CH; R1, R2, R3, R4, R5, R6=H; m=0; Y=H; R7=3-methylphenyl]

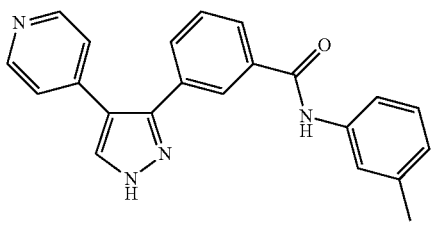 [SMILES: Cc1cccc(NC(=O)c2cccc(-c3n[nH]cc3-c3ccncc3)c2)c1]

HPLC (254 nm): R$_t$: 5.36 min $^1$H NMR (401 MHz, DMSO-d6) δ=13.40 (s, 1 H), 10.21 (s, 1 H), 8.48-8.44 (m, 2 H), 8.29 (s, 1 H), 8.08 (s, 1 H), 8.01-7.93 (m, 2 H), 7.67-7.51 (m, 3 H), 7.31-7.19 (m, 3 H), 6.96-6.89 (m, 1 H), 2.31 (s, 3 H). MS ESI (M+H) calc 355.1554; found. 355.1560 (C22H18N4O).

3-(4-pyridin-4-yl-1H-pyrazol-3-yl)-N-thiophen-2-yl-methyl-benzamide

[(I)K, X=CH; R1, R2, R3, R4, R5, R6=H; m=0; Y=H; R7=thiophen-2-yl-methyl]

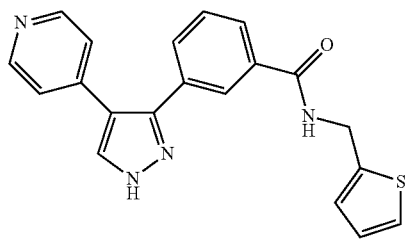 [SMILES: O=C(NCc1cccs1)c1cccc(-c2n[nH]cc2-c2ccncc2)c1]

HPLC (254 nm): R$_t$: 4.76 min $^1$H NMR (401 MHz, DMSO-d6) δ=13.37 (s, 1 H), 9.18 (t, J=5.7 Hz, 1 H), 8.45 (d, J=6.0 Hz, 2 H), 8.28 (br.s, 1 H), 8.11-7.83 (m, 2 H), 7.65-7.43 (m, 2 H), 7.38 (d, J=5.0 Hz, 1 H), 7.28-7.17 (m, 2 H), 7.00 (d, J=2.3 Hz, 1 H), 6.90-6.98 (m, 1 H), 4.55-4.68 (m, 2 H). MS ESI (M+H) calc 361.1118; found. 361.1125 (C20H16N4OS)

N-(3-Acetylamino-phenyl)-3-(4-pyridin-4-yl-1H-pyrazol-3-yl)-benzamide

[(I)K, X=CH; R1, R2, R3, R4, R5, R6=H; m=0; Y=H; R7=3-acetylamino]

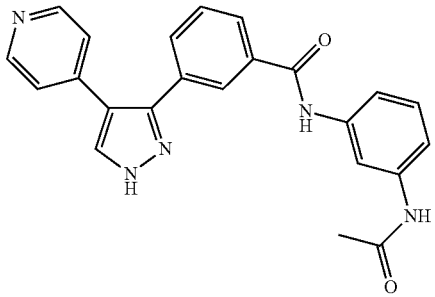 [SMILES: CC(=O)Nc1cccc(NC(=O)c2cccc(-c3n[nH]cc3-c3ccncc3)c2)c1]

HPLC (254 nm): R$_t$: 4.38 min $^1$H NMR (401 MHz, DMSO-d6) δ=13.39 (s, 1 H), 10.30 (s, 1 H), 9.95 (s, 1 H), 8.48-8.43 (m, 2 H), 8.29 (br.s, 1H), 7.67-7.22 (m, 7 H), 7.31-7.22 (m, 3 H), 2.05 (s, 3 H). MS ESI (M+H) calc 398.1612; found. 398.1619 (C23H19N5O2).

Example 17

Thiophene-3-sulfonic acid 3-(4-pyridin-4-yl-1H-pyrazol-3-yl)benzylamide

[(I)L, X=CH; R1, R2, R3, R4, R5, R6=H; m=0; R7'=3-thiophenyl]

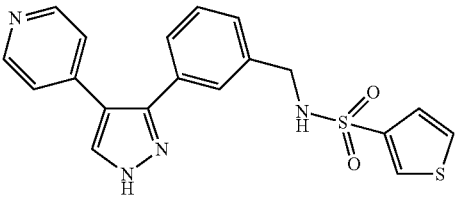 [SMILES: O=S(=O)(NCc1cccc(-c2n[nH]cc2-c2ccncc2)c1)c1ccsc1]

Method N

Step a: 3-[4-pyridin-4-yl-1-(2-trimethylsilanyl-ethoxymethyl)-1H-pyrazol-3yl]-benzonitrile Cesium carbonate (8.34 g, 25.6 mmol) and (2-chloromethoxy-ethyl)-trimethyl-silane (1.71 g, 10.24 mmol) were added to a solution of 3-(4-pyridin-4-yl-1H-pyrazol-3-yl)-benzonitrile (2.10 g, 8.54 mmol) in dry DMF (70 ml) and the reaction mixture was stirred at room temperature under nitrogen atmosphere for 24 h. A further addition of (2-chloromethoxy-ethyl)-trimethyl-silane (0.57 g, 3.41 mmol) was required to affect reaction completion; the solvent was then removed under reduced pressure and the residue was taken up with DCM (50 ml). The organic layer was washed with a saturated NaHCO$_3$ solution (1×50 ml), brine (1×50 ml), dried over Na$_2$SO$_4$. The filtrate was evaporated to dryness to give a brown oil, which was purified by flash chromatography, over silica gel, using DCM/MeOH/NH$_4$OH (9.8:0.2:0.1) as eluent, to afford 3-[4-pyridin-4-yl-1-(2-trimethylsilanyl-ethoxymethyl)-1H-pyrazol-3-yl]-benzonitrile (2.57 g, 6.82 mmol, 80%).

HPLC (254 nm): R$_t$: 7.19 min

1H NMR (401 MHz, DMSO-d6) δ=8.52 (m, 2 H), 8.44 (br.s., 1 H), 7.90-7.87 (m, 1 H), 7.84-7.80 (m, 1 H), 7.77-7.72 (m, 1 H), 7.63 (t, J=8.0 Hz, 1 H), 7.25-7.23 (m, 2 H), 5.51 (s, 2 H), 3.68 (t, J=8.0 Hz, 2 H), 0.90 (t, J=8.0 Hz, 2 H), −0.01 (s, 9 H). MS ESI (M+H) calc 377.1792; found. 377.1798 (C21H24N4OSi).

Method I

Step c: 3-[4-Pyridin-4-yl-1-(2-trimethylsilanyl-ethoxymethyl)-1H-pyrazol-3-yl]-benzylamine Lithium aluminium hydride (1 M in THF, 68.2 mmol, 10 eq) was added to a solution of 3-[4-pyridin-4-yl-1-(2-trim-ethylsilanyl-ethoxymethyl)-1H-pyrazol-3-yl]-benzonitrile (2.57 g, 6.82 mmol) in dry THF (45.0 mL) under nitrogen and the reaction mixture was stirred at reflux for 3 hours. The reaction was cooled down in an ice bath and distilled water was added dropwise followed by a 1M NaOH solution (7.5 ml). The organic layer was removed under vacuum and DCM was added (30 ml) to the water phase. The dichloromethane layer was washed with brine and dried over $Na_2SO_4$. The filtrate was evaporated to dryness to give an oil, which was purified over silica gel, using $DCM/MeOH/NH_4OH$ (9.8:0.2:0.05) as eluent, to afford 3-[4-pyridin-4-yl-1-(2-trimethylsi-lanyl-ethoxymethyl)-1H-pyrazol-3-yl]-benzylamine (1.48 g, 3.90 mmol, 56%).

HPLC (254 nm): $R_t$: 5.12 min
$^1$H NMR (401 MHz, DMSO-d6) δ=8.48-8.46 (m, 2 H), 8.40 (s, 1 H), 7.53-7.30 (m, 3 H), 7.25-7.14 (m, 3 H), 5.48 (s, 2 H), 3.73 (br.s, 2 H), 3.67 (t, J=8.0 Hz, 2 H), 0.89 (t, J=8.0 Hz, 2 H), −0.02 (s, 9 H). MS ESI (M+H) calc 381.2105; found. 381.2122 (C21H28N4OSi).

3-(1-Methyl-4-pyridin-4-yl-1H-pyrazol-3-yl)-benzy-lamine was an important side product (20%), which was also isolated and characterized.

3-(1-Methyl-4-pyridin-4-yl-1H-pyrazol-3-yl)-benzylamine

HPLC (254 nm): $R_t$: 3.36 min
$^1$H NMR (401 MHz, DMSO-d6) δ=8.42-8.48 (m, 2 H), 8.20 (s, 1 H), 7.52 (s, 1 H), 7.40-7.32 (m, 2 H), 7.23 (m, 1 H), 7.22-7.20 (m, 2 H), 3.32. (s, 2 H), 3.94 (s, 3 H). MS ESI (M+H) calc 265.1448; found. 265.1450 (C16H16N4). MS ESI (M+H) calc 265.1448; found. 265.1450 (C16H16N4).

Method I, Step d and Method M, Step a: General Procedure

The proper sulfonyl chloride (0.184 mmol, 2 eq) was added to a solution of 3-[4-pyridin-4-yl-1-(2-trimethylsilanyl-ethoxymethyl)-1H-pyrazol-3-yl]-benzylamine (0.035 g, 0.092 mmol) in dry DCM (1 ml) and the reaction mixture was stirred at room temperature for 24 h. The solvent was removed at Genevac Evaporator affording the SEM protected interme-diate, which was then stirred in HCl 4M in dioxane (1 mL) for 24 h at room temperature. The solvent was evaporated at Genevac and the crude was purified by reverse phase HPLC, affording the final sulfonylamide.

The following sulfonamides were prepared following this procedure:

Thiophene-3-sulfonic acid 3-(4-pyridin-4-yl-1H-pyrazol-3-yl)benzylamide

[(I)L, X=CH; R1, R2, R3, R4, R5, R6=H; m=0; R7'=3-thiophenyl]

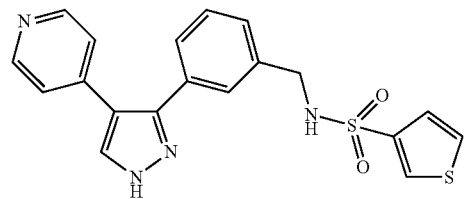 [SMILES: O=S(=O)(NCc1cccc(-c2n[nH]cc2-c2ccncc2)c1)c1ccsc1]

HPLC (254 nm): $R_t$: 4.81 min
$^1$H NMR (401 MHz, DMSO-d$_6$) (selected signals) δ=8.46-8.34 (m, 2 H), 8.09 (s, 1 H), 7.94 (br.s, 1 H), 7.61 (dd, J=3.0, 5.1 Hz, 1 H), 7.41 (s, 1 H), 7.32-7.28 (m, 2 H), 7.26-7.22 (m, 3 H), 7.21-7.18 (m, 1 H), 4.01 (s, 2 H). MS ESI (M+H) calc 397.0788; found. 397.0782 (C19H16N4O2S2).

Thiophene-2-sulfonic acid 3-(4-pyridin-4-yl-1H-pyrazol-3-yl)-benzylamide

[(I)L, X=CH; R1, R2, R3, R4, R5, R6=H; m=0; R7'=2-thiophenyl]

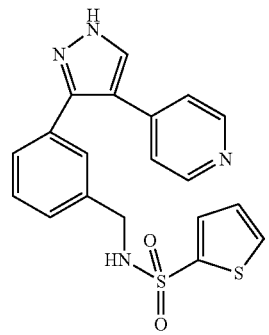 [SMILES: O=S(=O)(NCc1cccc(-c2n[nH]cc2-c2ccncc2)c1)c1cccs1]

HPLC (254 nm): $R_t$: 4.89 min
$^1$H NMR (401 MHz, DMSO-d6) δ=13.28 (br.s, 1 H), 8.43 (d, J=6.0 Hz, 2 H), 8.38 (t, J=6.0 Hz, 1 H), 8.24 (br.s., 1 H), 7.90 (dd, J=1.3, 5.0 Hz, 1 H), 7.57 (dd, J=1.3, 3.7 Hz, 1 H), 7.47-7.19 (m, 6 H), 7.15 (dd, J=3.8, 4.8 Hz, 1 H), 4.06 (m, 2 H). MS ESI (M+H) calc 397.0788; found. 397.0795 (C19H16N4O2S2).

[(I)L, X=CH; R1, R2, R3, R4, R5, R6=H; m=0; R7'=3-fluorophenyl]

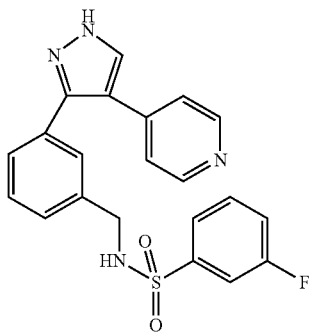 [SMILES: O=S(=O)(NCc1cccc(-c2n[nH]cc2-c2ccncc2)c1)c1cccc(F)c1]

HPLC (254 nm): $R_t$: 5.15 min.
$^1$H NMR (401 MHz, DMSO-d6) δ=13.28 (s, 1 H), 8.43 (dd, J=1.5, 4.6 Hz, 2 H), 8.33 (t, J=6.0 Hz, 1 H), 8.24 (s, 1 H), 7.65-7.15 (m, 10 H), 4.05 (d, J=6.2 Hz, 2 H). MS ESI (M+H) calc 409.1129; found. 409.1147 (C21H17FN4O2S).

Furan-2-sulfonic acid 3-(4-pyridin-4-yl-1H-pyrazol-3-yl)benzylamide

[(I)L, X=CH; R1, R2, R3, R4, R5, R6=H; m=0; R7'=2-furyl]

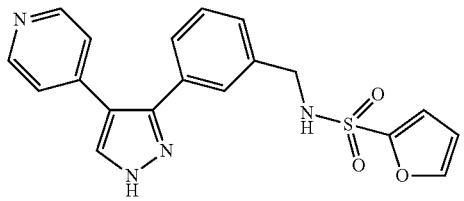 [SMILES: O=S(=O)(NCc1cccc(-c2n[nH]cc2-c2ccncc2)c1)c1ccco1]

HPLC (254 nm): $R_t$: 4.72 min
MS ESI (M+H) calc 381.1016; found. 381.1027 (C19H16N4O3S).

[(I)L, X=CH; R1, R2, R3, R4, R5, R6=H; m=0; R7'=phenyl]

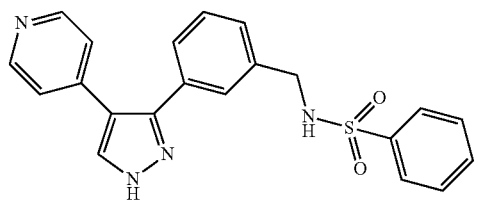 [SMILES: O=S(=O)(NCc1cccc(-c2n[nH]cc2-c2ccncc2)c1)c1ccccc1]

HPLC (254 nm): $R_t$: 4.96 min
MS ESI (M+H) calc 391.1223; found. 391.1215 (C21H18N4O2S)

4-Chloro-N-[3-(4-Pyridin-4-yl-1H-pyrazol-3-yl)-benzyl]-benzenesulfonamide

[(I)L, X=CH; R1, R2, R3, R4, R5, R6=H; m=0; R7'=4-chlorophenyl]

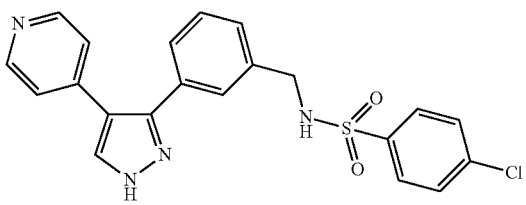 [SMILES: O=S(=O)(NCc1cccc(-c2n[nH]cc2-c2ccncc2)c1)c1ccc(Cl)cc1]

HPLC (254 nm): $R_t$: 5.40 min
$^1$H NMR (401 MHz, DMSO-d6) δ=13.32 (s, 1 H), 8.47-8.43 (m, 2 H), 8.13 (br. s., 1 H), 7.81-7.76 (m, 2 H), 7.66-7.59 (m, 2 H), 7.39 (s, 1 H), 7.25-7.22 (m, 2 H), 7.35-7.20 (m, 3 H), 4.03 (s, 2 H). MS ESI (M+H) calc 425.0834; found. 425.0853 (C21H17ClN4O2S)

N-[3-(4-Pyridin-4-yl-1H-pyrazol-3-yl)-benzyl]-3-trifluoromethyl-benzenesulfonamide

[(I)L, X=CH; R1, R2, R3, R4, R5, R6=H; m=0; R7'=3-trifluoromethylphenyl]

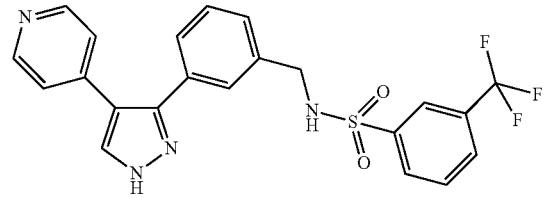 [SMILES: O=S(=O)(NCc1cccc(-c2n[nH]cc2-c2ccncc2)c1)c1cccc(C(F)(F)F)c1]

HPLC (254 nm): $R_t$: 5.63 min
$^1$H NMR (401 MHz, DMSO-d6) δ=13.29 (s, 1 H), 8.46-8.41 (m, 2 H), 8.40-8.34 (br.s, 1 H), 8.12 (br. s., 1 H), 8.09-8.02 (m, 2 H), 7.98 (d, J=7.9 Hz, 1 H), 7.79 (t, J=7.8 Hz, 1 H), 7.38 (s, 1 H), 7.33-7.23 (m, 3 H), 7.22 (dd, J=1.6, 4.5 Hz, 2 H), 4.07 (s, 2 H). MS ESI (M+H) calc 459.1097; found. 459.1096 (C22H17F3N4O2S).

N-[3-(4-Pyridin-4-yl-1H-pyrazol-3-yl)-benzyl]-4-trifluoromethyl-benzenesulfonamide

[(I)L, X=CH; R1, R2, R3, R4, R5, R6=H; m=0; R7'=4-trifluoromethylphenyl]

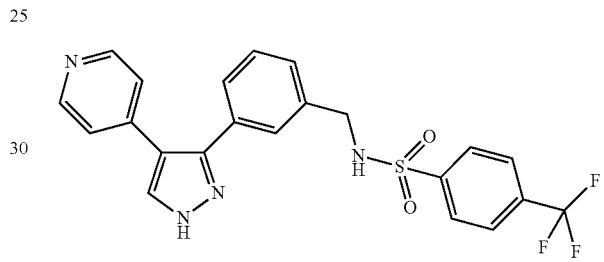

HPLC (254 nm): $R_t$:5.70 min
$^1$H NMR (401 MHz, DMSO-d6) δ=13.29 (s, 1 H), 8.47-8.41 (m, 2 H), 8.41-8.33 (br.s, 1 H), 8.13 (br.s., 1 H), 8.01-7.91 (m, 4 H), 7.40 (s, 1 H), 7.34-7.25 (m, 3 H), 7.25-7.22 (m, 2 H), 4.06 (s, 2 H). MS ESI (M+H) calc 459.1097; found. 459.1086 (C22H17F3N4O2S)

3,5-Difluoro-N-[3-(4-Pyridin-4-yl-1H-pyrazol-3-yl)-benzyl]-benzenesulfonamide

[(I)L, X=CH; R1, R2, R3, R4, R5, R6=H; m=0; R7'=3,5-difluorophenyl]

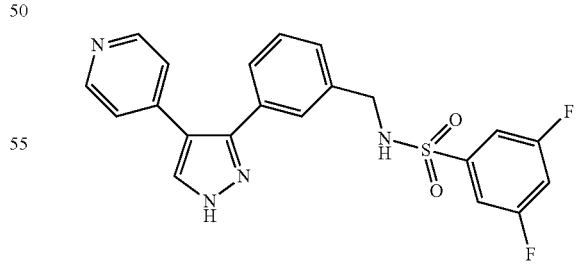

HPLC (254 nm): $R_t$ 5.33 min
$^1$H NMR (401 MHz, DMSO-d6) δ=13.31 (br. s., 1 H), 8.47-8.42 (m, 2 H), 8.41-8.30 (br.s, 1 H), 8.13 (br. s., 1 H), 7.57-7.51 (m, 1 H), 7.47-7.41 (m, 2 H), 7.39 (br.s, 1 H), 7.34-7.29 (m, 1 H), 7.29-7.20 (m, 4 H), 4.10 (s, 2 H). MS ESI (M+H) calc 427.1035; found: 427.1038 (C21H16F2N4O2S)

2,5-Difluoro-N-[3-(4-Pyridin-4-yl-1H-pyrazol-3-yl)-benzyl]-benzenesulfonamide

[(I)L, X=CH; R1, R2, R3, R4, R5, R6=H; m=0; R7'=2,5-difluorophenyl]

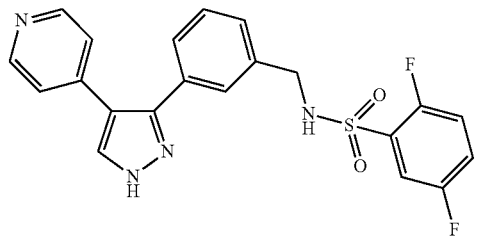 [SMILES: O=S(=O)(NCc1cccc(-c2n[nH]cc2-c2ccncc2)c1)c1cc(F)ccc1F]

HPLC (254 nm): $R_t$ 5.16 min
$^1$H NMR (401 MHz, DMSO-d6) δ=13.28 (s, 1 H), 8.71 (br. s., 1 H), 8.47-8.42 (m, 2 H), 8.12 (br. s., 1 H), 7.52-7.35 (m, 3 H), 7.33-7.25 (m, 4 H), 7.24-7.21 (m, 2 H), 4.16 (s, 2 H). MS ESI (M+H) calc 427.1035; found. 427.1040 (C21H16F2N4O2S).

Pyridine-4-sulfonicacid-[3-(4-Pyridin-4-yl-1H-pyrazol-3-yl)-benzyl]-benzylamide

[(I)L, X=CH; R1, R2, R3, R4, R5, R6=H; m=0; R7'=pyridyl]

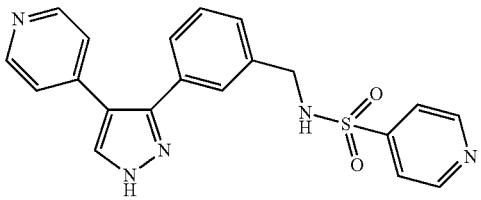 [SMILES: O=S(=O)(NCc1cccc(-c2n[nH]cc2-c2ccncc2)c1)c1ccncc1]

HPLC (254 nm): $R_t$ 4.29 min
$^1$H NMR (401 MHz, DMSO-d6) δ=13.32 (br. s., 1 H), 8.91 (dd, J=0.7, 2.4 Hz, 1 H), 8.77 (dd, J=1.6, 4.9 Hz, 1 H), 8.62-8.31 (br.s., 1 H), 8.46-8.44 (m, 2 H), 8.23-7.91 (m, 2 H), 7.58 (ddd, J=0.8, 4.8, 8.0 Hz, 1 H), 7.40 (s, 1 H), 7.34-7.18 (m, 5 H), 4.10 (s, 2 H). MS ESI (M+H) calc 392.1176; found. 392.1195 (C20H17N5O2S).

By removing the SEM protective group before derivatization the following primary amine was obtained:

3-(4-Pyridin-4-yl-1H-pyrazol-3-yl)-benzylamine

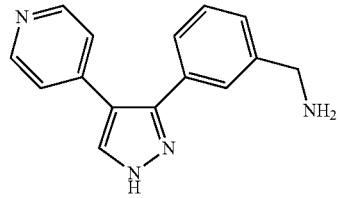 [SMILES: NCc1cccc(-c2n[nH]cc2-c2ccncc2)c1]

HPLC (254 nm): $R_t$: 2.42 min
$^1$H NMR (401 MHz, DMSO-d6) δ=13.26 (br.s, 1 H), 8.46-8.42 (m, 2 H), 8.10 (br. s., 1 H), 7.46-7.44 (m, 1 H), 7.42-7.30 (m, 2 H), 7.28-7.24 (m, 2 H), 7.22 (dt, J=1.8, 6.6 Hz, 1 H), 3.74 (s, 2 H). MS ESI (M+H) calc 251.1291; found. 251.1288 (C15H14N4).

Example 18

1-[3-(4-Pyridin-4-yl-1H-pyrazol-3-yl)-benzyl]-3-(3-trifluoromethyl-phenyl)-urea [(I)N, X=CH R1, R2, R3, R4, R5, R6=H; m=0; R7'=3-trifluoromethylphenyl]

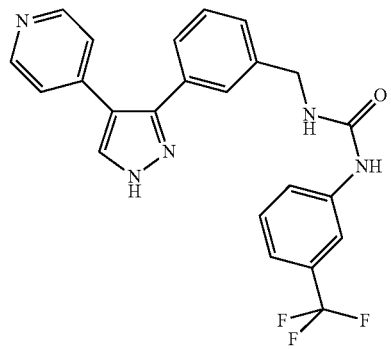 [SMILES: O=C(NCc1cccc(-c2n[nH]cc2-c2ccncc2)c1)Nc1cccc(C(F)(F)F)c1]

Method I, Step d and Method M, Step a

3-Trifluoromethylphenylisocyanate (0.184 mmol, 2 eq) was added to a solution of 3-[4-pyridin-4-yl-1-(2-trimethylsilanyl-ethoxymethyl)-1H-pyrazol-3-yl]-benzylamine (0.035 g, 0.092 mmol) (prepared as described in Example 19) in dry DCM (1 ml) and the reaction mixture was stirred at room temperature for 24 h. The solvent was removed at Genevac Evaporator affording the SEM protected intermediate, which was then stirred in HCl 4M in dioxane (1 mL) for 24 h at room temperature. The solvent was evaporated at Genevac and the crude was purified by reverse phase HPLC, affording the final urea.

HPLC (254 nm): $R_t$: 5.62 min
$^1$H NMR (401 MHz, DMSO-d6) δ=13.32 (br.s, 1 H), 8.95 (s, 1 H), 8.44-8.39 (m, 2 H), 8.12 (br.s, 1 H), 7.96 (s, 1 H), 7.54-7.21 (m, 9 H), 6.82 (t, J=5.9 Hz, 1 H), 4.33 (d, J=5.9 Hz, 2 H). MS ESI (M+H) calc 438.1536; found. 438.1535 (C23H18F3N5O).

Operating in an analogous way the following compounds were prepared:

1-(4-Chloro-3-trifluoromethylphenyl)-3-[3-(4-pyridin-4-yl-1H-pyrazol-3-yl)-benzyl]-urea

[(I)N, X=CH; R1, R2, R3, R4, R5, R6=H; m=0; R7'=4-chloro-3-trifluoromethylphenyl]

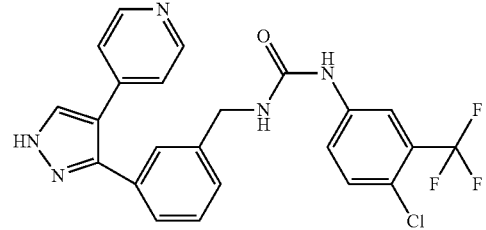 [SMILES: O=C(NCc1cccc(-c2n[nH]cc2-c2ccncc2)c1)Nc1ccc(Cl)c(C(F)(F)F)c1]

HPLC (254 nm): $R_t$:4.97 min

¹H NMR (401 MHz, DMSO-d6) (selected signals) δ=13.36 (br.s., 1 H), 8.42-8.39 (m, 2 H), 8.11-8.09 (m, 2 H), 7.61-7.59 (m, 1 H), 7.54 (m, 1 H), 7.45 (br.s, 1 H), 7.41-7.29 (m, 3 H), 7.28-7.23 (m, 2 H), 4.32 (d, J=6.0 Hz, 2 H). MS ESI (M+H) calc 472.1147; found. 472.1150 (C23H17ClF3N5O).

1-(4-Chloro-3-trifluoromethylphenyl)-3-[3-(1-methyl-4-pyridin-4-yl-1H-pyrazol-3-yl)-benzyl]-urea

[(I)N, X=CH; R2, R3, R4, R5, R6=H; m=0; R1=methyl; R7'=4-chloro-3-trifluoromethylphenyl]

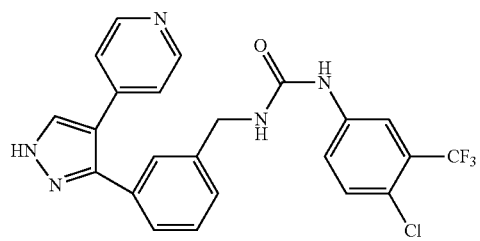 [SMILES: O=C(NCc1cccc(-c2n[nH]cc2-c2ccncc2)c1)Nc1ccc(Cl)c(C(F)(F)F)c1]

HPLC (254 nm): R$_t$: 6.36 min
¹H NMR (500 MHz, DMSO-d6) δ=9.07 (s, 1 H), 8.41 (dd, J=1.5, 4.5 Hz, 2 H), 8.19 (s, 1 H), 8.05 (d, J=2.3 Hz, 1 H), 7.57 (dd, J=2.4, 7.5 Hz, 1 H), 7.55 (br.s, 1 H), 7.43 (br. s., 1 H), 7.34-7.28 (m, 2 H), 7.21-7.17 (m, 3 H), 6.87 (t, J=5.9 Hz, 1 H), 4.31 (d, J=6.0 Hz, 2 H), 3.91 (s, 3 H). MS ESI (M+H) calc 486.1303; found: 486.1302 (C24H19ClF3N5O).

1-Phenyl-3-[3-(4-pyridin-4-yl-1H-pyrazol-3-yl)-benzyl]-urea

[(I)N, X=CH; R1, R2, R3, R4, R5, R6=H; m=0; R7'=phenyl]

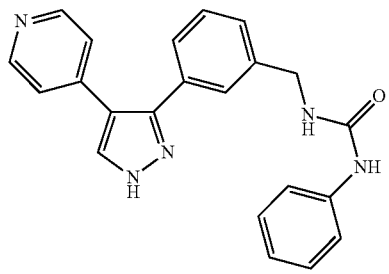 [SMILES: O=C(NCc1cccc(-c2n[nH]cc2-c2ccncc2)c1)Nc1ccccc1]

HPLC (254 nm): R$_t$: 4.77 min
¹H NMR (401 MHz, DMSO-d6) δ=13.31 (br.s, 1 H), 8.53 (s, 1 H), 8.44-8.41 (m, 2 H), 8.12 (br. s., 1 H), 7.45 (s, 1 H), 7.42-7.18 (m, 9 H), 6.92-6.87 (m, 1 H), 6.64 (t, J=6.0 Hz, 1 H), 4.32 (d, J=6.0 Hz, 2 H). MS ESI (M+H) calc 370.1663; found. 370.1678 (C22H19N5O).

1-(4-Chloro-phenyl)-3-[3-(4-pyridin-4-yl-1H-pyrazol-3-yl)-benzyl]-urea

[(I)N, X=CH; R1, R2, R3, R4, R5, R6=H; m=0; R7'=4-chlorophenyl]

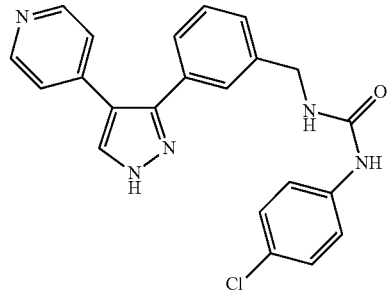 [SMILES: O=C(NCc1cccc(-c2n[nH]cc2-c2ccncc2)c1)Nc1ccc(Cl)cc1]

HPLC (254 nm): R$_t$: 5.31 min
¹H NMR (401 MHz, DMSO-d6) δ=13.32 (br. s., 1 H), 8.69 (s, 1 H), 8.45-8.39 (m, 2 H), 8.14 (br. s., 1 H), 7.46-7.20 (m, 10 H), 6.70 (t, J=5.9 Hz, 1 H), 4.32 (d, J=6.0 Hz, 2 H). MS ESI (M+H) calc 404.1273; found. 404.1277 (C22H18ClN5O).

1-(3-Methoxy-phenyl)-3-[3-(4-pyridin-4-yl-1H-pyrazol-3-yl)-benzyl]-urea

[(I)N, X=CH; R1, R2, R3, R4, R5, R6=H; m=0; R7'=3-methoxyphenyl]

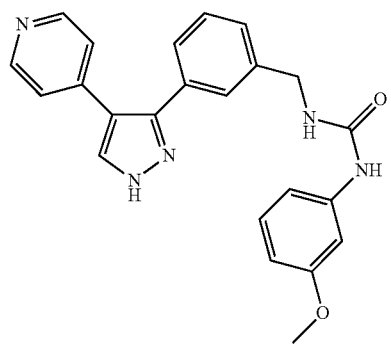 [SMILES: COc1cccc(NC(=O)NCc2cccc(-c3n[nH]cc3-c3ccncc3)c2)c1]

HPLC (254 nm): R$_t$: 4.84 min
¹H NMR (401 MHz, DMSO-d6) δ=13.30 (br. s., 1 H), 8.55 (s, 1 H), 8.44-8.41 (m, 2 H), 8.12 (br. s., 1 H), 7.44 (s, 1 H), 7.41-7.32 (m, 2 H), 7.27-7.22 (m, 3 H), 7.12-7.16 (m, 1 H), 7.08-7.12 (m, 1 H), 6.87 (dd, J=1.1, 8.2 Hz, 1 H), 6.65 (t, J=5.9 Hz, 1 H), 6.48 (dt, J=1.2, 8.2 Hz, 1 H), 4.32 (d, J=6.0 Hz, 2 H), 3.71 (s, 3 H). MS ESI (M+H) calc 400.1768; found. 400.1767 (C23H21N5O2).

1-[3-(4-Pyridin-4-yl-1H-pyrazol-3-yl)-benzyl]-3-p-tolyl-urea

[(I)N, X=CH; R1, R2, R3, R4, R5, R6=H; m=0; R7'=4-methylphenyl]

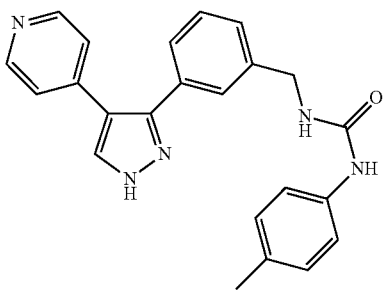 [SMILES: Cc1ccc(NC(=O)NCc2cccc(-c3n[nH]cc3-c3ccncc3)c2)cc1]

HPLC (254 nm) R$_t$: 5.07 min
$^1$H NMR (401 MHz, DMSO-d6) δ=13.29 (br. s., 1 H), 8.44-8.41 (m, 2 H), 8.39 (s, 1 H), 8.21 (br.s., 1 H), 7.48-7.20 (m, 8 H), 7.03 (d, J=8.2 Hz, 2 H), 6.58 (t, J=5.9 Hz, 1 H), 4.31 (d, J=6.0 Hz, 2 H), 2.22 (s, 3 H). MS ESI (M+H) calc 384.1819; found. 384.1803 (C23H21N5O).

1-(3-Fluoro-phenyl)-3-[3-(4-pyridin-4-yl-1H-pyrazol-3-yl)-benzyl]-urea

[(I)N, X=CH; R1, R2, R3, R4, R5, R6=H; m=0; R7'=3-fluorophenyl]

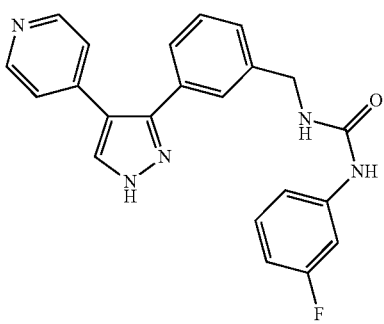 [SMILES: O=C(NCc1cccc(-c2n[nH]cc2-c2ccncc2)c1)Nc1cccc(F)c1]

HPLC (254 nm): R$_t$: 5.04 min
$^1$H NMR (401 MHz, DMSO-d6) δ=13.32 (br. s., 1 H), 8.80 (s, 1 H), 8.45-8.38 (m, 2 H), 8.12 (br. s., 1 H), 7.48-7.21 (m, 7 H), 7.06-7.02 (m, 2 H), 6.7-6.73 (m, 1 H), 6.73-6.67 (m, 1 H), 4.32 (d, J=6.0 Hz, 2 H). MS ESI (M+H) calc 388.1568; found. 388.1554 (C22H18FN5O).

1-(4-Fluoro-phenyl)-3-[3-(4-pyridin-4-yl-1H-pyrazol-3-yl)-benzyl]-urea

[(I)N, X=CH; R1, R2, R3, R4, R5, R6=H; m=0; R7'=4-fluorophenyl]

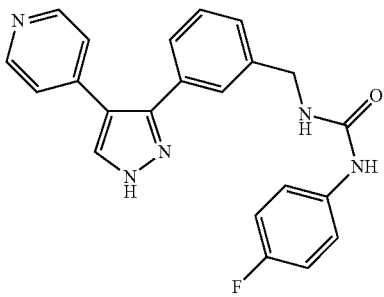 [SMILES: O=C(NCc1cccc(-c2n[nH]cc2-c2ccncc2)c1)Nc1ccc(F)cc1]

HPLC (254 nm): R$_t$: 4.91 min $^1$H NMR (401 MHz, DMSO-d6) δ=13.32 (br. s., 1 H), 8.57 (s, 1 H), 8.46-8.39 (m, 2 H), 8.12 (br. s., 1 H), 7.44 (s, 1 H), 7.42-7.32 (m, 4 H), 7.30-7.23 (m, 3 H), 7.01-7.09 (m, 2 H), 6.64 (t, J=6.0 Hz, 1 H), 4.32 (d, J=5.9 Hz, 2 H).
MS ESI (M+H) calc 388.1568; found. 388.1577 (C22H18FN5O).

1-(2,4-Difluoro-phenyl)-3-[3-(4-pyridin-4-yl-1H-pyrazol-3-yl)-benzyl]-urea

[(I)N, X=CH; R1, R2, R3, R4, R5, R6=H; m=0; R7'=2,4-difluorophenyl]

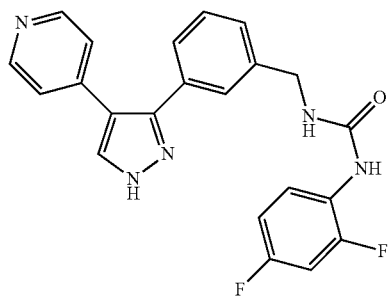 [SMILES: O=C(NCc1cccc(-c2n[nH]cc2-c2ccncc2)c1)Nc1ccc(F)cc1F]

HPLC (254 nm): R$_t$: 5.03 min
$^1$H NMR (401 MHz, DMSO-d6) δ=13.31 (br. s., 1 H), 8.41 (d, J=6.2 Hz, 2 H), 8.32 (d, J=1.6 Hz, 1 H), 8.11 (br. s., 1 H), 8.04 (td, J=6.3, 9.3 Hz, 1 H), 7.43 (s, 1 H), 7.41-7.26 (m, 4 H), 7.24 (d, J=6.2 Hz, 2 H), 7.04-6.94 (m, 2 H), 4.32 (d, J=5.9 Hz, 2 H). MS ESI (M+H) calc 406.1474; found. 406.1467 (C22H17F2N5O).

1-(4-Methoxy-phenyl)-3-[3-(4-pyridin-4-yl-1H-pyrazol-3-yl)-benzyl]-urea

[(I)N, X=CH; R1, R2, R3, R4, R5, R6=H; m=0; R7'=4-methoxyphenyl]

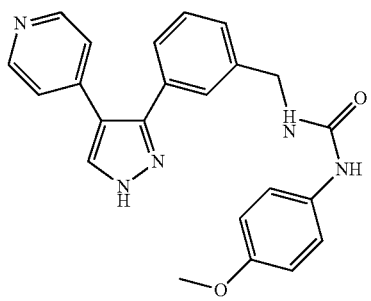 [SMILES: COc1ccc(NC(=O)NCc2cccc(-c3n[nH]cc3-c3ccncc3)c2)cc1]

HPLC (254 nm): R$_t$: 4.69 min
$^1$H NMR (401 MHz, DMSO-d6) δ=13.31 (br. s., 1 H), 8.42 (d, J=6.1 Hz, 2 H), 8.31 (s, 1 H), 8.11 (br. s., 1 H), 7.43 (s, 1 H), 7.41-7.22 (m, 7 H), 6.81 (d, J=9.0 Hz, 2 H), 6.53 (t, J=5.9 Hz, 1 H), 4.30 (d, J=6.0 Hz, 2 H), 3.69 (s, 3 H).
MS ESI (M+H) calc 400.1768; found. 400.1764. (C23H21N5O2).

1-[3-(4-Pyridin-4-yl-1H-pyrazol-3-yl)-benzyl]-3-m-tolyl-urea

[(I)N, X=CH; R1, R2, R3, R4, R5, R6=H; m=0; R7'=3-methylphenyl]

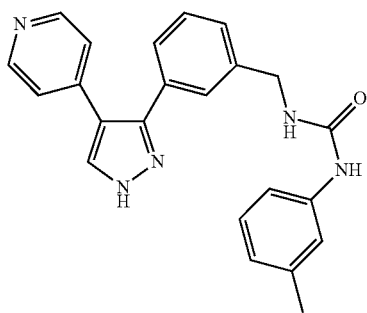 [SMILES: Cc1cccc(NC(=O)NCc2cccc(-c3n[nH]cc3-c3ccncc3)c2)c1]

HPLC (254 nm): R$_t$: 5.08 min $^1$H NMR (401 MHz, DMSO-d6) δ=13.30 (br. s., 1 H), 8.45 (s, 1 H), 8.42 (d, J=6.2 Hz, 2 H), 8.11 (br. s., 1 H), 7.43 (s, 1 H), 7.40-7.21 (m, 6 H), 7.16 (d, J=83.0 Hz, 1 H), 7.08 (t, J=7.7 Hz, 1 H), 6.71 (m, 1 H), 6.64 (t, J=5.9 Hz, 1 H), 4.30 (d, J=5.9 Hz, 2 H), 2.24 (s, 3 H). MS ESI (M+H) calc 384.1819; found. 384.1830 (C23H21N5O).

1-(2-Fluoro-4-trifluoromethyl-phenyl)-3-[3-(4-pyridin-4-yl-1H-pyrazol-3-yl)-benzyl]-urea

[(I)N, X═CH; R1, R2, R3, R4, R5, R6=H; m=0; R7'=2-fluoro-4-trifluoromethylphenyl]

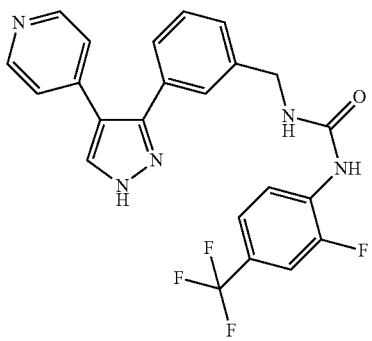 [SMILES: O=C(NCc1cccc(-c2n[nH]cc2-c2ccncc2)c1)Nc1ccc(C(F)(F)F)cc1F]

HPLC (254 nm): R$_t$: 5.77 min $^1$H NMR (401 MHz, DMSO-d6) δ=13.31 (br. s., 1 H), 8.72 (br. s., 1 H), 8.39 (d, J=6.1 Hz, 2 H), 8.11 (br. s., 1 H), 7.48-7.18 (m, 10 H), 4.35 (d, J=5.7 Hz, 2 H). MS ESI (M+H) calc 456.1442; found. 456.1436 (C23H17F4N5O).

1-(4-Cyano-phenyl)-3-[3-(4-pyridin-4-yl-1H-pyrazol-3-yl)-benzyl]-urea

[(I)N, X═CH; R1, R2, R3, R4, R5, R6=H; m=0; R7'=4-cyanophenyl]

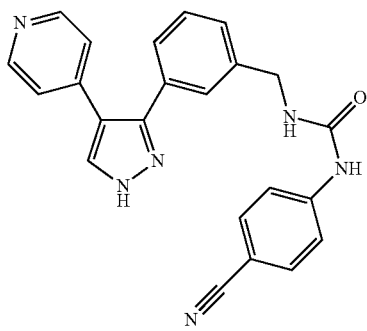 [SMILES: N#Cc1ccc(NC(=O)NCc2cccc(-c3n[nH]cc3-c3ccncc3)c2)cc1]

HPLC (254 nm): R$_t$:4.88 min $^1$H NMR (401 MHz, DMSO-d6) δ=13.29 (br. s., 1 H), 9.12 (br. s., 1 H), 8.46-8.35 (m, 2 H), 8.11 (br. s., 1 H), 7.70-7.63 (m, 2 H), 7.60-7.53 (m, 2 H), 7.43 (s, 1 H), 7.40-7.21 (m, 5 H), 6.90 (t, J=5.9 Hz, 1 H), 4.33 (d, J=5.9 Hz, 2 H). MS ESI (M+H) calc 395.1615; found. 395.1620 (C23H18N6O).

1-(4-Cyano-phenyl)-3-[3-(4-pyridin-4-yl-1H-pyrazol-3-yl)-benzyl]-urea

[(I)N, X═CH; R1, R2, R3, R4, R5, R6=H; m=0; R7'=4-trifluoromethylphenyl]

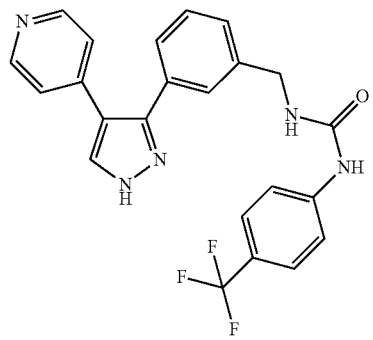 [SMILES: O=C(NCc1cccc(-c2n[nH]cc2-c2ccncc2)c1)Nc1ccc(C(F)(F)F)cc1]

HPLC (254 nm): R$_t$: 5.67 min $^1$H NMR (401 MHz, DMSO-d6) δ=13.31 (br. s., 1 H), 8.99 (s, 1 H), 8.41 (d, J=6.2 Hz, 2 H), 8.12 (br. s., 1 H), 7.62-7.53 (m, 4 H), 7.44 (s, 1 H), 7.41-7.22 (m, 5 H), 6.81 (t, J=5.9 Hz, 1 H), 4.33 (d, J=6.0 Hz, 2 H). MS ESI (M+H) calc 438.1536; found. 438.1547 (C23H18F3N5O).

1-Benzol[1,3]dioxol-5-yl-3-[3-(4-pyridin-4-yl-1H-pyrazol-3-yl)-benzyl]-urea

[(I)N, X═CH; R1, R2, R3, R4, R5, R6=H; m=0; R7'=benzol[1,3]dioxol-5-yl]

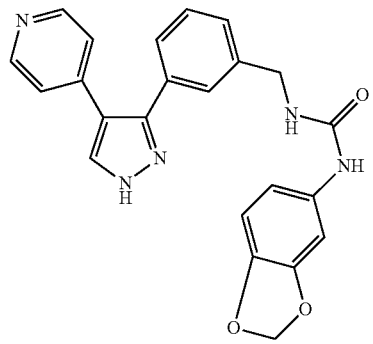 [SMILES: O=C(NCc1cccc(-c2n[nH]cc2-c2ccncc2)c1)Nc1ccc2c(c1)OCO2]

HPLC (254 nm): R$_t$: 4.69 min $^1$H NMR (401 MHz, DMSO-d6) δ=13.28 (s, 1 H), 8.42-8.40 (m, 2 H), 8.25 (s, 1 H), 7.49-7.18 (m, 7 H), 7.15 (d, J=1.8 Hz, 1 H), 6.76 (d, J=8.3 Hz, 1 H), 6.67 (dd, J=2.1, 8.4 Hz, 1 H), 6.55 (t, J=5.4 Hz, 1 H), 5.93 (s, 2 H), 4.29 (d, J=5.1 Hz, 2 H). MS ESI (M+H) calc 414.1561; found. 414.1567 (C23H19N5O3).

1-(4-Dimethylamino-phenyl)-3-[3-(4-pyridin-4-yl-1H-pyrazol-3-yl)-benzyl]-urea

[(I)N, X=CH; R1, R2, R3, R4, R5, R6=H; m=0; R7'=4-dimethylaminophenyl]

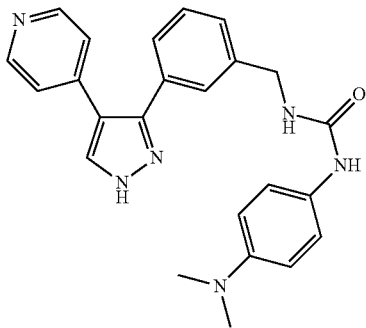 [SMILES: CN(C)c1ccc(NC(=O)NCc2cccc(-c3n[nH]cc3-c3ccncc3)c2)cc1]

HPLC (254 nm): R$_t$: 4.75 min
$^1$H NMR (401 MHz, DMSO-d6) δ=13.29 (s, 1 H), 8.43 (d, J=6.1 Hz, 2 H), 8.26 (s, 1 H), 8.13 (br.s., 1 H), 7.49-7.13 (m, 8 H), 6.66 (d, J=9.0 Hz, 2 H), 6.45 (t, J=5.8 Hz, 1 H), 4.29 (d, J=5.9 Hz, 2 H), 2.81 (s, 6 H). MS ESI (M+H) calc 413.2085; found: 413.2081 (C24H24N6O).

Example 19

N-[3-(4-Pyridin-4-yl-1H-pyrazol-3-yl)benzyl]-4-trifluoromethyl-benzamide

[(I)P, X=CH; R1, R2, R3, R4, R5, R6=H; m=0; R7=4-trifluoromethylphenyl]

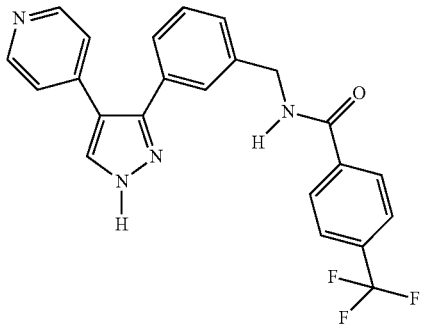 [SMILES: O=C(NCc1cccc(-c2n[nH]cc2-c2ccncc2)c1)c1ccc(C(F)(F)F)cc1]

Method I
Step h

N-{3-[4-Pyridin-4-yl-1-(2-trimethylsilanyl-ethoxymethyl)-1H-pyrazol-3-yl]-benzyl}-4-trifluoromethyl-benzamide 4-Trifluoromethylbenzoylchloride (0.054 g, 0.26 mmol) was added to a solution of 3-[4-pyridin-4-yl-1-(2-trimethylsilanyl-ethoxymethyl)-1H-pyrazol-3-yl]-benzylamine (0.10 g, 0.26 mmol) (prepared as described in Example 17) and triethylamine (0.08 g, 0.79 mmol) in dry DCM (2.0 ml) at 0° C. The reaction mixture was stirred at room temperature under nitrogen atmosphere for 6 h. The organic layer was washed with water (2.0 mL) and dried over Na$_2$SO$_4$. The filtrate was evaporated to dryness to give an oil which was purified by flash chromatography, over silica gel, using dichloromethane/MeOH (98:0.2) as eluent, to afford N-{3-[4-pyridin-4-yl-1-(2-trimethylsilanyl-ethoxymethyl)-1H-pyrazol-3-yl]-benzyl}-4-trifluoromethyl-benzamide (0.110 g, 0.20 mmol, 76%).

Method M
Step a

N-[3-(4-pyridin-4-yl-1H-pyrazol-3-yl)-benzyl]-4-trifluoromethyl-benzamide

N-{3-[4-pyridin-4-yl-1-(2-trimethylsilanyl-ethoxymethyl)-1H-pyrazol-3-yl]-benzyl}-4-trifluoromethyl-benzamide (0.10 g, 0.19 mmol) was stirred in HCl 4M in dioxane at room temperature for 4 h. The solvent was evaporated under vacuum and the crude product was purified by reverse phase HPLC yielding N-[3-(4-pyridin-4-yl-1H-pyrazol-3-yl)-benzyl]-4-trifluoromethyl-benzamide (0.025 g, 0.06 mmol, 31%) as a solid.

HPLC (254 nm): R$_t$: 5.54 min
$^1$H NMR (401 MHz, DMSO-d6) δ=13.42 (br. s, 1 H), 9.25 (t, J=5.9 Hz, 1 H), 8.39 (d, J=6.0 Hz, 2 H), 8.24 (br. s., 1 H), 8.03 (d, J=8.2 Hz, 2 H), 7.85 (d, J=8.2 Hz, 2 H), 7.5-7.2 (m, 6 H), 4.52 (d, J=6.0 Hz, 2 H). MS ESI (M+H) calc 423.1427; found. 423.1434 (C23H17F3N4O).

Example 20

1-{3-[4-(2-aminopyridin-4-yl)-1H-pyrazol-3-yl]phenyl}-3-[4(trifluoromethyl)-phenyl]urea (Cpd. 12)

[(I)U, R1, R3, R4, R5, R6=H; m=0; A=NHCONH; R7=4-trifluoromethylphenyl]

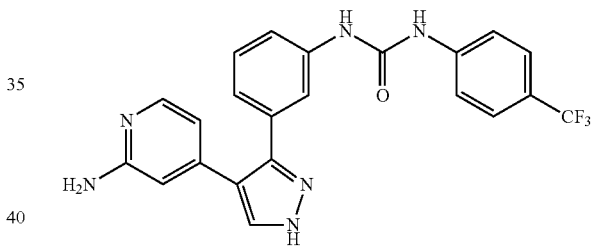

Method A

Step e: 1-(3-bromophenyl)-2-pyridin-4-ylethanone

To 66 ml (0.066 mol) of sodium 1,1,1,3,3,3-hexamethyldisilazane 1M in THF under nitrogen atmosphere at 0° C., 3.2 ml (0.033 mol) of 4-picoline were added. After stirring for 60 minutes 5 ml (7.15 g; 0.03 mol) of ethyl 3-bromo benzoate were added and the mixture maintained in the same conditions for 1.5 hours. HCl 2N was then added, the mixture made basic with NaOH 2N and extracted with ethyl acetate. The organic phase was dried over Na$_2$SO$_4$ and the solvent evaporated. 7.5 g (82% yield) of the title compound were obtained by crystallization from AcOEt-Et$_2$O.

$^1$H NMR (401 MHz, DMSO-d6) δ=8.52 (d, J=6.0 Hz, 2 H), 8.19 (t, J=1.7 Hz, 1 H), 8.05 (ddd, J=1.0, 1.6, 7.8 Hz, 1 H), 7.89 (ddd, J=1.0, 2.0, 8.0 Hz, 1 H), 7.54 (t, J=7.9 Hz, 1 H), 7.19-7.33 (m, 2 H), 4.53 (s, 2 H). MS-ESI (M+H) calc. 276.0019 found 276.0023 (C13H10BrNO)

Step f: (2E)-1-(3-bromophenyl)-3-(dimethylamino)-2-pyridin-4-ylprop-2-en-1-one

Dimethylformamide dimethylacetal (15 mL) were added to a solution of 7.2 g (0.026 ol) of 1-(3-bromophenyl)-2- pyridin-4-ylethanone in 15 ml of dry tetrahydrofuran. After stirring at 65° C. for 6 hours, the solvent was removed under reduced pressure. 8 g (93% yield) of the title compound as an oil were obtained and employed in the next step without any further purification.

Step g:
4-[3-(3-bromophenyl)-1H-pyrazol-4-yl]pyridine 8 g (0.024 mol) of 1-(3-bromophenyl)-3-(dimethylamino)-2-pyridin-4-ylprop-2-en-1-one were dissolved in 20 ml of ethanol and 3 mL (0.06 mol) of hydrazine hydrate were added. The solution was refluxed under stirring for 4 hours. The title compound was collected by filtration. The filtrate was evaporated, the residue taken up with dichloromethane and washed with water. The organic layer, dried over $Na_2SO_4$, was evaporated to dryness and triturated with diethylether affording a second crop of the title compound (7.2 g overall; 100% yield).

$^1$H NMR (401 MHz, DMSO-d6) δ=13.50 and 13.40 (2 br. s., 1H, mixture of tautomers), 8.48 (d, J=6.0 Hz, 2 H), 8.25 and 7.95 (2 br. s., 1H, mixture of tautomers), 7.55-7.70 (m, 2 H), 7.32-7.48 (m, 2 H), 7.26 (d, J=4.8 Hz, 2 H). MS-ESI (M+H) calc. 300.0131 found 300.0145 (C14H10BrN3).

Step h: 4-[3-(3-bromophenyl)-1-(4-methoxybenzyl)-1H-pyrazol-4-yl]pyridine 3 g (0.01 mol) of 4-[3-(3-bromophenyl)-1H-pyrazol-4-yl]pyridine were dissolved in 50 ml of dry dimethylformamide and 3.9 g (0.012 mol) of cesium carbonate and 1.6 ml (0.012 mol) of p-methoxybenzyl chloride were added. The mixture was stirred at 70° C. for 2 hours and the solvent removed in vacuo. The residue was taken up with dichoromethane and washed with water. The organic phase was dried over $Na_2SO_4$ and evaporated. Purification by column chromatography (dichloromethane-acetone 95/5) afforded 2 g (48% yield) of the title compound as an oil.

$^1$H NMR (401 MHz, DMSO-d6) (major regioisomer)=8.46-8.53 (m, 2 H), 8.30 (s, 1 H), 7.58 (m, 1 H), 7.33-7.38 (m, 5 H), 7.19-7.26 (m, 2 H), 6.95 (d, J=8.66 Hz, 2 H), 5.33 (s, 2 H), 3.75 (s, 3 H). MS-ESI (M+H) calc. 420.0706 found 420.0701 (C22H18BrN3O).
Method H Step f: N-(diphenylmethylidene)-3-[1-(4-methoxybenzyl)-4-pyridin-4-yl-1H-pyrazol-3-yl]aniline 1.9 g (4.5 mmol) of 4-[3-(3-bromophenyl)-1-(4-methoxybenzyl)-1H-pyrazol-4-yl]pyridine were dissolved in 60 ml of dry toluene under nitrogen atmosphere and 366 mg (0.4 mmol) of tris(dibenzylidene-acetone)dipalladium(0), 498 mg (0.8 mmol) of racemic 2,2'-bis(diphenylphosphino)-1,1'-binaphtalene, 562 mg (5.85 mmol) of sodium tertbutoxide and 975 L (5.85 mmol) of benzophenonimine were added to the solution successively. The mixture was refluxed for 3 hours. After cooling to room temperature the reaction mixture was filtered over a celite pad and the solvent evaporated. The residue was redissolved with ethylacetate and washed with water. The organic layer was dried over $Na_2SO_4$ and evaporated again to dryness. The crude was purified by chromatography on a silica gel column eluted by dichloromethane-methanol 95/5, affording 1.5 g (65% yield) of the title compound.

$^1$H NMR (401 MHz, DMSO-d6) δ=8.42 (d, J=6.0 Hz, 2 H), 8.24 (s, 1 H), 7.62-7.67 (m, 2 H), 7.50-7.56 (m, 1 H), 7.43-7.49 (m, 2 H), 7.31-7.38 (m, 5 H), 7.10-7.15 (m, 3 H), 7.04-7.07 (m, 2 H), 6.91-6.97 (m, 2 H), 6.86 (ddd, J=1.1, 1.3, 7.9 Hz, 1 H), 6.73 (t, J=1.7 Hz, 1 H), 6.65 (ddd, J=1.0, 2.1, 7.9 Hz, 1 H), 5.28 (s, 2 H), 3.75 (s, 3 H). MS-ESI (M+H) calc. 521.2336 found 521.2328 (C35H28N4O).
Method E Step a: N-(diphenylmethylidene)-3-[1-(4-methoxybenzyl)-4-(1-oxidopyridin-4-yl)-1H-pyrazol-3-yl]aniline 100 mg (0.19 mmol) of N-(diphenylmethylidene)-3-[1-(4-methoxybenzyl)-4-pyridin-4-yl-1H-pyrazol-3-yl]aniline were reacted with 36 mg (0.21 mmol) of m-chloroperbenzoic acid in 4 ml of dimethoxyethane. The solution was stirred at room temperature overnight. The reaction mixture was partitioned between dichloromethane and aqueous $NaHCO_3$, the organic layer dried over $Na_2SO_4$ and the solvent removed under reduced pressure. The residue was triturated with diethylether and collected by filtration giving 80 mg (78%) of the title compound.

$^1$H NMR (401 MHz, DMSO-d6) (selected signals, major regioisomer) δ=8.20 (s, 1 H), 8.06-8.10 (m, 2 H), 8.07 (m, 1 H), 7.12-7.15 (m, 3 H), 7.03-7.05 (m, 2 H), 6.93-6.95 (m, 2 H), 6.89 (ddd, J=1.1, 1.3, 7.9 Hz, 1 H), 6.73 (t, J=1.7 Hz, 1 H), 6.68 (ddd, J=1.0, 2.1, 7.9 Hz, 1 H), 5.27 (m, 2 H), 3.75 (s, 3 H). MS-ESI (M+H) calc. 537.2285 found 537.2286 (C35H28N4O2).

Step c: N-tert-butyl-4-[3-{3-[(diphenylmethylidene)amino]phenyl}-1-(4-methoxybenzyl)-1H-pyrazol-4-yl]pyridin-2-amine 200 mg (0.4 mmol) of N-(diphenylmethylidene)-3-[1-(4-methoxybenzyl)-4-(1-oxidopyridin-4-yl)-1H-pyrazol-3-yl]aniline were suspended in 50 ml of trifluoromethylbenzene and 210 μl (2 mmol) of tert-butylamine were added under stirring at room temperature. The mixture was cooled to 0° C. and 260 mg (0.8 mmol) of p-toluensulfonic anhydride were added. The reaction was maintained in the same conditions for 2.5 hours. Then the same amounts of reactants and 2 ml of dichloromethane to obtain a clear solution were added and after further 2 hours the reaction went to completion. The solvent was evaporated and the residue taken up in dichloromethane and washed with water. The organic phase was dried over $Na_2SO_4$ and evaporated to dryness, giving 161 mg (73% yield) of the title compound.

MS-ESI (M+H) calc. 592.3071 found 592.3065 (C39H37N5O)
Method H

Step g: 4-[3-(3-aminophenyl)-1-(4-methoxybenzyl)-1H-pyrazol-4-yl]-N-tert-butylpyridin-2-amine 120 mg (0.2 mmol) of N-tert-butyl-4-[3-{3-[(diphenylmethylidene)amino]phenyl}-1-(4-methoxybenzyl)-1H-pyrazol-4-yl]pyridin-2-amine were dissolved in 20 ml of 1,4-dioxane and 5 ml of HCl 4M in dioxane were added. After 4 hours the solvent was removed in vacuo and the residue dissolved in dichloromethane and washed with aqueous $NaHCO_3$. The organic layer was dried over $Na_2SO_4$ and evaporated to give, after trituration with diethylether, 40 mg (46% yield) of the title compound.
Method G Step e: 1-(3-{4-[2-(tert-butylamino)pyridin-4-yl]-1-(4-methoxybenzyl)-1H-pyrazol-3-yl}phenyl)-3-[4-(trifluoromethyl)phenyl]urea 40 mg (0,094 mmol) of 4-[3-(3-aminophenyl)-1-(4-methoxybenzyl)-1H-pyrazol-4-yl]-N-tert-butylpyridin-2-amine were dissolved in 2 ml of dry dimethylformamide and 12 μL (0.094 mmol) of p-trifluoromethylphenylisocyanate were added. The solution was stirred at room temperature for 3 hours. The reaction mixture was then poured into water and the product extracted several times with ethylacetate. The organic layer was dried over $Na_2SO_4$ and evaporated to dryness. The crude was purified by chromatography on a silica gel column eluted with dichloromethane-acetone 9/1, affording 40 mg (70% yield) of the title compound.

$^1$H NMR (401 MHz, DMSO-d6) δ=9.01 (s, 1 H), 8.84 (s, 1 H), 8.01 (s, 1 H), 7.84 (d, J=5.2 Hz, 1 H), 7.58-7.69 (m, 3 H), 7.55 (t, J=1.8 Hz, 1 H), 7.47-7.51 (m, 1 H), 7.31-7.36 (m, 2 H), 7.27 (t, J=7.9 Hz, 1 H), 7.00 (ddd, J=1.1, 1.3, 7.9 Hz, 1 H), 6.88-6.97 (m, 2 H), 6.42 (d, J=0.6 Hz, 1 H), 6.26 (dd, J=1.4, 5.3 Hz, 1 H), 6.02 (s, 1 H), 5.31 (s, 2 H), 3.75 (s, 3 H), 1.33 (s, 9 H). MS-EI (M+H) calc. 615.2690 found 615.2687 (C34H33F3N6O2).

Method K

Step d: 1-{3-[4-(2-aminopyridin-4-yl)-1H-pyrazol-3-yl]phenyl}-3-[4-(trifluoromethyl)-phenyl]urea 100 mg (0.16 mmol) of 1-(3-{4-[2-(tert-butylamino)pyridin-4-yl]-1-(4-methoxybenzyl)-1H-pyrazol-3-yl}phenyl)-3-[4-(trifluoromethyl)phenyl]urea were dissolved in 5 ml of trifluoroacetic acid and the mixture heated at 70° C. under stirring. After 16 hours the solution was poured into icy water, neutralized with aqueous $NaHCO_3$ and extracted with dichloromethane. The organic layer was then dried over $Na_2SO_4$ and evaporated to dryness. The product was purified by chromatography on a silica gel column eluted with dichloromethane-methanol (gradient from 1% to 5%) obtaining 50 mg (71% yield) of the title compound.

$^1$H NMR (401 MHz, DMSO-d6) (selected signals) δ=13.28 and 13.15 (2 br. s., 1 H, mixture of tautomers), 9.10 (br.s., 1 H), 8.85 (br.s., 1 H), 7.80 (d, J=5.4 Hz, 1 H), 7.60-7.68 (m, 4 H), 7.05 (d, J=7.2 Hz, 1 H), 6.41 (br. s., 1 H), 6.38 (dd, J=1.4, 5.3 Hz, 1 H), 5.83 (br. s., 2 H). MS-ESI (M+H) calc. 439.1489 found 439.1490 (C22H17F3N6O).

Example 21

N-(4-{3-[3-({[4-(trifluoromethyl)phenyl]carbamoyl}amino)phenyl]-1H-pyrazol-4-yl}pyridin-2-yl)thiophene-2-carboxamide

[(I)V, R1, R3, R4, R5, R6=H; R16=thiophen-2-yl; m=0; A=NHCONH; R7=4-trifluoromethylphenyl]

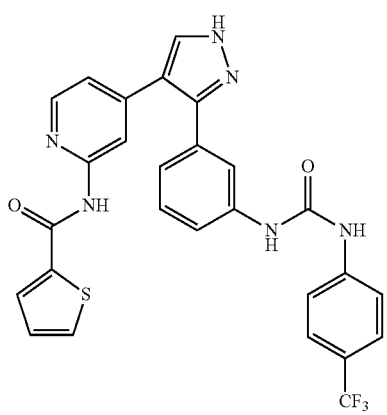 [SMILES: O=C(Nc1ccc(C(F)(F)F)cc1)Nc1cccc(-c2n[nH]cc2-c2ccnc(NC(=O)c3cccs3)c2)c1]

Method K

Step e

To a solution of 40 mg (0.09 mmol) of 1-{3-[4-(2-aminopyridin-4-yl)-1H-pyrazol-3-yl]phenyl}-3-[4-(trifluoromethyl)phenyl]urea (prepared as described in Example 20) in 4 ml of dry pyridine 1 mg (0.009 mmol) of 4-dimethylaminopyridine and 38 μl of 2-thienylcarbonyl chloride (0.36 mmol) were added. After 16 hours under stirring at room temperature the reaction mixture was poured into aqueous $NaHCO_3$ and extracted with dichloromethane, giving quantitatively (HPLC-MS analysis) N-(4-{1-(thiophen-2-ylcarbonyl)-3-[3-({[4-(trifluoromethyl)phenyl]carbamoyl}amino)phenyl]-1H-pyrazol-4-yl}pyridin-2-yl)thiophene-2-carboxamide as a regioisomeric mixture, that was submitted to the subsequent hydrolysis step without any further purification. The crude was then dissolved in 50 ml of methanol and 5 ml of triethylamine were added under stirring at room temperature. After 5 hours the solvent was removed in vacuo and the residue taken up with dichloromethane and washed with water. The product was extracted several times with a mixture dichloromethane-methanol 9/1 and then with ethylacetate. The crude was chromatographed on a silica gel column eluted with a mixture DCM/methanol (gradient from 1% to 5%), thus obtaining 40 mg (80% yield) of the title compound.

$^1$H NMR (401 MHz, DMSO-d6) (selected signals) δ=13.42 and 13.28 (2 br.s., 1H, mixture of tautomers), 10.83 (s, 1 H), 9.02-9.08 (2 br.s., 1H), 8.89-8.81 (2 br.s., 1 H), 8.25 (d, J=5.2 Hz, 1 H), 8.22 (d, J=3.54 Hz, 1H), 8.18 (m, 1H), 7.86 (d, 1 H), 7.58-7.66 (m, 4 H), 7.19 (m, 1 H), 7.02-7.12 (m, 1 H), 6.94-7.01 (m, 1 H). MS-ESI (M+H) calc. for C27H19F3N6O2S: 549.1315 found 549.1299.

Operating in an analogous way but using only methanol in place of a mixture methanol-triethylamine during the hydrolysis step, the following compound was obtained:

N-[4-(3-{3-[3-(4-Trifluoromethyl-phenyl)-ureido]-phenyl}-1H-pyrazol-4-yl)-pyridin-2-yl]-acetamide (Cmpd. 17)

[(I)V, R1, R3, R4, R5, R6=H; R16=methyl; m=0; A=NHCONH; R7=4-trifluoromethylphenyl]

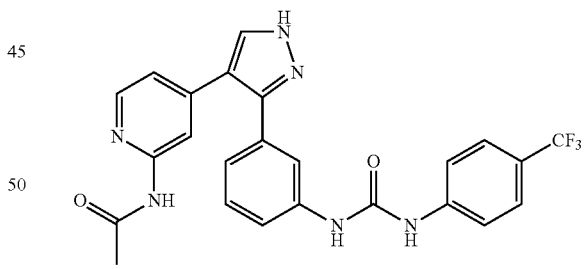

$^1$H-NMR (401 MHz, DMSO-d6) δ=13.38 and 13.25 (2 br.s., 1H, mixture of tautomers), 10.38 (s, 1 H), 9.13 and 9.07 (2 br.s., 1 H, mixture of tautomers), 8.92 and 8.83 (2 br.s., 1 H, mixture of tautomers), 8.16 (m, 1 H), 8.07-8.12 (m, 1 H), 7.82 (m, 1 H), 7.59-7.68 (m, 4 H), 7.47-7.56 (m, 1 H), 7.34-7.41 (m, 1 H), 7.24-7.30 (m, 1 H), 7.00-7.07 (m, 1 H), 6.88-6.94 (m, 1H), 2.05 (s, 3 H). MS-ESI (M+H) calc. for C24H19F3N6O2: 481.1595, found 481.1598.

Preparation of dibenzyl-(2,4-difluoro-phenyl)-amine

To 2,4-difluoroaniline (40.0 g, 0.31 mol) in N,N-dimethylformamide (400 mL) were added potassium carbonate (120 g, 0.92 mol, 3 eq) and benzyl bromide (112 mL, 0.71 mmol, 2.3 eq). The reaction was stirred with mechanical stirring at room temperature overnight. In order to quench the benzyl bromide in excess, NH$_4$OH (90 mL) was added and the reaction was stirred overnight. The mixture was filtered and DMF was evaporated under reduced pressure. Ethyl acetate was added and the organic layer was washed with water and brine, dried over anhydrous sodium sulfate and filtered. The filtrate was concentrated under reduced pressure and the oily crude was crystallized in methanol, obtaining after drying 71 g of dibenzyl-(2,4-difluoro-phenyl)-amine as a white solid (74%)

HPLC (254 nm): Rt: 8.25

$^1$H-NMR (401 MHz, DMSO-d6) δ=7.26-7.32 (m, 8 H), 7.19-7.25 (m, 2 H), 7.12-7.19 (m, 1 H), 6.97 (td, J=6.0, 9.4 Hz, 1 H), 6.82 (tt, J=1.4, 8.6 Hz, 1 H), 4.24 (s, 4 H). HRMS (ESI) calcd for C20H17F2N [M+H]+ 310.1402, found 310.1407.

Preparation of 3-dibenzylamino-2,6-difluoro-benzoic acid benzyl ester

To a solution of dibenzyl-(2,4-difluoro-phenyl)-amine (17.5 g, 0.056 mol) in THF (140 mL), under nitrogen atmosphere, cooled at −78° C., n-butyllithium (1.6 M in hexane, 38 mL, 0.06 mol) was slowly added. The reaction was stirred for 1 hour, and then quickly added via a cannula to a solution of benzyl chloroformate (11.78 mL, 0.084 mol) in THF (140 mL) previously cooled at −78° C. The reaction was then allowed to warm to room temperature, poured into water and extracted with ethyl acetate. The organic layer was washed with brine, dried over anhydrous sodium sulfate and filtered. The filtrate was concentrated and purified by silica gel column chromatography eluting with 5% ethyl acetate in hexane grading to 10% acetate (quant.).

HPLC (254 nm): Rt: 8.49

$^1$H-NMR (401 MHz, DMSO-d6) δ=7.20-7.46 (m, 15 H), 7.15 (td, J=5.7, 9.4 Hz, 1 H), 6.98 (td, J=1.5, 9.2 Hz, 1 H), 5.39 (s, 2 H), 4.27 (s, 4 H)

HRMS (ESI) calcd for C28H23F2NO2 [M+H]+ 444.177, found 444.1765.

Example 22

N-[2,4-Difluoro-3-(4-pyridin-4-yl-1H-pyrazol-3-yl)-phenyl]-2,5-difluoro-benzenesulfonamide (Cmpd. 18)

[(I)C, X═CH; R1, R2, R4, R5═H; R3, R6═F; m═0; R7'═2,5-difluoro-phenyl]

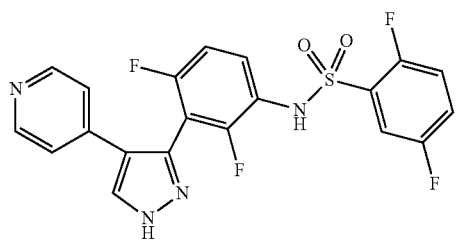 [SMILES: O=S(=O)(Nc1ccc(F)c(-c2n[nH]cc2-c2ccncc2)c1F)c1cc(F)ccc1F]

Method A

Step e: 1-(3-dibenzylamino-2,6-difluoro-phenyl)-2-pyridin-4-yl-ethanone

To 4-methyl-pyridine (806 4, 8.33 mmol) in anhydrous tetrahydrofuran (35 mL) was added at 0° C. sodium hexamethyldisilazide 1 M in tetrahydrofuran (16.66 mL, 16.66 mmol) and the reaction was stirred for 20 minutes. 3-Dibenzylamino-2,6-difluoro-benzoic acid benzyl ester (3.691 g, 8.33 mmol) was dissolved in tetrahydrofuran (5 mL) and added dropwise to the solution with 4-methyl-pyridine, the reaction was stirred at 0° C. for one hour. The reaction was poured into saturated ammonium chloride solution and extracted with ethyl acetate. The organic layer was washed with brine, dried over anhydrous sodium sulfate, filtrate and concentrated under reduced pressure. The crude was purified by silica gel column chromatography eluting with ethyl acetate 30% in hexane to give the title compound (1.775 g, 50%).

$^1$H NMR (401 MHz, DMSO-d$_6$) δ=8.50 (d, J=5.9 Hz, 2 H), 7.16-7.34 (m, 12 H), 7.09 (td, J=5.9, 9.3 Hz, 1 H), 6.91-6.99 (m, 1 H), 4.22-4.30 (M, 6 H).

HRMS (ESI) calcd for C27H22F2N20 [M+H]+ 429.1773, found 429.1767.

Step f: 1-(3-dibenzylamino-2,6-difluoro-phenyl)-3-dimethylamino-2-pyridin-4-yl-propenone To 1-(3-dibenzylamino-2,6-difluoro-phenyl)-2-pyridin-4-yl-ethanone (1.775 g, 4.14 mmol) in toluene (40 mL) dimethoxymethyldimethylamine (2.2 mL, 16.5 mmol) was added. The reaction was stirred at 80° C. for one hour and the solvent was concentrated under reduced pressure. The crude was used in the next step without further purification.

Step g: Dibenzyl-[2,4-difluoro-3-(4-pyridin-4-yl-1H-pyrazol-3-yl)-phenyl]-amine

To hydrazine 1M in tetrahydrofuran (16.56 mL) was added dibenzyl-[2,4-difluoro-3-(4-pyridin-4-yl-1H-pyrazol-3-yl)-phenyl]-amine (1.999 g, 4.14 mmol). The reaction was stirred under nitrogen atmosphere at 70° C. for one hour. The reaction was diluted with ethyl acetate (100 mL) and washed with water (3×50 mL) and brine (50 mL). The organic layer was dried over Na$_2$SO$_4$ concentrated under reduced pressure until a final volume of 5 mL. Ethyl ether was added and the mixture was stirred at room temperature for 30 minutes. The solid was filtered and dried at 50° C. for 1 h. Dibenzyl-[2,4-difluoro-3-(4-pyridin-4-yl-1H-pyrazol-3-yl)-phenyl]-amine was obtained as a pale yellow solid in 76% yield over the last two steps.

HPLC (254 nm): R$_t$: 6.88 min.

$^1$H NMR (401 MHz, DMSO-d6) (major tautomer) δ=13.53 (br. s., 1 H), 8.47 (m, 1 H), 8.37 (d, J=5.98 Hz, 2 H), 7.20-7.35 (m, 10 H), 7.10 (d, J=5.98 Hz, 2 H), 7.02-7.10 (m, 1 H), 6.91-6.98 (m, 1 H), 4.22-4.29 (m, 4 H). HRMS (ESI) calcd for C28H22F2N4 [M+H]+ 453.1886, found 453.1890.
Method G Step b: 2,4-difluoro-3-(4-pyridin-4-yl-1H-pyrazol-3-yl)-phenylamine To dibenzyl-[2,4-difluoro-3-(4-pyridin-4-yl-1H-pyrazol-3-yl)-phenyl]-amine (1.795 g, 3.97 mmol) in methanol (100 mL) was added 20% palladium hydroxide on carbon (646 mg). The reaction was stirred under hydrogen atmosphere for 12 hours (45 psi). The reaction was filtered to remove the catalyst, and then concentrated under reduced pressure. The crude was purified by silica gel column chromatography eluting with methanol 7% in methylene chloride to give 2,4-difluoro-3-(4-pyridin-4-yl-1H-pyrazol-3-yl)-phenylamine (yield 56% over three steps).

HPLC (254 nm): R$_t$: 3.93 min.

¹H NMR (401 MHz, DMSO-d6) δ=13.47 (br. s., 1 H), 8.35-8.48 (m, 3 H), 7.13-7.27 (m, 2 H), 6.74-6.95 (m, 2 H), 5.05 (br. s., 2 H). HRMS (ESI) calcd for C14H10F2N4 [M+H]+ 273.0947, found 273.0946.

Step c: N-[2,4-difluoro-3-(4-pyridin-4-yl-1H-pyrazol-3-yl)-phenyl]-2,5-difluoro-benzenesulfonamide To 2,4-difluoro-3-(4-pyridin-4-yl-1H-pyrazol-3-yl)-phenylamine (60 mg, 0.22 mmol) in anhydrous pyridine (0.2 M) 2,5-difluoro-benzenesulfonyl chloride(30 μL, 0.22 mmol) was added. The reaction was stirred at room temperature under nitrogen atmosphere overnight. The solvent was removed under reduced pressure and the residue was dissolved in ethylacetate and washed with NaHCO₃ saturated solution. The organic layer was dried over anhydrous sodium sulfate and filtered. The product was isolated by silica gel column chromatography eluting with methanol 7% in methylene chloride (yield 70%, white solid).

¹H NMR (401 MHz, DMSO-d₆) δ=13.57 (s, 1 H), 10.68 (br. s., 1 H), 8.45 (d, J=1.6 Hz, 1 H), 8.38 (m, 2 H), 7.54 (td, J=3.7, 8.2 Hz, 1 H), 7.38-7.49 (m, 3 H), 7.20 (td, J=0.9, 8.9 Hz, 1 H), 7.02 (m, 2 H).

HRMS (ESI) calcd for C20H12F4N4O2S [M+H]+ 449.069, found 449.0696

Operating in an analogous way the following compounds were prepared:

Propane-1-sulfonic acid [2,4-difluoro-3-(4-pyridin-4-yl-1H-pyrazol-3-yl)-phenyl]-amide (Cmpd. 21)

[(I)C, X=CH; R1, R2, R4, R5=H; R3, R6=F; m=0; R7'=propyl]

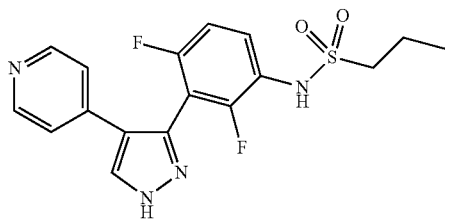 [SMILES: CCCS(=O)(=O)Nc1ccc(F)c(-c2n[nH]cc2-c2ccncc2)c1F]

HPLC (254 nm): R$_t$: 4.59 min.

¹H NMR (401 MHz, DMSO-d6) δ=13.61 (br, s, 1H), 9.65 8 (s, 1H), 8.50 (s, 1H), 8.40-8.42 (m, 2H), 7.50-7.60 (m, 1H), 7.20-7.40 (m, 1 H), 7.10-7.18 (m, 2H), 2.96-3.02 (m, 2H), 1.61-1.71 (m, 2H), 0.85-0.95 (m, 3H). HRMS (ESI) calcd for C17H16F2N4O2S [M+H]+ 379.1035, found 379.1039

Thiophene-3-sulfonic acid [2,4-difluoro-3-(4-pyridin-4-yl-1H-pyrazol-3-yl)-phenyl]-amide (Cmpd. 19)

[(I)C, X=CH; R1, R2, R4, R5=H; R3, R6=F; m=0; R7'=thiophen-3-yl]

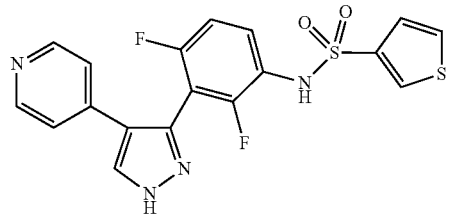 [SMILES: O=S(=O)(Nc1ccc(F)c(-c2n[nH]cc2-c2ccncc2)c1F)c1ccsc1]

HPLC (254 nm): R$_t$: 4.82 min.

¹H NMR (401 MHz, DMSO-d6) δ=13.56 (s, 1 H), 10.16 (br. s., 1 H), 8.46 (d, J=1.7 Hz, 1 H), 8.41 (d, J=6.0 Hz, 2 H), 8.08 (dd, J=1.3, 3.0 Hz, 1 H), 7.67 (dd, J=1.3, 5.1 Hz, 1 H), 7.40 (td, J=5.9, 8.8 Hz, 1 H), 7.23 (dd, J=1.2, 5.1 Hz, 1 H), 7.18 (td, J=1.2, 8.9 Hz, 1 H), 7.04 (dd, J=1.5, 4.8 Hz, 2 H). HRMS (ESI) calcd for C18H12F2N4O2S [M+H]+ 419.0443, found 419.0451.

Furan-2-sulfonic acid [2,4-difluoro-3-(4-pyridin-4-yl-1H-pyrazol-3-yl)-phenyl]amide (Cmpd. 20)

[(I)C, X=CH; R1, R2, R4, R5=H; R3, R6=F; m=0; R7'=furan-2-yl]

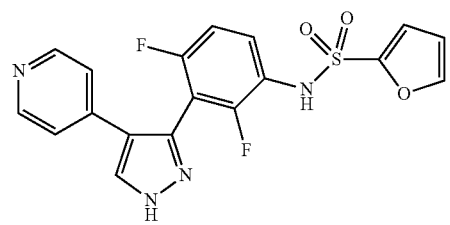 [SMILES: O=S(=O)(Nc1ccc(F)c(-c2n[nH]cc2-c2ccncc2)c1F)c1ccco1]

HPLC (254 nm): R$_t$: 4.70 min.

¹H NMR (401 MHz, DMSO-d₆) δ=13.55 (s, 1 H), 10.51 (br. s., 1 H), 8.44 (d, J=1.6 Hz, 1 H), 8.39 (d, J=5.6 Hz, 1 H), 8.11 (s, 1 H), 7.87 (dd, J=0.9, 1.7 Hz, 1 H), 7.37 (td, J=5.8, 8.8 Hz, 1 H), 7.18 (t, J=8.9 Hz, 1 H), 7.03 (d, J=6.1 Hz, 2 H), 6.99 (d, J=3.4 Hz, 1 H), 6.52 (dd, J=1.8, 3.5 Hz, 1 H). HRMS (ESI) calcd for C18H12F2N4O2S [M+H]+ 403.0671, found 403.067.

2,2,2-Trifluoro-ethanesulfonic acid [2,4-difluoro-3-(4-pyridin-4-yl-1H-pyrazol-3-yl)-phenyl]amide (Cmpd. 27)

[(I)C, X=CH; R1, R2, R4, R5=H; R3, R6=F; m=0; R7'=2,2,2-trifluoroethyl]

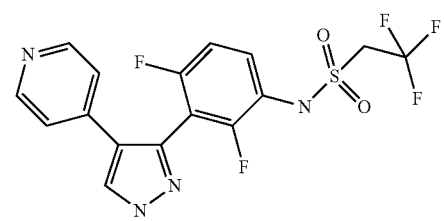 [SMILES: O=S(=O)(CC(F)(F)F)Nc1ccc(F)c(-c2n[nH]cc2-c2ccncc2)c1F]

HPLC (254 nm): Rt: 4.78

¹H NMR (401 MHz, DMSO-d6) δ=13.62 (s, 1 H), 10.36 (br. s., 1 H), 8.50 (d, J=1.7 Hz, 1 H), 8.40 (d, J=6.0 Hz, 2 H), 7.54-7.71 (m, 1 H), 7.21-7.39 (m, 1 H), 7.18 (d, J=6.1 Hz, 2 H), 4.51 (q, J=9.7 Hz, 2 H)

HRMS (ESI) calcd for C16H11F5N4O2S [M+H]+ 419.0596, found 419.0593.

Propane-2-sulfonic acid [2,4-difluoro-3-(4-pyridin-4-yl-1H-pyrazol-3-yl)-phenyl]-amide

[(I)C, X=CH; R1, R2, R4, R5=H; R3, R6=F; m=0; R7'=2-propyl]

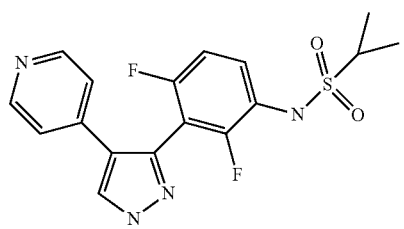 [SMILES: CC(C)S(=O)(=O)Nc1ccc(F)c(-c2n[nH]cc2-c2ccncc2)c1F]

HPLC (254 nm): Rt: 4.52
¹H NMR (401 MHz, DMSO-d6) δ=13.61 (s, 1 H), 9.64 (s, 1 H), 8.50 (d, J=1.7 Hz, 1 H), 8.39-8.45 (m, 2 H), 7.53-7.59 (m, 1 H), 7.19-7.26 (m, 1 H), 7.15-7.17 (m, 2 H), 3.11-3.18 (m, 1 H), 1.21 (d, J=6.71 Hz, 6 H).
HRMS (ESI) calcd for C17H16F2N4O2S [M+H]+ 379.1035, found 379.1034.

Cyclopropanesulfonic acid [2,4-difluoro-3-(4-pyridin-4-yl-1H-pyrazol-3-yl)-phenyl]amide (Cmpd. 26)

[(I)C, X=CH; R1, R2, R4, R5=H; R3, R6=F; m=0; R7'=cyclopropyl]

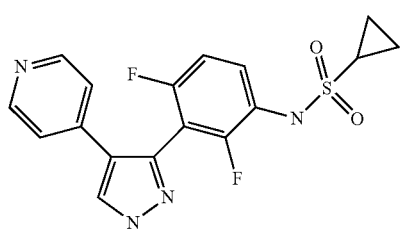 [SMILES: O=S(=O)(Nc1ccc(F)c(-c2n[nH]cc2-c2ccncc2)c1F)C1CC1]

HPLC (254 nm): Rt: 4.43
¹H NMR (401 MHz, DMSO-d6) δ=13.50 (s, 1 H), 9.64 (s, 1 H), 8.39-8.50 (m, 3 H), 7.51-7.59 (m, 1 H), 7.19-7.27 (m, 1 H), 7.14-7.16 (m, 2 H), 2.32-2.34 (m, 1 H), 0.82-0.86 (m, 4 H).
HRMS (ESI) calcd for C17H14F2N4O2S [M+H]+ 377.0879, found 377.088.

Cyclohexanesulfonic acid [2,4-difluoro-3-(4-pyridin-4-yl-1H-pyrazol-3-yl)-phenyl]-amide (Cmpd. 29)

[(I)C, X=CH; R1, R2, R4, R5=H; R3, R6=F; m=0; R7'=cyclohexyl]

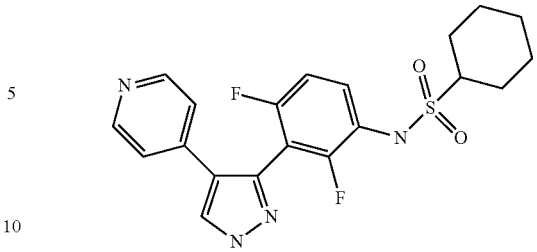

HPLC (254 nm): Rt: 5.19
¹H NMR (401 MHz, DMSO-d6) δ=13.61 (br. s., 1 H), 8.49 (d, J=1.5 Hz, 1 H), 8.42 (d, J=6.0 Hz, 2 H), 7.56 (s, 1 H), 7.18-7.35 (m, 1 H), 7.15 (d, J=6.0 Hz, 2 H), 2.84 (br. s., 1 H), 1.96-2.08 (m, 2 H), 1.69 (br. s., 2 H), 1.57 (br. s., 2 H), 1.32 (br. s., 2 H), 0.99-1.21 (m, 3 H)
HRMS (ESI) calcd for C20H20F2N4O2S [M+H]+ 419.1348, found 419.1346.

Example 23

1-[2,4-Difluoro-3-(4-pyridin-4-yl-1H-pyrazol-3-yl)-phenyl]-3-(4-trifluoromethyl-phenyl)-urea

[(I)E, X=CH; R1, R2, R4, R5=H; R3, R6=F; m=0; Y=H; R7=4-trifluoromethylphenyl]

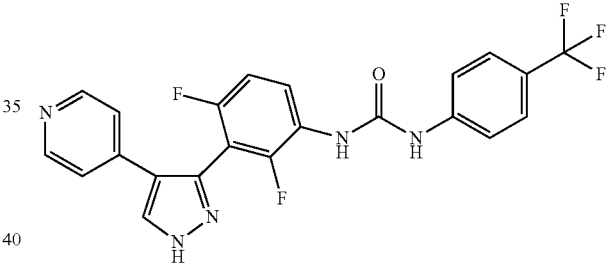

Method G
Step e
To 2,4-difluoro-3-(4-pyridin-4-yl-1H-pyrazol-3-yl)-phenylamine (70 mg, 0.25 mmol) (prepared as described in Example 22) in anhydrous N,N-dimethylformamide (2.5 mL) was added trifluoromethyl-phenylisocyanate (35 μL, 0.25 mmol) at 0° C. The reaction was allowed to warm to room temperature and it was stirred under nitrogen atmosphere for two days to yield a mixture of mono- and di-urea derivatives. Solvent was removed under reduced pressure. To the crude of reaction in methanol (3 mL) triethylamine (138 μL, 1 mmol) was added and the reaction was stirred at room temperature for two hours in order to transform the di-urea into the mono-urea derivative. The solvent was removed under reduced pressure and the residue was dissolved in ethyl acetate and washed successively with NaHCO₃ saturated solution. The organic layer was dried over anhydrous sodium sulfate and filtered. The product was isolated by silica gel column chromatography eluting with methanol 10% in methylene chloride.
HPLC (254 nm): R_t: 6.02 min.
¹H NMR (401 MHz, DMSO-d₆) δ=13.5 (s, 1H), 9.40 (s, 1 h), 8.70-8.80 (m, 5H), 7.58-7.70 (m, 4 H), 7.10-7.20 (m, 3H).
HRMS (ESI) calcd for C22H14F5N5O [M+H]+ 460.1192, found 460.1182.

Example 24

N-[2,4-difluoro-3-(4-pyridin-4-yl-1H-pyrazol-3-yl)-phenyl]-2-(4-trifluoromethyl-phenyl)-acetamide

[(I)G, X=CH; R1, R2, R4, R5=H; R3, R6=F; m=0; R7=4-trifluoromethylphenylmethyl]

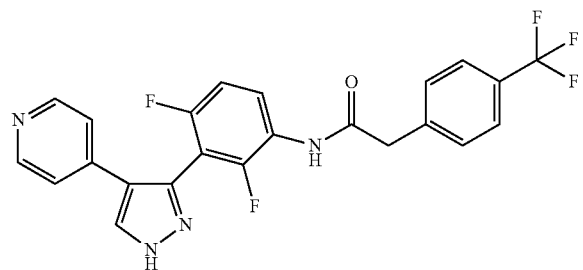 [SMILES: O=C(Cc1ccc(C(F)(F)F)cc1)Nc1ccc(F)c(-c2n[nH]cc2-c2ccncc2)c1F]

Method G
Step h

To (4-trifluoromethyl-phenyl)-acetic acid (49 mg, 0.24 mmol) in anhydrous tetrahydrofuran (3 mL) 1-ethyl-3-(3-dimethylaminopropyl)carbodiimide hydrochloride (63 mg, 0.24 mmol) was added, after 10 minutes 1-hydroxybenzotriazole (38 mg, 0.28 mmol) and after 30 minutes 2,4-difluoro-3-(4-pyridin-4-yl-1H-pyrazol-3-yl)-phenylamine (60 mg, 0.22 mmol) (prepared as described in Example 22) were added. The reaction was stirred under nitrogen atmosphere at room temperature overnight to yield a mixture of mono- and bis-amide (3:1 ratio at 254 nm). The reaction was concentrated under reduced pressure and the residue was dissolved in ethyl acetate, washed successively with NaHCO$_3$ saturated solution and the organic layer was dried over anhydrous sodium sulfate and filtered. The monoamide derivative was isolated by silica gel column chromatography eluting with ethanol 7% in methylene chloride.

HPLC (254 nm): R$_t$: 5.76 min.

$^1$H NMR (401 MHz, DMSO-d$_6$) δ=13.59 (br. s., 1 H), 10.07 (br. s., 1 H), 8.49 (s, 1 H), 8.40-8.45 (m, 2 H), 7.90-7.98 (m, 1 H), 7.68 (d, J=8.1 Hz, 2 H), 7.54 (d, J=8.1 Hz, 2 H), 7.09-7.25 (m, 3 H), 3.83 (s, 2 H). HRMS (ESI) calcd for C23H15F5N4O [M+H]+ 459.1239, found 459.1243.

Example 25

N-[3-(1-Ethyl-4-pyridin-4-yl-1H-pyrazol-3-yl)-2,4-difluoro-phenyl]-2,5-difluoro-benzenesulfonamide
(Cmpd. 51)

[(I)C, X=CH; R1, R2, R4, R5=H; R3, R6=F; m=2; R7'=2,5-difluoro-phenyl]

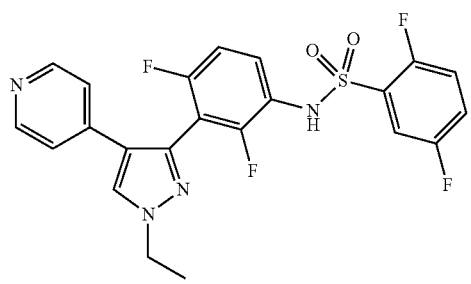 [SMILES: CCn1cc(-c2ccncc2)c(-c2c(F)ccc(NS(=O)(=O)c3cc(F)ccc3F)c2F)n1]

Method A
Step h

Dibenzyl-[3-(1-ethyl-4-pyridin-4-yl-1H-pyrazol-3-yl)-2,4-difluoro-phenyl]-amine

Dibenzyl-[2,4-difluoro-3-(4-pyridin-4-yl-1H-pyrazol-3-yl)-phenyl]-amine (prepared as described in Example 22) (4 g, 8.84 mmol) was suspended in DCM (44 mL) and 32% NaOH (44 mL) was added followed by tetrabutylammonium bromide (400 mg, 1.24 mmol, 0.14 eq). Neat ethyliodide (1.07 mL, 13.27 mmol, 1.5 eq) was then added and the biphasic mixture was vigorously stirred at room temperature for 1 h. By HPLC analysis at 254 nm the regioisomeric ratio was 55:45 in favour of the most polar N1-substituted pyrazole. The reaction mixture was then diluted with water (50 mL) and DCM (50 mL) and the two layers were separated. Aqueous phase was extracted with DCM (2×50 mL) and combined organic layers were washed with water (2×50 mL) and brine (50 mL), dried over Na$_2$SO$_4$ and evaporated to dryness. The two reagioisomers were separated by flash chromatography on silica gel (n-hexane/ethyl acetate 1:1) and the desired N$^1$-ethylpyrazole was obtained as a white solid in 52% yield.

HPLC (254 nm): R$_t$: 7.38 min.

$^1$H-NMR (401 MHz, DMSO-d$_6$) δ=8.47 (s, 1 H), 8.37 (d, J=6.0 Hz, 2 H), 7.20-7.33 (m, 10 H), 7.03-7.10 (m, 3 H), 6.89-6.97 (m, 1 H), 4.18-4.30 (m, 6 H), 1.47 (t, J=7.3 Hz, 3 H). HRMS (ESI) calcd for C30H26F2N4 [M+H]+ 481.2199, found 481.2197.

Method G
Step b 3-(1-Ethyl-4-pyridin-4-yl-1H-pyrazol-3-yl)-2,4-difluoro-phenylamine Dibenzyl-[3-(1-ethyl-4-pyridin-4-yl-1H-pyrazol-3-yl)-2,4-difluoro-phenyl]-amine (2.35 g, 4.89 mmol) was dissolved in methanol (140 mL). 20% Palladium hydroxide on carbon (500 mg) was added and the reaction was stirred under hydrogen atmosphere (50 psi) for 7 h. A further addition of catalyst was made (500 mg) and hydrogenation was continued for 6 more hours. The reaction mixture was filtered over a Celite pad and then concentrated under reduced pressure. The crude product was purified by flash chromatography on silica gel (DCM/methanol 95:5) to give 1.16 g of the desired product as a colourless foam (79% yield).

HPLC (254 nm): Rt: 4.56 min.

$^1$H-NMR (401 MHz, DMSO-d$_6$) δ=8.46 (s, 1 H), 8.39-8.43 (m, 2 H), 7.11-7.18 (m, 2 H), 6.81-6.93 (m, 2 H), 5.05 (s, 2 H), 4.23 (q, J=7.3 Hz, 2 H), 1.46 (t, J=7.3 Hz, 3 H). HRMS (ESI) calcd for C16H14F2N4 [M+H]+ 301.1260, found 301.1251.

Step b

N-[3-(1-Ethyl-4-pyridin-4-yl-1H-pyrazol-3-yl)-2,4-difluoro-phenyl]-2,5-difluoro-benzenesulfonamide 3-(1-Ethyl-4-pyridin-4-yl-1H-pyrazol-3-yl)-2,4-difluoro-phenylamine (1.146 g, 3.816 mmol) was dissolved in anhydrous pyridine (30 M) under nitrogen atmosphere and cooled to 0° C. 2,5-Difluoro-benzenesulfonyl chloride (0.513 mL, 3.816 mmol, 1 eq) was added and the mixture was allowed to stir at the same temperature. Further additions of sulfonyl chloride (for a total amount of 0.650 mL) were needed to drive the reaction to completion. The reaction mixture was kept at 0° C. overnight and then it was allowed to reach room temperature. The solvent was removed under reduced pressure and the residue was dissolved in ethyl acetate and washed with NaHCO$_3$ saturated aqueous solution. The organic layer was dried over anhydrous sodium sulfate and evaporated to dryness. The crude product was slurried in methanol at 50° C. for 10 minutes and the solid was filtered and washed with ethyl ether. After drying at 40° C. for 5 hours 1.13 g of the title compound were obtained as a white solid (62% yield).

HPLC (254 nm): Rt: 5.68 min.

$^{1}$H-NMR (401 MHz, DMSO-$d_{6}$) δ=10.68 (br. s., 1 H), 8.45 (s, 1 H), 8.38 (d, J=6.0 Hz, 2 H), 7.50-7.58 (m, 1 H), 7.40-7.49 (m, 3 H), 7.15-7.23 (m, 1 H), 6.96-7.02 (m, 2 H), 4.22 (q, J=7.2 Hz, 4 H), 1.44 (t, J=7.3 Hz, 3 H).

HRMS (ESI) calcd for C22H16F4N4O2S [M+H]+ 477.1003, found 477.0997.

Operating in an analogous way the following compounds were obtained:

N-[3-(1-Ethyl-4-pyridin-4-yl-1H-pyrazol-3-yl)-2,4-difluoro-phenyl]-2-fluoro-benzenesulfonamide (Cmpd. 57)

[(I)C, X=CH; R1, R2, R4, R5=H; R3, R6=F; m=2; R7'=2-fluoro-phenyl]

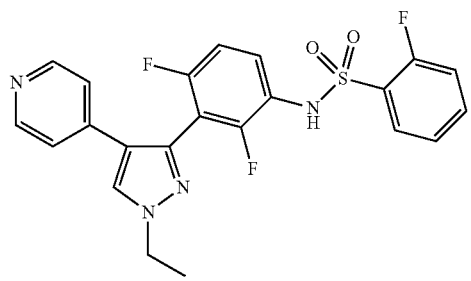 [SMILES: CCn1cc(-c2ccncc2)c(-c2c(F)ccc(NS(=O)(=O)c3ccccc3F)c2F)n1]

HPLC (254 nm): Rt: 5.53 min.

$^{1}$H-NMR (401 MHz, DMSO-$d_{6}$) δ=10.49 (s, 1 H), 8.44 (s, 1 H), 8.37-8.40 (m, 2 H), 7.59-7.73 (m, 2 H), 7.42 (td, J. 6.0, 8.9 Hz, 1 H), 7.28-7.38 (m, 2 H), 7.14-7.21 (m, 1 H), 6.92-6.98 (m, 2 H), 4.14-4.27 (m, 2 H), 1.44 (t, J=7.3 Hz, 3 H).

HRMS (ESI) calcd for C22H18F3N4O2S [M+H]+ 459.1097, found 459.1091.

Operating in an analogous way the following compounds were obtained:

N-[3-(1-Ethyl-4-pyridin-4-yl-1H-pyrazol-3-yl)-2,4-difluoro-phenyl]-3-fluoro-benzenesulfonamide (Cmpd. 58)

[(I)C, X=CH; R1, R2, R4, R5=H; R3, R6=F; m=2; R7'=3-fluoro-phenyl]

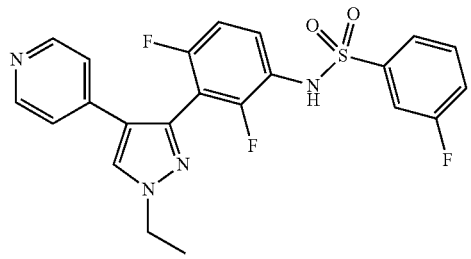 [SMILES: CCn1cc(-c2ccncc2)c(-c2c(F)ccc(NS(=O)(=O)c3cccc(F)c3)c2F)n1]

HPLC (254 nm): Rt: 5.67 min.

$^{1}$H-NMR (401 MHz, DMSO-$d_{6}$) δ=10.38 (s, 1 H), 8.44 (s, 1 H), 8.35-8.42 (m, 2 H), 7.44-7.62 (m, 4 H), 7.40 (td, J. 5.9, 8.9 Hz, 1 H), 7.18 (td, J=1.5, 8.9 Hz, 1 H), 6.98 (d, J=6.1 Hz, 2 H), 4.21 (q, J=7.3 Hz, 2 H), 1.44 (t, J=7.3 Hz, 3 H).

HRMS (ESI) calcd for C22H18F3N4O2S [M+H]+ 459.1097, found 459.1100.

Example 26

N-{2,4-Difluoro-3-[4-(2-methylamino-pyridin-4-yl)-1H-pyrazol-3-yl]-phenyl}-2,5-difluoro-benzene-sulfonamide) (Cmpd. n° 53)

[(I)C, X=CH; R1, R4, R5=H; R2=methylamino; R3, R6=F; m=2; R7'=2,5-difluoro-phenyl]

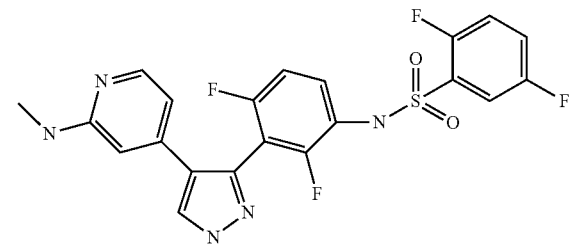 [SMILES: CNc1cc(-c2c[nH]nc2-c2c(F)ccc(NS(=O)(=O)c3cc(F)ccc3F)c2F)ccn1]

Method A

Step e 1-(3-Dibenzylamino-2,6-difluoro-phenyl)-2-(2-fluoro-pyridin-4-yl)-ethanone To a solution of 2-fluoro-4-methyl-pyridine (5.76 mL, 0.056 mol) in anhydrous tetrahydrofuran (200 mL) at 0° C. sodium hexamethyldisilazide (NaHMDS, 2 M in tetrahydrofuran, 36 mL, 0112 mol) was added and the reaction was stirred for 1 hour. A solution of 3-dibenzylamino-2,6-difluoro-benzoic acid benzyl ester (25 g, 0.056 mol) in tetrahydrofuran (80 mL) was then added dropwise to the reaction mixture, which was stirred at 0° C. for one hour and allowed to warm at room temperature. The reaction mixture was then poured into saturated aqueous ammonium chloride and extracted with ethyl acetate. The organic layer was washed with brine, dried over anhydrous sodium sulfate, filtered and concentrated under reduced pressure. The crude was purified by silica gel column chromatography eluting with ethyl acetate 15% in hexane (40.7%).

HPLC (254 nm): Rt: 7.89

$^{1}$H-NMR (401 MHz, DMSO-d6) δ=8.19 (d, J=5.1 Hz, 1 H), 7.09 (s, 1 H), 7.02-7.17 (m, 2 H), 6.93-7.02 (m, 1 H), 4.40 (s, 2 H), 4.25-4.29 (m, 4 H).

HRMS (ESI) calcd for C13H9F3N2O [M+H]+ 447.1679, found 447.1666.

Step f (E)-1-(3-Dibenzylamino-2,6-difluoro-phenyl)-3-dimethylamino-2-(2-fluoro-pyridin-4-yl)-propenone To 1-(3-Dibenzylamino-2,6-difluoro-phenyl)-2-(2-fluoro-pyridin-4-yl)-ethanone (5 g, 0.01 mol) in toluene (100 mL) was added dimethoxymethyl-dimethyl-amine (6 mL, 0.04 mol). The reaction was stirred at 80° C. for one hour and the solvent was concentrated under reduced pressure. The crude was used in the next step without further purification.

Step g1

Dibenzyl-{2,4-difluoro-3-[4-(2-fluoro-pyridin-4-yl)-1H-pyrazol-3-yl]-phenyl}-amine To (E)-1-(3-Dibenzylamino-2,6-difluoro-phenyl)-3-dimethylamino-2-(2-fluoro-pyridin-4-yl)-propenone (5.6 g, 0.01 mol) was added hydrazine in tetrahydrofuran 1M (40 mL, 0.04 mol). The reaction mixture was stirred under nitrogen atmosphere at 70° C. for one hour. The reaction was concentrated under reduced pressure and the crude was used in the next step without further purification.

HPLC (254 nm): Rt: 7.3

$^1$H-NMR (401 MHz, DMSO-d6) δ=13.64 (br. s., 1 H), 8.58 (d, J=1.7 Hz, 1 H), 8.04 (d, J=5.2 Hz, 1 H), 6.89 (s, 1 H), 6.85-7.35 (m, 13 H), 4.15-4.32 (m, 4 H)

HRMS (ESI) calcd for C28H21F3N4 [M+H]+ 471.1791, found 447.1795.

Method E
Step b1

{4-[3-(3-Dibenzylamino-2,6-difluoro-phenyl)-1H-pyrazol-4-yl]-pyridin-2-yl}-methyl-amine To a solution of dibenzyl-{2,4-difluoro-3-[4-(2-fluoro-pyridin-4-yl)-1H-pyrazol-3-yl]-phenyl}-amine (400 mg, 0.849 mmol) in DMSO (4.24 mL), a 40% methyl amine solution in water (3.5 mL) was added. The mixture was irradiated in the microwave oven at 120° C. for one hour and then poured into water and extracted with ethyl acetate. The organic layer was washed three times with saturated aqueous NaHCO$_3$ and once with brine, dried over anhydrous sodium sulfate and filtered. The filtrate was concentrated under reduce pressure and the crude product was used in the following step without further purification.

HPLC (254 nm): Rt: 6.66

$^1$H-NMR (401 MHz, DMSO-d6) δ=13.39 (br. s., 1 H), 8.27 (s, 1 H), 7.78 (d, J=5.5 Hz, 1 H), 7.16-7.33 (m, 12 H), 6.17-6.30 (m, 3 H), 4.22 (s, 4 H), 2.58 (d, J=4.4 Hz, 3 H). HRMS (ESI) calcd for C29H25F2N5 [M+H]+ 482.2151, found 482.2149.

Method G
Step b

{4-[3-(3-Amino-2,6-difluoro-phenyl)-1H-pyrazol-4-yl]-pyridin-2-yl}-methyl-amine To a solution of {4-[3-(3-dibenzylamino-2,6-difluoro-phenyl)-1H-pyrazol-4-yl]-pyridin-2-yl}-methyl-amine (408 mg, 0.849 mmol) in toluene (4.30 mL) trifluoro-methanesulfonic acid (4.30 mL) was added and the mixture was irradiated in the microwave oven at 120° C. for 30 minutes. The reaction was then poured into water and extracted with ethyl acetate. The organic layer was washed with saturated aqueous NaHCO$_3$ and brine, dried over anhydrous sodium sulfate and filtered. The filtrate was concentrated under reduced pressure and purified by silica gel column chromatography eluting with 5% methanol in methylene chloride (60% over 4 steps).

HPLC (254 nm): Rt: 3.37

$^1$H-NMR (401 MHz, DMSO-d6) δ=13.31 (s, 1 H), 8.15 (s, 1 H), 7.80 (d, J=5.37 Hz, 1 H), 6.79-6.98 (m, 2 H), 6.34-6.36 (m, 1 H), 6.27 (br. s, 1 H), 6.21 (br. s, 1 H), 5.00 (br.s., 2 H), 2.60-2.68 (m, 3 H).

HRMS (ESI) calcd for C15H13F2N5 [M+H]+ 302.1212, found 302.1206.

Step c

N-{2,4-Difluoro-3-[4-(2-methylamino-pyridin-4-yl)-1H-pyrazol-3-yl]-phenyl}-2,5-difluoro-benzene-sulfonamide To a solution of {4-[3-(3-amino-2,6-difluoro-phenyl)-1H-pyrazol-4-yl]-pyridin-2-yl}-methyl-amine (144 mg, 0.48 mmol) in anhydrous pyridine (0.2 M), 2,5-difluoro-benzenesulfonyl chloride (64 μL, 0.48 mmol) was added and the reaction mixture was stirred at room temperature under nitrogen atmosphere overnight. The solvent was removed under reduced pressure and the residue was dissolved in ethyl acetate and washed with saturated aqueous NaHCO$_3$. The organic layer was dried over anhydrous sodium sulfate and filtered. The product was isolated by silica gel column chromatography eluting with methanol 5% in methylene chloride (58%).

HPLC (254 nm): Rt: 4.73

$^1$H-NMR (401 MHz, DMSO-d6) δ=13.42 (s, 1 H), 10.73 (br. S, 1 H), 8.26 (d, J=1.47, 1 H), 7.75-7.79 (m, 1 H), 7.10-7.59 (m, 5 H), 6.10-6.40 (m, 3 H), 2.60-2.70 (m, 3 H). HRMS (ESI) calcd for C21H15F4N5O2S [M+H]+ 478.0956, found 478.0947.

Operating in an analogous way the following ethylaminopyridine analog was prepared:

N-{3-[4-(2-Ethylamino-pyridin-4-yl)-1H-pyrazol-3-yl]-2,4-difluoro-phenyl}-2,5-difluoro-benzene-sulfonamide (Cmpd. n° 54) [(I)C, X=CH; R1, R4, R5=H; R2=ethylamino; R3, R6=F; m=2; R7'=2,5-difluoro-phenyl]

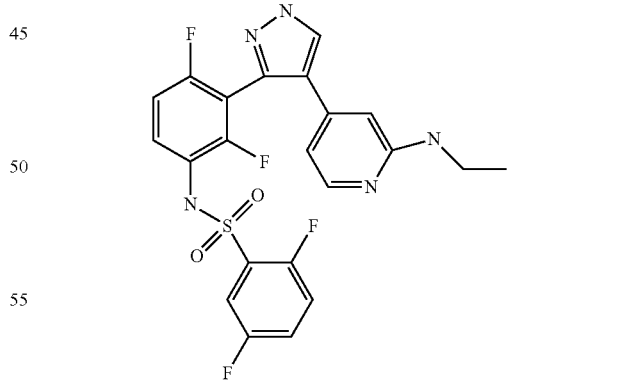

HPLC (254 nm): Rt: 5.04

$^1$H-NMR (401 MHz, DMSO-d6) δ=1H NMR (401 MHz, DMSO-d6)=13.42 (s, 1 H), 10.74 (br. s., 1 H), 8.25 (br. s, 1 H), 7.74-7.78 (m, 1 H), 7.10-7.60 (m, 5 H), 6.08-6.40 (m, 3 H), 3.04-3.18 (m, 2 H), 1.00-1.07 (t, J=7.20 Hz, 3 H).

HRMS (ESI) calcd for C22H17F4N5O2S [M+H]+ 492.1112, found 492.11

Example 27

N-(4-{3-[3-({[4-(trifluoromethyl)phenyl]carbamoyl}amino)phenyl]-1H-pyrazol-4-yl}pyridin-2-yl)propanamide (Cmpd. n° 39) [(I)V, R1, R3, R4, R5, R6=H; m=0; A=NHCONH; R7=4-trifluoromethylphenyl; R16=ethyl]

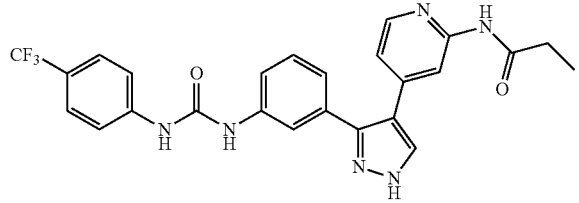 [SMILES: CCC(=O)Nc1cc(-c2c[nH]nc2-c2cccc(NC(=O)Nc3ccc(C(F)(F)F)cc3)c2)ccn1]

Method C
Step a (2E)-3-(dimethylamino)-1-(3-nitrophenyl)prop-2-en-1-one 5 g (30 mmol) of 3-nitro-acetophenone were dissolved in 20 ml of dry tetrahydrofuran and 5 ml (38 mmol) of dimethylformamide dimethylacetal were added. The mixture was stirred at 65° C. for 3 hours, then the solvent removed under reduced pressure. The crude was triturated with diisopropylether and collected by filtration, giving 6.5 g of the title compound.

$^1$H NMR (401 MHz, DMSO-d6) δ ppm 2.97 (s, 3 H) 3.19 (s, 3 H) 5.91 (d, J=12.08 Hz, 1 H) 7.74 (t, J=8.00 Hz, 1 H) 7.83 (d, J=11.96 Hz, 1 H) 8.30-8.37 (m, 2 H) 8.61 (t, J=1.89 Hz, 1 H).

HRMS (ESI): calcd for C11H12N2O3 [M+H]+ 221.0921 found 221.0915

Step b 3-(3-nitrophenyl)-1H-pyrazole 2.5 g (11 mmol) of (2E)-3-(dimethylamino)-1-(3-nitrophenyl)prop-2-en-1-one were dissolved in 25 ml of ethanol and 2.3 ml of hydrazine hydrate 98% (46 mmol) were added. The resulting solution was refluxed under stirring for 5 hours. The solvent was then evaporated and the crude was dissolved with dichloromethane and washed with water. The organic layer was dried over sodium sulphate and the solvent removed in vacuo. The residue was then triturated with diisopropylether and collected by filtration, giving 2.1 g of the title compound (98%).

$^1$H NMR (401 MHz, DMSO-d6) δ ppm 6.93 (d, J=2.32 Hz, 1 H) 7.71 (t, J=7.99 Hz, 1 H) 7.86 (br. s., 1 H) 8.14 (d, J=8.18 Hz, 1 H) 8.26 (d, J=7.32 Hz, 1 H) 8.61 (t, J=1.89 Hz, 1 H) 13.12 (br. s., 1 H).

MS (ESI) (−) 188 m/z [M−H]−; 248 m/z [M+AcOH—H]−

Step c 4-iodo-3-(3-nitrophenyl)-1H-pyrazole 2.1 g (11 mmol) of 3-(3-nitrophenyl)-1H-pyrazole were dissolved in 25 ml of dry dimethylformamide and 2.63 g (11.7 mmol) of N-iodosuccinimide were added. After 5 hours under stirring at 70° C. the most part of solvent was removed in vacuo and an aqueous solution of sodium thiosulphate was added and the product extracted several times with dichloromethane. The organic phase was then dried over sodium sulphate and evaporated to give, after trituration with diisopropylether, 2.6 g (74%) of the title compound.

$^1$H NMR (401 MHz, DMSO-d6) δ ppm 7.79 (t, J=7.99 Hz, 1 H) 8.08 (br. s., 1 H) 8.21-8.33 (m, 2 H) 8.68 (s, 1 H) 13.62 (br. s., 1 H).

MS (ESI) (−) 314 m/z [M−H].

Step d 4-iodo-1-(4-methoxybenzyl)-3-(3-nitrophenyl)-1H-pyrazole 2 g (6.3 mmol) of 4-iodo-3-(3-nitrophenyl)-1H-pyrazole were dissolved in 20 ml of dry dimethylformamide and 2.46 g (7.5 mmol) of cesium carbonate and 0.85 ml (6.3 mmol) of p-methoxybenzyl chloride were added successively. The reaction mixture was heated at 70° C. under stirring for 5 hours. Water was then added and the product extracted with dichloromethane. The organic phase was dried over sodium sulphate and the solvent evaporated under reduced pressure. 2.4 g (86%) of the title compound crystallized from a mixture diethylether-diisopropylether.

$^1$H NMR (401 MHz, DMSO-d6) δ ppm 3.73 (s, 3 H) 5.32 (s, 2 H) 6.90-6.95 (m, 2 H) 7.27-7.34 (m, 2 H) 7.76 (t, J=8.06 Hz, 1 H) 8.16 (s, 1 H) 8.23 (ddd, J=8.24, 2.38, 0.98 Hz, 1 H) 8.27 (ddd, J=7.75, 1.65, 1.10 Hz, 1 H) 8.64 (t, J=1.89 Hz, 1 H).

HRMS (ESI): calcd for C17H14IN3O3[M+H]+ 436.0153 found 436.0166.

Step h

4-[1-(4-methoxybenzyl)-3-(3-nitrophenyl)-1H-pyrazol-4-yl]pyridine

To a solution of 100 mg (0.23 mol) of 4-iodo-1-(4-methoxybenzyl)-3-(3-nitrophenyl)-1H-pyrazole in 16 ml of dioxane and 4 ml of water, 90 mg (0.46 mmol) of 4-(4,4,5,5-tetramethyl-1,3,2-dioxaborolan-2-yl)pyridine, 52 mg (0.046 mmol) of palladium tetrakis and 150 mg (0.46 mmol) mg of cesium carbonate were added successively. The mixture was submitted to microwave irradiation at 120° C. for 30 minutes in a sealed vial. The reaction was filtered through a celite pad and the solvent evaporated to dryness. The crude was then partitioned between dichloromethane and water, the organic layer dried over sodium sulphate and the solvent removed in vacuo. After purification by flash-chromatography on a silica gel column (CH$_2$Cl$_2$-CH$_3$COCH$_3$) 78 mg (88%) of the title compound were obtained.

$^1$H NMR (401 MHz, DMSO-d6) δ ppm 3.74 (s, 3 H) 5.36 (s, 2 H) 6.91-6.98 (m, 2 H) 7.24-7.27 (m, 2 H) 7.34-7.39 (m, 2 H) 7.60-7.65 (m, 1 H) 7.80 (ddd, J=7.87, 1.34, 1.16 Hz, 1 H) 8.19-8.21 (m, 1 H) 8.21-8.23 (m, 1 H) 8.34 (s, 1 H) 8.48-8.51 (m, 2 H).

HRMS (ESI): calcd for C22H18N4O3[M+H]+ 387.1452 found 387.1452.

Method E
Step a

4-[1-(4-methoxybenzyl)-3-(3-nitrophenyl)-1H-pyrazol-4-yl]pyridine 1-oxide 100 mg (0.26 mmol) of 4-[1-(4-methoxybenzyl)-3-(3-nitrophenyl)-1H-pyrazol-4-yl]-pyridine were dissolved in 3 mL of dichloromethane and 80 mg (0.52 mmol) of m-chloroperbenzoic acid were added. The mixture was stirred at room temperature for 4 hours, diluted with the same solvent and washed with aqueous sodium hydrogenocarbonate. The organic layer was then dried over sodium sulphate and evaporated to afford, after crystallization from ethylacetate, 49 mg (47%) of the title compound.

$^1$H NMR (401 MHz, DMSO-d6) δ ppm 3.74 (s, 3 H) 5.35 (s, 2 H) 6.88-6.98 (m, 2 H) 7.22-7.29 (m, 2 H) 7.33-7.39 (m, 2 H) 7.64-7.71 (m, 1 H) 7.83 (ddd, J=7.93, 1.34, 1.10 Hz, 1 H) 8.10-8.17 (m, 2 H) 8.19-8.24 (m, 2 H) 8.31 (s, 1 H).

HRMS (ESI): calcd for C22H18N4O4 [M+H]+ 403.1401 found 403.1415.

Step c

N-tert-butyl-4-[1-(4-methoxybenzyl)-3-(3-nitrophenyl)-1H-pyrazol-4-yl]pyridin-2-amine 580 mg (1.44 mmol) of 4-[1-(4-methoxybenzyl)-3-(3-nitrophenyl)-1H-pyrazol-4-yl]pyridine 1-oxide were suspended in a mixture of 16 ml of trifluoromethylbenzene and 4 ml of dry dichloromethane and 756 µl of tert-butylamine were added. At 0° C. 936 mg (7.2 mmol) of p-toluensulfonic anhydride were added. After 6 hours under stirring in the same conditions the solvent was removed under reduced pressure, the residue partitioned between dichloromethane and water, the organic layer dried over sodium sulphate and evaporated. The crude was then purified by flash-chromatography on a silica gel column (CH2Cl2-CH3COCH3 19/1), giving 500 mg (75%) of the title compound.

$^1$H NMR (401 MHz, DMSO-d6) δ ppm 1.33 (s, 9 H) 3.74 (s, 3 H) 5.34 (s, 2 H) 6.09 (s, 1 H) 6.27 (dd, J=5.31, 1.40 Hz, 1 H) 6.39 (dd, J=1.28, 0.67 Hz, 1 H) 6.94 (d, J=8.79 Hz, 2 H) 7.35 (d, J=8.67 Hz, 2 H) 7.66 (t, J=7.99 Hz, 1 H) 7.84 (ddd, J=7.69, 1.46, 1.10 Hz, 1 H) 7.88 (dd, J=5.25, 0.49 Hz, 1 H) 8.09 (s, 1 H) 8.18 (ddd, J=8.27, 2.35, 0.98 Hz, 1 H) 8.27 (t, J=1.83 Hz, 1 H).

HRMS (ESI): calcd for C26H27N5O3[M+H]+ 458.2187 found 458.2190.

Method G

Step a

4-[3-(3-aminophenyl)-1-(4-methoxybenzyl)-1H-pyrazol-4-yl]-N-tert-butylpyridin-2-amine 400 mg (0.87 mmol) of N-tert-butyl-4-[1-(4-methoxybenzyl)-3-(3-nitrophenyl)-1H-pyrazol-4-yl]pyridin-2-amine were dissolved in 15 ml of dioxane and 4 ml of water and 227 mg (3.48 mmol) of metallic zinc and 461 (8.7 mmol) of ammonium chloride were added. The mixture was stirred at 100° C. for 4 hours, then filtered through a celite pad. The filtrate was evaporated and the residue partitioned between dichloromethane and aqueous sodium hydrogenocarbonate. The organic phase was then dried and evaporated and the residue purified by flash-chromatography on a silica gel column (CH2Cl2-CH3COCH3 from 9/1 to 7/3), giving 180 mg (48%) of the title compound.

HRMS (ESI): calcd for C26H29N5O [M+H]+ 428.2445 found 428.2452.

Step e

1-(3-{4-[2-(tert-butylamino)pyridin-4-yl]-1-(4-methoxybenzyl)-1H-pyrazol-3-yl}phenyl)-3-[4-(trifluoromethyl)phenyl]urea 350 mg (0.82 mmol) of 4-[3-(3-aminophenyl)-1-(4-methoxybenzyl)-1H-pyrazol-4-yl]-N-tert-butyl-pyridin-2-amine were dissolved in 30 ml of dry dimethylformamide and 110 µl (0.82 mmol) of p-trifluoromethyl-phenyl isocyanate were added to the resulting solution. The mixture was stirred overnight at room temperature, then poured into an aqueous solution of sodium hydrogenocarbonate and extracted with dichloromethane. The organic phase was dried over sodium sulphate and evaporated in vacuo. The residue was chromatographed on a silica gel column (dichloromethane-acetone 9/1), affording 302 mg (60%) of the title compound.

$^1$H NMR (401 MHz, DMSO-d6) δ ppm 1.33 (s, 9 H) 3.75 (s, 3 H) 5.31 (s, 2 H) 6.02 (s, 1 H) 6.26 (dd, J=5.30, 1.40 Hz, 1 H) 6.42 (d, J=0.61 Hz, 1 H) 6.88-6.97 (m, 2 H) 7.00 (ddd, J=7.86, 1.28, 1.10 Hz, 1 H) 7.27 (t, J=7.87 Hz, 1 H) 7.31-7.36 (m, 2 H) 7.47-7.51 (m, 1 H) 7.55 (t, J=1.77 Hz, 1 H) 7.58-7.69 (m, 4 H) 7.84 (d, J=5.24 Hz, 1 H) 8.01 (s, 1 H) 8.84 (s, 1 H) 9.01 (s, 1 H).

HRMS (ESI): calcd for C34H33F3N6O2 [M+H]+ 615.2690 found 615.2687.

Method K

Step d

1-{3-[4-(2-aminopyridin-4-yl)-1H-pyrazol-3-yl]phenyl}-3-[4-(trifluoromethyl)phenyl]urea 100 mg (0.16 mmol) of 1-(3-{4-[2-(tert-butylamino)pyridin-4-yl]-1-(4-methoxybenzyl)-1H-pyrazol-3-yl}phenyl)-3-[4-(trifluoromethyl)phenyl]urea were dissolved with 5 ml of trifluoroacetic acid and the solution stirred at 70° C. for 6 hours. The mixture was then poured into icy water, neutralized with aqueous sodium hydrogenocarbonate and extracted with ethylacetate. The organic layer was dried over sodium sulphate and evaporated to dryness. The residue was purified by flash-chromatography on a silica gel column (dichloromethane-methanol, from 1% to 10%), giving 63 mg (90%) of the title compound.

$^1$H NMR (401 MHz, DMSO-d6) (mixture of tautomers) δ ppm 5.83 (br. s., 2 H) 6.38 (dd, J=5.30, 1.40 Hz, 1 H) 6.41 (br. s., 1 H) 7.05 (d, J=7.19 Hz, 1 H) 7.29-8.02 (many br signals, 4 H) 7.60-7.68 (m, 4 H) 7.80 (d, J=5.37 Hz, 1 H) 8.80-8.98 (m, 1 H) 9.10 (br.s., 1 H) 13.28 and 13.15 (2 br.s., 1 H).

HRMS (ESI): calcd for C22H17F3N5O [M+H]+ 439.1489 found 439.1490.

Step e

N-(4-{3-[3-({[4-(trifluoromethyl)phenyl]carbamoyl}amino)phenyl]-1H-pyrazol-4-yl}pyridin-2-yl)propanamide 35 mg (0.08 mmol) of 1-{3-[4-(2-aminopyridin-4-yl)-1H-pyrazol-3-yl]phenyl}-3-[4-(trifluoromethyl)-phenyl]urea were dissolved in 2 ml of dry tetrahydrofuran and 27 µl (0.16 mmol) of N,N-diisopropylethylamine and 14 µl of propionyl chloride (0.16 mmol) were added consecutively. The mixture was stirred overnight at room temperature, then poured into aqueous sodium hydrogenocarbonate, extracted with dichloromethane, dried over sodium sulphate ed evaporated. Without any further purification the crude was redissolved with 10 mL of methanol and 5 mL of triethylamine were added. After 7 hours at room temperature the solvent was removed in vacuo, the residue partitioned between dichloromethane and water, dried over sodium sulphate and evaporated. After trituration with diethylether, 30 mg (77%) of the title compound were collected by filtration.

$^1$H NMR (401 MHz, DMSO-d6) (mixture of tautomers) δ=1.03 (t, J=7.6, 3 H), 2.31-2.41 (q, J=7.6, 2 H), 6.85-6.91 (m, 1 H), 7.00-7.09 (m, 1 H), 7.23-7.56 (3 m, 3 H), 7.59-7.67 (m, 4 H), 8.09-8.18 (m, 2 H), 8.15 (d, J=5.3, 1 H), 8.73-8.91 (m, 1 H), 8.97-9.11 (m, 1 H), 10.33 (s, 1 H), 13.38 and 13.25 (2 br. s., 1 H). HRMS (ESI): calcd for C25H21F3N6O2 [M+H]+ 495.1751 found 495.1746.

Operating in an analogous way the following compounds were obtained:

2-methyl-N-(4-{3-[3-({[4-(trifluoromethyl)phenyl]carbamoyl}amino)phenyl]-1H-pyrazol-4-yl}pyridin-2-yl)propanamide (Cmpd. n° 40)

[(I)V, R1, R3, R4, R5, R6=H; m=0; A=NHCONH; R7=4-trifluoromethylphenyl; R16=isopropyl]

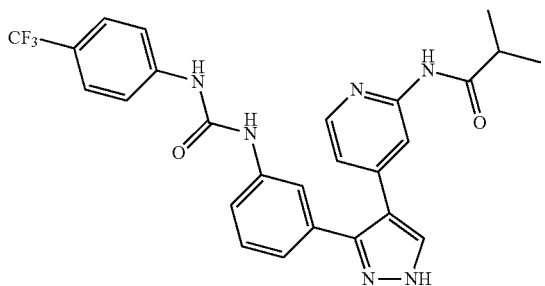 [SMILES: CC(C)C(=O)Nc1cc(-c2c[nH]nc2-c2cccc(NC(=O)Nc3ccc(C(F)(F)F)cc3)c2)ccn1]

$^1$H NMR (401 MHz, DMSO-d6) δ=1.03-1.08 (m, 6 H) 2.67-2.79 (m, 1 H) 6.83-6.89 (m, 1 H) 6.99-7.08 (m, 1 H) 7.20-7.57 (m, 3 H) 7.58-7.67 (m, 4 H) 7.81 (br.s., 1 H) 8.10-8.21 (m, 3 H) 8.80 (br. s, 1 H) 9.04 (br. s, 1 H) 10.33 (s, 1 H).

HRMS (ESI): calcd for C26H24F3N6O2 [M+H]+ 509.1908 found 509.1896.

Example 28

4-hydroxy-N-(4-{3-[3-({[4-(trifluoromethyl)phenyl]carbamoyl}amino)phenyl]-1H-pyrazol-4-yl}pyridin-2-yl)butanamide (Cpd. n° 43)

[(I)V, R1, R3, R4, R5, R6=H; m=0; A=NHCONH; R7=4-trifluoromethylphenyl; R16=3-hydroxypropyl]

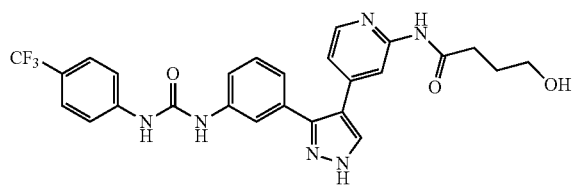 [SMILES: O=C(CCCO)Nc1cc(-c2c[nH]nc2-c2cccc(NC(=O)Nc3ccc(C(F)(F)F)cc3)c2)ccn1]

Method K
Step e 30 mg (0.068 mmol) of 1-{3-[4-(2-aminopyridin-4-yl)-1H-pyrazol-3-yl]phenyl}-3-[4-(trifluoromethyl)phenyl]urea were dissolved in 2 ml of dry tetrahydrofuran and 15 μl (0.34 mmol) of γ-butyrolactone were added. The reaction mixture was cooled to 0° C. and a solution of 680 μl (0.68 mmol) of hexamethyldisilazane sodium salt 1M in THF in 2 ml of the same solvent were added dropwise. The mixture was maintained at 0° C. for 6 hours and at room temperature overnight, then partitioned between dichloromethane and water. The organic phase was dried over sodium sulphate and evaporated. The crude was finally purified by preparative HPLC in reverse phase conditions (basic eluant), giving 20 mg (59%) of the title compound.

$^1$H NMR (401 MHz, DMSO-d6) (mixture of tautomers) δ=13.39-13.25 (2 br.s., 1H), 10.34 (s, 1H); 9.05 (m, 1H), 8.81 (m, 1H), 8.13-8.18 (m, 2H), 8.13 and 7.82 (2bs, 1H), 7.58-7.68 (m, 4H), 7.22-7.56 (3 m, 3H) 7.04 (m, 1H), 6.85 (m, 1H), 4.45 (t, J=5.4 Hz, 1H), 3.39 (m, 2H), 2.39 (t, J=7.45 Hz, 2H), 1.69 (tt, J=6.59, 6.59 Hz, 2H).

HRMS (ESI): calcd for C26H24F3N6O3[M+H]+ 525.1857 found 525.1856.

Example 29

1-(3-{4-[2-(methylamino)pyridin-4-yl]-1H-pyrazol-3-yl}phenyl)-3-[4-(trifluoromethyl)phenyl]urea

[(I)E, X=CH; R1, R3, R4, R5, R6=H; m=0; R2=methylamino; Y=H; R7=4-trifluoromethylphenyl]

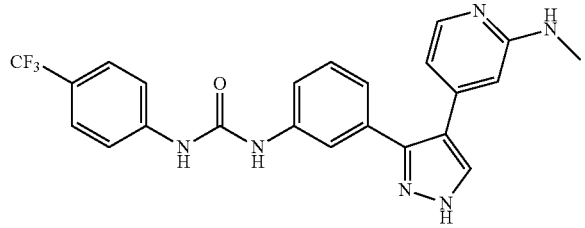 [SMILES: CNc1cc(-c2c[nH]nc2-c2cccc(NC(=O)Nc3ccc(C(F)(F)F)cc3)c2)ccn1]

Method C
Step h 2-fluoro-4-[1-(4-methoxybenzyl)-3-(3-nitrophenyl)-1H-pyrazol-4-yl]pyridine 1 g (2.3 mmol) of 4-iodo-1-(4-methoxybenzyl)-3-(3-nitrophenyl)-1H-pyrazole (prepared as described in Example 27) were dissolved in a mixture of 20 ml of dioxane and 5 ml of water in a nitrogen atmosphere. 750 mg (2.3 mmol) of cesium carbonate, 350 mg (0.3 mmol) of palladium tetrakis and 486 mg (3.45 mmol) of 2-fluoro-pyridyl boronic acid were added and the reaction stirred at 100° C. for 4 hours. The mixture was then filtered through a celite pad and the filtrate evaporated under reduced pressure. The residue was re-dissolved with dichloromethane and washed with water. The organic layer was dried over sodium sulphate and evaporated. 680 mg (73%) of the title compound crystallized from diethylether.

$^1$H NMR (401 MHz, DMSO-d6) δ=3.74 (s, 3 H) 5.36 (s, 2 H) 6.91-6.99 (m, 2 H) 7.16-7.18 (m, 1 H) 7.34-7.39 (m, 2 H) 7.45-7.48 (m, 1 H) 7.68 (dd, J=8.79, 7.81 Hz, 1 H) 7.78-7.83 (m, 1 H) 8.15 (d, J=5.25 Hz, 1 H) 8.20-8.28 (m, 2H) 8.43 (s, 1 H).

HRMS (ESI): calcd for C22H18FN4O3[M+H]+ 405.1358 found 405.1369.

Method E
Step c1

4-[1-(4-methoxybenzyl)-3-(3-nitrophenyl)-1H-pyrazol-4-yl]-N-methylpyridin-2-amine 500 mg (1.24 mmol) of 2-fluoro-4-[1-(4-methoxybenzyl)-3-(3-nitrophenyl)-1H-pyrazol-4-yl]pyridine were dissolved in a mixture of 6 ml of methylamine 40% in water and 12 ml of dioxane and the mixture submitted to microwave irradiation at 130° C. for 2 hours in a sealed vial. The solvent was the removed under reduced pressure and the residue taken up with dichloromethane and washed with water. The organic layer was dried over sodium sulphate and evaporated. The crude was finally purified by flash-chromatography on a silica gel column (CH2Cl2-CH3COCH3 9/1), giving 300 mg (58%) of the title compound.

¹H NMR (401 MHz, DMSO-d6) δ=2.70 (d, J=4.88 Hz, 3 H) 3.74 (s, 3 H) 5.34 (s, 2 H) 6.29-6.31 (m, 1 H) 6.34 (dd, J=5.25, 1.46 Hz, 1 H) 6.40 (q, J=4.60 Hz, 1 H) 6.85-6.97 (m, 2 H) 7.33-7.38 (m, 2 H) 7.65 (t, J=8.06, 1 H) 7.83 (dt, J=1.2, 8.1 Hz, 1 H), 7.90 (d, J=5.25 Hz, 1 H) 8.17 (s, 1 H) 8.16-8.21 (m, 1 H) 8.27 (t, J=1.89 Hz, 1 H).

HRMS (ESI): calcd for C23H21N5O3[M+H]+ 416.1717 found 416.1720.

Operating in an analogous way the following intermediates were obtained:

N-ethyl-4-[1-(4-methoxybenzyl)-3-(3-nitrophenyl)-1H-pyrazol-4-yl]pyridin-2-amine ¹H NMR (401 MHz, DMSO-d6) δ=1.07 (t, J=7.14 Hz, 3 H) 3.13-3.23 (m, 2 H) 3.74 (s, 3 H) 5.34 (s, 2 H) 6.29-6.35 (m, 2 H) 6.44 (br.s., 1 H) 6.90-6.98 (m, 2 H) 7.32-7.38 (m, 2 H) 7.64 (t, J=8.05, 1 H) 7.84 (dt, J=7.90, 1.24 Hz, 1 H) 7.89 (d, J=5.25 Hz, 1 H) 8.17 (s, 1 H) 8.17-8.21 (m, 1 H) 8.26 (t, J=1.89 Hz, 1 H).

HRMS (ESI): calcd for C24H23N5O3[M+H]+ 430.1874 found 430.1877.

N'-{4-[1-(4-methoxybenzyl)-3-(3-nitrophenyl)-1H-pyrazol-4-yl]pyridin-2-yl}-N,N-dimethylethane-1,2-diamine ¹H NMR (401 MHz, DMSO-d6) δ=2.23 (bs, 6 H) 2.45 (bs, 2 H) 3.31 (bs, 2 H) 3.74 (s, 3 H) 5.34 (s, 2 H) 6.32-6.38 (m, 3 H) 6.89-6.96 (m, 2 H) 7.30-7.39 (m, 2 H) 7.62-7.68 (m, 1 H) 7.84 (dt, J=7.96, 1.21 Hz, 1 H) 7.90 (m, J=5.86 Hz, 1 H) 8.16 (s, 1 H) 8.19 (ddd, J=8.21, 2.35, 1.04 Hz, 1 H) 8.25 (t, J=1.89 Hz, 1 H).

HRMS (ESI): calcd for C26H28N6O3[M+H]+ 473.2296 found 473.2304.

4-[1-(4-methoxybenzyl)-3-(3-nitrophenyl)-1H-pyrazol-4-yl]-N-(2-methoxyethyl)pyridin-2-amine HRMS (ESI): calcd for C25H25N5O4[M+H]+ 460.1980 found 460.1964.

Method G
Step a

4-[3-(3-aminophenyl)-1-(4-methoxybenzyl)-1H-pyrazol-4-yl]-N-methylpyridin-2-amine 300 mg (0.72 mmol) of 4-[1-(4-methoxybenzyl)-3-(3-nitrophenyl)-1H-pyrazol-4-yl]-N-methylpyridin-2-amine were dissolved in a mixture of 20 ml of dioxane and 4 ml of water and 381 mg (7.2 mmol) of ammonium chloride and 190 mg (2.9 mmol) of metallic zinc were added. The reaction was maintained at 100° C. under stirring for 6 hours. The mixture was then filtered through a celite pad and the solvent removed in vacuo. The residue was partitioned between dichloromethane and water, dried over sodium sulphate and evaporated again, giving, after trituration with diethylether, 260 mg (93%) of the title compound.

¹H NMR (401 MHz, DMSO-d6) δ=2.68 (d, J=4.76 Hz, 3 H) 3.74 (s, 3 H) 5.04 (bs, 2 H) 5.26 (s, 2 H) 6.24-6.31 (m, 1 H) 6.30 (s, 1 H) 6.33 (dd, J=5.37, 1.46 Hz, 1 H) 6.44-6.53 (m, 2 H) 6.70 (t, J=1.83 Hz, 1 H) 6.90-6.94 (m, 2 H) 6.94-6.98 (m, 1 H) 7.27-7.32 (m, 2 H) 7.83 (dd, J=5.31, 0.43 Hz, 1 H) 8.05 (s, 1 H).

HRMS (ESI): calcd for C23H23N5O [M+H]+ 386.1986 found 386.1991.

Operating in an analogous way the following intermediates were obtained:

4-[3-(3-aminophenyl)-1-(4-methoxybenzyl)-1H-pyrazol-4-yl]-N-methylpyridin-2-amine Yield 77%.

¹H NMR (401 MHz, DMSO-d6) δ=1.03-1.10 (m, 3 H) 3.09-3.21 (m, 2 H) 3.74 (s, 3 H) 5.04 (s, 2 H) 5.26 (s, 2 H) 6.27 (t, J=5.43 Hz, 1 H) 6.32 (d, J=1.46 Hz, 1 H) 6.30 (s, 1 H) 6.47 (dt, J=8.88, 1.30 Hz, 1 H) 6.49-6.52 (m, 1 H) 6.70 (t, J=1.89 Hz, 1 H) 6.90-7.00 (m, 3 H) 7.24-7.35 (m, 2 H) 7.82 (dd, J=5.13, 0.73 Hz, 1 H) 8.02 (s, 1 H).

HRMS (ESI): calcd for C24H25N5O [M+H]+ 400.2132 found 400.2141.

N'-{4-[3-(3-aminophenyl)-1-(4-methoxybenzyl)-1H-pyrazol-4-yl]pyridin-2-yl}-N,N-dimethylethane-1,2-diamine Yield 74%

HRMS (ESI): calcd for C26H30N5O [M+H]+ 443.2554 found 443.2555.

4-[3-(3-aminophenyl)-1-(4-methoxybenzyl)-1H-pyrazol-4-yl]-N-(2-methoxyethyl)pyridin-2-amine Yield 54%

¹H NMR (401 MHz, DMSO-d6) δ=3.15-3.21 (m, 2 H) 3.24 (s, 3 H) 3.37-3.42 (m, 2 H) 3.74 (s, 3 H) 5.04 (br. s., 2 H) 5.26 (s, 2 H) 6.32 (dd, J=5.37, 1.22 Hz, 1 H) 6.34-6.41 (m, 2 H) 6.47 (dt, J=7.60, 1.14 Hz, 1 H) 6.50 (ddd, J=7.96, 2.23, 0.92 Hz, 1 H) 6.70 (t, J=1.77 Hz, 1 H) 6.90-6.99 (m, 3 H) 7.28-7.32 (m, 2 H) 7.81 (d, J=5.25 Hz, 1 H) 8.01 (s, 1 H).

HRMS (ESI): calcd for C25H27N5O2[M+H]+ 430.2238 found 430.2242.

Method G
Step e

1-(3-{1-(4-methoxybenzyl)-4-[2-(methylamino)pyridin-4-yl]-1H-pyrazol-3-yl}phenyl)-3-[4-(trifluoromethyl)phenyl]urea 250 mg (0.65 mmol) of 4-[3-(3-aminophenyl)-1-(4-methoxybenzyl)-1H-pyrazol-4-yl]-N-methylpyridin-2-amine were dissolved in 10 ml of dry dimethylformamide and 92 μl of p-trifluoromethyl-phenylisocyanate were added. The reaction was stirred at room temperature overnight, poured into aqueous sodium hydrogenocarbonate and extracted with dichloromethane. The organic phase was then dried over sodium sulphate and evaporated. The residue was purified by flash-chromatography on a silica gel column CH2Cl2-CH3COCH3; from 9/1 to 8/2), giving 234 mg (63%) of the title compound.

¹H NMR (401 MHz, DMSO-d6) δ=2.69 (d, J=4.88 Hz, 3 H) 3.74 (s, 3 H) 5.30 (s, 2 H) 6.31 (s, 1 H) 6.29-6.35 (m, 2 H) 6.94 (d, J=8.79 Hz, 2 H) 7.00 (dt, J=7.75, 1.25 Hz, 1 H) 7.26 (m, J=8.79 Hz, 1 H) 7.33 (d, J=8.79 Hz, 2 H) 7.47-7.55 (m, 2 H) 7.58-7.69 (m, 4 H) 7.87 (d, J=5.25 Hz, 1 H) 8.10 (s, 1 H) 8.83 (s, 1 H) 9.01 (s, 1 H).

HRMS (ESI): calcd for C31H28F3N6O2 [M+H]+ 573.2221 found 573.2216.

Operating in an analogous way the following intermediates ureas were obtained:

1-(3-{4-[2-(ethylamino)pyridin-4-yl]-1-(4-methoxybenzyl)-1H-pyrazol-3-yl}phenyl)-3-[4-(trifluoromethyl)phenyl]urea Yield 58%

$^1$H NMR (401 MHz, DMSO-d6) δ=1.06 (t, J=7.14 Hz, 3 H) 3.09-3.21 (m, 2 H) 3.74 (s, 3 H) 5.30 (s, 2 H) 6.28-6.35 (m, 3 H) 6.91-6.96 (m, 2 H) 6.97-7.03 (m, 1 H) 7.26 (t, J=7.87 Hz, 1 H) 7.30-7.37 (m, 2 H) 7.48-7.54 (m, 2 H) 7.58-7.68 (m, 4 H) 7.82-7.87 (m, 1 H) 8.08 (s, 1 H) 8.83 (s, 1 H) 9.02 (s, 1 H).

HRMS (ESI): calcd for C32H30F3N6O2 [M+H]+ 587.2377 found 587.2374.

1-{3-[4-(2-{[2-(dimethylamino)ethyl]amino}pyridin-4-yl)-1-(4-methoxybenzyl)-1H-pyrazol-3-yl]phenyl}-3-[4-(trifluoromethyl)phenyl]urea Yield 50%

$^1$H NMR (401 MHz, DMSO-d6) δ=2.16-2.23 (m, 6H) 2.41-2.53 (m, 2H) 3.21-3.37 (m, 2H) 3.74 (s, 3H) 5.30 (s, 2 H) 6.27 (bs, 1 H) 6.35 (dd, J=5.31, 1.28 Hz, 1 H) 6.37 (s, 1 H) 6.91-6.96 (m, 2 H) 6.96-7.01 (m, 1 H) 7.26 (t, J=7.87 Hz, 1 H) 7.33 (d, J=8.67 Hz, 2 H) 7.48-7.52 (m, 1 H) 7.52-7.54 (m, 2 H) 7.58-7.67 (m, 4 H) 7.86 (d, J=5.13 Hz, 1 H) 8.88 (s, 1 H) 9.06 (s, 1 H).

HRMS (ESI): calcd for C34H34F3N7O2[M+H]+ 630.2799 found 630.2822.

Method M

Step a

1-(3-{4-[2-(methylamino)pyridin-4-yl]-1H-pyrazol-3-yl}phenyl)-3-[4-(trifluoromethyl)phenyl]urea 200 mg (0.35 mmol) of 1-(3-{1-(4-methoxybenzyl)-4-[2-(methylamino)pyridin-4-yl]-1H-pyrazol-3-yl}phenyl)-3-[4-(trifluoromethyl)phenyl]urea were dissolved with 10 ml of trifluoroacetic acid and the solution was stirred at 70° C. for 6 hours. The solvent was then evaporated and the residue taken up with dichloromethane and washed with aqueous sodium hydrogenocarbonate. The organic layer was dried over sodium sulphate and evaporated again, affording, after trituration with diethylether, 100 mg (63%) of the title compound.

$^1$H NMR (401 MHz, DMSO-d6) (mixture of tautomers) δ=13.13 and 13.26 (2s, 1H), 9.03 (m, 1H), 8.80 (m, 1H), 7.77 and 8.04 (2bs, 1H), 7.86 (d, J=5.37 Hz, 1H), 7.61-7.66 (m, 4H), 7.43-7.58 (3 m, 3 H) 7.28 (m, 1H), 6.21-6.42 (m, 3H), 2.68 (d, J=4.88 Hz, 3H).

HRMS (ESI): calcd for C23H20F3N5O [M+H]+ 453.1645 found 453.1638.

Operating in an analogous way the following compounds were obtained:

1-(3-{4-[2-(ethylamino)pyridin-4-yl]-1H-pyrazol-3-yl}phenyl)-3-[4-(trifluoromethyl)phenyl]urea

[(I)E, X=CH; R1, R3, R4, R5, R6=H; m=0; R2=ethylamino; Y=H; R7=4-trifluoromethylphenyl]

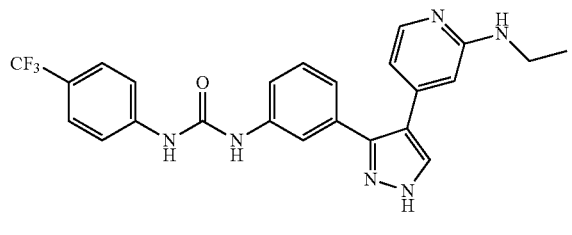 [SMILES: CCNc1cc(-c2c[nH]nc2-c2cccc(NC(=O)Nc3ccc(C(F)(F)F)cc3)c2)ccn1]

$^1$H NMR (401 MHz, DMSO-d6) δ=1.06 (t, J=7.08 Hz, 3 H) 3.15 (dq, J=7.08, 12.69 Hz, 2 H) 6.30 (t, J=4.64 Hz, 1 H) 6.33-6.38 (m, 2 H), 7.03-7.08 (m, 1 H) 7.25-7.42 (m, 1 H) 7.44-7.59 (2m, 2H) 7.56-7.69 (m, 4H), 7.83-7.88 (m, 1H), 7.75 and 8.03 (2bs, 1H) 8.91 and 8.82 (2bs, 1H) 9.11 and 9.05 (2 bs, 1H) 13.13 and 13.26 (2bs, 1H).

HRMS (ESI): calcd for C24H21F3N5O [M+H]+ 467.1802 found 467.1808.

1-{3-[4-(2-{[2-(dimethylamino)ethyl]amino}pyridin-4-yl)-1H-pyrazol-3-yl]phenyl}-3-[4-(trifluoromethyl)phenyl]urea

[(I)E, X=CH; R1, R3, R4, R5, R6=H; m=0; R2=(2-dimethylamino)ethylamino; Y=H; R7=4-trifluoromethylphenyl]

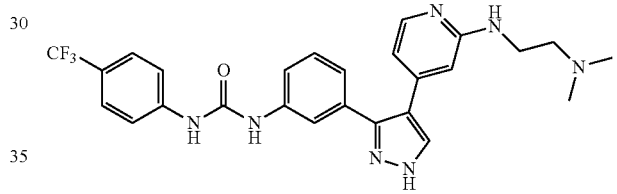

$^1$H NMR (401 MHz, DMSO-d6) (selected signals) (mixture of tautomers) δ=2.12 (s, 6H), 2.34 (t, J=6.71, 2H), 3.22 (q, J=6.23 Hz, 2H), 6.16 (t, J=5.37, 1 H), 6.37 (dd, J=5.25, 1.22, 1 H), 6.39-6.45 (br.s., 1 H), 7.04 (d, J=7.63 Hz, 1H), 7.59-7.67 (m, 4H), 7.86 (d, J=5.19 Hz, 1H), 13.25 and 13.12 (2 br.s., 1 H).

HRMS (ESI): calcd for C26H26F3N7O [M+H]+ 510.2224 found 510.2226.

Example 30

2,5-difluoro-N-(3-{4-[2-(methylamino)pyridin-4-yl]-1H-pyrazol-3-yl}phenyl)benzenesulfonamide

[(I)C, X=CH; R1, R3, R4, R5, R6=H; m=0; R2=methylamino; R7'=2,5-difluorophenyl]

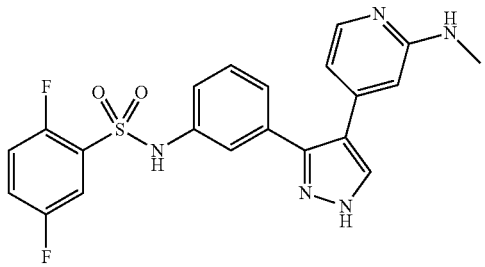 [SMILES: CNc1cc(-c2c[nH]nc2-c2cccc(NS(=O)(=O)c3cc(F)ccc3F)c2)ccn1]

Method G
Step c

2,5-difluoro-N-(3-{1-(4-methoxybenzyl)-4-[2-(methylamino)pyridin-4-yl]-1H-pyrazol-3-yl}phenyl)benzenesulfonamide

250 mg (0.65 mmol) of 4-[3-(3-aminophenyl)-1-(4-methoxybenzyl)-1H-pyrazol-4-yl]-N-methylpyridin-2-amine (prepared as described in Example 29) were dissolved in 10 ml of dry pyridine and 87 μl of 2,5-difluorobenzensulfonyl-chloride were added The reaction was stirred at room temperature overnight, then poured into aqueous sodium hydrogenocarbonate and extracted with dichloromethane. The organic layer was dried over sodium sulphate and evaporated in vacuo. The residue was then triturated with diethylether, giving 300 mg of the title compound (82%).

$^1$H NMR (401 MHz, DMSO-d6) δ=2.66 (d, J=4.88 Hz, 3 H) 3.74 (s, 3 H) 5.27 (s, 2 H) 6.19 (dd, J=5.25, 1.34 Hz, 1 H) 6.21 (s, 1 H) 6.30 (m, J=3.30 Hz, 1 H) 6.90-6.97 (m, 2 H) 7.03-7.10 (m, 2 H) 7.19-7.25 (m, 2 H) 7.28-7.34 (m, 2 H) 7.44-7.60 (m, 2 H) 7.81 (d, J=5.25, 1 H) 8.07 (s, 1 H) 10.78 (bs, 1 H).

HRMS (ESI): calcd for C29H25F2N5O3S[M+H]+ 562.1719 found 562.1727.

Operating in an analogous way the following intermediate sulphonamide was also obtained:

2,5-difluoro-N-{3-[1-(4-methoxybenzyl)-4-{2-[(2-methoxyethyl)amino]pyridin-4-yl}-1H-pyrazol-3-yl]phenyl}benzenesulfonamide

Yield 86%

$^1$H NMR (401 MHz, DMSO-d6) δ=3.23 (s, 3 H) 3.27-3.42 (m, 4 H), 3.74 (s, 3 H) 5.27 (s, 2 H) 6.16 (dd, J=5.31, 1.40 Hz, 1 H) 6.31 (s, 1 H) 6.34-6.40 (m, 1 H) 6.91-6.95 (m, 2 H) 7.02-7.10 (m, 2 H) 7.19-7.24 (m, 1 H) 7.23 (d, J=2.07 Hz, 1 H) 7.29-7.33 (m, 2 H) 7.45-7.58 (m, 3 H) 7.79 (d, J=5.49 Hz, 1 H) 8.03 (s, 1 H) 10.77 (s, 1 H).

HRMS (ESI): calcd for C31H29F2N5O4S[M+H]+ 606.1981 found 606.1988.

Method M
Step a

2,5-difluoro-N-(3-{4-[2-(methylamino)pyridin-4-yl]-1H-pyrazol-3-yl}phenyl)benzenesulfonamide

300 mg (0.53 mmol) of 2,5-difluoro-N-(3-{1-(4-methoxybenzyl)-4-[2-(methylamino)-pyridin-4-yl]-1H-pyrazol-3-yl}phenyl)benzenesulfonamide were dissolved in 10 ml of trifluoroacetic acid and the mixture heated at 70° C. under stirring for 4 hours. The solvent was then removed in vacuo, the residue partitioned between dichloromethane and a saturated aqueous solution of sodium hydrogenocarbonate. The organic layer was dried over sodium sulphate and evaporated to dryness. The crude was finally purified by flash-chromatography on a silica gel column (CH2Cl2-CH3COCH3; from 9/1 to 8/2), giving 47 mg (20%) of the title compound.

$^1$H NMR (401 MHz, DMSO-d6) (mixture of tautomers) δ=13.14 and 13.25 (2bs, 1H), 10.78 (bs, 1H), 8.02 (s, 1H), 7.81 (m, 1 H) 7.44-7.60 (m, 3 H) 7.05-7.39 (several m, 4H), 6.26-6.30 (m, 3H), 2.66 (d, J=4.88 Hz, 3H).

HRMS (ESI): calcd for C21H17F2N5O2S[M+H]+ 442.1144 found 442.1156.

Operating in an analogous way the following sulphonamide was also obtained:

2,5-difluoro-N-[3-(4-{2-[(2-methoxyethyl)amino]pyridin-4-yl}-1H-pyrazol-3-yl)phenyl]benzenesulfonamide

[(I)C, X=CH; R1, R3, R4, R5, R6=H; m=0; R2=(2-methoxy)ethylamino; R7'=2,5-difluorophenyl]

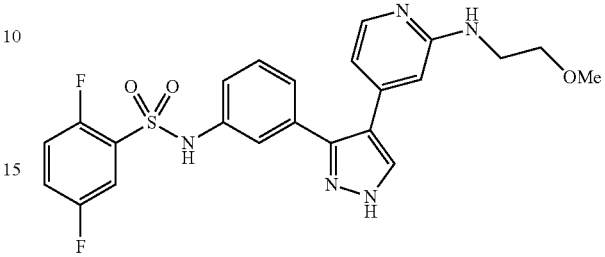

Yield 33%

$^1$H NMR (401 MHz, DMSO-d6) (selected signals) δ=13.14 and 13.25 (2s, 1H), 10.78 (bs, 1H), 7.0-8.0 (several m, 8H), 3.33 (m, 2H), 3.31 (m, 2H), 3.24 (s, 3H).

HRMS (ESI): calcd for C23H21F2N5O3S[M+H]+ 486.1406 found 486.1396.

Example 31

1-{3-[4-(2-aminopyrimidin-4-yl)-1H-pyrazol-3-yl]phenyl}-3-[4-(trifluoromethyl)-phenyl]urea (Cpd. n° 31)

[(I)E, X=N; R1, R3, R4, R5, R6=H; m=0; R2=NH2; Y=H; R7=4-trifluoromethylphenyl]

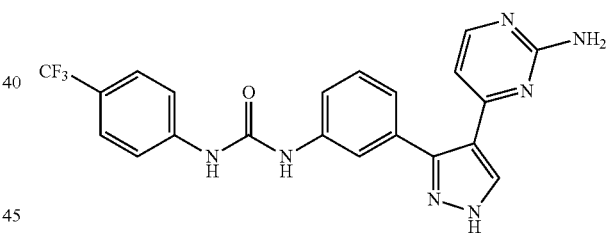

Method C
Step i

3-(3-nitrophenyl)-4-[(trimethylsilyl)ethynyl]-1H-pyrazole

415 mg (1.32 mmol) of 4-iodo-3-(3-nitrophenyl)-1H-pyrazole (prepared as described in Example 27) were dissolved in 15 ml of dry tetrahydrofuran and 494 μL (3.42 mmol) of triethylamine, 80 mg (0.106 mmol) of palladium(II)-bis(triphenylphosphine) dichloride, 26 mg (0.166 mmol) of cuprous iodide and 406 μL (2.9 mmol) of trimethylsilylacetylene were added consecutively in a nitrogen atmosphere. The reaction was refluxed under stirring for 4 hours. The solvent was then removed in vacuo and the residue re-dissolved with dichloromethane and washed with water. The organic phase was dried over sodium sulphate and evaporated, affording, after trituration with diisopropylether, 300 mg (80%) of the title compound, that was employed for the next step without any further purification.

Step j

4-Ethynyl-3-(3-nitrophenyl)-1H-pyrazole 300 mg (1.05 mmol) of 3-(3-nitrophenyl)-4-[(trimethylsilyl)ethynyl]-1H-pyrazole were suspended in 60 ml of methanol and 120 mg (2.1 mmol) of potassium fluoride were added and the mixture stirred at room temperature overnight. After this time the solvent was removed under reduced pressure and the residue taken up with dichloromethane and washed with water. The organic layer was then dried over sodium sulphate and evaporated. The crude was finally purified by flash-chromatography on a silica gel column (CH2Cl2-CH3COCH3 9/1), giving 150 mg (67%) of the title compound.

$^1$H NMR (401 MHz, DMSO-d6) δ=4.37 (s, 1 H) 7.78 (t, J=7.93 Hz, 1 H) 8.24 (d, J=8.30 Hz, 1 H)) 8.26-8.29 (m, 1H) 8.47 (d, J=8.06 Hz, 1 H) 8.91 (s, 1 H) 13.50 (bs, 1 H). MS (ESI) (−) 212 m/z [M−H].

Step I

1-[3-(3-nitrophenyl)-1H-pyrazol-4-yl]ethanone

To a solution of 350 mg (1.6 mmol) of 4-ethynyl-3-(3-nitrophenyl)-1H-pyrazole in a mixture of 50 ml of dioxane and 0.5 ml (28 mmol) of water, 0.5 ml (6.5 mmol) of trifluoroacetic acid were added. The reaction was heated at 100° C. under stirring for 2 hours. The organic solvent was removed under reduced pressure and the residue partitioned between ethylacetate and aqueous sodium hydrogenocarbonate. The organic layer was then dried over sodium sulphate and evaporated to dryness, affording, after trituration with diethylether, 251 mg (68%) of the title compound.

$^1$H NMR (401 MHz, DMSO-d6) δ=2.47 (s, 3 H) 7.70 (t, J=7.93 Hz, 1 H) 8.22 (t, J=7.14 Hz, 2 H) 8.64 (bs, 1 H) 8.72 (s, 1 H) 13.67 (bs, 1 H).

HRMS (ESI): calcd for C11H9N3O3 [M+H]+ 232.0717 found 232.0719.

Protection of the Pyrazole:

1-[1-(4-methoxybenzyl)-3-(3-nitrophenyl)-1H-pyrazol-4-yl]ethanone 320 mg (1.39 mmol) of 1-[3-(3-nitrophenyl)-1H-pyrazol-4-yl]ethanone were dissolved with 15 ml of dry dimethylformamide and 540 mg (1.66 mmol) of cesium carbonate and 189 μl (1.39 mmol) of p-methoxybenzyl chloride were added. The reaction mixture was maintained at 70° C. under stirring for 8 hours. The solvent was then removed under reduced pressure and the residue taken up with dichloromethane and washed with water. The organic layer was dried over sodium sulphate and evaporated. The crude was finally purified by flash-chromatography on a silica gel column (cyclohexane-ethylacetate; from 4/1 to 3/2), giving 470 mg (97%) of the title compound.

$^1$H NMR (401 MHz, DMSO-d6) δ=2.44 (s, 3 H) 3.74 (br.s., 3 H) 5.34-5.37 (m, 2 H) 6.91-6.97 (m, 2 H) 7.31-7.37 (m, 2 H) 7.69 (t, J=8.06 Hz, 1 H) 8.14-8.19 (m, 1 H) 8.23 (ddd, J=8.21, 2.41, 1.10 Hz, 1 H) 8.58-8.60 (m, 1 H) 8.80 (s, 1 H).

HRMS (ESI): calcd for C19H17N3O4[M+H]+ 352.1292 found 352.1308.

Method C

Step m

(2E)-3-(dimethylamino)-1-[1-(4-methoxybenzyl)-3-(3-nitrophenyl)-1H-pyrazol-4-yl]prop-2-en-1-one 460 mg (1.3 mmol) of 1-[1-(4-methoxybenzyl)-3-(3-nitrophenyl)-1H-pyrazol-4-yl]-ethanone were dissolved in 25 ml of dry tetrahydrofuran and 15 ml of dimethylformamide di-tert-butylacetale (62 mmol) were added to the resulting solution. The reaction was heated at 70° C. under stirring for 6 hours. The solvent was then evaporated in vacuo and the residue diluted with dichloromethane and washed with water. The organic layer was finally dried over sodium sulphate and evaporated, giving 500 mg (96%) of the title compound as an oil.

$^1$H NMR (401 MHz, DMSO-d6) δ=2.65-3.12 (m, 6H) 3.73 (s, 3 H) 5.32 (s, 2 H) 5.47 (d, J=12.33 Hz, 1 H) 6.89-6.97 (m, 2 H) 7.27-7.36 (m, 2 H) 7.58 (d, J=12.45 Hz, 1 H) 7.64 (t, J=8.06 Hz, 1 H) 8.15-8.23 (m, 2 H) 8.50 (s, 1 H) 8.67-8.71 (m, 1 H). HRMS (ESI): calcd for C22H22N4O4 [M+H]+ 407.1714 found 407.1724.

Step n

4-[1-(4-methoxybenzyl)-3-(3-nitrophenyl)-1H-pyrazol-4-yl]pyrimidin-2-amine 450 mg (1.1 mmol) of (2E)-3-(dimethylamino)-1-[1-(4-methoxybenzyl)-3-(3-nitrophenyl)-1H-pyrazol-4-yl]prop-2-en-1-one were dissolved in 10 ml of dry dimethylformamide and 1.2 g (6.66 mmol) of guanidine carbonate and 910 mg (6.66 mmol) of potassium carbonate were added. After 16 hours at 120° C. the solvent was removed in vacuo and the residue taken up with dichloromethane and washed with water. The organic phase was then dried over sodium to sulphate and evaporated. The crude was finally purified by flash-chromatography on a silica gel column (CH2Cl2-CH3COCH3 9/1), giving 300 mg (68%) of the title compound.

$^1$H NMR (401 MHz, DMSO-d6) δ=3.74 (s, 3 H) 5.36 (s, 2 H) 6.42 (s, 2 H) 6.52 (d, J=5.13 Hz, 1 H) 6.94 (d, J=8.79 Hz, 2 H) 7.34 (d, J=8.79 Hz, 2 H) 7.68 (t, J=8.06 Hz, 1 H) 8.07 (ddd, J=7.81, 1.59, 1.10 Hz, 1 H) 8.13 (d, J=5.13 Hz, 1 H) 8.21 (ddd, J=8.24, 2.38, 0.98 Hz, 1 H) 8.37 (s, 1 H) 8.49 (t, J=1.89 Hz, 1 H).

HRMS (ESI): calcd for C21H18N6O3 [M+H]+ 403.1513 found 403.1509.

Method G

Step a

4-[3-(3-aminophenyl)-1-(4-methoxybenzyl)-1H-pyrazol-4-yl]pyrimidin-2-amine 1.6 g (3.98 mmol) of 4-[1-(4-methoxybenzyl)-3-(3-nitrophenyl)-1H-pyrazol-4-yl]-pyrimidin-2-amine were dissolved in a mixture of 100 ml of dioxane and 30 ml of water and 2.12 g (40 mmol) of ammonium chloride and 1.05 g (16 mmol) of metallic zinc were added successively. The reaction mixture was stirred at 100° C. for 6 hours. The suspension was then filtered through a celite pad and the filtrate evaporated. The residue was partitioned between dichloromethane and aqueous sodium hydrogenocarbonate, dried over sodium sulphate and evaporated again, giving 1 g (67%) of the title compound.

HRMS (ESI): calcd for C21H20N5O [M+H]+ 373.1772 found 373.1771.

Step e

1-{3-[4-(2-aminopyrimidin-4-yl)-1-(4-methoxybenzyl)-1H-pyrazol-3-yl]phenyl}-3-[4-(trifluoromethyl)phenyl]urea 1 g (2.7 mmol) of 4-[3-(3-aminophenyl)-1-(4-methoxybenzyl)-1H-pyrazol-4-yl]-pyrimidin-2-amine was dissolved in 290 ml of dry dimethylformamide and 386 μl of p-trifluoromethyl-phenylisocyanate were added. The reaction was then stirred at room temperature overnight. The mixture was poured into aqueous sodium hydrogenocarbonate and extracted with dichloromethane. The organic layer was then dried over sodium sulphate and evaporated. The crude was purified by flash-chromatography on a silica gel column (CH2Cl2-CH3COCH3; from 9/1 to 8/2), affording 800 mg (53%) of the title compound.

$^1$H NMR (401 MHz, DMSO-d6) δ=3.74 (s, 3 H) 5.32 (s, 2 H) 6.31 (d, J=5.25 Hz, 1 H) 6.42-6.47 (m, 2 H) 6.93-6.96 (m, 2 H) 7.10 (dt, J=7.69, 0.92 Hz, 1 H) 7.32-7.36 (m, 2 H) 7.60-7.68 (m, 4 H) 8.04 (d, J=5.25 Hz, 1 H) 8.19 (s, 1 H) 8.93 (s, 1 H) 9.10 (s, 1 H).

HRMS (ESI): calcd for C29H24F3N7O2 [M+H]+ 560.2017 found 560.2004.

Method M
Step a

1-{3-[4-(2-aminopyrimidin-4-yl)-1H-pyrazol-3-yl]phenyl}-3-[4-(trifluoromethyl)-phenyl]urea 800 mg (1.4 mmol) of 1-{3-[4-(2-aminopyrimidin-4-yl)-1-(4-methoxybenzyl)-1H-pyrazol-3-yl]phenyl}-3-[4-(trifluoromethyl)phenyl]urea were dissolved in 20 ml of trifluoroacetic acid and the mixture stirred at 70° C. for 4 hours. The solvent was then removed under reduced pressure and the residue taken up with dichloromethane and washed with aqueous sodium hydrogenocarbonate. The organic phase was dried over sodium sulphate and evaporated. The product was finally purified by flash-chromatography on a silica gel column (CH2Cl2-CH3OH; from 99/1 to 95/5), giving 450 mg (73%) of the title compound.

$^1$H NMR (401 MHz, DMSO-d6) δ=6.39 (d, J=5.13 Hz, 1H) 6.45 (bs, 2H), 7.15 (d, J=7.57 Hz, 1H) 7.27-7.70 (several m, 7H), 7.96 and 8.18 (2s, 1H, tautomers), 8.05 (d, J=5.25 Hz, 1H) 8.90 (2s, 1H, tautomers) 9.10 (2s, 1H, tautomers), 13.23 and 13.33 (2s, 1H tautomers).

HRMS (ESI): calcd for C21H16F3N7O [M+H]+ 440.1441 found 440.1436.

Example 32

N-(4-{3-[3-({[4-(trifluoromethyl)phenyl]carbamoyl}amino)phenyl]-1H-pyrazol-4-yl}pyrimidin-2-yl)acetamide (Cmpd. n° 32) [(I)Z, R1, R3, R4, R5, R6=H; m=0; A=NHCONH; R7=4-trifluoromethylphenyl; R16=methyl]

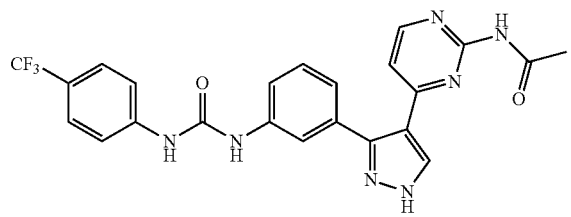 [SMILES: CC(=O)Nc1nccc(-c2c[nH]nc2-c2cccc(NC(=O)Nc3ccc(C(F)(F)F)cc3)c2)n1]

Method L
Step d 144 mg (0.33 mmol) of 1-{3-[4-(2-aminopyrimidin-4-yl)-1H-pyrazol-3-yl]phenyl}-3-[4-(trifluoromethyl)phenyl]urea were dissolved in 10 ml of dry tetrahydrofuran and 226 μl (1.32 mmol) of N,N-diisopropyl-N-ethylamine and 94 μl of acetyl chloride were added consecutively. After 8 hours at room temperature the solvent was removed in vacuo and the residue taken up with dichloromethane and washed with an aqueous solution of sodium hydrogenocarbonate. The residue was re-dissolved with 10 ml of methanol and stirred at room temperature overnight. The solvent was then evaporated and the crude purified by preparative HPLC(CH2Cl2-ethanol 9/1), giving 79 mg (50%) of the title compound.

$^1$H NMR (401 MHz, DMSO-d6) δ=2.13 (s, 3 H) 6.95 (m, 1 H) 7.17 (m, 1 H) 7.60-7.67 (m, 7 H) 8.21 (2s, 1H, tautomers) 8.44 (d, J=5.25 Hz, 1 H) 8.91 (2s, 1H, tautomers) 9.10 (2s, 1H, tautomers) 10.26 (s, 1 H) 13.39-13.40 (2s, 1 H, tautomers).

HRMS (ESI): calcd for C23H18F3N7O2 [M+H]+ 482.1547 found 482.1540.

Example 33

N-{3-[4-(2-aminopyrimidin-4-yl)-1H-pyrazol-3-yl]phenyl}-2,5-difluorobenzene-sulfonamide (Cmpd. n° 34)

[(I)A, X═N; R3, R4, R5, R6=H; R2=NH2; A=—NHSO2-; R7=2,5-difluorophenyl]

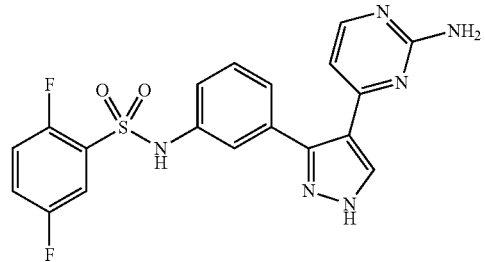 [SMILES: Nc1nccc(-c2c[nH]nc2-c2cccc(NS(=O)(=O)c3cc(F)ccc3F)c2)n1]

Method G
Step c

N-{3-[4-(2-aminopyrimidin-4-yl)-1-(4-methoxybenzyl)-1H-pyrazol-3-yl]phenyl}-2,5-difluorobenzene-sulfonamide 175 mg (0.47 mmol) of 4-[3-(3-aminophenyl)-1-(4-methoxybenzyl)-1H-pyrazol-4-yl]-pyrimidin-2-amine were dissolved with 10 ml of dry pyridine and 63 μl of 2,5-difluorobenzensulfonylchloride were added under stirring. The solution was maintained at room temperature overnight. The reaction mixture was then poured into aqueous sodium hydrogenocarbonate and extracted with dichloromethane. The organic layer was dried over sodium sulphate and evaporated to dryness. The residue was purified by flash-chromatography on a silica gel column (CH2Cl2-CH3COCH3; from 9/1 to 8/2), giving 80 mg (31%) of the title compound.

$^1$H NMR (401 MHz, DMSO-d6) δ=3.74 (s, 3 H) 5.29 (s, 2 H) 6.12 (d, J=5.13 Hz, 1 H) 6.45 (s, 2 H) 6.90-6.97 (m, 2 H) 7.12-7.19 (m, 2H) 7.24-7.35 (m, 4 H) 7.47-7.60 (m, 3H) 7.97 (d, J=5.13 Hz, 1 H) 8.16 (s, 1 H) 10.79 (s, 1 H).

HRMS (ESI): calcd for C27H22F2N6O3S [M+H]+ 549.1515 found 549.1520.

Method M
Step a

N-{3-[4-(2-aminopyrimidin-4-yl)-1H-pyrazol-3-yl]phenyl}-2,5-difluorobenzene-sulfonamide 80 mg (0.14 mmol) of N-{3-[4-(2-aminopyrimidin-4-yl)-1-(4-methoxybenzyl)-1H-pyrazol-3-yl]phenyl}-2,5-difluorobenzenesulfonamide were dissolved in 5 ml of trifluoroacetic acid and the resulting solution was heated at 70° C. under stirring for 2 hours. The solvent was removed in vacuo and the residue taken up with dichloromethane and washed with aqueous sodium hydrogenocarbonate. The organic phase was then dried over sodium sulphate and evaporated, giving, after trituration with diethylether, 10 mg (17%) of the title compound.

$^1$H NMR (401 MHz, DMSO-d6) δ=6.19 (bs, 1 H) 6.43 (bs, 2 H) 7.10-8.18 (several m, 9H), 10.79 and 10.92 (2s, 1H, tautomers), 13.24 and 13.30 (2s, 1H, tautomers).

HRMS (ESI): calcd for C19H14F2N6O2S [M+H]+ 429.0940 found 429.0945.

Example 34

N-(3-{4-[2-(ethylamino)pyrimidin-4-yl]-1H-pyrazol-3-yl}phenyl)-2,5-difluorobenzenesulfonamide (Cmpd. n° 55) (I)A, X=N; R3, R4, R5, R6=H; R2=ethylamino; A=—NHSO2—; R7=2,5-difluorophenyl]

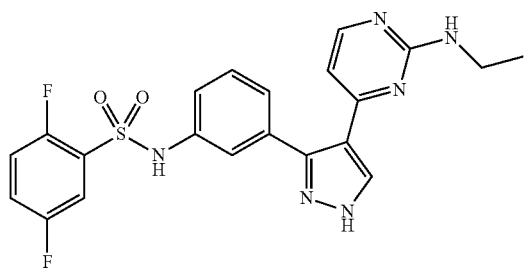 [SMILES: CCNc1nccc(-c2c[nH]nc2-c2cccc(NS(=O)(=O)c3cc(F)ccc3F)c2)n1]

Method C
Step o 1-(4-methoxybenzyl)-3-(3-nitrophenyl)-4-(4,4,5,5-tetramethyl-1,3,2-dioxaborolan-2-yl)-1H-pyrazole 1 g (2.3 mmol) of 4-iodo-1-(4-methoxybenzyl)-3-(3-nitrophenyl)-1H-pyrazole (prepared as described in Example 27) was dissolved in 20 ml of dry toluene and 3.18 ml of 4,4,5,5-tetramethyl-1,3,2-dioxaborolane (23 mmol), 20 mg (0.08 mmol) of palladium(II) chloride diacetonitrile complex, 80 mg (0.005 mmol) of S-Phos (2-dicyclohexylphosphino-2',6'-dimethoxy-1,1'-biphenyl) and 774 µl (5.7 mmol) of triethylamine were added successively. The reaction mixture was submitted to microwave irradiation in a sealed vial at 90° C. for 30 minutes. The mixture was then filtered through a celite pad and the filtrate evaporated in vacuo. The residue was taken up with dichloromethane and washed with water and the organic layer dried over sodium sulphate and evaporated again. The crude was finally purified by flash-chromatography on a silica gel column (CH2Cl2-CH3COCH3 1%), affording 800 mg (80%) of the title compound, crystallized from diethylether.

$^1$H NMR (401 MHz, DMSO-d6) δ=1.28 (s, 12 H) 3.73 (s, 3 H) 5.33 (s, 2 H) 6.75-7.05 (m, 2 H) 7.26-7.36 (m, 2 H) 7.67 (t, J=7.99 Hz, 1 H) 8.13 (s, 1 H) 8.17 (ddd, J=8.24, 2.38, 0.98 Hz, 1 H) 8.25-8.37 (m, 1 H) 8.91 (t, J=1.95 Hz, 1H).

HRMS (ESI): calcd for C23H26BN3O5 [M+H]+ 435.2075 found 435.2066.

Step p

4-[1-(4-methoxybenzyl)-3-(3-nitrophenyl)-1H-pyrazol-4-yl]-2-(methylsulfanyl)-pyrimidine 2.6 g (6 mmol) of 1-(4-methoxybenzyl)-3-(3-nitrophenyl)-4-(4,4,5,5-tetramethyl-1,3,2-dioxaborolan-2-yl)-1H-pyrazole were dissolved in a mixture of 520 ml of dioxane and 130 ml of water under a nitrogen atmosphere. 709 µl (6 mmol) of 2-methylthio-4-chloro-pyrimidine, 3.9 g (12 mmol) of cesium carbonate and 650 mg (0.6 mmol) of palladium tetrakis were added consecutively to the resulting solution under stirring. The reaction mixture was heated at 100° C. for 6 hours, then filtered through a celite pad and concentrated under reduced pressure. The residue was partitioned between dichloromethane and water, the organic layer dried over sodium sulphate and evaporated to dryness. The crude was finally purified by flash-chromatography on a silica gel column (cyclohexane-ethylacetate; from 9/1 to 4/1), giving 2.3 g (88%) of the title compound.

$^1$H NMR (401 MHz, DMSO-d6) δ=2.16 (s, 3 H) 3.71 (s, 3 H) 5.35 (s, 2 H) 6.87-6.96 (m, 2 H) 7.18 (d, J=5.25 Hz, 1 H) 7.28-7.39 (m, 2 H) 7.66 (t, J=8.06 Hz, 1 H) 7.94 (dt, J=7.99, 1.13 Hz, 1 H) 8.21 (ddd, J=8.24, 2.38, 1.10 Hz, 1 H) 8.31 (t, J=1.83 Hz, 1 H) 8.47 (d, J=5.25 Hz, 1 H) 8.64 (s, 1 H).

HRMS (ESI): calcd for C22H19N5O3S [M+H]+ 434.1282 found 434.1278.

Method F
Step a

4-[1-(4-methoxybenzyl)-3-(3-nitrophenyl)-1H-pyrazol-4-yl]-2-(methylsulfonyl)-pyrimidine 2.3 g (5 mmol) of 4-[1-(4-methoxybenzyl)-3-(3-nitrophenyl)-1H-pyrazol-4-yl]-2-(methylsulfanyl)pyrimidine were dissolved with 50 ml of dry dichloromethane and 2.24 g (10 mmol) of m-chloroperbenzoic acid 77% were added to the resulting solution. The reaction was maintained at room temperature for 4 hours under stirring, then diluted with the same solvent and washed with a saturated aqueous solution of sodium hydrogenocarbonate. The organic phase was dried over sodium sulphate and evaporated under reduced pressure. The residue was triturated with diisopropylether and collected by filtration, giving 2.2 g (95%) of the title compound.

$^1$H NMR (401 MHz, DMSO-d6) δ=3.05 (s, 3 H) 3.71 (s, 3 H) 5.38 (s, 2 H) 6.86-7.03 (m, 2 H) 7.24-7.44 (m, 2 H) 7.66 (t, J=8.00 Hz, 1 H) 7.78 (d, J=5.37 Hz, 1 H) 7.89-8.06 (m, 1 H) 8.23 (ddd, J=8.24, 2.38, 1.10 Hz, 1 H) 8.31 (t, J=1.95 Hz, 1 H) 8.82 (s, 1 H) 8.87 (d, J=5.37 Hz, 1 H).

HRMS (ESI): calcd for C22H19N5O5S [M+H]+ 466.1180 found 466.1168.

Method F
Step b

N-ethyl-4-[1-(4-methoxybenzyl)-3-(3-nitrophenyl)-1H-pyrazol-4-yl]pyrimidin-2-amine 450 mg (0.97 mmol) of 4-[1-(4-methoxybenzyl)-3-(3-nitrophenyl)-1H-pyrazol-4-yl]-2-(methylsulfonyl)pyrimidine were dissolved in a mixture of 10 ml of dioxane and 5 ml of ethylamine 70% in water. The resulting solution was submitted to microwave irradiation in a sealed vial at 140° C. for 45 minutes. The solvent was then removed and the residue was partitioned between dichloromethane and aqueous sodium hydrogenocarbonate. The organic phase was then dried over sodium sulphate and evaporated to dryness. 391 mg (94%) of the title compound were obtained by trituration with diethylether.

¹H NMR (401 MHz, DMSO-d6) δ=0.77-1.05 (m, 3 H) 2.83-3.18 (m, 2 H) 3.74 (s, 3 H) 5.35 (s, 2 H) 6.60 (br. s., 1 H) 6.86 (d, J=8.67 Hz, 1 H) 6.91-6.98 (m, 2 H) 7.30-7.38 (m, 2 H) 7.67 (t, J=8.06 Hz, 1 H) 8.03 (d, J=7.69 Hz, 1 H) 8.16 (d, J=5.00 Hz, 1 H) 8.21 (ddd, J=8.21, 2.41, 0.98 Hz, 1 H) 8.39 (bs, 1 H) 8.46 (bs, 1 H).

HRMS (ESI): calcd for C23H22N6O3 [M+H]+ 431.1826 found 431.1811.

Operating in an analogous way the following intermediate was obtained:

4-[1-(4-methoxybenzyl)-3-(3-nitrophenyl)-1H-pyrazol-4-yl]-N-(1-methylpiperidin-4-yl)pyrimidin-2-amine (Microwave Irradiation was Performed at 130° C. for 1H. Yield: 81%)

¹H NMR (401 MHz, DMSO-d6) δ=1.19-1.95 (several m, 4H) 2.05-2.82 (several m, 7H) 3.21-3.69 (m, 1H) 3.74 (s, 3 H) 5.35 (s, 2 H) 6.65 (br. s., 1 H) 6.86 (d, J=8.67 Hz, 1 H) 6.91-6.97 (m, 2 H) 7.31-7.39 (m, 2 H) 7.68 (t, J=8.06 Hz, 1 H) 7.99 (bs, 1 H) 8.19 (d, J=5.13 Hz, 1 H) 8.22 (ddd, J=8.18, 2.26, 1.04 Hz, 1 H) 8.33 (bs, 1 H) 8.45 (bs, 1 H).

HRMS (ESI): calcd for C27H29N7O3 [M+H]+ 500.2405 found 500.2387.

Method G
Step a

4-[3-(3-aminophenyl)-1-(4-methoxybenzyl)-1H-pyrazol-4-yl]-N-ethylpyrimidin-2-amine 391 mg (0.91 mmol) of N-ethyl-4-[1-(4-methoxybenzyl)-3-(3-nitrophenyl)-1H-pyrazol-4-yl]pyrimidin-2-amine were dissolved in a mixture of 20 ml of dioxane and 4 ml of water. 239 mg (3.64 mmol) of metallic zinc and 485 mg (9.1 mmol) of ammonium chloride were then added to the resulting solution. The reaction was carried out at 100° C. under stirring for 5 hours. The suspension was then filtered through a celite pad and the filtrate evaporated in vacuo. The residue was partitioned between dichloromethane and aqueous sodium hydrogenocarbonate and the organic layer dried over sodium sulphate and concentrated to give a crude purified by flash-chromatography on a silica gel column (CH2Cl2-CH3COCH3; from 9/1 to 7/3), affording 340 mg (93%) of the title compound.

¹H NMR (401 MHz, DMSO-d6) δ=1.08 (t, J=7.14 Hz, 3 H) 3.20-3.29 (m, 2 H) 3.74 (s, 3 H) 5.08 (bs, 2 H) 5.29 (s, 2 H) 6.31 (d, J=5.13 Hz, 1 H) 6.51-6.58 (m, 2 H) 6.70 (t, J=1.65 Hz, 1 H) 6.87 (t, J=5.74 Hz, 1 H) 6.91-6.96 (m, 2 H) 7.01 (t, J=7.81 Hz, 1 H) 7.27-7.34 (m, 2 H) 8.03 (d, J=5.13 Hz, 1 H) 8.21 (bs, 1 H).

HRMS (ESI): calcd for C23H24N5O [M+H]+ 401.2085 found 401.2093.

Operating in an analogous way the following intermediate was obtained:

4-[3-(3-aminophenyl)-1-(4-methoxybenzyl)-1H-pyrazol-4-yl]-N-(1-methylpiperidin-4-yl)pyrimidin-2-amine Yield: 82%

¹H NMR (401 MHz, DMSO-d6) δ=1.39-1.53 (m, 2H), 1.70-1.80 (m, 2H), 1.88-2.06 (m, 2H), 2.18 (s, 3H), 2.68-2.76 (m, 2H), 3.55-3.59 (m, 1H), 3.74 (s, 3H), 5.07 (bs, 2H), 5.29 (s, 2H), 6.34 (bs, 1H), 6.68-6.80 (m, 4H), 6.93-6.96 (m, 2H), 7.00 (t, J=7.8 Hz, 1H), 7.30-7.34 (m, 2H), 8.04 (d, J=5.0 Hz, 1H), 8.09-8.19 (bs, 1H).

HRMS (ESI): calcd for C27H31N7O [M+H]+ 470.2663 found 470.2668.

Step c

N-(3-{4-[2-(ethylamino)pyrimidin-4-yl]-1-(4-methoxybenzyl)-1H-pyrazol-3-yl}phenyl)-2,5-difluorobenzenesulfonamide 340 mg (0.85 mmol) of 4-[3-(3-aminophenyl)-1-(4-methoxybenzyl)-1H-pyrazol-4-yl]-N-ethylpyrimidin-2-amine were dissolved in 10 ml of dry pyridine and 114 μl (0.85 mmol) of 2,5-difluorobenzensulfonyl chloride were added. The resulting solution was stirred at room temperature overnight. The mixture was then poured into aqueous sodium hydrogenocarbonate and extracted with dichloromethane. The organic layer was finally dried over sodium sulphate and evaporated, giving 450 mg (91%) of the title compound.

¹H NMR (401 MHz, DMSO-d6) δ=0.98 (bs, 3 H) 3.10 (bs, 2 H) 3.75 (s, 3 H) 5.30 (s, 2 H) 6.24 (bs, 1 H) 6.86 (t, J=5.37 Hz, 1H) 6.94 (d, J=8.54 Hz, 2 H) 7.10-7.20 (m, 2 H) 7.23-7.28 (m, 2 H) 7.32 (d, J=8.67 Hz, 2 H) 7.45-7.61 (m, 3 H) 8.02 (d, J=5.25 Hz, 1 H) 8.27 (bs, 1 H) 10.78 (s, 1 H).

HRMS (ESI): calcd for C29H26F2N6O3S [M+H]+ 577.1828 found 577.1821.

Operating in an analogous way the following intermediate was obtained:

2,5-difluoro-N-{3-[1-(4-methoxybenzyl)-4-{3-[(1-methylpiperidin-4-yl)amino]phenyl}-1H-pyrazol-3-yl]phenyl}benzenesulfonamide Yield: 89%

¹H NMR (401 MHz, DMSO-d6) δ=1.36-1.50 (m, 2H), 1.73-1.83 (m, 2H), 1.90-2.08 (m, 2H), 2.16 (s, 3H), 2.65-2.73 (m, 2H), 3.55-3.59 (m, 1H), 3.74 (s, 3H), 5.29 (s, 2H), 6.40 (bs, 1H), 6.79 (bs, 1H), 6.92-6.97 (m, 2H), 7.13-7.19 (m, 2H), 7.26-7.34 (m, 4H), 7.47-7.60 (m, 3H), 8.04 (d, J=5.1 Hz, 1H), 8.16 (s, 1H), 10.79 (s, 1H).

HRMS (ESI): calcd for C33H33F2N7O3S [M+H]+ 646.2407 found 646.2419.

Method M
Step a

N-(3-{4-[2-(ethylamino)pyrimidin-4-yl]-1H-pyrazol-3-yl}phenyl)-2,5-difluorobenzenesulfonamide 450 mg (0.78 mmol) of N-(3-{4-[2-(ethylamino)pyrimidin-4-yl]-1-(4-methoxybenzyl)-1H-pyrazol-3-yl}phenyl)-2,5-difluorobenzenesulfonamide were dissolved in 10 ml of trifluoroacetic acid and the resulting solution heated at 70° C. under stirring for 4 hours. After this time the solvent was evaporated and the residue taken up with dichloromethane and washed with aqueous sodium hydrogenocarbonate. The organic phase was then dried over sodium sulphate and evaporated again. The crude was finally purified by flash-chromatography on a silica gel column (CH2Cl2-CH3COCH3; from 9/1 to 8/2), giving 80 mg (22%) of the title compound.

¹H NMR (401 MHz, DMSO-d6) δ=1.02 (t, J=7.02 Hz, 3H). 3.15 (q, J=5.80 Hz, 2H) 6.35 (d, J=5.19 Hz, 1H) 6.49 (bs, 1H) 7.08-7.39 (m, 5H),), 7.39-7.54 (2m, 2H) 8.02 (m, 1H), 8.10 (m, 1H) 10.53 (bs, 1H) 13.04 (bs, 1H).

HRMS (ESI): calcd for C21H18F2N6O2S [M+H]+ 457.1253 found 457.1250.

Operating in an analogous way the following compound was obtained:

2,5-difluoro-N-[3-(4-{2-[(1-methylpiperidin-4-yl)amino]pyrimidin-4-yl}-1H-pyrazol-3-yl)phenyl]benzenesulfonamide

[(I)A, X═N; R3, R4, R5, R6═H; R2═(1-methylpiperidin-4-yl)amino; A═—NHSO2—; R7═2,5-difluorophenyl]

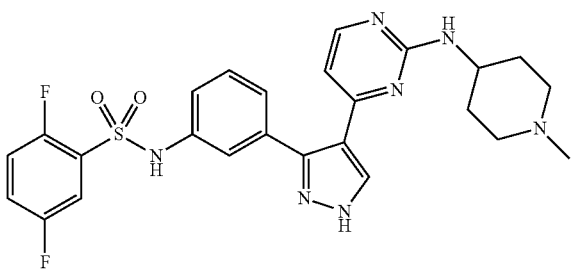 [SMILES: CN1CCC(Nc2nccc(-c3c[nH]nc3-c3cccc(NS(=O)(=O)c4cc(F)ccc4F)c3)n2)CC1]

Yield: 26%

¹H NMR (401 MHz, DMSO-d6) δ=2.25 (s, 3H) 2.50 (m, 4H) 2.73 (m, 4H) 3.38 (m, 1H) 6.40 (bs, 1H), 6.79 (d, J=7.32 Hz, 1H) 7.05-7.29 (m, 4H) 7.38-7.64 (m, 3H) 8.04 (m, 2H) 10.47 (bs, 1H) 13.22 (bs, 1H).

HRMS (ESI): calcd for C21H18F2N6O2S [M+H]+ 526.1831 found 526.1834.

Example 35

N-[3-(1-Methyl-4-pyridin-4-yl-1H-pyrazol-3-yl)-2,4-difluoro-phenyl]-2,5-difluoro-benzenesulfonamide
(Cmpd. n°52)

[(I)C, X═CH; R1═Me, R2, R4, R5═H; R3, R6═F; m═0; R7'═2,5-difluorophenyl]

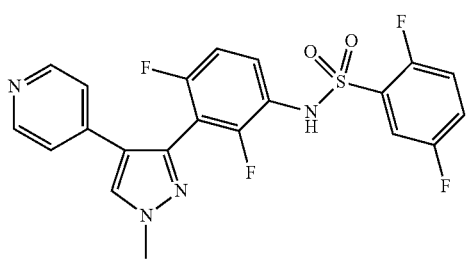 [SMILES: Cn1cc(-c2ccncc2)c(-c2c(F)ccc(NS(=O)(=O)c3cc(F)ccc3F)c2F)n1]

Preparation of 2-bromo-1,3-difluoro-4-nitrobenzene
[(35), G=NO2; L'=Br; R3, R6=F; R4, R5=H]

To a stirred, ice-cooled, solution of 1,3-difluoro-2-bromobenzene (1.74 g, 9.0 mmol) in 96% sulphuric acid (2 mL), a mixture of 96% sulphuric acid (0.6 mL) and fuming nitric acid (0.6 mL) was slowly added, keeping the temperature below 55° C. After addition, the reaction mixture was stirred at room temperature for 2 h, then poured onto ice. The precipitate was filtered, washed with water and dried. The title compound was obtained as a yellowish solid (1.7 g, 80%).

HPLC (254 nm): Rt: 6.26 min.

¹H-NMR (401 MHz, DMSO-d6) δ=8.1 (m, 1 H) 7.1 (m, 1 H).

Preparation of 1-(tetrahydro-2H-pyran-2-yl)-5-(4,4,5,5-tetramethyl-1,3,2-dioxaborolan-2-yl)-1H-pyrazole

[(21), PG3=tetrahydro-2H-pyran-2-yl; M=4,4,5,5-tetramethyl-1,3,2-dioxaborolan-2-yl]

To a cooled (−78° C.), stirred solution of 1-(tetrahydro-2H-pyran-2-yl)-1H-pyrazole (prepared as described in the literature: J. Med. Chem. 2004, 47, 2995-3008 and JOC 2008, 73, 4309-4312) (11.8 g, 78 mmol) in anhydrous THF (200 mL), 2.5 M n-BuLi in n-hexane (40 mL, 100 mmol) was slowly added, keeping T<−70° C. After addition the mixture was stirred at −78° C. for 1 h, then triisopropyl borate (23 mL, 100 mmol) was added dropwise, keeping T<−70° C. After addition the mixture was let to reach room temperature in about 2 h, then a solution of 2,3-dimethyl-2,3-butandiol (12.5 g, 105 mmol) in anhydrous THF (30 mL) was added, followed after 10 min by glacial acetic acid (6 mL, 100 mmol). The colorless jelly precipitate was filtered on a thick celite pad and washed thoroughly with diethyl ether. The filtrate was concentrated to yield a colorless oil that crystallized upon addition of n-heptane. The title compound was obtained as colorless crystalline powder (14.7 g, 53%).

HPLC (254 nm): Rt: 5.81 min.

¹H-NMR (401 MHz, DMSO-d6) δ=7.55 (s, 1 H) 6.7 (s, 1 H) 5.75 (m, 1 H) 4.05 (m, 1 H) 3.7 (m, 1 H) 2.5 (m, 1 H) 1.85-2.2 (m, 2 H) 1.4-1.75 (m, 3 H) 1.2 (s, 12 H).

ESI (+) MS: m/z 279 (MH+).

Method C

Step q 5-(2,6-Difluoro-3-nitrophenyl)-1-(tetrahydro-2H-pyran-2-yl)-1H-pyrazole

To a solution of tetrakis(triphenylphosphine)palladium(0) (1.2 g, 1.04 mmol) in dimethoxyethane (30 mL), 2-bromo-1,3-difluoro-4-nitrobenzene (2.38 g, 10 mmol) in dimethoxyethane (20 mL) was added and the mixture was insufflated with nitrogen for 10 min. To the solution, 1-(tetrahydro-2H-pyran-2-yl)-5-(4,4,5,5-tetramethyl-1,3,2-dioxaborolan-2-yl)-1H-pyrazole (4 g, 15 mmol) in dimethoxyethane (30 mL) was added and the mixture was insufflated with nitrogen for 2 min, then 2 M sodium carbonate solution (40 mL) was added and the mixture was refluxed for 4 h. The mixture was cooled and the organic phase was concentrated to oil. By addition of diethyl ether a precipitate was obtained, filtered off and discarded. The filtrate was concentrated and purified by flash chromatography (eluant: dichloromethane/ethyl acetate 20:1). The title compound was obtained as oil (1.27 g, 40%).

HPLC (254 nm): Rt: 4.38 min.

¹H-NMR (401 MHz, DMSO-d6) δ=8.4 (m, 1 H) 7.7 (s, 1 H) 7.5 (m, 1 H) 6.6 (s, 1 H) 5.2 (m, 1 H) 3.7 (m, 1 H) 3.3 (m, 1 H) 2.2 (m, 1 H) 1.9 (m, 2 H) 1.6 (m, 1 H) 1.4 (m, 2 H). ESI (+) MS: m/z 310 (MH+).

Step r 4-bromo-5-(2,6-difluoro-3-nitrophenyl)-1-(tetrahydro-2H-pyran-2-yl)-1H-pyrazole A solution of 5-(2,6-difluoro-3-nitrophenyl)-1-(tetrahydro-2H-pyran-2-yl)-1H-pyrazole (1.23 g, 4 mmol) and N-bromosuccinimide (1.25 g, 7 mmol) in dichloromethane (10 mL) was stirred at room temperature for 18 h. The solution was washed with water, dried over anhydrous sodium sulfate and concentrated. Crude 4-bromo-5-(2,6-difluoro-3-nitrophenyl)-1-(tetrahydro-2H-pyran-2-yl)-1H-pyrazole was obtained.

HPLC (254 nm): Rt: 7.08 min.
¹H-NMR (401 MHz, DMSO-d6) δ=8.5 (m, 1 H) 7.9 (s, 1 H) 7.6 (m, 1 H) 5.25 (m, 1 H) 3.7 (m, 1 H) 3.4 (m, 1 H) 2.2 (m, 1 H) 1.9 (m, 2 H) 1.6 (m, 1 H) 1.4 (m, 2 H).
ESI (+) MS: m/z 390 (MH+).
Step s 4-Bromo-5-(2,6-difluoro-3-nitrophenyl)-1H-pyrazole The crude product was dissolved in 1.25 M hydrochloric acid in methanol (10 mL) and stirred at room temperature for 3 h. A saturated aqueous solution of sodium hydrogencarbonate was added and the product was extracted with dichloromethane. The organic layer was dried over anhydrous sodium sulfate and concentrated to oil. After addition of a 1:1 mixture of diisopropyl ether and petroleum ether the desired compound crystallized as an off-white solid (0.67 g, 55% two steps).
HPLC (254 nm): Rt: 3.97 min.
¹H NMR (401 MHz, DMSO-d6, hydrochloride) δ=7.51-7.59 (m, 1 H) 8.19 (bs, 1 H) 8.35-8.48 (m, 1 H) 13.78 (bs, 1 H).
ESI (+) MS: m/z 303 (MH−).
Step d 4-Bromo-3-(2,6-difluoro-3-nitrophenyl)-1-methyl-1H-pyrazole To a mixture of 4-bromo-5-(2,6-difluoro-3-nitrophenyl)-1H-pyrazole (0.88 g, 2.9 mmol) and methyl iodide (2 mL, 32 mmol) in dichloromethane (20 mL), tetrabutylammonium bromide (0.32 g, 1 mmol) in 7 N sodium hydroxide (20 mL) was added and the mixture was rapidly stirred at room temperature for 3 h. The phases were separated and the organic layer was washed with water, dried over anhydrous sodium sulfate and concentrated. The crude residue was purified by flash chromatography (eluant: dichloromethane/petroleum ether 2:1). The title compound, mixture of the two regioisomers, was obtained as a waxy solid (0.53 g, 57%).
HPLC (254 nm): Rt: 4.42 min.
ESI (+) MS: m/z 319 (MH+).

Preparation of N-[3-(4-bromo-1-methyl-1H-pyrazol-3-yl)-2,4-difluorophenyl]-2,5-difluorobenzene-sulfonamide A mixture of 4-bromo-3-(2,6-difluoro-3-nitrophenyl)-1-methyl-1H-pyrazole and its regioisomer 4-bromo-5-(2,6-difluoro-3-nitrophenyl)-1-methyl-1H-pyrazole (0.35 g, 1.1 mmol), powdered zinc (0.39 g, 6 mmol) and ammonium chloride (0.6 g, 11 mmol) in dioxane (6 mL) and water (2 mL) were refluxed under good stirring for 3 h. After cooling, the mixture was filtered and the filtrate was concentrated. The residue was taken up with dichloromethane, washed with saturated aqueous solution of sodium hydrogen carbonate and water, dried over anhydrous sodium sulfate and concentrated. The crude mixture of 3-(4-bromo-1-methyl-1H-pyrazol-3-yl)-2,4-difluoroaniline and its regioisomer 3-(4-bromo-1-methyl-1H-pyrazol-5-yl)-2,4-difluoroaniline was obtained as a brownish solid (0.33 g, 95%).
HPLC (254 nm): Rt: 3.49 min and 3.81 min.
ESI (+) MS: m/z 290 (MH+).
To an ice-cooled solution of a mixture of 3-(4-bromo-1-methyl-1H-pyrazol-3-yl)-2,4-difluoroaniline and its regioisomer 3-(4-bromo-1-methyl-1H-pyrazol-5-yl)-2,4-difluoroaniline in anhydrous pyridine (3 mL), 2,5-difluorosulfonyl chloride (0.23 g, 1.1 mmol) was added and the reaction mixture was stirred at room temperature for 18 h. More sulfonyl chloride (0.14 g, 0.7 mmol) was added and, after 2 h stirring, dichloromethane was added and the solution was washed twice with 2 N hydrochloric acid, with saturated aqueous solution of sodium hydrogen carbonate, dried over anhydrous sodium sulfate and concentrated. The residue was crystallized from diethyl ether and the title compound was obtained as a yellow solid (0.35 g, 68%).
HPLC (254 nm): Rt: 4.59 min.
¹H NMR (401 MHz, DMSO-d6) δ=3.88 (s, 3 H) 7.16 (t, J=8.61 Hz, 1 H) 7.40 (td, J=8.94, 5.92 Hz, 1 H) 7.44-7.61 (m, 2 H) 8.07 (s, 1 H) 10.68 (bs, 1 H).
ESI (+) MS: m/z 466 (MH+).
Step h N-[3-(1-methyl-4-pyridin-4-yl-1H-pyrazol-3-yl)-2,4-difluoro-phenyl]-2,5-difluoro-benzenesulfonamide To a solution of tetrakis(triphenylphosphine)palladium(0) (0.12 g, 0.1 mmol) in dimethoxyethane (3 mL), N-[3-(4-bromo-1-methyl-1H-pyrazol-3-yl)-2,4-difluoro-phenyl]-2,5-difluorobenzenesulfonamide (0.14 g, 0.3 mmol) in dimethoxyethane (3 mL) was added and the mixture was insufflated with nitrogen for 5 min. A solution of 4-(4,4,5,5-tetramethyl-1,3,2-dioxaborolan-2-yl)pyridine (0.13 g, 0.63 mmol) in dimethoxyethane (3 mL) was added and the mixture was insufflated with nitrogen for 10 min, then 2 M sodium carbonate solution (2.5 mL) was added and the mixture was heated at 110° C. in a microwave cavity for 3 h. The mixture was cooled and the organic phase was concentrated. The crude oil was purified by flash chromatography (eluant: dichloromethane/ethyl acetate 1:1). The title compound was obtained as a white solid (0.05 g, 36%).
HPLC (254 nm): Rt: 5.33 min.
¹H-NMR (401 MHz, DMSO-d6) δ=10.68 (bs, NH) 8.22-8.51 (m, 3 H), 7.51-7.59 (m, 1 H) 7.37-7.49 (m, 3 H), 7.20 (td, J=8.85, 1.46 Hz, 1 H), 6.92-7.01 (m, 2 H), 3.93 (s, 3 H).
HRMS (ESI) calcd for C21H14F4N4O2S [M+H]+ 463.0847, found 463.0851.

Example 36

N-[3-(1-i-Butyl-4-pyridin-4-yl-1H-pyrazol-3-yl)-2,4-difluoro-phenyl]-2,5-difluoro-benzenesulfonamide (Cm pd. n°56) [(I)C, X=CH; R1=isobutyl; R2, R4, R5=H; R3, R6=F; m=0; R7'=2,5-difluorophenyl]

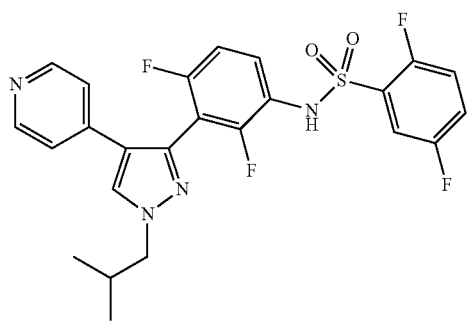 [SMILES: CC(C)Cn1cc(-c2ccncc2)c(-c2c(F)ccc(NS(=O)(=O)c3cc(F)ccc3F)c2F)n1]

Method C
Steps s and d

N-{3[4-bromo-1-(2-methylpropyl)-1H-pyrazol-3-yl]-2,4-difluorophenyl}-2,5-difluorobenzenesulfonamide 4-Bromo-5-(2,6-difluoro-3-nitrophenyl)-1-(tetrahydro-2H-pyran-2-yl)-1H-pyrazole (prepared as described in Example 35) (0.53 g, 1.38 mmol), powdered zinc (0.52 g, 8 mmol) and ammonium chloride (0.8 g, 15 mmol) in dioxane (10 mL) and water (5 mL) were refluxed under vigorous stirring for 1.5 h. After cooling, the mixture was filtered and the filtrate was concentrated. The residue was taken up with dichloromethane, washed with saturated aqueous solution of sodium hydrogen carbonate and water, dried over anhydrous sodium sulfate and concentrated. To the crude 3-[4-bromo-1-(tetrahydro-2H-pyran-2-yl)-1H-pyrazol-5-yl]-2,4-difluoroaniline, dissolved in toluene (10 mL) and anhydrous pyridine (2 mL), 2,5-difluorobenzenesulfonyl chloride (0.64 g, 3 mmol) was added and the reaction mixture was stirred at room temperature for 18 h. Dichloromethane and water were added and the organic layer was washed twice with 0.5 N hydrochloric acid, with saturated aqueous solution of sodium hydrogen carbonate, dried over anhydrous sodium sulfate and concentrated. Crude N-{3[4-bromo-1-(tetrahydro-2H-pyran-2-yl)-1H-pyrazol-5-yl]-2,4-difluorophenyl}-N-[(2,5-difluoro-phenyl)sulfonyl]-2,5-difluorobenzene sulfonamide was isolated as a yellow oily foam in quantitative yield.

HPLC (254 nm): Rt: 6.07 min.

ESI (+) MS: m/z 712 (MH+).

The raw product was dissolved in 1.25 M hydrochloric acid in methanol (8 mL) and stirred at room temperature for 18 h. After solvent removal crude N-[3-(4-bromo-1H-pyrazol-3-yl)-2,4-difluorophenyl]-N-[(2,5-difluorophenyl)sulfonyl]-2,5-difluoro-benzenesulfonamide was obtained (quant.).

HPLC (254 nm): Rt: 5.24 min.

ESI (+) MS: m/z 628 (MH+).

To the residue, dissolved in dichloromethane (10 mL), isobutyl bromide (1 mL, 9 mmol) and tetrabutylammonium bromide (0.16 g, 0.5 mmol) in 7 N sodium hydroxide (10 mL) were added and the mixture was vigorously stirred at room temperature. After 2 h, only N-[3-(4-bromo-1H-pyrazol-3-yl)-2,4-difluorophenyl]-2,5-difluorobenzene-sulfonamide was present. Upon addition of more isobutyl bromide (3 mL, 27 mmol) and tetrabutylammonium bromide (0.45 g, 1.4 mmol) and after 18 h additional stirring the reaction was completed. The phases were separated and the organic layer was washed with water, dried over anhydrous sodium sulfate and concentrated. The crude residue was purified by flash chromatography (eluant: dichloromethane). First the regioisomer N-{3-[4-bromo-1-(2-methyl propyl)-1H-pyrazol-5-yl]-2,4-difluorophenyl}-2,5-difluoro-benzenesulfonamide (0.065 g, 0.13 mmol) was isolated, then the title product was obtained as a white solid (0.12 g, 0.2 mmol, 15% four steps).

HPLC (254 nm): Rt: 5.29 min.

¹H-NMR (401 MHz, DMSO-d6) δ=10.67 (s, NH) 8.12 (s, 1 H), 7.57-7.64 (m, 1 H) 7.51-7.57 (m, 1 H) 7.47 (td, J=5.19, 2.69 Hz, 1 H) 7.38-7.45 (m, 1 H), 7.21 (td, J=8.94, 1.40 Hz, 1 H), 3.95 (d, J=7.20 Hz, 2 H), 2.09 (m, 1 H), 0.83 (d, J=6.59 Hz, 6 H).

HRMS (ESI) calcd for C19H16BrF4N3O2S [M+H]+ 506.0156, found 506.0161.

Step h

N-[3-(1-i-butyl-4-pyridin-4-yl-1H-pyrazol-3-yl)-2,4-difluoro-phenyl]-2,5-difluoro-benzenesulfonamide To a solution of tetrakis(triphenylphosphine)palladium(0) (0.035 g, 0.03 mmol) in dimethoxyethane (1 mL), N-{3-[4-bromo-1-(2-methylpropyl)-1H-pyrazol-3-yl]-2,4-difluorophenyl}-2,5-difluorobenzenesulfonamide (0.09 g, 0.18 mmol) in dimethoxyethane (1 mL) was added and the mixture was insufflated with nitrogen for 5 min. A solution of 4-(4,4, 5,5-tetramethyl-1,3,2-dioxaborolan-2-yl)pyridine (0.08 g, 0.4 mmol)) in dimethoxyethane (1 mL) was added and the mixture was insufflated with nitrogen for 10 min, then 2 M sodium carbonate solution (1 mL) was added and the mixture was heated at 110° C. in a microwave cavity for 1 h. More tetrakis(triphenylphosphine)palladium(0) (0.012 g, 0.01 mmol) and 4-(4,4,5,5-tetramethyl-1,3,2-dioxaborolan-2-yl) pyridine (0.016 g, 0.08 mmol) were added and the process was resumed for 0.5 h. The mixture was cooled and the organic phase was concentrated. The crude oil was purified by flash chromatography (eluant: dichloromethane/methanol 30:1). The title compound was obtained as a white solid (0.025 g, 28%).

HPLC (254 nm): Rt: 4.62 min.

¹H-NMR (401 MHz, DMSO-d6) δ=10.66 (bs, NH) 8.43 (s, 1 H), 8.35-8.41 (m, 2 H), 7.51-7.59 (m, 1 H) 7.39-7.50 (m, 3 H) 7.14-7.27 (m, 1 H), 6.96-7.03 (m, 2 H) 4.00 (d, J=7.20 Hz, 2 H), 2.15 (m, 1 H), 0.88 (d, J=6.71 Hz, 6 H).

HRMS (ESI) calcd for C24H20F4N4O2S [M+H]+ 505.1316, found 505.1305.

Example 37

(2,5-Difluoro-benzyl)-[2,4-difluoro-3-(4-pyridin-4-yl-1H-pyrazol-3-yl)-phenyl]-amine [(I), X=CH; R1, R2, R4, R5=H; R3, R6=F; m=0; A=—NHCH2—; R7=2,5-difluorophenyl]

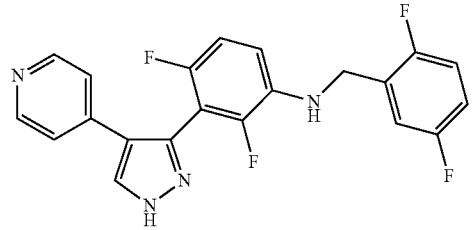 [SMILES: Fc1ccc(F)c(CNc2ccc(F)c(-c3n[nH]cc3-c3ccncc3)c2F)c1]

Dibenzyl-[2,4-difluoro-3-(4-pyridin-4-yl-1H-pyrazol-3-yl)-phenyl]-amine (prepared as described in Example 22) (150 mg, 0.551 mmol) was dissolved in a 1:1:1 mixture of methanol, acetic acid and water (18 mL). Freshly distilled 2,5-difluorobenzaldehyde (0.180 mL, 1.653 mmol, 3 eq) was then added, followed by sodiumcyanoborohydride (2.424 mmol, 4.4 eq) and the mixture was stirred at room temperature for 5 hours. It was then poured into water, basified to pH 10 by addition of a saturated aqueous solution of Na₂CO₃ and extracted with ethyl acetate (3×30 mL). The combine dorganic layers were washed with brine, dried over $_{Na2SO4}$ and evaporated to dryness. The crude product was purified by flash chromatography on silica gel (DCM/MeOH 96:4) to give 124 mg (85%) of (2,5-difluoro-benzyl)-[2,4-difluoro-3-(4-pyridin-4-yl-1H-pyrazol-3-yl)-phenyl]-amine a white solid.

HPLC (254 nm): Rt: 5.75 min.

¹H-NMR (401 MHz, DMSO-d6) δ=13.51 (s, 1 H), 8.46-8.49 and 8.13-8.15 (2 m, 1H, 2 tautomers), 8.38-8.44 (m, 2 H), 7.19-7.30 (m, 2 H), 7.10-7.19 (m, 3 H), 6.91-7.07 (m, 1 H), 6.65-6.81 (m, 1 H), 6.11 and 6.28 (2t, 1H, 2 tautomers), 4.37-4.43 (m, 1H).

HRMS (ESI) calcd for C21H15F4N4 [M+H]+ 399.1228, found 399.1236.

Preparation of N-(3-Acetyl-2,4-difluoro-phenyl)-2,5-difluoro-N-(2-methoxyethoxymethyl)-benzene-sulfonamide

[(1), R4, R5=H; R3, R6=F; G=N-(methoxyethoxymethyl)-(2,5-difluorobenzenesulfonylamino)]

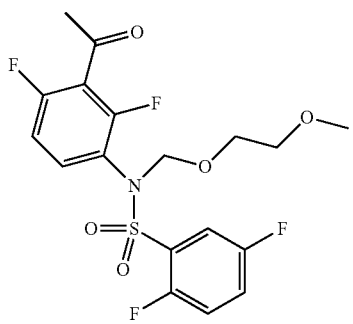 [SMILES: COCCOCN(c1ccc(F)c(C(C)=O)c1F)S(=O)(=O)c1cc(F)ccc1F]

N-(3-acetyl-2,4-difluoro-phenyl)-2,5-difluoro-benzenesulfonamide 1-(2,6-Difluoro-3-nitro-phenyl)-ethanone (*J. Het. Chem.* 1987, 24, 1509) (3.8 g, 18.9 mmol) was dissolved in ethyl acetate (40 mL). Pd/C5% (1.2 g) was added and the mixture was shaken under hydrogen atmosphere (2 atm) in a Parr apparatus for 8 hours. The reaction mixture was then filtered on a Celite pad and the filtrate was evaporated to dryness. The crude 1-(3-amino-2,6-difluoro-phenyl)-ethanone was immediately dissolved in dry pyridine (80 mL) under nitrogen atmosphere, neat 2,5-difluorobenzenesulfonylchloride was then added dropwise (2.55 mL, 18.9 mmol, 1 eq) and the mixture was stirred at room temperature overnight. The solvent was then concentrated under reduced pressure and the residue was taken up with DCM (100 mL) and washed with half-saturated aqueous ammonium chloride and brine. The organic phase was dried over $Na_2SO_4$ and evaporated to dryness. The crude was treated with a 1:1 diethyl ether/n-hexane mixture and stirred until a solid was obtained. The solid was filtered and dried under vacuum at 45° C. for 2 hours to give 5.4 g of N-(3-acetyl-2,4-difluoro-phenyl)-2,5-difluoro-benzenesulfonamide as a light orange powder (82% over two steps).

HPLC (254 nm): Rt: 5.79 min.

$^1$H-NMR (401 MHz, DMSO-$d_6$) δ=10.75 (br. s., 1 H), 7.39-7.72 (m, 4 H), 7.20 (td, J=1.6, 9.2 Hz, 1 H), 2.48 (t, J=1.6 Hz, 3 H).

N-(3-Acetyl-2,4-difluoro-phenyl)-2,5-difluoro-N-(2-methoxy-ethoxymethyl)-benzenesulfonamide N-(3-acetyl-2,4-difluoro-phenyl)-2,5-difluoro-benzenesulfonamide (2.88 g, 8.293 mmol) was dissolved in dry DCM (75 mL) under nitrogen atmosphere. DIPEA (1.55 mL, 9.12 mmol, 1.1 eq) was then added, followed by 2-methoxy-ethoxymethyl chloride (0.98 mL, 9.12 mmol, 1.1 eq) and the mixture was stirred at room temperature for 1 h. It was then diluted with DCM and washed with water and brine, dried over Na2SO4 and evaporated to dryness. The crude product was purified by chromatography on silica gel (n-hexane/ethyl acetate 7:3) to give 2.25 g (62%) of N-(3-acetyl-2,4-difluoro-phenyl)-2,5-difluoro-N-(2-methoxy-ethoxymethyl)-benzene-sulfonamide as a yellow oil.

HPLC (254 nm): Rt: 6.38 min.

$^1$H-NMR (401 MHz, DMSO-$d_6$) δ=7.65-7.73 (m, 1 H), 7.57-7.65 (m, 1 H), 7.47-7.57 (m, 2 H), 7.29 (td, J=1.5, 9.2 Hz, 1 H), 5.11 (s, 2 H), 3.65-3.70 (m, 2 H), 3.40-3.45 (m, 2 H), 3.29 (s, 3 H), 3.21 (s, 3 H).

HRMS (ESI) calcd for C18H18F4NO5F [M+H]+: 453.1120, found: 453.1104.

Example 38

N-{3-[4-(2-Amino-pyridin-4-yl)-1-ethyl-1H-pyrazol-3-yl]-2,4-difluoro-phenyl}-2,5-difluoro-benzene-sulfonamide (Cpd. n°68) [(I)U, R1, R4, R5=H; R3, R6=F; m=2; A=—NHSO2—; R7=2,5-difluorophenyl]

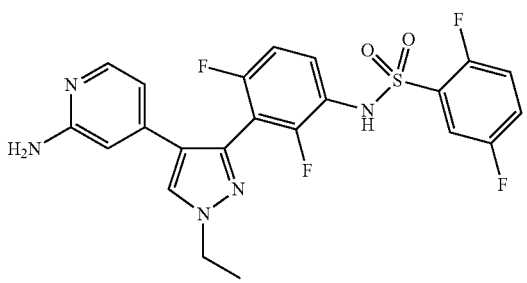 [SMILES: CCn1cc(-c2ccnc(N)c2)c(-c2c(F)ccc(NS(=O)(=O)c3cc(F)ccc3F)c2F)n1]

Method C
Steps a and b

N-[2,4-Difluoro-3-(1H-pyrazol-3-yl)-phenyl]-2,5-difluoro-N-(2-methoxyethoxy-methyl)-benzenesulfonamide

[(23), R4, R5=H; R3, R6=F; G=N-(methoxy-ethoxymethyl)-(2,5-difluorobenzenesulfonylamino)]

N-(3-acetyl-2,4-difluoro-phenyl)-2,5-difluoro-N-(2-methoxy-ethoxymethyl)-benzene-sulfonamide (1.7 g, 3.91 mmol) was dissolved in dry toluene (40 mL) under nitrogen atmosphere. N,N-dimethylformamidedimethylacetal (2.1 mL, 15.64 mmol, 4 eq) was added and the mixture was heated to 100° C. and stirred at this temperature for 4 hours. The solvent was then evaporated to dryness. The crude intermediate enaminone was kept under high vacuum for 2 hours and then dissolved in absolute ethanol (26 mL). Monohydrate hydrazine was added (0.57 mL, 11.7 mmol, 3 eq) and the reaction mixture was heated to 60° C. and stirred at this temperature for 2 hours. It was then concentrated under reduced pressure, taken up with DCM and washed with water and brine. The crude product was purified by chromatography on silica gel (DCM/MeOH 95:5) to give 1.27 g of N-[2,4-difluoro-3-(1H-pyrazol-3-yl)-phenyl]-2,5-difluoro-N-(2-methoxyethoxy-methyl)-benzenesulfonamide as a yellow amorphous solid.

HPLC (254 nm): Rt: 5.89 min.

$^1$H-NMR (401 MHz, DMSO-$d_6$) δ=13.22 (br. s., 1 H), 7.87 (br. s., 1 H), 7.51-7.74 (m, 3 H), 7.30-7.39 (m, J=6.8 Hz, 1 H), 7.15-7.27 (m, 1 H), 6.43 (br. s., 1 H), 5.13 (s, 2 H), 3.64-3.80 (m, 2 H), 3.40-3.49 (m, 2 H), 3.22 (s, 3 H).

HRMS (ESI) calcd for C19H18F4N3O4F [M+H]+: 460.0949, found: 460.0949.

Method C
Step c

N-[3-(4-Bromo-1H-pyrazol-3-yl)-2,4-difluoro-phenyl]-2,5-difluoro-N-(2-methoxy-ethoxymethyl)-benzene-sulfonamide

[(25), R4, R5=H; R3, R6=F; Hal=Br; G=N-(methoxyethoxymethyl)-(2,5-difluorobenzene-sulfonylamino)]
N-[2,4-difluoro-3-(1H-pyrazol-3-yl)-phenyl]-2,5-difluoro-N-(2-methoxyethoxy-methyl)-benzenesulfonamide (1.27 g, 2.76 mmol) was dissolved in dry DCM (10 mL). N-bromosuccinimide was then added (737 mg, 4.14 mmol, 1.5.eq) and the reaction was stirred at room temperature for 3 hours. The reaction mixture was then diluted with DCM and washed with 10% aqueous $NaHSO_3$ and brine. The organic phase was dried over $Na_2SO_4$ and evaporated to dryness. The desired N-[3-(4-bromo-1H-pyrazol-3-yl)-2,4-difluoro-phenyl]-2,5-difluoro-N-(2-methoxyethoxymethyl)-benzenesulfonamide was isolated from the crude mixture by chromatography on silica gel (DCM/MeOH 95:5) obtaining 584 mg (39%) of off-white solid.

$^1$H-NMR (300 MHz, DMSO-$d_6$) δ=13.61 (br. s., 1 H), 8.14 (br. s., 1 H), 7.46-7.73 (m, 4 H), 7.25-7.39 (m, 1 H), 5.13 (s, 2 H), 3.68-3.75 (m, 2 H), 3.40-3.49 (m, 2 H), 3.22 (s, 3 H).

Step d

N-[3-(4-Bromo-1-ethyl-1H-pyrazol-3-yl)-2,4-difluoro-phenyl]-2,5-difluoro-N-(2-methoxy-ethoxymethyl)-benzenesulfonamide [(26), R1, R4, R5=H; R3, R6=F; m=2; Hal=Br; G=N-(methoxyethoxymethyl)-(2,5-difluorobenzenesulfonylamino)]

N-[3-(4-bromo-1H-pyrazol-3-yl)-2,4-difluoro-phenyl]-2,5-difluoro-N-(2-methoxy-ethoxymethyl)-benzenesulfonamide (584 mg, 1.085 mmol) was dissolved in DCM (5 mL). 32% sodium hydroxide was added (5 mL) followed by ethyl iodide (0.13 mL, 1.628 mmol, 1.5 eq) and TBAB (58 mg, 0.18 mmol, 0.17 eq) and the biphasic mixture was vigorously stirred at room temperature for 3 hours. The reaction mixture was then diluted with DCM, washed with water and brine, dried over $Na_2SO_4$ and evaporated to dryness. The two ethyl pyrazole regioisomers have been separated by chromatography on silica gel (n-hexane/ethyl acetate 7:3): 308 mg (50% yield) of the desired regioisomer N-[3-(4-bromo-1-ethyl-1H-pyrazol-3-yl)-2,4-difluoro-phenyl]-2,5-difluoro-N-(2-methoxy-ethoxymethyl)-benzenesulfonamide were obtained along with 160 mg (26% yield) of the minor regioisomer N-[3-(4-bromo-2-ethyl-2H-pyrazol-3-yl)-2,4-difluoro-phenyl]-2,5-difluoro-N-(2-methoxy-ethoxymethyl)-benzenesulfonamide.

HPLC (254 nm): Rt: 6.92 min.

$^1$H-NMR (401 MHz, DMSO-$d_6$) δ=8.15 (s, 1 H), 7.63-7.70 (m, 1 H), 7.55-7.63 (m, 1 H), 7.47-7.55 (m, 2 H), 7.30 (td, J=1.4, 8.9 Hz, 1 H), 5.13 (s, 2 H), 4.18 (q, J=7.3 Hz, 2 H), 3.67-3.73 (m, 2 H), 3.41-3.47 (m, 2 H), 3.22 (s, 3 H), 1.38 (t, J=7.3 Hz, 3 H).

HRMS (ESI) calcd for $C_{21}H_{21}BrF_4N_3O_4S$ [M+H]+: 566.0367, found: 566.0354.

Step h

N-[3-(1-Ethyl-4-pyridin-4-yl-1H-pyrazol-3-yl)-2,4-difluoro-phenyl]-2,5-difluoro-N-(2-methoxy-ethoxymethyl)-benzenesulfonamide

[(II), X=CH; R1, R2, R4, R5=H; R3, R6=F; m=2; G=N-(methoxyethoxymethyl)-2,5-difluorobenzene-sulfonylamino]

In a vial suitable for microwave irradiation N-[3-(4-Bromo-1-ethyl-1H-pyrazol-3-yl)-2,4-difluoro-phenyl]-2,5-difluoro-N-(2-methoxy-ethoxymethyl)-benzenesulfonamide (288 mg, 0.509 mmol) was dissolved in dimethoxyethane (4.5 mL) and Ar was bubbled through the solution for 5 minutes. Water (0.5 mL) was added, followed by 4-pyridyl-boronic acid pinacol ester (209 mg, 1.018 mmol, 2 eq), cesium carbonate (497 mg, 1.527 mmol, 3 eq) and Pd(dppf)$Cl_2$.DCM (42 mg, 0.051 mmol, 0.1 eq). The vial was sealed and irradiated in the microwave oven at 100° C. for 30 minutes. The reaction mixture was then filtered over a Celite pad and concentrated under reduced pressure. The residue was taken up with ethyl acetate and washed with saturated aqueous $NaHCO_3$ and brine. The organic phase was dried over $Na_2SO_4$ and evaporated to dryness. The crude product was purified by chromatography on silica gel (DCM/MeOH 97:3) to give 247 mg (86% yield) of N-[3-(1-ethyl-4-pyridin-4-yl-1H-pyrazol-3-yl)-2,4-difluoro-phenyl]-2,5-difluoro-N-(2-methoxy-ethoxymethyl)-benzenesulfonamide as an off-white solid.

HPLC (254 nm): Rt: 6.14 min.

$^1$H-NMR (401 MHz, DMSO-$d_6$) δ=8.47 (s, 1 H), 8.39-8.42 (m, 2 H), 7.57-7.65 (m, 1 H), 7.45-7.55 (m, 3 H), 7.24-7.31 (m, 1 H), 7.01-7.07 (m, 2 H), 5.11 (s, 2 H), 4.23 (q, J=7.4 Hz, 2 H), 3.62-3.68 (m, 2 H), 3.36-3.42 (m, 2 H), 3.20 (s, 3 H), 1.45 (t, J=7.3 Hz, 3 H).

HRMS (ESI) calcd for $C_{26}H_{25}F_4N_4O_4S$ [M+H]+: 565.1527, found: 565.1506.

Method E

Steps a, c, d

N-{3-[4-(2-Amino-pyridin-4-yl)-1-ethyl-1H-pyrazol-3-yl]-2,4-difluoro-phenyl}-2,5-difluoro-benzene-sulfonamide

[(I)U, R1, R4, R5=H; R3, R6=F; m=2; A=—NHSO2-; R7=2,5-difluorophenyl]

N-[3-(1-ethyl-4-pyridin-4-yl-1H-pyrazol-3-yl)-2,4-difluoro-phenyl]-2,5-difluoro-N-(2-methoxy-ethoxymethyl)-benzenesulfonamide (123 mg, 0.217 mmol) was dissolved in dry DCM, mCPBA (75 mg, 2 eq) was added and the reaction mixture was stirred at room temperature for 3 hours. A further addition of mCPBA was made (50 mg) and the mixture was stirred for 2 more hours. It was then diluted with DCM, washed with saturated aqueous $NaHCO_3$ and brine, dried over $Na_2SO_4$ and evaporated to dryness. The crude intermediate N-oxide (130 mg) was dissolved in dry trifluoromethylbenzene (1.5 mL), the solution was cooled to 0° C. and t-butyl amine (0.118 mL 1.12 mmol, 5 eq) was added. Tosylanhydride (150 mg, 0.448 mmol, 2 eq) was then added in portions. After 1 h stirring at 0° C., further additions of t-butyl amine (0.03 mL, 1.25 eq) and tosylanhydride (40 mg, 0.5 eq) were made and the reaction mixture was stirred at 0° C. for 30 more minutes. Trifluoroacetic acid (1.5 mL) was then added and the mixture was hated to 70° C. and stirred at this temperature for 1.5 h. The solvent was evaporated and the residue taken up with DCM and water. The aqueous phase was neutralized with 32% aq. NaOH and extracted 3 times with DCM. The combined organic layers were washed with brine, dried over $Na_2SO_4$ and evaporated to dryness. The crude product was purified by chromatography on silica gel (DCM/MeOH 95:5) to give 46 mg of N-{3-[4-(2-amino-pyridin-4-yl)-1-ethyl-1H-pyrazol-3-yl]-2,4-difluoro-phenyl}-2,5-difluoro-benzenesulfonamide as a white solid.

HPLC (254 nm): Rt: 5.19 min.

$^1$H-NMR (401 MHz, DMSO-$d_6$) δ=9.87-11.05 (m, 1 H), 8.22 (s, 1 H), 7.68 (d, J=5.5 Hz, 1 H), 7.51-7.58 (m, 1 H), 7.33-7.50 (m, 3 H), 7.06-7.21 (m, 1 H), 6.25 (d, J=0.7 Hz, 1 H), 6.02 (dd, J=1.3, 5.3 Hz, 1 H), 5.85 (br. s., 2 H), 4.19 (q, J=7.2 Hz, 2 H), 1.42 (t, J=7.3 Hz, 3 H).

The invention claimed is:
1. A compound of formula (I):

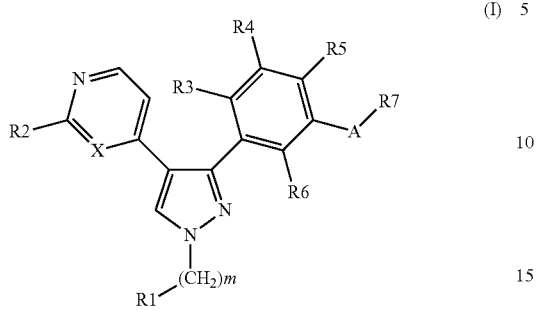

wherein:
m is an integer from 0 to 6;
R1 is hydrogen, trichloromethyl, trifluoromethyl, halogen, cyano, OH, OR8, NR9R10, NR21COR22, COOH, COOR11, CONR12R13, or a group optionally substituted selected from straight or branched ($C_1$-$C_8$) alkyl, ($C_2$-$C_8$) alkenyl or ($C_2$-$C_8$) alkynyl, ($C_3$-$C_8$) cycloalkyl, ($C_3$-$C_8$) cycloalkenyl, heterocyclyl, aryl and heteroaryl, wherein:
R8 and R11 are each independently a group optionally substituted selected from straight or branched ($C_1$-$C_8$) alkyl, ($C_3$-$C_8$) cycloalkyl, heterocyclyl, aryl and heteroaryl;
R9, R10, R12 and R13 the same or different, are each independently hydrogen or a group optionally substituted selected from straight or branched ($C_1$-$C_8$) alkyl, ($C_3$-$C_8$) cycloalkyl, heterocyclyl, aryl and heteroaryl, or taken together with the nitrogen atom to which they are bonded either R9 and R10 as well as R12 and R13 may form an optionally substituted heterocyclyl or heteroaryl, optionally containing one additional heteroatom or heteroatomic group selected from S, O, N or NH;
R21 and R22 the same or different, are each independently hydrogen or a group optionally substituted selected from straight or branched ($C_1$-$C_8$) alkyl, ($C_3$-$C_8$) cycloalkyl, heterocyclyl, aryl and heteroaryl, or taken together with the atoms to which they are bonded R21 and R22 may form an optionally substituted heterocyclyl, optionally containing one additional heteroatom or heteroatomic group selected from S, O, N or NH;
X is —CH or N;
R2 is hydrogen, halogen, NR14R15, SR23 or SO$_2$R23, wherein:
R14 and R15 are independently hydrogen or a group optionally substituted selected from straight or branched ($C_1$-$C_8$) alkyl, ($C_3$-$C_8$) cycloalkyl, heterocyclyl, aryl and heteroaryl; or taken together with the nitrogen atom to which they are bonded R14 and R15 may form an optionally substituted 3 to 8 membered heterocyclyl or heteroaryl, optionally containing one additional heteroatom or heteroatomic group selected from S, O, N or NH; or R14 is hydrogen and R15 is COR 16, wherein:
R16 is OR17, NR18R19 or a group optionally substituted selected from straight or branched ($C_1$-$C_8$) alkyl, ($C_2$-$C_8$) alkenyl or ($C_2$-$C_8$) alkynyl, ($C_3$-$C_8$) cycloalkyl, ($C_3$-$C_8$) cylcoalkenyl, heterocyclyl, aryl and heteroaryl, wherein:
R17 is a group optionally substituted selected from straight or branched ($C_1$-$C_8$) alkyl, ($C_3$-$C_8$) cycloalkyl, heterocyclyl, aryl and heteroaryl;
R18 and R19 are each independently a group optionally substituted selected from straight or branched ($C_1$-$C_8$) alkyl, ($C_3$-$C_8$) cycloalkyl, heterocyclyl, aryl and heteroaryl, or taken together with the nitrogen atom to which they are bonded R18 and R19 may form an optionally substituted 3 to 8 membered heterocyclyl or heteroaryl, optionally containing one additional heteroatom or heteroatomic group selected from S, O, N or NH;
R23 is a group optionally substituted selected from straight or branched ($C_1$-$C_8$) alkyl, ($C_3$-$C_8$) cycloalkyl, heterocyclyl, aryl and heteroaryl;
R3, R4, R5 and R6 are each independently hydrogen, halogen, trifluoromethyl, trichloromethyl, cyano, OR20 or a group optionally substituted selected from straight or branched ($C_1$-$C_8$) alkyl, and ($C_3$-$C_8$) cycloalkyl, wherein:
R20 is a group optionally substituted selected from straight or branched ($C_1$-$C_8$) alkyl and ($C_3$-$C_8$) cycloalkyl;
A is —CON(Y)—, —CON(Y)O—, —CON(Y)N(Y)—, —CON(Y)SO$_2$—, —SO$_2$N(Y)—, —SO$_2$N(Y)O—, —SO$_2$N(Y)N(Y)—, —SO$_2$N(Y)CO—, —SO$_2$N(Y)CON(Y)—, —SO$_2$N(Y)SO$_2$—, —N(Y)CO—, —N(Y)SO$_2$—, —N(Y)CON(Y)—, —N(Y)CSN(Y)—, —N(Y)CON(Y)N(Y)—, —N(Y)COO—, —N(Y)CON(Y)SO$_2$—, —N(Y)SO$_2$N(Y)—, —C(R'R")CON(Y)—, —C(R'R")CSN(Y)—, —C(R'R")CON(Y)O—, —C(R'R")CON(Y)N(Y)—, —C(R'R")CON(Y)SO$_2$—, —C(R'R")SO$_2$N(Y)—, —C(R'R")SO$_2$N(Y)O—, —C(R'R")SO$_2$N(Y)N(Y)—, —C(R'R")SO$_2$N(Y)CO—, —C(R'R")SO$_2$N(Y)SO$_2$—, —C(R'R")N(Y)CO, —C(R'R")N(Y)SO$_2$—, —C(R'R")N(Y)CON(Y)—, —C(R'R")N(Y)CSN(Y)—, —C(R'R")N(Y)COO—, —C(R'R")N(Y)SO$_2$N(Y)—or —N(Y)C(R'R")—, wherein:
Y is hydrogen or an optionally substituted straight or branched ($C_1$-$C_3$) alkyl;
and R' and R" are independently hydrogen or an optionally further substituted straight or branched ($C_1$-$C_6$) alkyl, or taken together with the carbon atom to which they are bonded R' and R" may form an optionally substituted ($C_3$-$C_8$) cycloalkyl;
R7 is hydrogen or an optionally substituted group selected from straight or branched ($C_1$-$C_8$) alkyl, ($C_2$-$C_8$) alkenyl, or ($C_3$-$C_8$) cycloalkyl, ($C_2$-$C_8$) alkynyl, ($C_3$-$C_8$) cylcoalkenyl, heterocyclyl, aryl and heteroaryl;
or a pharmaceutically acceptable salts thereof.
2. A compound of formula (I) as defined in claim 1 wherein:
m is an integer from 0 to 2; or a pharmaceutically acceptable salt thereof.
3. A compound of formula (I) as defined in claim 1 wherein:
A is —CON(Y)—, —CON(Y)O—, —CON(Y)N(Y)—, —CON(Y)SO$_2$—, —SO$_2$N(Y)—, —N(Y)CO—, —N(Y)SO$_2$—, —N(Y)CON(Y)—, —N(Y)CSN(Y)—, —N(Y)COO—, —C(R'R")CON(Y)—, —C(R'R")N(Y)CO, —C(R'R")N(Y)CON(Y)—, wherein:
Y, R' and R" are as defined in claim 1, or a pharmaceutically acceptable salt thereof.

4. A compound of formula (I) as defined in claim 1 wherein:
R1 is hydrogen, trichloromethyl, trifluoromethyl, halogen, cyano, OH, OR8, NR9R10, CONR12R13, or a group optionally substituted selected from straight or branched ($C_1$-$C_8$) alkyl, ($C_2$-$C_8$) alkenyl or ($C_2$-$C_8$) alkynyl, ($C_3$-$C_8$) cycloalkyl, ($C_3$-$C_8$) cycloalkenyl, heterocyclyl, aryl and heteroaryl, wherein:
R8, R9, R10, R12 and R13 are as defined in claim 1; or a pharmaceutically acceptable salt thereof.

5. A compound of formula (I) as defined in claim 3, wherein:
R1 is hydrogen, trichloromethyl, trifluoromethyl, halogen and cyano; or a pharmaceutically acceptable salt thereof.

6. A compound of formula (I) as defined in claim 3 wherein:
R2 is hydrogen or NR14R15, wherein:
R14 and R15 are independently hydrogen or a group optionally substituted selected from straight or branched ($C_1$-$C_8$) alkyl, ($C_3$-$C_8$) cycloalkyl, heterocyclyl, aryl and heteroaryl; or a pharmaceutically acceptable salt thereof.

7. A compound of formula (I) as defined in claim 6 wherein:
R3, R4, R5 and R6 are each independently hydrogen, halogen, trifluoromethyl, trichloromethyl or cyano; or a pharmaceutically acceptable salt thereof.

8. A compound of formula (I) as defined in claim 1 wherein:
R7 is an optionally substituted group selected from straight or branched ($C_1$-$C_8$) alkyl, ($C_3$-$C_8$) cylcoalkyl, ($C_3$-$C_8$) cycloalkenyl, heterocyclyl, aryl and heteroaryl; or a pharmaceutically acceptable salt thereof.

9. A compound of formula (I) or a pharmaceutically acceptable salt thereof as defined in claim 1 which is selected from the group consisting of:
1-[3-(4-pyridin-4-yl-1H-pyrazol-3-yl)-phenyl]-3-(4-trifluoromethyl-phenyl)-urea, 2,5-difluoro-N-[3-(4-pyridin-4-yl-1H-pyrazol-3-yl)-phenyl]-benzenesulfonamide, N-(4-chloro-phenyl)-3-(4-pyridin-4-yl-1H-pyrazol-3-yl)-benzamide,
N-(4-tert-Butyl-phenyl)-3-(4-pyridin-4-yl-1H-pyrazol-3-yl)-benzamide,
1-(4-chloro-3-trifluoromethyl-phenyl)-3-{3-[1-(2-fluoro-ethyl)-4-pyridin-4-yl-1H-pyrazol-3-yl]-phenyl}-urea,
furan-2-sulfonic acid[3-(4-pyridin-4-yl-1H-pyrazol-3-yl)-phenyl]-amide,
thiophene-3-sulfonic acid[3-(4-pyridin-4-yl-1H-pyrazol-3-yl)-phenyl]-amide,
1-[3-(4-pyridin-4-yl-1H-pyrazol-3-yl)-phenyl]-3-p-tolyl-urea,
1-(4-chloro-phenyl)-3-[3-(4-pyridin-4-yl-1H-pyrazol-3-yl)-phenyl]-urea,
1-[3-(1-ethyl-4-pyridin-4-yl-1H-pyrazol-3-yl)-phenyl]-3-(4-trifluoromethyl-phenyl)-urea,
1-[3-(1-cyanomethyl-4-pyridin-4-yl-1H-pyrazol-3-yl)-phenyl]-3-(4-trifluoromethyl-phenyl)-urea,
1-{3-[4-(2-amino-pyridin-4-yl)-1H-pyrazol-3-yl]-phenyl}-3-(4-trifluoromethyl-phenyl)-urea,
1-{3-[1-(2-fluoro-ethyl)-4-pyridin-4-yl-1H-pyrazol-3-yl]-phenyl}-3-(4-trifluoromethyl-phenyl)-urea,
1-{3-[1-(2-hydroxy-ethyl)-4-pyridin-4-yl-1H-pyrazol-3-yl]-phenyl}-3-(4-trifluoromethyl-phenyl)-urea,
1-{3-(1-piperidin-4-yl-4-pyridin-4-yl-1H-pyrazol-3-yl]-phenyl]-3-(4-trifluoromethyl-phenyl)-urea,
N-[3-(4-pyridin-4-yl-1H-pyrazol-3-yl)-phenyl]-2-(4-trifluoromethyl-phenyl)-acetamide,
N-[4-(3-{3-[3-(4-trifluoromethyl-phenyl)-ureido]-phenyl}-1H-pyrazol-4-yl)-pyridin-2-yl]-acetamide,
N-[2,4-difluoro-3-(4-pyridin-4-yl-1H-pyrazol-3-yl)-phenyl]-2,5-difluoro-benzenesulfonamide,
thiophene-3-sulfonic acid[2,4-difluoro-3-(4-pyridin-4-yl-1H-pyrazol-3-yl)-phenyl]-amide,
furan-2-sulfonic acid[2,4-difluoro-3-(4-pyridin-4-yl-1H-pyrazol-3-yl)-phenyl]-amide,
propane-1-sulfonic acid[2,4-difluoro-3-(4-pyridin-4-yl-1H-pyrazol-3-yl)-phenyl]-amide,
1-(4-tert-butyl-phenyl)-3-[3-(4-pyridin-4-yl-1H-pyrazol-3-yl)-phenyl]-urea,
1-[4-(cyano-dimethyl-methyl)-phenyl]-3-[3-(4-pyridin-4-yl-1H-pyrazol-3-yl)-phenyl]-urea,
1-[2-ffluoro-5-(4-pyridin-4-yl-1H-pyrazol-3-yl)-phenyl]-3-(4-trifluoromethyl-phenyl)-urea,
1-(2-fluoro-4-trifluoromethyl-phenyl)-3-[3-(4-pyridin-4-yl-1H-pyrazol-3-yl)-phenyl]-urea,
cyclopropanesulfonic acid[2,4-difluoro-3-(4-pyridin-4-yl-1H-pyrazol-3-yl)-phenyl]-amide,
2,2,2-trifluoro-ethanesulfonic acid[2,4-difluoro-3-(4-pyridin-4-yl-1H-pyrazol-3-yl)-phenyl]-amide,
N-[2,4-difluoro-3-(4-pyridin-4-yl-1H-pyrazol-3-yl)-phenyl]-trifluoro-methanesulfonamide,
cyclohexanesulfonic acid[2,4-difluoro-3-(4-pyridin-4-yl-1H-pyrazol-3-yl)-phenyl]-amide,
1-[3-(4-pyrimidin-4-yl-1H-pyrazol-3-yl)-phenyl]-3-(4-trifluoromethyl-phenyl)-urea,
1-{3-[4-(2-amino-pyrimidin-4-yl)-1H-pyrazol-3-yl]-phenyl}-3-(4-trifluoromethyl-phenyl)-urea,
N-[4-(3-{3-[3-(4-trifluoromethyl-phenyl)-ureido]-phenyl}-1H-pyrazol-4-yl)- pyrimidin-2-yl]-acetamide,
2,5-difluoro-N-[3-(4-pyrimidin-4-yl-1H-pyrazol-3-yl)-phenyl]-benzenesulfonamide,
N-{3-[4-(2-amino-pyrimidin-4-yl)-1H-pyrazol-3-yl]-phenyl}-2,5-difluoro-benzenesulfonamide,
N-(4-{3-[3(2,5-difluoro-benzenesulfonylamino)-phenyl]-1H-pyrazol-4-yl}-pyrimidin-2-yl)-acetamide,
N-[2,4-difluoro-3-(4-pyrimidin-4-yl-1H-pyrazol-3-yl)-phenyl]-2,5-difluoro-benzenesulfonamide,
N-{3-[4-(2-amino-pyrimidin-4-yl)-1H-pyrazol-3-yl]-2,4-difluoro-phenyl}-2,5-difluoro-benzenesulfonamide,
N-(4-{3-[3-(2,5-difluoro-benzenesulfonylamino)-2,6-difluoro-phenyl]-1H-pyrazol-4-yl}-pyrimidin-2-yl)-acetamide,
N-[4-(3-{3-[3-(4-trifluoromethyl-phenyl)-ureido]-phenyl}-1H-pyrazol-4-yl)-pyridin-2-yl]-propionamide,
N-[4-(3-{3-[3-(4-trifluoromethyl-phenyl)-ureido]-phenyl}-1H-pyrazol-4-yl)-pyridin-2-yl]-isobutyramide,
cyclopentanecarboxylic acid[4-(3-{3-[3-(4-trifluoromethyl-phenyl)-ureido]-phenyl}-1H-pyrazol-4-yl)-pyridin-2-yl]-amide,
2-[3-(4-pyridin-4-yl-1H-pyrazol-3-yl)-phenyl]-N-(4-trifluoromethyl-phenyl)-acetamide,
4-hydroxy-N-[4-(3-{3-[3-(4-trifluoromethyl-phenyl)-ureido]-phenyl}-1H-pyrazol-4-yl)-pyridin-2-yl]-butyramide,
N-(4-{3-[3-(2,5-difluoro-benzenesulfonylamino)-phenyl]-1H-pyrazol-4-yl}-pyridin-2-yl)-acetamide,
N-(4-{3-[3-(2,5-difluoro-benzenesulfonylamino)-2,6-difluoro-phenyl]-1H-pyrazol-4-yl}-pyridin-2-yl)-acetamide, 3-(4-pyridin-4-yl-1H-pyrazol-3-yl)-N-(4-trifluoromethyl-phenyl)-benzamide, 4-pyridin-4-yl-3-{3-[3-(4-trifluoromethyl-phenyl)-ureido]-phenyl}-pyrazole-1-carboxylic acid ethyl ester 1-[3-(1-methyl-4-pyridin-4-yl-1H-pyrazol-3-yl)-phenyl]-3-(4-trifuoromethyl-phenyl)-urea, 1-[3-(1-butyl-4-pyridin-4-yl-1H-pyrazol-3-yl)-phenyl]-3-(4-trifuoromethyl-phenyl)-urea, 1-[3-(1-Isobutyl-4-pyridin-4-yl-1H-pyrazol-3-yl)-phenyl]-3-(4-trifluoromethyl-phenyl)-urea, N-[3-(1-ethyl-4-pyridin-4-yl-1H-pyrazol-3-yl)-2,4-difluoro-phenyl]-2,5-difluoro-benzenesulfonamide, N-[2,4-difluoro-3-(1-methyl-4-pyridin-4-yl-1H-pyrazol-3-yl)-phenyl]-2,5-difluoro-benzenesulfonamide, N-{2,4-difluoro-3-[4-(2-methylamino-pyridin-4-yl)-1H-pyrazol-3-yl]-phenyl}-2,5-difluoro-benzenesulfonamide, N-{3-[4-(2-ethylamino-pyridin-4-yl)-1H-pyrazol-3-yl]-2,4-difluoro-phenyl}-2,5-difluoro-benzenesulfonamide, N-{3-[4-(2-ethylamino-pyrimidin-4-yl)-1H-pyrazol3-yl]-phenyl}-2,5-difluoro-benzenesulfonamide, N-[2,4-difluoro-3-(1-isobutyl-4-pyridin-4-yl-1H-pyrazol-3-yl)-phenyl]-2,5-difluoro-benzenesulfonamide, N-[3-(1-ethyl-4-pyridin-4-yl-1H-pyrazol-3-yl)-2,4-difluoro-phenyl]-2-fluoro-benzenesulfonamide, N-[3-(1-ethyl-4-pyridin-4-yl-1H-pyrazol-3-yl)-2,4-difluoro-phenyl]-3-fluoro-benzenesulfonamide, N-[3-(1-ethyl-4-pyridin-4-yl-1H-pyrazol-3-yl)-4-fluoro-phenyl]-2,5-difluoro-benzenesulfonamide, N-[3-(1-ethyl-4-pyridin-4-yl-1H-pyrazol-3-yl)-2-fluoro-phenyl]-2,5-difluoro-benzenesulfonamide, N-{3-[4-(2-amino-pyrimidin-4-yl)-1-ethyl-1H-pyrazol3-yl]-2,4-difluoro-phenyl}-2,5-difluoro-benzenesulfonamide, N-{2,4-difluoro-3-[1-(2-piperidin-1-yl-ethyl)-4-pyridin-4-yl-1H-pyrazol3-yl]-phenyl}-2,5-difluoro-enzenesulfonamide, N-{2,4-difluoro-3-[1-(2-morpholin-4-yl-ethyl)-4-pyridin-4-yl-1H-pyrazol3-yl]-phenyl}-2,5-difluoro-enzenesulfonamide, N-(2,4-difluoro-3-{1-[2-(4-methyl-piperazin-1-yl)-ethyl]-4-pyridin-4-yl-1H-pyrazol-3-yl}-phenyl)-2,5-difluoro-benzenesulfonamide, N-{3-[1-(2-dimethylamino-ethyl)-4-pyridin-4-yl-1H-pyrazol3-yl]-2,4-difluoro-phenyl}-2,5-difluoro-benzenesulfonamide, (2,5-difluoro-benzyl)-[3-(1-ethyl-4-pyridin-4-yl-1H-pyrazol-3-yl)-2,4-difluoro-phenyl]-amine, 4-{3-[3-(2,5-difluoro-benzyloxy)-2,6-difluoro-phenyl]-1-ethyl-1H-pyrazol4-yl}-pyridine and N-{3-[4-(2-Amino-pyridin-4-yl)-1-ethyl-1H-pyrazol-3-yl]-2,4-difluoro-phenyl}-2,5-difluoro-benzenesulfonamide.

10. A method for treating a disease caused by and/or associated with a deregulated protein kinase activity which comprises administering to a mammal in need thereof an effective amount of a compound of formula (I) as defined in claim 1.

11. The method according to claim 10 for treating a disease caused by and/or associated with a deregulated Raf family kinase activity.

12. The method according to claim 10 wherein the disease is selected from the group consisting of cancer and cell proliferative disorders.

13. The method according to claim 12 wherein the cancer is selected from the group consisting of carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

14. The method according to claim 12 wherein the cell proliferative disorder is selected from the group consisting of benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

15. The method according to claim 10 further comprising subjecting the mammal in need thereof to a radiation therapy or chemotherapy regimen in combination with at least one cytostatic or cytotoxic agent.

16. The method according to claim 10 wherein the mammal in need thereof is a human.

17. An in vitro method for inhibiting the RAF family activity which comprises contacting the said receptor with an effective amount of a compound as defined in claim 1.

18. The method according to claim 10 which provides tumor angiogenesis and metastasis inhibition.

19. A pharmaceutical composition comprising a therapeutically effective amount of a compound of formula (I) or a pharmaceutically acceptable salt thereof, as defined in claim 1, and at least one pharmaceutically acceptable excipient, carrier or diluent.

20. A pharmaceutical composition according to claim 19 further comprising one or more chemotherapeutic agents.

21. A product or kit comprising a compound of formula (I) or a pharmaceutically acceptable salt thereof, as defined in claim 1, or a pharmaceutical compositions comprising a therapeutically effective amount of a compound accordinq to claim 1 or a pharmaceutically acceptable salt thereof and at least one pharmaceutically acceptable excipient, carrier or diluent, and one or more chemotherapeutic agents, as a combined preparation for simultaneous, separate or sequential use in anticancer therapy.

* * * * *

UNITED STATES PATENT AND TRADEMARK OFFICE
CERTIFICATE OF CORRECTION

PATENT NO. : 8,541,575 B2  Page 1 of 1
APPLICATION NO. : 13/054853
DATED : September 24, 2013
INVENTOR(S) : Pulici et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 218 days.

Signed and Sealed this

Fifteenth Day of September, 2015

Michelle K. Lee
*Director of the United States Patent and Trademark Office*